(12) United States Patent  (10) Patent No.: US 8,426,631 B2
Rheinheimer et al.  (45) Date of Patent: Apr. 23, 2013

(54) FUNGICIDAL COMPOUNDS, METHOD FOR THE PRODUCTION THEREOF, AND USE THEREOF TO COMBAT DAMAGING FUNGI, AND AGENTS COMPRISING THE SAME

(75) Inventors: Joachim Rheinheimer, Ludwigshafen (DE); Barbara Nave, Ruppertsberg (DE); Doris Kremzow, Heidelberg (DE); Stefan Redlich, Ludwigshafen (DE); Christian Pilger, Ludwigshafen (DE); Claudia Rosenbaum, Heidelberg (DE); Wassilios Grammenos, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 470 days.

(21) Appl. No.: 12/739,606

(22) PCT Filed: Oct. 9, 2008

(86) PCT No.: PCT/EP2008/063519
§ 371 (c)(1),
(2), (4) Date: Apr. 23, 2010

(87) PCT Pub. No.: WO2009/053250
PCT Pub. Date: Apr. 30, 2009

(65) Prior Publication Data
US 2010/0304966 A1 Dec. 2, 2010

(30) Foreign Application Priority Data
Oct. 26, 2007 (EP) .................................... 07119391

(51) Int. Cl.
*C07C 229/00* (2006.01)
*A01N 25/26* (2006.01)
(52) U.S. Cl.
USPC ............................................ 560/35; 504/100
(58) Field of Classification Search ........................ None
See application file for complete search history.

(56) References Cited

U.S. PATENT DOCUMENTS 3,890,442 A 6/1975 Meiser et al.

FOREIGN PATENT DOCUMENTS

| DE | 22 47 186 | 3/1974 |
| JP | 63162673 | * 7/1988 |
| WO | WO 00/46184 | 8/2000 |
| WO | WO 03/093224 | 11/2003 |
| WO | WO 2007/031508 | 3/2007 |
| WO | WO 2007/031512 | 3/2007 |
| WO | WO 2007/031513 | 3/2007 |
| WO | WO 2007/031523 | 3/2007 |
| WO | WO 2007/031524 | 3/2007 |
| WO | WO 2007/031526 | 3/2007 |

OTHER PUBLICATIONS

International Search Report for International Application No. PCT/EP2008/063519, 2009.
International Preliminary Report on Patentability for International Application No. PCT/EP2008/063519, 2010.

* cited by examiner

*Primary Examiner* — Susanna Moore
*Assistant Examiner* — Jennifer C Sawyer
(74) *Attorney, Agent, or Firm* — Brinks Hofer Gilson & Lione

(57) ABSTRACT

Compounds of the formula I

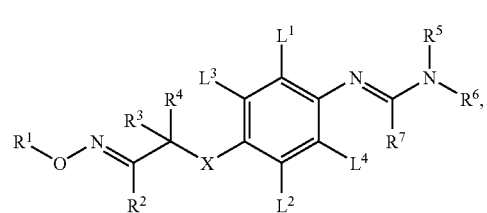

in which the substituents have the meaning given in the description, processes for preparing these compounds, compositions comprising them and their use for controlling harmful fungi.

20 Claims, No Drawings

FUNGICIDAL COMPOUNDS, METHOD FOR THE PRODUCTION THEREOF, AND USE THEREOF TO COMBAT DAMAGING FUNGI, AND AGENTS COMPRISING THE SAME

This application is a National Stage application of International Application No. PCT/EP2008/063519 filed Oct. 9, 2008, the entire contents of which is hereby incorporated herein by reference. This application also claims the benefit under 35 U.S.C. §119 of European Patent Application No. 07119391.6, filed Oct. 26, 2007, the entire contents of which is hereby incorporated herein by reference.

DESCRIPTION

The present invention relates to compounds of the formula I

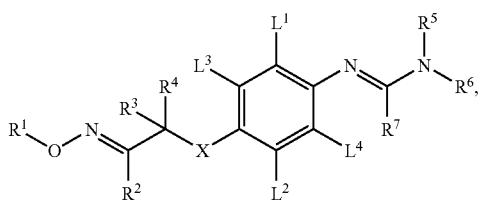

in which the substituents have the following meaning:

$R^1$ is $C_1$-$C_8$-alkyl, $C_2$-$C_8$-alkenyl, $C_2$-$C_8$-alkynyl, $C_3$-$C_8$-cycloalkyl, $C_3$-$C_8$-cycloalkenyl, phenyl or a three- to ten-membered saturated, partially unsaturated or aromatic mono- or bicyclic heterocyclyl which, in addition to carbon atoms, contains one to four heteroatoms from the group consisting of O, N and S as ring members;

$R^2$ is amino, $C_1$-$C_8$-alkyl, $C_2$-$C_8$-alkenyl, $C_2$-$C_8$-alkynyl, $C_1$-$C_8$-alkoxy, $C_3$-$C_8$-cycloalkyl, $C_3$-$C_8$-cycloalkenyl, phenyl or a three- to ten-membered saturated, partially unsaturated or aromatic mono- or bicyclic heterocyclyl which, in addition to carbon atoms, contains one to four heteroatoms from the group consisting of O, N and S as ring members, where the groups $R^2$ may be attached directly or via a carbonyl group;

$R^3,R^4$ independently of one another are hydrogen, $C_1$-$C_8$-alkyl, $C_1$-$C_8$-haloalkyl, $C_1$-$C_8$-alkylcarbonyl or $C_1$-$C_8$-alkoxycarbonyl;

$R^5,R^6$ independently of one another are $C_1$-$C_8$-alkyl, $C_1$-$C_8$-haloalkyl, $C_1$-$C_4$-alkoxy or $C_3$-$C_8$-cycloalkyl;

$R^7$ is hydrogen, $C_1$-$C_8$-alkyl, $C_1$-$C_8$-haloalkyl, $C_1$-$C_4$-alkoxy or $C_1$-$C_8$-haloalkoxy; and aliphatic and cyclic groups $R^1$ to $R^6$ may carry one, two, three or up to the maximum possible number of identical or different groups $R^a$ which independently of one another are selected from:

$R^a$ is halogen, hydroxyl, oxo, nitro, cyano, carboxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_3$-$C_6$-cycloalkyl, $C_3$-$C_8$-cycloalkenyl, $C_2$-$C_6$-alkenyloxy, $C_3$-$C_6$-alkynyloxy, $C_1$-$C_4$-alkoxyimino, $C_2$-$C_8$-alkylidene, $C_3$-$C_8$-cycloalkylidene, $C_1$-$C_{12}$-alkylamino, $C_1$-$C_4$-alkoxycarbonyl, $C_1$-$C_4$-alkylcarbonyloxy, $NR^AR^B$, $C_2$-$C_8$-alkylene, $C_2$-$C_8$-oxyalkylene, $C_1$-$C_8$-oxyalkyleneoxy, phenyl, naphthyl or a three- to ten-membered saturated, partially unsaturated or aromatic mono- or bicyclic heterocyclyl which, in addition to carbon atoms, contains one to four heteroatoms from the group consisting of O, N and S as ring members; where the cyclic groups $R^a$ may be attached directly or via a nitrogen or oxygen atom;

where in the divalent groups $R^a$ the carbon chains may be interrupted by one to four heteroatoms from the group consisting of O, N and S and the free valencies may be attached to the same atom or to two adjacent atoms; where the aliphatic or cyclic groups $R^a$ for their part may be partially or fully halogenated and/or may carry one, two, three or up to the maximum possible number of identical or different groups $R^b$:

$R^b$ is halogen, hydroxyl, nitro, cyano, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy, $C_1$-$C_4$-halo-alkoxy, $C_1$-$C_8$-alkylcarbonylamino, phenyl, phenoxy, pyridyl, pyridyl-oxy or $C_3$-$C_8$-cycloalkylcarbonylamino;

where the cyclic groups $R^b$ for their part may be partially or fully halogenated and/or may carry one, two, three or up to the maximum possible number of identical or different groups $R^c$:

$R^c$ is halogen, hydroxyl, nitro, cyano, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy or $C_1$-$C_4$-haloalkoxy;

$R^A,R^B$ independently of one another are hydrogen, $C_1$-$C_8$-alkyl, $C_1$-$C_8$-halo-alkyl or $C_1$-$C_8$-alkylcarbonyl;

$L^1,L^2,L^3,L^4$ independently of one another are hydrogen, halogen, $C_1$-$C_4$-alkyl, $C_1$-$C_4$-haloalkyl, $C_1$-$C_4$-alkoxy or $C_1$-$C_4$-haloalkoxy;

where $R^1$ and $R^2$ or $R^1$ and $R^3$ or $R^2$ and $R^3$ or $R^3$ and $R^4$ and/or $R^5$ and $R^6$ in each case together with the atoms linking them may form a five- to ten-membered saturated or partially unsaturated cyclic group which, in addition to the carbon atoms, may contain one to three heteroatoms from the group consisting of N, O and S and/or may be partially or fully halogenated and/or may carry one, two, three or up to the maximum possible number of identical or different groups $R^a$;

X is oxygen or sulfur;

and agriculturally acceptable salts of the compounds of the formula I.

Moreover, the invention relates to processes for preparing these compounds, to compositions comprising them and to their use for controlling harmful fungi.

Phenylamidines are known in a general manner from WO 2000/046184. Further phenylamidines are disclosed in WO 2003/093224, WO 2007/031508, WO 2007/031512, WO 2007/031513, WO 2007/031523, WO 2007/031524, WO 2007/031526. These compounds are known to be suitable for controlling harmful fungi.

In many cases, in particular at low application rates, the fungicidal activity of the known compounds is unsatisfactory. Based on this fact, it is an object of the present invention to provide compounds having improved activity and/or a broader activity spectrum.

This object has been achieved by the compounds defined at the outset. Furthermore, we have found processes for their preparation, compositions comprising them and methods for controlling harmful fungi using the compounds I.

The compounds I according to the invention can be obtained by different routes. Advantageously, they are prepared by reacting compounds of the formula II in which Y represents a nucleophilically replaceable group such as halogen, alkylsulfonyloxy and arylsulfonyloxy, preferably chlorine, bromine or iodine, particularly preferably chlorine, with appropriate O-substituted hydroxylamines of the formula III.

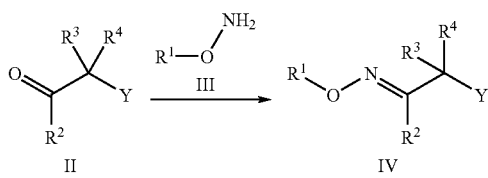

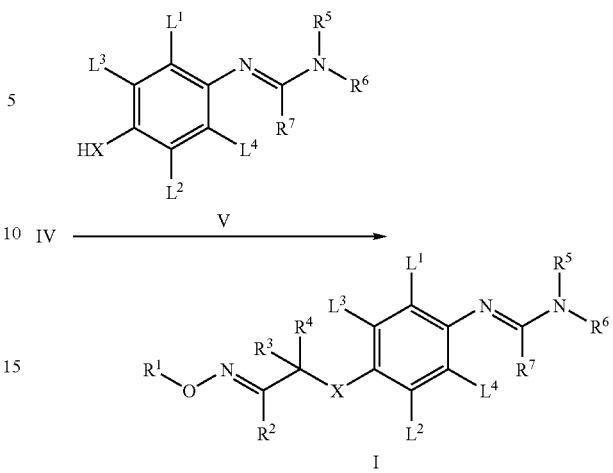

This reaction is usually carried out at from −20° C. to 150° C., preferably at from 0° C. to 120° C., in an inert organic solvent. With particular preference, the reaction is carried out in a neutral or slightly acidic medium which, if appropriate, may be prepared by addition of an acid or, if the salt of the hydroxylamine is used, by addition of a base.

Suitable solvents are aliphatic hydrocarbons, aromatic hydrocarbons, ethers, such as diethyl ether, diisopropyl ether, tert-butyl methyl ether, dioxane, anisole and tetrahydrofuran, alcohols, such as methanol, ethanol, n-propanol, isopropanol, n-butanol and tert-butanol, and also dimethyl sulfoxide, dimethylformamide and dimethylacetamide. Particular preference is given to methanol, ethanol, propanol, tetrahydrofuran and dioxane. It is also possible to use mixtures of the solvents mentioned.

Suitable bases are, in general, inorganic compounds, such as alkali metal and alkaline earth metal hydroxides, alkali metal and alkaline earth metal oxides, alkali metal and alkaline earth metal hydrides, alkali metal amides, alkali metal and alkaline earth metal carbonates, such as lithium carbonate, sodium carbonate, potassium carbonate and calcium carbonate, and also alkali metal bicarbonates, alkali metal and alkaline earth metal alkoxides, moreover organic bases, for example tertiary amines, such as trimethylamine, triethylamine, tributylamine, diisopropylethylamine and N-methylpiperidine, pyridine, substituted pyridines, and also bicyclic amines. Particular preference is given to sodium carbonate, potassium carbonate, sodium bicarbonate, and also to tertiary amines. The bases are generally employed in catalytic amounts; however, they can also be used in equimolar amounts, in excess or, if appropriate, as solvents.

Suitable for use as acids and acidic catalysts are inorganic acids, such as hydrochloric acid, hydrobromic acid, sulfuric acid and perchloric acid, and also organic acids, such as formic acid, acetic acid, propionic acid, oxalic acid, toluenesulfonic acid, benzenesulfonic acid, camphorsulfonic acid, citric acid and trifluoroacetic acid. The acids are generally employed in catalytic amounts; however, they can also be used in equimolar amounts, in excess or, if appropriate, as solvents.

The starting materials are generally reacted with one another in equimolar amounts. In terms of yield, it may be advantageous to use the hydroxylamine III in excess, based on the ketone II. This reaction may also be carried out in two steps by initially reacting hydroxylamine (formula III where $R^1$=hydrogen) or a salt thereof under the conditions described above. The product can then be alkylated to the compound IV using a known process.

Under basic conditions, the compounds of the formula IV are condensed with N-4-mercapto- or N-4-hydroxyphenylamidines of the formula V.

This reaction is usually carried out at from −40° C. to 150° C., preferably from −20° C. to 120° C., in an inert organic solvent in the presence of a base.

Suitable solvents are aliphatic hydrocarbons, aromatic hydrocarbons, such as toluene, o-, m- and p-xylene, halogenated hydrocarbons, ethers, such as diethyl ether, diisopropyl ether, tert-butyl methyl ether (MTBE), dioxane, anisole and tetrahydrofuran (THF), nitriles, such as acetonitrile and propionitrile, ketones, and also dimethyl sulfoxide (DMSO), dimethylformamide (DMF) and dimethylacetamide. Particular preference is given to DMSO, DMF and dimethylacetamide, toluene, MTBE, dioxane, acetonitrile, propionitrile and THF. It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, alkali metal and alkaline earth metal hydrides, such as lithium hydride, sodium hydride, potassium hydride and calcium hydride, alkali metal amides, alkali metal and alkaline earth metal carbonates, such as lithium carbonate, sodium carbonate, potassium carbonate and calcium carbonate, and also alkali metal bicarbonates, organometallic compounds, alkylmagnesium halides, and also alkali metal and alkaline earth metal alkoxides, such as sodium methoxide, sodium ethoxide, potassium ethoxide, potassium tert-butoxide and dimethoxymagnesium, moreover organic bases, for example tertiary amines, such as trimethylamine, triethylamine, tributylamine, diisopropylethylamine and N-methylpiperidine, pyridine, substituted pyridines, such as collidine, lutidine and 4-dimethylaminopyridine, and also bicyclic amines. Particular preference is given to sodium hydroxide, potassium hydroxide, sodium hydride, potassium hydride, sodium carbonate, potassium carbonate, sodium methoxide, sodium ethoxide, potassium ethoxide, potassium tert-butoxide, and also to tertiary amines. The bases are generally employed in equimolar amounts; however, they can also be used in excess or, if appropriate, as solvent.

The starting materials are generally reacted with one another in equimolar amounts.

Alternatively, compounds of the formula I in which $R^2$ is $CH_2$—$R^{2a}$, where $R^{2a}$ is a group $R^a$ which is attached via oxygen, can be obtained by condensing compounds of the formula II.1 in which $Y^1$ and $Y^2$ independently of one another are a nucleophilically replaceable group, such as halogen, alkylsulfonyloxy and arylsulfonyloxy, preferably chlorine, bromine and iodine, particularly preferably chlorine, with O-substituted hydroxylamines of the formula III, preferably under the conditions described above for the reaction of compounds of the formula II with compounds of the formula III.

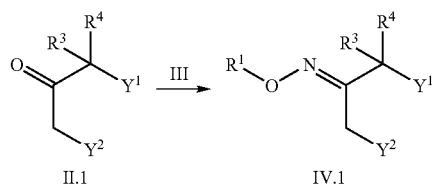

If advantageous with a view to the total yield of the reactions, this reaction can also be carried out in two steps by initially reacting hydroxylamine (where $R^1$ is hydrogen) or a salt thereof under the conditions described above. Using known processes, the product can then be alkylated to compound IV.1.

The compounds of the formula IV.I in which $Y^1$ and $Y^2$ are each independently of one another a nucleophilically replaceable group, such as halogen, alkylsulfonyloxy and arylsulfonyloxy, preferably chlorine, bromine or iodine, particularly preferably chlorine, are reacted further under basic conditions with compounds of the formula V. The resulting compounds correspond to the formula VI.

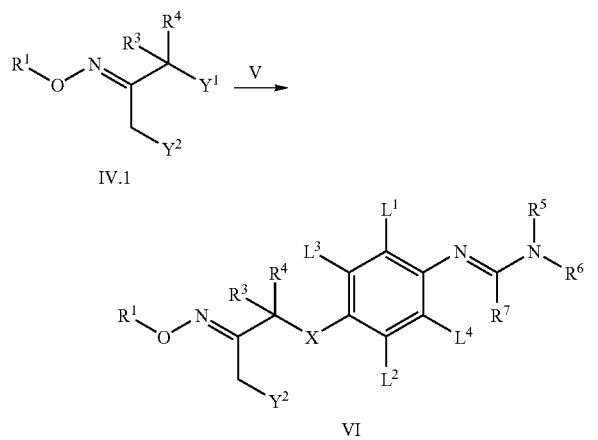

This reaction is usually carried out at from $-40°$ C. to $150°$ C., preferably from $-20°$ C. to $100°$ C., in an inert organic solvent in the presence of a base, the other reaction conditions corresponding to the reaction of compounds of the formula IV with compounds of the formula V.

The starting materials are generally reacted with one another in equimolar amounts. In terms of yield, it may be advantageous to use an excess of the compound IV.1, based on the compound V.

Under basic conditions, the compounds of the formula VI are reacted further with compounds of the formula VII, it being preferred to use the conditions described above for reacting compounds of the formula IV.1 with compounds of the formula V. The resulting compounds correspond to the formula I.1.

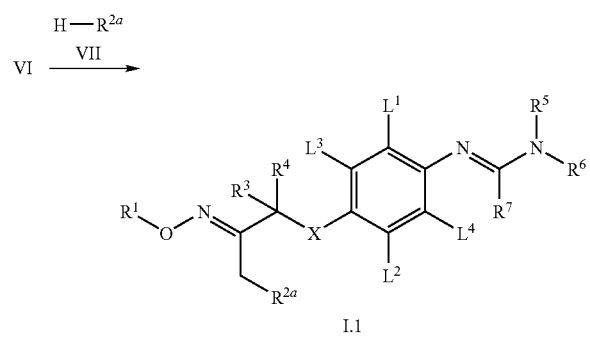

The starting materials are generally reacted with one another in equimolar amounts. In terms of yield, it may be advantageous to use an excess of the compound VII, based on the compound VI.

The order of these synthesis steps may also be changed such that initially compounds of the formula IV.1 are reacted with compounds of the formula VII. By reacting the intermediate with compounds of the formula V, it is then possible to obtain compounds of the formula I.1. To this end, the conditions described above for the reaction of compounds of the formula IV.1 with compounds of the formula V may be employed.

Compounds of the formula I in which $R^2$ and $R^3$ together with the atoms linking them form a cyclic group and $R^2$ is optionally $R^a$-substituted $C_1$-alkyl can be obtained as described above. These compounds correspond to the formula I.2

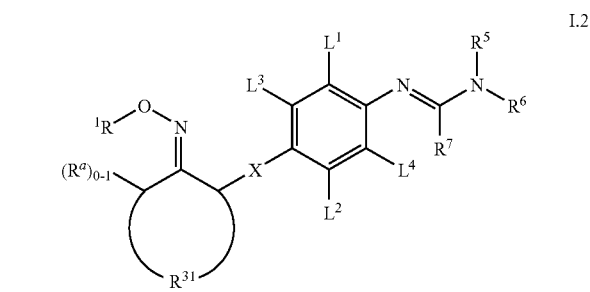

in which $R^{31}$ together with the a carbon atom of $R^2$ and the carbon atoms of the skeleton linking the $R^2$ and $R^3$ groups form a five- to ten-membered saturated or partially unsaturated cyclic group which, in addition to the carbon atoms, may contain one to three heteroatoms from the group consisting of N, O and S and/or may be partially or fully halogenated and/or may carry one, two, three or up to the maximum possible number of identical or different groups $R^a$.

The compounds I.2 can be obtained by condensing compounds of the formula II.2 in which $Y^1$ is a nucleophilically replaceable group such as halogen, alkylsulfonyloxy and arylsulfonyloxy, preferably chlorine, bromine and iodine, particularly preferably chlorine, and $Y^2$ is hydrogen or one of the groups mentioned above with O-substituted hydroxylamines of the formula III.

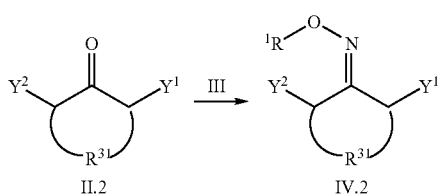

Under basic conditions, the compounds of the formula IV.2 are reacted further with compounds of the formula V. The resulting compounds correspond to those of the formula VI.1.

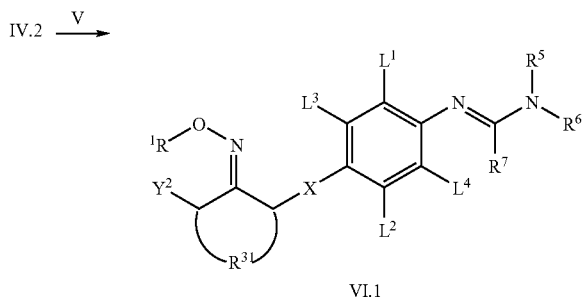

The starting materials are generally reacted with one another in equimolar amounts. In terms of yield, it may be advantageous to employ an excess of IV.2, based on V.

If desired, the compounds of the formula VI.1 are reacted under basic conditions with compounds of the formula VIII. The resulting compounds correspond to those of the formula I.2.

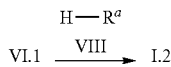

The starting materials are generally reacted with one another in equimolar amounts. In terms of yield, it may be advantageous to employ an excess of the compounds of the formula VIII, based on the compounds of the formula VI.1.

The order of these synthesis steps may also be changed such that initially compounds of the formula IV.2 are reacted with compounds of the formula VIII. By reacting the intermediate with compounds of the formula V, it is then possible to obtain compounds of the formula I.2. To this end, the conditions described above for the reaction of compounds of the formula IV.1 with compounds of the formula V may be employed.

The reaction mixtures are worked up in a customary manner, for example by mixing with water, separating the phases and, if appropriate, chromatographic purification of the crude products. Some of the intermediates and end products are obtained in the form of colorless or slightly brownish viscous oils which are purified or freed from volatile components under reduced pressure and at moderately elevated temperature. If the intermediates and end products are obtained as solids, purification can also be carried out by recrystallization or digestion.

The starting materials required for preparing the compounds I are known from the literature or can be prepared in accordance with the literature cited. If individual compounds of the formula I can not be obtained by the routes described above, they can be prepared by derivatization of other compounds I.

If the synthesis yields mixtures of isomers, a separation is generally not necessarily required since in some cases the individual isomers can be interconverted during preparation for application or during application (for example under the action of light, acid or bases). Such conversions may also take place after application, for example in the case of the treatment of plants in the treated plants or in the harmful fungus to be controlled.

In the definitions of the symbols given in the above formulae, collective terms were used which are generally representative for the following substituents:

halogen: fluorine, chlorine, bromine and iodine;

alkyl: saturated straight-chain or branched hydrocarbon groups having 1 to 4, 6 or 8 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methyl-pentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 2, 4 or 6 carbon atoms (as mentioned above), where some or all of the hydrogen atoms in these groups may be replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoro-prop-2-yl;

alkenyl: unsaturated straight-chain or branched hydrocarbon groups having 2 to 4, 6 or 8 carbon atoms and one or two double bonds in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 4, 6 or 8 carbon atoms and one or two triple bonds in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: mono- or bicyclic saturated hydrocarbon groups having 3 to 6 or 8 carbon ring members, for example $C_3$-$C_8$-cycloalkyl, such as cyclopropyl, cyclobutyl, cyclopentyl, cyclohexyl, cycloheptyl and cyclooctyl;

cycloalkenyl: mono- or bicyclic unsaturated hydrocarbon groups having 3 to 6 or 8 carbon ring members and one or two double bonds in any position, for example $C_3$-$C_8$-cycloalkenyl, such as cyclopropenyl, cyclobutenyl, cyclopentenyl, cyclohexenyl, cycloheptenyl and cyclooctenyl;

aryl or aromatic ring: a ring comprising mono-, bi- or tricyclic aromatic hydrocarbon groups and having 6, 8, 10, 12 or 14 ring members, such as phenyl, naphthyl or anthracenyl, preferably phenyl or naphthyl, in particular phenyl;

heterocyclyl: three- to ten-membered saturated, partially unsaturated or aromatic mono- or bicyclic heterocyclyl which contains one, two, three or four heteroatoms from the group consisting of O, N and S: in particular having five or six ring members non-aromatic saturated or partially unsaturated 5- or 6-membered heterocyclyl which contains one to three nitrogen atoms and/or one oxygen or sulfur atom or one or two oxygen and/or sulfur atoms, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazoiidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydro-pyridazinyl, 2-hexahydropyrimidinyl, 4-hexahydropyrimidinyl, 5-hexahydropyrimidinyl and 2-piperazinyl;

5-membered heteroaryl which contains one to four nitrogen atoms or one to three nitrogen atoms and one sulfur or oxygen atom: 5-membered heteroaryl groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, and 1,3,4-triazol-2-yl;

6-membered heteroaryl which contains one to three or one to four nitrogen atoms: 6-membered heteroaryl groups which, in addition to carbon atoms, may contain one to three or one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl;

cyclic groups: cycloalkyl, cycloalkenyl, aryl or heterocyclyl groups as mentioned above;

alkoxy: alkyl groups as mentioned above which are attached to the skeleton via oxygen, for example $C_1$-$C_8$-alkoxy, such as $OCH_3$, $OCH_2CH_3$, $O(CH_2)_2CH_3$, $O(CH_2)_3CH_3$, $O(CH_2)_4CH_3$, $O(CH_2)_5CH_3$, $O(CH_2)_6CH_3$ and $O(CH_2)_7CH_3$;

alkenoxy: alkenyl groups as mentioned above which are attached to the skeleton via oxygen, for example $C_2$-$C_8$-alkenoxy, such as $OCH=CH_2$, $OCH_2CH=CH_2$, $OCH_2CH=CHCH_3$; $O(CH_2)_2CH=CHCH_3$ and $O(CH_2)_3CH=CHCH_3$;

alkynoxy: alkynyl groups as mentioned above which are attached to the skeleton via oxygen, for example $C_3$-$C_8$-alkynoxy, such as $OCH_2C\equiv CH$, $O(CH_2)_2CH\equiv CH$, $O(CH_2)_3CH\equiv CH$ and $O(CH_2)_4CH\equiv CH$;

alkylcarbonyl: alkyl groups as mentioned above which are attached to the skeleton via a carbonyl group, for example $C_1$-$C_8$-alkylcarbonyl, such as $COCH_3$, $COCH_2CH_3$, $CO(CH_2)_2CH_3$, $CO(CH_2)_3CH_3$, $CO(CH_2)_4CH_3$, $CO(CH_2)_5CH_3$, $CO(CH_2)_6CH_3$ and $CO(CH_2)_7CH_3$;

alkoxycarbonyl: alkoxy groups as mentioned above which are attached to the skeleton via a carbonyl group, for example $C_1$-$C_4$-alkoxycarbonyl, such as $COOCH_3$, $COOCH_2CH_3$, $COO(CH_2)_2CH_3$, $COO(CH_2)_3CH_3$, $COO(CH_2)_4CH_3$, $COO(CH_2)_5CH_3$, $COO(CH_2)_6CH_3$ and $COO(CH_2)_7CH_3$;

alkylcarbonyloxy or alkylcarboxyl: alkylcarbonyl groups as mentioned above which are attached to the skeleton via oxo, for example $C_1$-$C_4$-alkylcarbonyloxy, such as $OCOCH_3$, $OCOCH_2CH_3$, $OCO(CH_2)_2CH_3$ and $OCO(CH_2)_3CH_3$;

alkylcarbonylamino: alkylcarbonyl groups as mentioned above which are attached to the skeleton via amino, for example $C_1$-$C_8$-alkylcarbonylamino, such as $NHCOCH_3$, $NHCOCH_2CH_3$, $NHCO(CH_2)_2CH_3$, $NHCO(CH_2)_3CH_3$, $NHCO(CH_2)_4CH_3$, $NHCO(CH_2)_5CH_3$, $NHCO(CH_2)_6CH_3$ and $NHCO(CH_2)_7CH_3$;

cycloalkylcarbonyl: cycloalkyl groups as mentioned above which are attached to the skeleton via a carbonyl group, for example $C_3$-$C_8$-cycloalkylcarbonyl, such as cyclopropylcarbonyl, cyclobutylcarbonyl, cyclopentylcarbonyl, cyclohexylcarbonyl, cycloheptylcarbonyl and cyclooctylcarbonyl;

cycloalkylcarbonylamino: cycloalkylcarbonyl groups as mentioned above which are attached to the skeleton via amino, for example $C_3$-$C_8$-cycloalkylcarbonylamino, such as cyclopropylcarbonylamino, cyclobutylcarbonylamino, cyclopentylcarbonylamino, cyclohexylcarbonylamino, cycloheptylcarbonylamino and cyclooctylcarbonylamino;

alkylene: divalent unbranched chains of 2 to 8 $CH_2$ groups, for example $CH_2CH_2$, $CH_2CH_2CH_2$, $CH_2CH_2CH_2CH_2$, $CH_2CH_2CH_2CH_2CH_2$, $CH_2CH_2CH_2CH_2CH_2CH_2$, $CH_2CH_2CH_2CH_2CH_2CH_2CH_2$ and $CH_2CH_2CH_2CH_2CH_2CH_2CH_2CH_2$;

oxyalkylene: divalent unbranched chains of 2 to 4 $CH_2$ groups where one valency is attached via an oxygen atom to the skeleton, for example $OCH_2CH_2$, $OCH_2CH_2CH_2$ and $OCH_2CH_2CH_2CH_2$;

oxyalkyleneoxy: divalent unbranched chains of 1 to 3 $CH_2$ groups where both valencies are attached via an oxygen atom to the skeleton, for example $OCH_2O$, $OCH_2CH_2O$ and $OCH_2CH_2CH_2O$.

alkylidene: divalente straight-chain or branched hydrocarbon groups which have 2 to 4, 6 or 8 carbon atoms and are attached to the skeleton via a double bond, for example $C_1$-$C_8$-alkylidene, such as methylidene, ethylidene, propylidene, isopropylidene, butylidene, hexylidene and octylidene;

cycloalkylidene: cycloalkyl groups as mentioned above which are attached to the skeleton via a double bond, for example $C_3$-$C_8$-cycloalkylidene, such as cyclopropylidene, cyclobutylidene, cyclopentylidene, cyclohexylidene, cycloheptylidene and cyclooctylidene;

alkoxyimino: alkoxy groups as mentioned above which are attached to the skeleton via imino, for example $C_1$-$C_4$-alkoxyimino, such as =$NOCH_3$, =$NOCH_2CH_3$, =$NO(CH_2)_2CH_3$, =$NO(CH_2)_3CH_3$, =$NO(CH_2)_4CH_3$, =$NO(CH_2)_5CH_3$, =$NO(CH_2)_6CH_3$ and =$NO(CH_2)_7CH_3$;

and divalent groups: oxo, alkylene, oxyalkylene, oxyalkyleneoxy, alkylidene and cycloalkylidene groups as mentioned above.

Agriculturally useful salts include in particular the salts of those cations or the acid addition salts of those acids whose cations and anions, respectively, have no adverse effect on the fungicidal action of the compounds of the formula I. Thus, suitable cations are in particular the ions of the alkali metals, preferably sodium and potassium, of the alkaline earth metals, preferably calcium, magnesium and barium, and of the transition metals, preferably manganese, copper, zinc and iron, and also the ammonium ion which, if desired, may carry from one to four ($C_1$-$C_4$)-alkyl substituents and/or one phenyl or benzyl substituent, preferably diisopropylammonium, tetramethylammonium, tetrabutylammonium, trimethylbenzylammonium, and also phosphonium ions, sulfonium ions, preferably tri($C_1$-$C_4$)-alkylsulfonium, and sulfoxonium ions, preferably tri($C_1$-$C_4$)-alkylsulfoxonium.

Anions of useful acid addition salts are, primarily, chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and also the anions of ($C_1$-$C_4$)-alkanoic acids, preferably formate, acetate, propionate and butyrate. They can be formed by reacting the compounds of formula I with an acid of the corresponding anion, preferably hydrochloric acid, hydrobromic acid, sulfuric acid, phosphoric acid or nitric acid.

The scope of the present invention includes the (R)- and (S)-isomers and the racemates of compounds of the formula I having chiral centers.

As a result of hindered rotation of asymmetrically substituted groups, atrope isomers of compounds of the formula I may be present. They also form part of the subject matter of the invention.

The embodiments of the intermediates with respect to the variables correspond to those of the formula I.

With a view to the intended use of the compounds of the formula I and the compounds of all subformulae mentioned herein, such as formulae I.1 to 1.10 and I.3A to I.3E, for example, particular preference is given to the following meanings of the substituents $R^1$, $R^2$, $R^3$, $R^4$, $R^5$, $R^6$, $R^7$, $L^1$, $L^2$, $L^3$, $L^4$ and X, in each case on their own or in combination:

In the compounds according to the invention, $R^1$ is preferably $C_1$-$C_8$-alkyl, $C_2$-$C_8$-alkenyl, $C_2$-$C_8$-alkynyl, $C_3$-$C_8$-cycloalkyl, phenyl or a five- or six-membered saturated, partially unsaturated or aromatic heterocyclyl which, in addition to carbon atoms, contains one to three heteroatoms from the group consisting of O, N and S as ring members, where $R^1$ may carry one, two, three or up to the maximum possible number of identical or different groups $R^a$ which are not heterocyclic groups.

One embodiment relates to compounds I in which $R^1$ is optionally $R^a$-substituted $C_1$-$C_8$-alkyl, $C_2$-$C_8$-alkenyl, $C_3$-$C_8$-cycloalkyl, phenyl, pyridyl, pyrazolyl, imidazolyl or triazolyl.

A further embodiment relates to compounds I in which $R^1$ is optionally $R^a$-substituted $C_1$-$C_8$-alkyl, $C_2$-$C_8$-alkenyl, $C_3$-$C_8$-cycloalkyl or phenyl.

A further embodiment relates to compounds I in which $R^1$ is optionally $R^a$-substituted $C_1$-$C_8$-alkyl.

A further embodiment relates to compounds I in which $R^1$ is optionally $R^a$-substituted $C_2$-$C_8$-alkenyl.

A further embodiment relates to compounds I in which $R^1$ is optionally $R^a$-substituted $C_3$-$C_8$-cycloalkyl.

A further embodiment relates to compounds I in which $R^1$ is optionally $R^a$-substituted phenyl.

A further embodiment relates to compounds I in which the α carbon atom in $R^1$ does not carry a cyclic group.

A further embodiment relates to compounds I in which $R^1$ is optionally $R^a$-substituted $C_1$-$C_4$-alkyl or $C_2$-$C_4$-alkenyl.

A further embodiment relates to compounds I in which $R^1$ is optionally $R^a$-substituted methyl.

A further embodiment relates to compounds I in which $R^1$ is unsubstituted.

Further embodiments relate to compounds I in which $R^1$ is in each case one of the following groups I-1 to I-19 in table I:

TABLE I

| No. | $R^1$ |
|---|---|
| I-1 | $CH_3$ |
| I-2 | $CH_2CH_3$ |
| I-3 | $CH(CH_3)_2$ |
| I-4 | $CH_2CH_2CH_3$ |
| I-5 | $CH_2CF_3$ |
| I-6 | $CHF_2$ |
| I-7 | $CH_2OCH_3$ |
| I-8 | $CH_2CH_2CH_2CH_3$ |
| I-9 | $CH(CH_3)CH_2CH_3$ |
| I-10 | $CH_2CH(CH_3)_2$ |
| I-11 | (S)—$CHCF_3CH_3$ |
| I-12 | (R)—$CHCF_3CH_3$ |
| I-13 | cyclopropylmethyl |
| I-14 | 2-buten-1-yl |
| I-15 | 3-methyl-2-buten-1-yl |
| I-16 | propargyl |
| I-17 | 1-butyn-3-yl |
| I-18 | 2-butyn-1-yl |
| I-19 | E-3-chloro-2-propen-1-yl |

In the compounds according to the invention, $R^2$ is preferably optionally substituted amino, $C_1$-$C_8$-alkyl, $C_2$-$C_8$-alkenyl, $C_2$-$C_8$-alkynyl, $C_1$-$C_8$-alkylcarbonyl, $C_1$-$C_8$-alkoxycarbonyl, $C_3$-$C_8$-cycloalkyl, phenyl or five- or six-membered saturated, partially unsaturated or aromatic heterocyclyl which, in addition to carbon atoms, contains one to three heteroatoms from the group consisting of O, N and S as ring members.

One embodiment relates to compounds I in which $R^2$ is optionally $R^a$-substituted amino, $C_1$-$C_8$-alkyl, $C_2$-$C_8$-alkenyl, $C_2$-$C_8$-alkynyl, $C_1$-$C_8$-alkylcarbonyl, $C_1$-$C_8$-alkoxycarbonyl, $C_3$-$C_8$-cycloalkyl, phenyl or five- or six-membered saturated, partially unsaturated or aromatic heterocyclyl which, in addition to carbon atoms, contains one to three heteroatoms from the group consisting of O, N and S as ring members.

A further embodiment relates to compounds I in which $R^2$ is optionally $R^a$-substituted $C_1$-$C_8$-alkyl or phenyl.

A further embodiment relates to compounds I in which $R^2$ is optionally $R^a$-substituted phenyl or heterocyclyl.

A further embodiment relates to compounds I in which $R^2$ is optionally $R^a$-substituted $C_1$-$C_8$-alkyl.

A further embodiment relates to compounds I in which $R^2$ is optionally $R^a$-substituted phenyl.

A further embodiment relates to compounds I in which $R^2$ is a substituted $C_1$-$C_8$-alkyl which carries a phenyl or heterocyclyl group and optionally a further one, two, three or four identical or different $R^a$ groups.

A further embodiment relates to compounds I in which $R^2$ is a substituted $C_1$-$C_8$-alkyl which carries a phenyl or heterocyclyl group attached via oxygen and optionally substituted by $R^b$, and optionally carries a further one, two, three or four identical or different $R^a$ groups.

A further embodiment relates to compounds I in which $R^2$ is $CH_2$—$R^{2a}$ where $R^{2a}$ is a group $R^a$-attached via oxygen. These compounds correspond to the formula I.1.

A further embodiment relates to compounds I in which $R^2$ is a substituted methyl which carries a phenyl or heterocyclyl group which is attached via oxygen and optionally substituted by $R^b$.

A further embodiment relates to compounds I in which $R^2$ is unsubstituted.

Further embodiments relate to compounds I in which $R^2$ is in each case one of the following groups II-1 to II-325 in table II:

TABLE II

| No. | $R^2$ (# defines the bond to the skeleton) |
|---|---|
| II-1 | (2-methylpyridyl-5-oxy)methyl |
| II-2 | (2-trifluoromethylpyridyl-5-oxy)methyl |
| II-3 | (3-(4-chlorophenyl)-4-methyl-pyrazol-1-yl)methyl |
| II-4 | (3,4-dimethylpyrazol-1-yl)methyl |
| II-5 | (3-chloro-2-fluoropyridyl-5-oxy)methyl |
| II-6 | (3-chloropyridyl-5-oxy)methyl |
| II-7 | (4-(4-methylphenyl)pyrazol-1-yl)methyl |
| II-8 | (4-chlorophenyl)methoxymethyl |
| II-9 | (4-methylpyrazol-1-yl)methyl |
| II-10 | (imidazolazol-1-yl)methyl |
| II-11 | (pyrazol-1-yl)methyl |
| II-12 | (pyridyl-3-oxy)methyl |
| II-13 | (pyrimidinyl-5-oxy)methyl |
| II-14 | (R)-1-methyl-2,2,2-trifluoroethyl-aminomethyl |
| II-15 | (S)-1-methyl-2,2,2-trifluoroethyl-aminomethyl |
| II-16 | [1,2,4]-triazol-1-ylmethyl |
| II-17 | 1-methylpyrazol-5-yloxymethyl |
| II-18 | 2-(3,4-dimethoxyphenyl)ethoxymethyl |
| II-19 | 2-(3,4-dimethoxyphenyl)ethyl-aminomethyl |
| II-20 | 2,2,2-trifluoroethoxymethyl |
| II-21 | 2,2,2-trifluoroethyl |
| II-22 | 2,3,4-trichlorophenoxymethyl |
| II-23 | 2-fluorophenoxymethyl |
| II-24 | 2-trifluoromethylphenoxymethyl |
| II-25 | 4-trifluoromethylphenoxymethyl |
| II-26 | 2-bromophenoxymethyl |
| II-27 | 4-bromophenoxymethyl |
| II-27 | 4-bromophenoxymethyl |
| II-28 | 2-chlorophenoxymethyl |
| II-29 | 2,6-dichlorophenoxymethyl |
| II-30 | 3,4,5-trifluorophenoxymethyl |
| II-31 | 4-chloro-3-fluorophenoxymethyl |
| II-32 | 2-chloro-4-fluorophenoxymethyl |
| II-33 | 4-chloro-2-fluorophenoxymethyl |
| II-34 | 4-chloro-2-trifluoromethyl-phenoxymethyl |
| II-35 | 4-chloro-6-trifluoromethyl-phenoxymethyl |
| II-36 | 2-fluoro-6-trifluoromethylphenoxymethyl |

TABLE II-continued

| No. | $R^2$ (# defines the bond to the skeleton) |
|---|---|
| II-37 | 2-fluoro-4-trifluoromethylphenoxymethyl |
| II-38 | 2,3,4-trichlorophenyl |
| II-39 | 2,3,4-trifluorophenoxymethyl |
| II-40 | 2,3,4-tetrafluoro-4-trifluoro-methylphenoxymethyl |
| II-41 | 2,3,6-trichlorophenoxymethyl |
| II-42 | 2,3-dichlorophenoxymethyl |
| II-43 | 2,4,5-trifluorophenoxymethyl |
| II-44 | 2,4,6-trifluorophenoxymethyl |
| II-45 | 2,4-dichloro-3-methylphenyl |
| II-46 | 2,4-dichloro-5-methoxyphenoxymethyl |
| II-47 | 2,4-dichlorophenoxymethyl |
| II-48 | 2,4-dichlorophenyl |
| II-49 | 2,4-difluorophenoxymethyl |
| II-50 | 2,4-difluorophenyl |
| II-51 | 2,5-dichlorophenoxymethyl |
| II-52 | 2,5-dichlorophenyl |
| II-53 | 2,6-dichloro-4-fluorophenoxymethyl |
| II-54 | 2,6-dichloro-4-methylphenoxymethyl |
| II-55 | 2,6-difluorophenoxymethyl |
| II-56 | 2,6-dimethylphenoxymethyl |
| II-57 | 2-bromo-4,5-difluorophenoxymethyl |
| II-58 | 2-chloro-4-trifluoromethyl-phenoxymethyl |
| II-59 | 2-chloro-5-trifluoromethyl-phenoxymethyl |
| II-60 | 2-chloro-6-fluorophenoxymethyl |
| II-61 | 2-fluoro-3-trifluoromethyl-phenoxymethyl |
| II-62 | 2-fluoro-5-trifluoromethylphenoxymethyl |
| II-63 | 2-methoxyphenyl |
| II-64 | 2-propaniminoxymethyl |
| II-65 | 3-(2,4-dichlorophenyl)pyrazol-1-yl-methyl |
| II-66 | 3-(4-chlorophenoxy)phenoxymethyl |
| II-67 | 3-(trifluoromethyl)phenoxymethyl |
| II-68 | 3,4,5-trichlorophenoxymethyl |
| II-69 | 3,4,5-trimethylpyrazol-1-ylmethyl |
| II-70 | 3,4-dichlorophenoxymethyl |
| II-71 | 3,4-dichlorophenyl |
| II-72 | 3,4-difluorophenoxymethyl |
| II-73 | 3,4-difluorophenyl |
| II-74 | 3,4-dimethoxyphenoxymethyl |
| II-75 | 3,4-ethylenedioxyphenyl |
| II-76 | 3,4-methylenedioxyphenoxymethyl |
| II-77 | 3,5-bis(2-methylphenyl)pyrazol-1-ylmethyl |
| II-78 | 3,5-bistrifluoromethylphenoxymethyl |
| II-79 | 3,5-dichlorophenoxymethyl |
| II-80 | 3,5-dimethoxyphenoxymethyl |
| II-81 | 3,5-dimethylpyrazol-1-ylmethyl |
| II-82 | 3-acetamino-2,4-dimethylphenyl |
| II-83 | 3-acetaminophenyl |
| II-84 | 3-bromo-4-fluorophenoxymethyl |
| II-85 | 3-bromophenoxymethyl |
| II-86 | 3-chloro-2-fluoro-5-trifluoromethyl-phenoxymethyl |
| II-87 | 3-chloro-4-(3-chloro-5-trifluoro-methylpyridin-2-yloxy)phenoxymethyl |
| II-88 | 3-chloro-4-(phenylcarbonyl)-phenoxymethyl |
| II-89 | 3-chloro-4-bromophenoxymethyl |
| II-90 | 3-chloro-4-ethoxycarbonyl-phenoxymethyl |
| II-91 | 3-chloro-4-fluorophenoxymethyl |
| II-92 | 3-chloro-4-methylphenoxymethyl |
| II-93 | 3-chlorophenoxymethyl |
| II-94 | 3-chlorophenyl |

TABLE II-continued

| No. | R² (# defines the bond to the skeleton) |
|---|---|
| II-95 | 3-cyanophenoxymethyl |
| II-96 | 3-difluoromethoxyphenoxymethyl |
| II-97 | 3-fluorophenoxymethyl |
| II-98 | 3-isopropylphenoxymethyl |
| II-99 | 3-isopropylpyrazol-1-ylmethyl |
| II-100 | 3-methyl-4-phenylpyrazol-1-yl-methyl |
| II-101 | 3-methylpyrazol-1-ylmethyl |
| II-102 | 3-phenoxyphenoxymethyl |
| II-103 | 3-phenylphenoxymethyl |
| II-104 | 3-trifluoromethyl-4-cyano-phenoxymethyl |
| II-105 | 3-trifluoromethylphenoxymethyl |
| II-106 | 4-(3-chloro-5-trifluoromethyl-pyridin-2-yloxy)phenyl |
| II-107 | 4-(4-chlorophenoxy)phenyl |
| II-108 | 4-(4-chlorophenyl)phenyl |
| II-109 | 4-(4-fluorophenyl)pyrazol-1-yl-methyl |
| II-110 | 4-(methylsulfonylamino)phenyl |
| II-111 | 4,5-difluoro-2-methylphenoxy-methyl |
| II-112 | 4,6-dimethyl-2-(1-oxo-1-ethyl)-phenoxymethyl |
| II-113 | 4-bromophenyl |
| II-114 | 4-chloro-1-naphthoxymethyl |
| II-115 | 4-chloro-2,5-dimethylphenoxy-methyl |
| II-116 | 4-chloro-2-fluoro-5-methylphenyl |
| II-117 | 4-chloro-2-phenylphenoxymethyl |
| II-118 | 4-chloro-3-(phenylcarbonyl)-phenoxymethyl |
| II-119 | 4-chloro-3,5-dimethylphenoxy-methyl |
| II-120 | 4-chloro-3-ethylphenoxymethyl |
| II-121 | 4-chloro-3-methylphenoxymethyl |
| II-122 | 4-chloro-3-trifluoromethoxy-phenoxymethyl |
| II-123 | 4-chlorophenoxymethyl |
| II-124 | 4-chlorophenyl |
| II-125 | 4-chloropyrazol-1-ylmethyl |
| II-126 | 4-cyano-3-trifluoromethyl-phenoxymethyl |
| II-127 | 4-cyanophenoxymethyl |
| II-128 | 4-fluoro-2-methylphenoxymethyl |
| II-129 | 4-fluoro-2-trifluoromethyt-phenoxymethyl |
| II-130 | 4-fluoro-3-methylphenoxymethyl |
| II-131 | 4-fluoro-3-trifluoromethylphenoxy-methyl |
| II-132 | 4-fluorophenoxymethyl |
| II-133 | 4-fluorophenyl |
| II-134 | 4-methoxyphenyl |
| II-135 | 4-methyl-2,3,5,6-tetrafluoro-phenoxymethyl |
| II-136 | 4-methyl-3-phenylpyrazol-1-yl-methyl |
| II-137 | 4-methylphenoxymethyl |
| II-138 | 4-phenoxyphenyl |
| II-139 | 4-phenylpyrazol-1-ylmethyl |
| II-140 | 4-tert-butylphenoxymethyl |
| II-141 | 4-tert-butylphenyl |
| II-142 | 4-trifluoromethylphenyl |
| II-143 | 5-bromo-2-chloro-4-fluoro-phenoxymethyl |
| II-144 | 5-bromo-2-chloro-4-iodophenoxy-methyl |
| II-145 | 5-chloro-2-methoxyphenyl |
| II-146 | $C(CH_3)_3$ |
| II-147 | $CCH_3{=}NOCH_3$ |
| II-148 | $CH_2CH_3$ |
| II-149 | $CH_2CH_2CH_3$ |
| II-150 | $CH_2CN$ |
| II-151 | $CH_2COOCH_2CH_3$ |
| II-152 | $CH_2OCH_3$ |
| II-153 | $CH_3$ |
| II-154 | $COOCH_2CH_3$ |
| II-155 | $COOCH_3$ |
| II-156 | cyanoaminomethyl |
| II-157 | hydroxymethyl |
| II-158 | isopropyloxymethyl |
| II-159 | methoxycarbonylmethyl |
| II-160 | morpholin-4-ylmethyl |
| II-161 | N-ethyl-N-methylaminomethyl |
| II-162 | $NH_2$ |
| II-163 | phenyl |
| II-164 | piperidin-1-ylmethyl |
| II-165 | piperidin-1-yl |
| II-166 | pyrrolidin-1-yl |
| II-167 | 2-pyrolidon-1-yl |
| II-168 | pyrazol-1-yl |
| II-169 | trifluoromethyl |
| II-170 | isopropyl |
| II-171 | 3-(4-chlorophenyl)propyl |
| II-172 | 2-(2,3,4-trichlorophenyl)ethyl |
| II-173 | 2-(2-fluorophenyl)ethyl |
| II-174 | 2-(2-trifluoromethylphenyl)ethyl |
| II-175 | 2-(4-trifluoromethylphenyl)ethyl |
| II-176 | 2-(2-bromophenyl)ethyl |
| II-177 | 2-(4-bromophenyl)ethyl |
| II-178 | 2-(2-chlorophenyl)ethyl |
| II-179 | 2-(2,6-dichlorophenyl)ethyl |
| II-180 | 2-(3,4,5-trifluorophenyl)ethyl |
| II-181 | 2-(4-chloro-3-fluoro.phenyl)ethyl |
| II-182 | 2-(2-chloro-4-fluorophenyl)ethyl |
| II-183 | 2-(4-chloro-2-fluorophenyl)ethyl |
| II-184 | 2-(4-chloro-2-trifluoromethyl-phenyl)ethyl |
| II-185 | 2-(4-chloro-6-trifluoromethyl-phenyl)ethyl |
| II-186 | 2-(2-fluoro-6-trifluoromethylphenyl)ethyl |
| II-187 | 2-(2-fluoro-4-trifluoromethyphenyl)ethyl |
| II-188 | 2-(2,3,4-trifluorophenyl)ethyl |
| II-189 | 2-(2,3,6-trichlorophenyl)ethyl |
| II-190 | 2-(2,3-dichlorophenyl)ethyl |
| II-191 | 2-(2,4,5-trifluorophenyl)ethyl |
| II-192 | 2-(2,4,6-trifluorophenyl)ethyl |
| II-193 | 2-(2,4-dichloro-5-methoxy-phenyl)ethyl |
| II-194 | 2-(2,4-dichlorophenyl)ethyl |
| II-195 | 2-(2,4-difluorophenyl)ethyl |
| II-196 | 2-(2,5-dichlorophenyl)ethyl |
| II-197 | 2-(2,6-dichloro-4-fluorophenyl)-ethyl |
| II-198 | 2-(2,6-dichloro-4-methylphenyl)-ethyl |
| II-199 | 2-(2, 6-difluorophenyl)ethyl |
| II-200 | 2-(2, 6-dimethylphenyl)ethyl |
| II-201 | 2-(2-bromo-4,5-difluorophenyl)-ethyl |
| II-202 | 2-(2-chloro-4-trifluoromethyl-phenyl)ethyl |
| II-203 | 2-(2-chloro-5-trifluoromethyl-phenyl)ethyl |
| II-204 | 2-(2-chloro-6-fluorophenyl)ethyl |
| II-205 | 2-(2-fluoro-3-trifluoromethyl-phenyl)-ethyl |
| II-206 | 2-(2-fluoro-5-trifluoromethyl-phenyl)-ethyl |
| II-207 | 2-(3-(4-chlorophenylthio)phenyl)-ethyl |
| II-208 | 2-(3-(trifluoromethyl)phenyl)ethyl |
| II-209 | 2-(3,4,5-trichlorophenyl)ethyl |
| II-210 | 2-(3,4-dichlorophenyl)ethyl |
| II-211 | 2-(3,4-difluorophenyl)ethyl |
| II-212 | 2-(3,4-dimethoxyphenyl)ethyl |
| II-213 | 2-(3,5-bistrifluoromethylphenyl)ethyl |
| II-214 | 2-(3,5-dichlorophenyl)ethyl |
| II-215 | 2-(3,5-dimethoxyphenyl)ethyl |
| II-216 | 2-(3-bromo-4-fluorophenyl)ethyl |
| II-217 | 2-(3-bromophenyl)ethyl |
| II-218 | 2-(3-chloro-2-fluoro-5-trifluoro-methylphenyl)ethyl |

TABLE II-continued

| No. | R² (# defines the bond to the skeleton) |
|---|---|
| II-219 | 2-(3-chloro-4-(3-chloro-5-trifluoro-methylpyridin-2-yloxy)phenyl)ethyl |
| II-220 | 2-(3-chloro-4-(phenyl-carbonyl)-phenyl)ethyl |
| II-221 | 2-(3-chloro-4-bromophenyl)ethyl |
| II-222 | 2-(3-chloro-4-fluoro-phenyl)ethyl |
| II-223 | 2-(3-chloro-4-methyl-phenyl)ethyl |
| II-224 | 2-(3-cyanophenyl)ethyl |
| II-225 | 2-(3-difluoromethoxyphenyl)ethyl |
| II-226 | 2-(3-fluorophenyl)ethyl |
| II-227 | 2-(3-isopropylphenyl)ethyl |
| II-228 | 2-(3-phenoxyphenyl)ethyl |
| II-229 | 2-(3-phenylphenyl)ethyl |
| II-230 | 2-(3-trifluoromethylphenyl)ethyl |
| II-231 | 2-(4,5-difluoro-2-methylphenyl)ethyl |
| II-232 | 2-(4-chloro-2,5-dimethylphenyl)ethyl |
| II-233 | 2-(4-chloro-2-phenylphenyl)ethyl |
| II-234 | 2-(4-chloro-3,5-dimethylphenyl)ethyl |
| II-235 | 2-(4-chloro-3-ethylphenyl)ethyl |
| II-236 | 2-(4-chloro-3-methylphenyl)ethyl |
| II-237 | 2-(4-chloro-3-trifluoromethoxy-phenyl)ethyl |
| II-238 | 2-(4-chlorophenyl)ethyl |
| II-239 | 2-(4-cyanophenyl)ethyl |
| II-240 | 2-(4-fluoro-2-methylphenyl)ethyl |
| II-241 | 2-(4-fluoro-2-trifluoromethyl- |
| II-242 | 2-(4-fluoro-3-methylphenyl)ethyl |
| II-243 | 2-(4-fluoro-3-trifluoromethyl-phenyl)ethyl |
| II-244 | 2-(4-fluorophenyl)ethyl |
| II-245 | 2-(4-methylphenyl)ethyl |
| II-246 | 2-(4-tert.-Butylphenyl)ethyl |
| II-247 | 2-(5-bromo-2-chloro-4-fluoro-phenyl)ethyl |
| II-248 | 2-(5-bromo-2-chloro-4-iodo-phenyl)ethyl |
| II-249 | 2-(3-chlorophenyl)ethyl |
| II-250 | N-(2-chlorophenyl)aminomethyl |
| II-251 | N-(2-bromophenyl)aminomethyl |
| II-252 | N-(2-trifluoromethylphenyl)-aminomethyl |
| II-253 | N-(3-chlorophenyl)aminomethyl |
| II-254 | N-(3-bromophenyl)aminomethyl |
| II-255 | N-(3-trifluoromethylphenyl)-aminomethyl |
| II-256 | N-(4-chlorophenyl)aminomethyl |
| II-257 | N-(4-bromophenyl)aminomethyl |
| II-258 | N-(4-trifluoromethylphenyl)-aminomethyl |
| II-259 | N-(3,4-dichlorophenyl)-aminomethyl |
| II-260 | N-(2,6-dichlorophenyl)-aminomethyl |
| II-261 | N-(2-chloro-6-fluorophenyl)-1-aminomethyl |
| II-262 | 3-(3-chlorophenyl)propyl |
| II-263 | 3-(3-bromophenyl)propyl |
| II-264 | 3-(3-trifluoromethylphenyl)propyl |
| II-265 | 3-(4-bromophenyl)propyl |
| II-266 | 3-(4-trifluoromethylphenyl)propyl |
| II-267 | 3-(3,4-dichlorophenyl)propyl |
| II-268 | 3-(2,6-dichlorophenyl)propyl |
| II-269 | 3-(2-chloro-6-fluorophenyl)propyl |
| II-270 | 4-(3-chlorophenyl)butyl |
| II-271 | 4-(3-bromophenyl)butyl |
| II-272 | 4-(3-trifluoromethylphenyl)butyl |
| II-273 | 4-(4-chlorophenyl)butyl |
| II-274 | 4-(4-bromophenyl)butyl |
| II-275 | 4-(4-trifluoromethylphenyl)butyl |
| II-276 | 4-(3,4-dichlorophenyl)butyl |
| II-277 | 4-(2,6-dichlorophenyl)butyl |
| II-278 | 4-(2-chloro-6-fluorophenyl)butyl |
| II-279 | 3-chlorophenylmethyl |
| II-280 | 3-bromophenylmethyl |
| II-281 | 3-trifluoromethylphenylmethyl |
| II-282 | 4-fluorophenylmethyl |
| II-283 | 4-chlorophenylmethyl |
| II-284 | 4-bromophenylmethyl |
| II-285 | 4-trifluoromethylphenylmethyl |
| II-286 | 3,4-dichlorophenylmethyl |
| II-287 | 3,4-difluorophenylmethyl |
| II-288 | 2,6-dichlorophenylmethyl |
| II-289 | 2-chloro-6-fluorophenylmethyl |
| II-290 | 2,4-dichlorophenylmethyl |
| II-291 | 2,4-difluorophenylmethyl |
| II-292 | 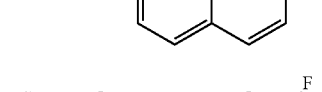 |
| II-293 | 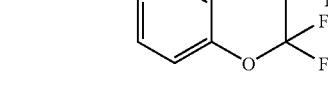 |
| II-294 | 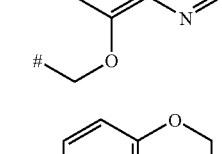 |
| II-295 | 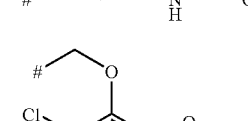 |
| II-296 | 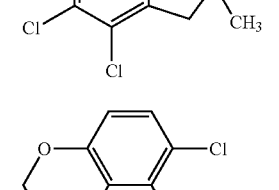 |
| II-297 | 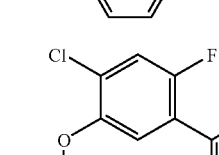 |
| II-298 | 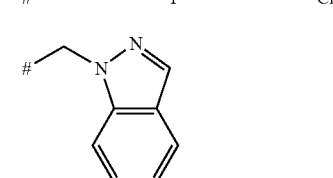 |
| II-299 | 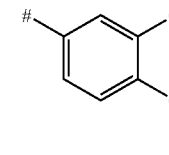 |
| II-300 |  |

TABLE II-continued

| No. | R² (# defines the bond to the skeleton) |
|---|---|
| II-301 | 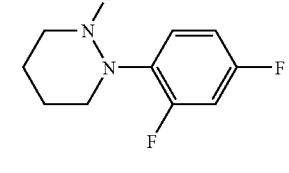 |
| II-302 | 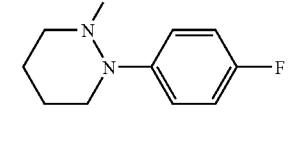 |
| II-303 | 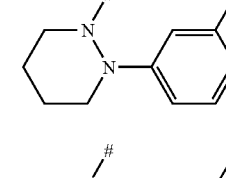 |
| II-304 | 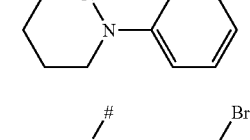 |
| II-305 | 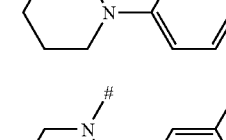 |
| II-306 | 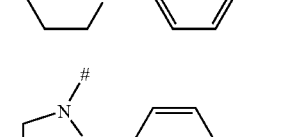 |
| II-307 | 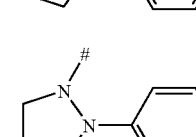 |
| II-308 | 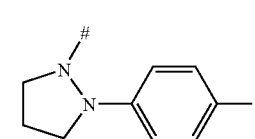 |
| II-309 | 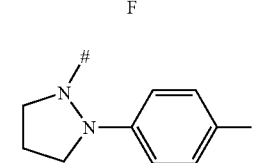 |
| II-310 | (2,4-dichlorophenyl piperidazinyl) |
| II-311 | (2,4-difluorophenyl piperidazinyl) |
| II-312 | (4-fluorophenyl piperidazinyl) |
| II-313 | (3-chlorophenyl piperidazinyl) |
| II-314 | (3-trifluoromethylphenyl piperidazinyl) |
| II-315 | (3-bromophenyl piperidazinyl) |
| II-316 | (3,4-dichlorophenyl piperidazinyl) |
| II-317 | (phenyl pyrazolidinyl) |
| II-318 | (4-fluorophenyl pyrazolidinyl) |
| II-319 | (2,4-difluorophenyl pyrazolidinyl) |
| II-320 | (2,4-dichlorophenyl pyrazolidinyl) |

TABLE II-continued

| No. | R² (# defines the bond to the skeleton) |
|---|---|
| II-321 | 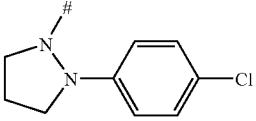 |
| II-322 | 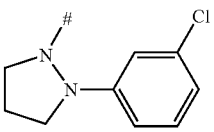 |
| II-323 | 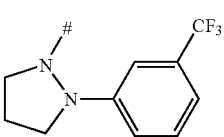 |
| II-324 | 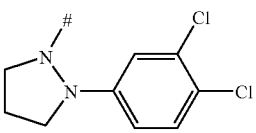 |
| II-325 | 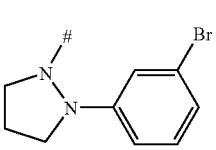 |

One embodiment relates to compounds I in which X is oxygen. These compounds correspond to the formula I.3:

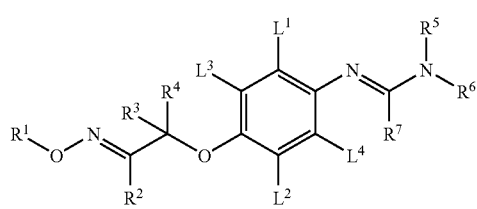

I.3

A further embodiment relates to compounds I in which X is sulfur.

One embodiment relates to compounds I in which $R^3$ is $C_1$-$C_4$-alkyl or $C_1$-$C_8$-haloalkyl.

A further embodiment relates to compounds I in which $R^3$ is $C_1$-$C_4$-alkyl.

A further embodiment relates to compounds I in which $R^3$ is $C_1$-$C_8$-haloalkyl.

A further embodiment relates to compounds I in which $R^3$ is methyl.

A further embodiment relates to compounds I in which $R^4$ is hydrogen. These compounds correspond to the formula I.4:

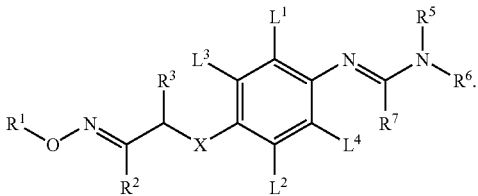

I.4

A further embodiment relates to compounds I in which $R^3$ and $R^4$ are hydrogen. These compounds correspond to the formula I.5:

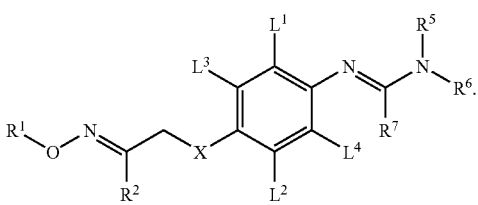

I.5

A further embodiment relates to compounds I in which $R^3$ and $R^4$ are not hydrogen.

A further embodiment relates to compounds I in which X is oxygen and $R^3$ and $R^4$ are hydrogen. These compounds correspond to the formula I.3A:

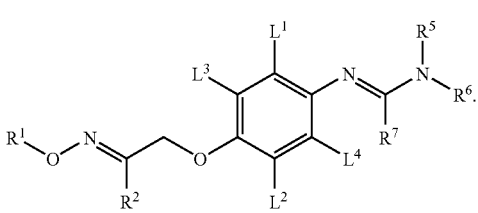

I.3A

A further embodiment relates to compounds I in which X is oxygen, $R^3$ is methyl and $R^4$ is hydrogen. These compounds correspond to the formula I.3B:

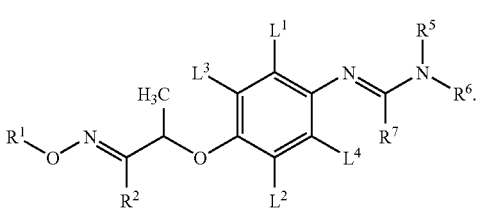

I.3B

A further embodiment relates to compounds I in which X is oxygen and $R^3$ and $R^4$ are methyl. These compounds correspond to the formula I.3C:

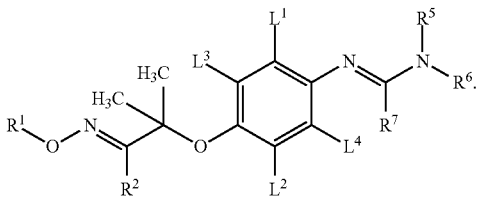

I.3C

A further embodiment relates to compounds I in which X is oxygen, $R^3$ is ethyl and $R^4$ is hydrogen. These compounds correspond to the formula I.3D:

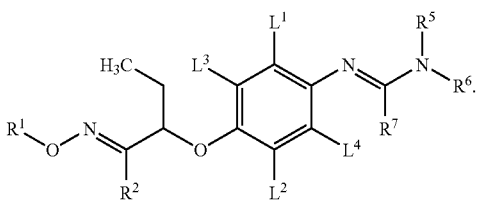

I.3D

A further embodiment relates to compounds I in which X is oxygen, $R^3$ is ethyl and $R^4$ is methyl. These compounds correspond to the formula I.3E:

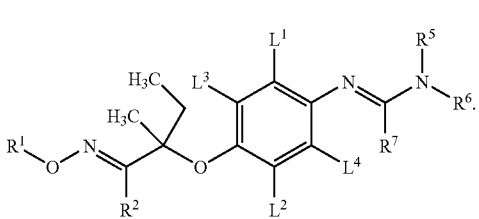

I.3E

One embodiment relates to compounds I in which $R^5$ is methyl or ethyl.

A further embodiment relates to compounds I in which $R^5$ is methyl.

One embodiment relates to compounds I in which $R^6$ is ethyl.

Further embodiments relate to compounds I in which $R^5$ and $R^6$ are one of the following combinations III-1 to III-43 in table III:

TABLE III

| No. | $R^5$ | $R^6$ |
|---|---|---|
| III-1 | $CH_3$ | $CH_2CH_3$ |
| III-2 | $CH_3$ | $CH_2CF_3$ |
| III-3 | $CH_3$ | $CH_3$ |
| III-4 | $CH_3$ | $CH(CH_3)_2$ |
| III-5 | $CH_3$ | $CHF_2$ |
| III-6 | $CH_3$ | $CF_3$ |
| III-7 | $CH_3$ | $CH_2CH_2CH_3$ |
| III-8 | $CH_3$ | $CH_2OCH_3$ |
| III-9 | $CH_3$ | $C(CH_3)_3$ |
| III-10 | $CH_3$ | $OCH_3$ |
| III-11 | $CH_3$ | $OCH_2CH_3$ |
| III-12 | $CH_3$ | $OCH_2CH_2CH_3$ |
| III-13 | $CH_3$ | $OCH(CH_3)_2$ |
| III-14 | $CH_3$ | $OCHF_2$ |
| III-15 | $CH_3$ | $CH_2CH_2CH_3$ |
| III-16 | $CH_3$ | $CH_2CH_2CF_3$ |

TABLE III-continued

| No. | $R^5$ | $R^6$ |
|---|---|---|
| III-17 | $CH_3$ | $CH_2CHF_2$ |
| III-18 | $CH_3$ | $CH_2CH_2CH_2CH_3$ |
| III-19 | $CH_3$ | $CH(CH_3)CH_2CH_3$ |
| III-20 | $CH_3$ | $CH_2CH(CH_3)_2$ |
| III-21 | $CH_3$ | (S)—$CHCF_3CH_3$ |
| III-22 | $CH_3$ | (R)—$CHCF_3CH_3$ |
| III-23 | $CH_3$ | cyclopropylmethyl |
| III-24 | $CH_3$ | 2-buten-1-yl |
| III-25 | $CH_3$ | 3-methyl-2-buten-1-yl |
| III-26 | $CH_3$ | propargyl |
| III-27 | $CH_3$ | 1-butyn-3-yl |
| III-28 | $CH_3$ | 2-butyn-1-yl |
| III-29 | $CH_3$ | E-3-chloro-2-propen-1-yl |
| III-30 | $CH_3$ | cyclopropyl |
| III-31 | $CH_3$ | cyclopropylmethyl |
| III-32 | | —$CH_2CH_2CH_2CH_2$— |
| III-33 | | —(S)—$CH(CH_3)CH_2CH_2CH_2$— |
| III-34 | | —(R)—$CH(CH_3)CH_2CH_2CH_2$— |
| III-35 | | —$CH(CH_3)CH_2CH_2CH(CH_3)$— |
| III-36 | | —$CH_2CH_2CH_2CH_2CH_2$— |
| III-37 | | —(S)—$CH(CH_3)CH_2CH_2CH_2CH_2$— |
| III-38 | | —(R)—$CH(CH_3)CH_2CH_2CH_2CH_2$— |
| III-39 | | —$CH(CH_3)CH_2CH_2CH_2CH(CH_3)$— |
| III-40 | | —$CH_2CH_2CH(CH_3)CH_2CH_2$— |
| III-41 | | —$CH_2CH_2OCH_2CH_2$— |
| III-42 | | —$CH_2CH_2N(CH_3)CH_2CH_2$— |
| III-43 | | —$CH_2N(CH_3)CH_2CH_2CH_2$— |

One embodiment relates to compounds I in which $L^1$ and $L^2$ independently of one another are halogen or $C_1$-$C_4$-alkyl or haloalkyl.

One embodiment relates to compounds I in which $L^1$ and $L^2$ independently of one another are halogen, such as chlorine or fluorine.

A further embodiment relates to compounds I in which $L^1$ and $L^2$ independently of one another are methyl or halomethyl, such as $CF_3$, $CCl_3$, $CH_2Cl$, $CH_2F$, $CHF_2$ or $CHCl_2$.

A further embodiment relates to compounds in which $L^1$ and $L^2$ are methyl.

One embodiment relates to compounds I in which $L^3$ and $L^4$ are hydrogen. These compounds correspond to the formula I.6:

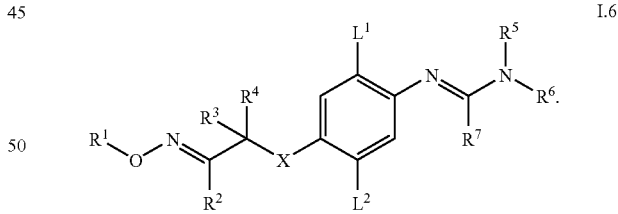

I.6

A preferred embodiment relates to compounds I in which $L^1$ and $L^2$ independently of one another are halogen or $C_1$-$C_4$-alkyl and $L^3$ and $L^4$ are hydrogen.

Preferably, $R^5$ and $R^6$ in the compounds I according to the invention are $C_1$-$C_4$-alkyl which may carry one, two, three, four or five identical or different groups $R^a$.

One embodiment relates to compounds I in which $R^5$ and $R^6$ are $C_1$-$C_4$-alkyl.

One embodiment relates to compounds I in which $R^7$ is unsubstituted.

One embodiment relates to compounds I in which $R^7$ is hydrogen. These compounds correspond to the formula I.7:

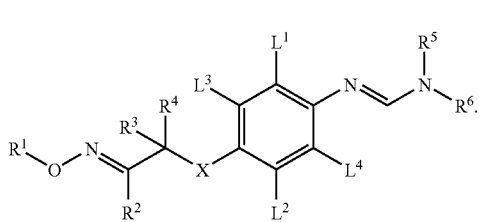

1.7

A further embodiment relates to compounds I in which $R^7$ is methyl.

One embodiment relates to compounds I in which $R^3$ and $R^4$ together are not able to form a cyclic group as described at the outset.

A further embodiment relates to compounds I in which $R^1$ and $R^2$, $R^1$ and $R^3$, $R^2$ and $R^3$ and also $R^3$ and $R^4$ are in each case not able to form cyclic groups as described at the outset.

A further embodiment relates to compounds I in which $R^2$ and $R^3$ together with the atoms linking them form a cyclic group and $R^2$ is optionally $R^a$-substituted $C_1$-alkyl. These compounds correspond to the formula I.2.

In the compounds according to the invention, $R^a$ is preferably halogen, $C_1$-$C_4$-alkyl, $C_1$-$C_4$-haloalkyl, $C_1$-$C_4$-alkoxy, $C_1$-$C_4$-haloalkoxy, phenyl or a five- or six-membered saturated, partially unsaturated or aromatic heterocyclyl which, in addition to carbon atoms, contains one to three heteroatoms from the group consisting of O, N and S as ring members, where the cyclic groups $R^a$ may be attached directly or via a nitrogen or oxygen atom; where the aliphatic and cyclic groups $R^a$ for their part may be partially or fully halogenated and/or may carry one, two, three or up to the maximum possible number of identical or different groups $R^b$, where $R^b$ is halogen, $C_1$-$C_4$-alkyl, $C_1$-$C_4$-haloalkyl, $C_1$-$C_4$-alkoxy or $C_1$-$C_4$-haloalkoxy.

In the compounds according to the invention, $R^a$ is in particular halogen, $C_1$-$C_4$-alkyl, $C_1$-$C_4$-alkoxy, $C_1$-$C_4$-haloalkoxy, phenyl, pyridyl, pyrimidinyl, pyridazinyl, triazinyl, pyrazolyl, imidazolyl or triazolyl, where the cyclic groups $R^a$ may be attached directly or via an oxygen atom, where the aromatic and heterocyclic groups $R^a$ for their part may be partially or fully halogenated and/or may carry one, two, three or up to the maximum possible number of identical or different groups $R^b$, where $R^b$ is halogen, $C_1$-$C_4$-alkyl, $C_1$-$C_4$-haloalkyl, $C_1$-$C_4$-alkoxy or $C_1$-$C_4$-haloalkoxy.

In a further preferred embodiment, $R^a$ in the compounds according to the invention is halogen, $C_1$-$C_4$-alkyl, $C_1$-$C_4$-alkoxy, $C_1$-$C_4$-haloalkoxy, phenyl or pyridyl, where the cyclic groups $R^a$ may be attached directly or via an oxygen atom, where the aromatic and heterocyclic groups $R^a$ for their part may be partially or fully halogenated and/or may carry one, two, three or up to the maximum possible number of identical or different groups $R^b$, where $R^b$ is halogen, $C_1$-$C_4$-alkyl, $C_1$-$C_4$-haloalkyl, $C_1$-$C_4$-alkoxy or $C_1$-$C_4$-haloalkoxy.

A further embodiment relates to compounds I in which $R^4$, $R^7$, $L^3$ and $L^4$ are hydrogen and X is oxygen. These compounds correspond to the formula I.8:

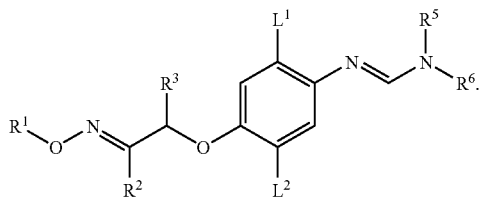

1.8

A further embodiment relates to compounds I in which $R^4$, $R^7$ and $L^4$ are hydrogen and X is oxygen. These compounds correspond to the formula I.9:

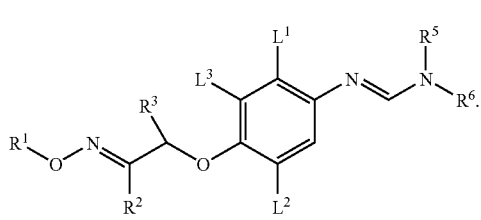

1.9

According to a preferred embodiment of the compounds I:
$R^1$ is $C_1$-$C_8$-alkyl, $C_2$-$C_8$-alkenyl, $C_3$-$C_8$-cycloalkyl, phenyl, pyridyl, pyrazoloyl, imidazolyl or triazolyl, where $R^1$ may carry one, two, three or up to the maximum possible number of identical or different groups $R^a$ which are not heterocyclic groups;
$R^2$ is amino, $C_1$-$C_8$-alkyl, $C_2$-$C_8$-alkenyl, $C_3$-$C_8$-cycloalkyl, phenyl, pyridyl, pyrimidinyl, pyrazinyl, triazinyl, pyrazolyl, imidazolyl or triazolyl, where $R^2$ may carry one, two, three or up to the maximum possible number of identical or different groups $R^a$;
$R^a$ is halogen, $C_1$-$C_4$-alkyl, $C_1$-$C_4$-haloalkyl, $C_1$-$C_4$-alkoxy, $C_1$-$C_4$-haloalkoxy, phenyl, pyrimidinyl, pyradizinyl, triazinyl, pyrazolyl, imidazolyl or triazolyl; where the cyclic groups $R^a$ may be attached directly or via an oxygen atom and/or for their part may be partially or fully halogenated and/or may carry one, two, three or up to the maximum possible number of identical or different groups $R^b$:
$R^b$ is halogen, $C_1$-$C_4$-alkyl, $C_1$-$C_4$-haloalkyl, $C_1$-$C_4$-alkoxy or $C_1$-$C_4$-haloalkoxy;
$R^3$, $R^4$ independently of one another are hydrogen, $C_1$-$C_4$-alkyl or $C_1$-$C_8$-haloalkyl;
$R^5$, $R^6$ is $C_1$-$C_4$-alkyl;
$R^7$ is hydrogen;
$L^1$, $L^2$ independently of one another are halogen or $C_1$-$C_4$-alkyl;
$L^3$, $L^4$ are hydrogen; and
X is oxygen.
These compounds correspond to the formula I.10:

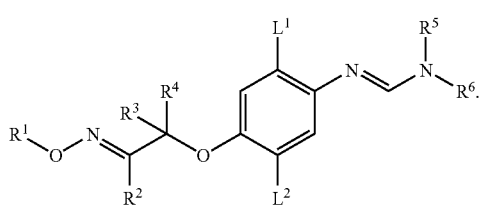

1.10

According to a further preferred embodiment of the compounds I:
$R^1$ $C_1$-$C_8$-alkyl, $C_2$-$C_8$-alkenyl, $C_3$-$C_8$-cycloalkyl or phenyl, where $R^1$ may carry one, two, three or up to the maximum possible number of identical or different groups $R^a$ which are not heterocyclic groups;
$R^2$ is $C_1$-$C_8$-alkyl or phenyl, where $R^2$ may carry one, two, three or up to the maximum possible number of identical or different groups $R^a$;
$R^a$ is halogen, $C_1$-$C_4$-alkyl, $C_1$-$C_4$-haloalkyl, $C_1$-$C_4$-alkoxy, $C_1$-$C_4$-haloalkoxy, phenyl or pyridyl;
where the cyclic groups $R^a$ may be attached directly or via an oxygen atom and/or for their part may be partially or fully halogenated and/or may carry one, two, three or up to the maximum possible number of identical or different groups $R^b$:
$R^b$ is halogen, $C_1$-$C_4$-alkyl, $C_1$-$C_4$-haloalkyl, $C_1$-$C_4$-alkoxy or $C_1$-$C_4$-haloalkoxy; and
$R^3$,$R^4$ independently of one another are hydrogen, $C_1$-$C_4$-alkyl or $C_1$-$C_8$-haloalkyl;
$R^5$,$R^6$ are $C_1$-$C_4$-alkyl;
$R^7$ is hydrogen;
$L^1$, $L^2$ independently of one another are halogen or $C_1$-$C_4$-alkyl;
$L^3$, $L^4$ are hydrogen; and
X is oxygen.
These compounds correspond to the formula I.10.

With a view to their intended use, preference is given in particular to the compounds of the formula I compiled in tables 1 to 2655250 below in which the definitions for the substituents $R^1$ are selected from groups I-1 to I-19 in table I, the definitions for $R^2$ are selected from groups II-1 to II-325 in table II, the definitions for $R^5$ and $R^6$ are selected from the combinations III-1 to III-43 in table III and the definitions for $L^1$, $L^2$, $L^3$ and $L^4$ are selected from the combinations A-1 to A-386 of table A and additionally the definitions of X, $R^3$ and $R^4$ correspond to those in the subformulae I.3A to I.3E. The groups mentioned for a substituent in the tables are furthermore per se, independently of the combination in which they are mentioned, a particularly preferred embodiment of the substituent in question.

Table 1. Compounds of the formula I.3A in which $R^7$ is hydrogen and $R^2$ corresponds to row II-1 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 2. Compounds of the formula I.3A in which $R^7$ is hydrogen and $R^2$ corresponds to row II-2 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 3. Compounds of the formula I.3A, in which $R^7$ is hydrogen and $R^2$ corresponds to row II-3 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 4. Compounds of the formula I.3A, in which $R^7$ is hydrogen and $R^2$ corresponds to row II-4 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 5. Compounds of the formula I.3A, in which $R^7$ is hydrogen and $R^2$ corresponds to row II-5 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 6. Compounds of the formula I.3A, in which $R^7$ is hydrogen and $R^2$ corresponds to row II-6 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 7. Compounds of the formula I.3A, in which $R^7$ is hydrogen and $R^2$ corresponds to row II-7 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 8. Compounds of the formula I.3A, in which $R^7$ is hydrogen and $R^2$ corresponds to row II-8 of table II, $R^1$ corresponds to row I-1 of table II, the combination of the radicals $R^3$ and $R^4$ corresponds to row III-1 of table III the combination of the radicals $L^1$, $L^2$, $L^3$ and $L^4$ for a compound corresponds in each case to one row of table A.

Table 9. Compounds of the formula I.3A, in which $R^7$ is hydrogen and $R^2$ corresponds to row II-9 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 10. Compounds of the formula I.3A, in which $R^7$ is hydrogen and $R^2$ corresponds to row II-10 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 11. Compounds of the formula I.3A, in which $R^7$ is hydrogen and $R^2$ corresponds to row II-11 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 12. Compounds of the formula I.3A, in which $R^7$ is hydrogen and $R^2$ corresponds to row II-12 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 13. Compounds of the formula I.3A, in which $R^7$ is hydrogen and $R^2$ corresponds to row II-13 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 14. Compounds of the formula I.3A, in which $R^7$ is hydrogen and $R^2$ corresponds to row II-14 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 15. Compounds of the formula I.3A, in which $R^7$ is hydrogen and $R^2$ corresponds to row II-15 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 16. Compounds of the formula I.3A, in which $R^7$ is hydrogen and $R^2$ corresponds to row II-16 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 17. Compounds of the formula I.3A, in which $R^7$ is hydrogen and $R^2$ corresponds to row II-17 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 18. Compounds of the formula I.3A, in which $R^7$ is hydrogen and $R^2$ corresponds to row II-18 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 19. Compounds of the formula I.3A, in which $R^7$ is hydrogen and $R^2$ corresponds to row II-19 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 20. Compounds of the formula I.3A, in which $R^7$ is hydrogen and $R^2$ corresponds to row II-20 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 21. Compounds of the formula I.3A, in which $R^7$ is hydrogen and $R^2$ corresponds to row II-21 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 22. Compounds of the formula I.3A, in which $R^7$ is hydrogen and $R^2$ corresponds to row II-22 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 23. Compounds of the formula I.3A, in which $R^7$ is hydrogen and $R^2$ corresponds to row II-23 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 24. Compounds of the formula I.3A, in which $R^7$ is hydrogen and $R^2$ corresponds to row II-24 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 25. Compounds of the formula I.3A, in which $R^7$ is hydrogen and $R^2$ corresponds to row II-25 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 26. Compounds of the formula I.3A, in which $R^7$ is hydrogen and $R^2$ corresponds to row II-26 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of fable A.

Table 27. Compounds of the formula I.3A, in which $R^7$ is hydrogen and $R^2$ corresponds to row II-27 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 28. Compounds of the formula I.3A, in which $R^7$ is hydrogen and $R^2$ corresponds to row II-28 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 29. Compounds of the formula I.3A, in which $R^7$ is hydrogen and $R^2$ corresponds to row II-29 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 30. Compounds of the formula I.3A, in which $R^7$ is hydrogen and $R^2$ corresponds to row II-30 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 31. Compounds of the formula I.3A, in which $R^7$ is hydrogen and $R^2$ corresponds to row II-31 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 32. Compounds of the formula I.3A, in which $R^7$ is hydrogen and $R^2$ corresponds to row II-32 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 33. Compounds of the formula I.3A, in which $R^7$ is hydrogen and $R^2$ corresponds to row II-33 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 34. Compounds of the formula I.3A, in which $R^7$ is hydrogen and $R^2$ corresponds to row II-34 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 35. Compounds of the formula I.3A, in which $R^7$ is hydrogen and $R^2$ corresponds to row II-35 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 36. Compounds of the formula I.3A, in which $R^7$ is hydrogen and $R^2$ corresponds to row II-36 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 37. Compounds of the formula I.3A, in which $R^7$ is hydrogen and $R^2$ corresponds to row II-37 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 38. Compounds of the formula I.3A, in which $R^7$ is hydrogen and $R^2$ corresponds to row II-38 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 39. Compounds of the formula I.3A, in which $R^7$ is hydrogen and $R^2$ corresponds to row II-39 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 40. Compounds of the formula I.3A, in which $R^7$ is hydrogen and $R^2$ corresponds to row II-40 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 41. Compounds of the formula I.3A, in which $R^7$ is hydrogen and $R^2$ corresponds to row II-41 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 42. Compounds of the formula I.3A, in which $R^7$ is hydrogen and $R^2$ corresponds to row II-42 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 43. Compounds of the formula I.3A, in which $R^7$ is hydrogen and $R^2$ corresponds to row II-43 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 44. Compounds of the formula I.3A, in which $R^7$ is hydrogen and $R^2$ corresponds to row II-44 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 45. Compounds of the formula I.3A, in which $R^7$ is hydrogen and $R^2$ corresponds to row II-45 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 46. Compounds of the formula I.3A, in which $R^7$ is hydrogen and $R^2$ corresponds to row II-46 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 47. Compounds of the formula I.3A, in which $R^7$ is hydrogen and $R^2$ corresponds to row II-47 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 48. Compounds of the formula I.3A, in which $R^7$ is hydrogen and $R^2$ corresponds to row II-48 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 49. Compounds of the formula I.3A, in which $R^7$ is hydrogen and $R^2$ corresponds to row II-49 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 50. Compounds of the formula I.3A, in which $R^7$ is hydrogen and $R^2$ corresponds to row II-50 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 51. Compounds of the formula I.3A, in which $R^7$ is hydrogen and $R^2$ corresponds to row II-51 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 52. Compounds of the formula I.3A, in which $R^7$ is hydrogen and $R^2$ corresponds to row II-52 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 53. Compounds of the formula I.3A, in which $R^7$ is hydrogen and $R^2$ corresponds to row II-53 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 54. Compounds of the formula I.3A, in which $R^7$ is hydrogen and $R^2$ corresponds to row II-54 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 55. Compounds of the formula I.3A, in which $R^7$ is hydrogen and $R^2$ corresponds to row II-55 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 56. Compounds of the formula I.3A, in which $R^7$ is hydrogen and $R^2$ corresponds to row II-56 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 57. Compounds of the formula I.3A, in which $R^7$ is hydrogen and $R^2$ corresponds to row II-57 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 58. Compounds of the formula I.3A, in which $R^7$ is hydrogen and $R^2$ corresponds to row II-58 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 59. Compounds of the formula I.3A, in which $R^7$ is hydrogen and $R^2$ corresponds to row II-59 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 60. Compounds of the formula I.3A, in which $R^7$ is hydrogen and $R^2$ corresponds to row II-60 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 61. Compounds of the formula I.3A, in which $R^7$ is hydrogen and $R^2$ corresponds to row II-61 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 62. Compounds of the formula I.3A, in which $R^7$ is hydrogen and $R^2$ corresponds to row II-62 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 63. Compounds of the formula I.3A, in which $R^7$ is hydrogen and $R^2$ corresponds to row II-63 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 64. Compounds of the formula I.3A, in which $R^7$ is hydrogen and $R^2$ corresponds to row II-64 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 65. Compounds of the formula I.3A, in which $R^7$ is hydrogen and $R^2$ corresponds to row II-65 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 66. Compounds of the formula I.3A, in which $R^7$ is hydrogen and $R^2$ corresponds to row II-66 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 67. Compounds of the formula I.3A, in which $R^7$ is hydrogen and $R^2$ corresponds to row II-67 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 68. Compounds of the formula I.3A, in which $R^7$ is hydrogen and $R^2$ corresponds to row II-68 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 69. Compounds of the formula I.3A, in which $R^7$ is hydrogen and $R^2$ corresponds to row II-69 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 70. Compounds of the formula I.3A, in which $R^7$ is hydrogen and $R^2$ corresponds to row II-70 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 71. Compounds of the formula I.3A, in which $R^7$ is hydrogen and $R^2$ corresponds to row II-71 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 72. Compounds of the formula I.3A, in which $R^7$ is hydrogen and $R^2$ corresponds to row II-72 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 73. Compounds of the formula I.3A, in which $R^7$ is hydrogen and $R^2$ corresponds to row II-73 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 74. Compounds of the formula I.3A, in which $R^7$ is hydrogen and $R^2$ corresponds to row II-74 of table II, $R^1$ corresponds to row I-1 of table II, the combination of the radicals $R^3$ and $R^4$ corresponds to row III-1 of table III and the combination of the radicals. $L^1$, $L^2$, $L^3$ and $L^4$ for a compound corresponds in each case to one row of table A.

Table 75. Compounds of the formula I.3A, in which $R^7$ is hydrogen and $R^2$ corresponds to row II-75 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 76. Compounds of the formula I.3A, in which $R^7$ is hydrogen and $R^2$ corresponds to row II-76 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 77. Compounds of the formula I.3A, in which $R^7$ is hydrogen and $R^2$ corresponds to row II-77 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 78. Compounds of the formula I.3A, in which $R^7$ is hydrogen and $R^2$ corresponds to row II-78 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 79. Compounds of the formula I.3A, in which $R^7$ is hydrogen and $R^2$ corresponds to row II-79 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 80. Compounds of the formula I.3A, in which $R^7$ is hydrogen and $R^2$ corresponds to row II-80 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 81. Compounds of the formula I.3A, in which $R^7$ is hydrogen and $R^2$ corresponds to row II-81 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 82. Compounds of the formula I.3A, in which $R^7$ is hydrogen and $R^2$ corresponds to row II-82 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 83. Compounds of the formula I.3A, in which $R^7$ is hydrogen and $R^2$ corresponds to row II-83 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 84. Compounds of the formula I.3A, in which $R^7$ is hydrogen and $R^2$ corresponds to row II-84 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 85. Compounds of the formula I.3A, in which $R^7$ is hydrogen and $R^2$ corresponds to row II-85 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 86. Compounds of the formula I.3A, in which $R^7$ is hydrogen and $R^2$ corresponds to row II-86 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 87. Compounds of the formula I.3A, in which $R^7$ is hydrogen and $R^2$ corresponds to row II-87 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 88. Compounds of the formula I.3A, in which $R^7$ is hydrogen and $R^2$ corresponds to row II-88 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 89. Compounds of the formula I.3A, in which $R^7$ is hydrogen and $R^2$ corresponds to row II-89 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 90. Compounds of the formula I.3A, in which $R^7$ is hydrogen and $R^2$ corresponds to row II-90 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 91. Compounds of the formula I.3A, in which $R^7$ is hydrogen and $R^2$ corresponds to row II-91 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 92. Compounds of the formula I.3A, in which $R^7$ is hydrogen and $R^2$ corresponds to row II-92 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 93. Compounds of the formula I.3A, in which $R^7$ is hydrogen and $R^2$ corresponds to row II-93 of table II, $R^1$ corresponds to row I-1 of table II, the combination of the radicals $R^3$ and $R^4$ corresponds to row III-1 of table III and the Table 94. Compounds of the formula I.3A, in which $R^7$ is hydrogen and $R^2$ corresponds to row II-94 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 95. Compounds of the formula I.3A, in which $R^7$ is hydrogen and $R^2$ corresponds to row II-95 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 96. Compounds of the formula I.3A, in which $R^7$ is hydrogen and $R^2$ corresponds to row II-96 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 97. Compounds of the formula I.3A, in which $R^7$ is hydrogen and $R^2$ corresponds to row II-97 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 98. Compounds of the formula I.3A, in which $R^7$ is hydrogen and $R^2$ corresponds to row II-98 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 99. Compounds of the formula I.3A, in which $R^7$ is hydrogen and $R^2$ corresponds to row II-99 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 100. Compounds of the formula I.3A, in which $R^7$ is hydrogen and $R^2$ corresponds to row II-100 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 101. Compounds of the formula I.3A, in which $R^7$ is hydrogen and $R^2$ corresponds to row II-101 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 102. Compounds of the formula I.3A, in which $R^7$ is hydrogen and $R^2$ corresponds to row II-102 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 103. Compounds of the formula I.3A, in which $R^7$ is hydrogen and $R^2$ corresponds to row II-103 of table II, $R^1$ corresponds to row I-1 of table II, the combination of the radicals $R^3$ and $R^4$ corresponds to row III-1 of table III and the combination of the radicals $L^1, L^2, L^3$ and $L^4$ for a compound corresponds in each case to one row of table A.

Table 104. Compounds of the formula I.3A, in which $R^7$ is hydrogen and $R^2$ corresponds to row II-104 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 105. Compounds of the formula I.3A, in which $R^7$ is hydrogen and $R^2$ corresponds to row II-105 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 106. Compounds of the formula I.3A, in which $R^7$ is hydrogen and $R^2$ corresponds to row II-106 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 107. Compounds of the formula I.3A, in which $R^7$ is hydrogen and $R^2$ corresponds to row II-107 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 108. Compounds of the formula I.3A, in which $R^7$ is hydrogen and $R^2$ corresponds to row II-108 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 109. Compounds of the formula I.3A, in which $R^7$ is hydrogen and $R^2$ corresponds to row II-109 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 110. Compounds of the formula I.3A, in which $R^7$ is hydrogen and $R^2$ corresponds to row II-110 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 111. Compounds of the formula I.3A, in which $R^7$ is hydrogen and $R^2$ corresponds to row II-111 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 112. Compounds of the formula I.3A, in which $R^7$ is hydrogen and $R^2$ corresponds to row II-112 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 113. Compounds of the formula I.3A, in which $R^7$ is hydrogen and $R^2$ corresponds to row II-113 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 114. Compounds of the formula I.3A, in which $R^7$ is hydrogen and $R^2$ corresponds to row II-114 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 115. Compounds of the formula I.3A, in which $R^7$ is hydrogen and $R^2$ corresponds to row II-115 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 116. Compounds of the formula I.3A, in which $R^7$ is hydrogen and $R^2$ corresponds to row II-116 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 117. Compounds of the formula I.3A, in which $R^7$ is hydrogen and $R^2$ corresponds to row II-117 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 118. Compounds of the formula I.3A, in which $R^7$ is hydrogen and $R^2$ corresponds to row II-118 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 119. Compounds of the formula I.3A, in which $R^7$ is hydrogen and $R^2$ corresponds to row II-119 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 120. Compounds of the formula I.3A, in which $R^7$ is hydrogen and $R^2$ corresponds to row II-120 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 121. Compounds of the formula I.3A, in which $R^7$ is hydrogen and $R^2$ corresponds to row II-121 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 122. Compounds of the formula I.3A, in which $R^7$ is hydrogen and $R^2$ corresponds to row II-122 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 123. Compounds of the formula I.3A, in which $R^7$ is hydrogen and $R^2$ corresponds to row II-123 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 124. Compounds of the formula I.3A, in which $R^7$ is hydrogen and $R^2$ corresponds to row II-124 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 125. Compounds of the formula I.3A, in which $R^7$ is hydrogen and $R^2$ corresponds to row II-125 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 126. Compounds of the formula I.3A, in which $R^7$ is hydrogen and $R^2$ corresponds to row II-126 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 127. Compounds of the formula I.3A, in which $R^7$ is hydrogen and $R^2$ corresponds to row II-127 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 128. Compounds of the formula I.3A, in which $R^7$ is hydrogen and $R^2$ corresponds to row II-128 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 129. Compounds of the formula I.3A, in which $R^7$ is hydrogen and $R^2$ corresponds to row II-129 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 130. Compounds of the formula I.3A, in which $R^7$ is hydrogen and $R^2$ corresponds to row II-130 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 131. Compounds of the formula I.3A, in which $R^7$ is hydrogen and $R^2$ corresponds to row II-131 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 132. Compounds of the formula I.3A, in which $R^7$ is hydrogen and $R^2$ corresponds to row II-132 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 133. Compounds of the formula I.3A, in which $R^7$ is hydrogen and $R^2$ corresponds to row II-133 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 134. Compounds of the formula I.3A, in which $R^7$ is hydrogen and $R^2$ corresponds to row II-134 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 135. Compounds of the formula I.3A, in which $R^7$ is hydrogen and $R^2$ corresponds to row II-135 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 136. Compounds of the formula I.3A, in which $R^7$ is hydrogen and $R^2$ corresponds to row II-136 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 137. Compounds of the formula I.3A, in which $R^7$ is hydrogen and $R^2$ corresponds to row II-137 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 138. Compounds of the formula I.3A, in which $R^7$ is hydrogen and $R^2$ corresponds to row II-138 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 139. Compounds of the formula I.3A, in which $R^7$ is hydrogen and $R^2$ corresponds to row II-139 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 140. Compounds of the formula I.3A, in which $R^7$ is hydrogen and $R^2$ corresponds to row II-140 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 141. Compounds of the formula I.3A, in which $R^7$ is hydrogen and $R^2$ corresponds to row II-141 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 142. Compounds of the formula I.3A, in which $R^7$ is hydrogen and $R^2$ corresponds to row II-142 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 143. Compounds of the formula I.3A, in which $R^7$ is hydrogen and $R^2$ corresponds to row II-143 of table II, $R^1$ corresponds to row I-1 of table II, the combination of the radicals $R^3$ and $R^4$ corresponds to row III-1 of table III and the combination of the radicals $L^1$, $L^2$, $L^3$ and $L^4$ for a compound corresponds in each case to one row of table A.

Table 144. Compounds of the formula I.3A, in which $R^7$ is hydrogen and $R^2$ corresponds to row II-144 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 145. Compounds of the formula I.3A, in which $R^7$ is hydrogen and $R^2$ corresponds to row II-145 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 146. Compounds of the formula I.3A, in which $R^7$ is hydrogen and $R^2$ corresponds to row II-146 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 147. Compounds of the formula I.3A, in which $R^7$ is hydrogen and $R^2$ corresponds to row II-147 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 148. Compounds of the formula I.3A, in which $R^7$ is hydrogen and $R^2$ corresponds to row II-148 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 149. Compounds of the formula I.3A, in which $R^7$ is hydrogen and $R^2$ corresponds to row II-149 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 150. Compounds of the formula I.3A, in which $R^7$ is hydrogen and $R^2$ corresponds to row II-150 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 151. Compounds of the formula I.3A, in which $R^7$ is hydrogen and $R^2$ corresponds to row II-151 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 152. Compounds of the formula I.3A, in which $R^7$ is hydrogen and $R^2$ corresponds to row II-152 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 153. Compounds of the formula I.3A, in which $R^7$ is hydrogen and $R^2$ corresponds to row II-153 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 154. Compounds of the formula I.3A, in which $R^7$ is hydrogen and $R^2$ corresponds to row II-154 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 155. Compounds of the formula I.3A, in which $R^7$ is hydrogen and $R^2$ corresponds to row II-155 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 156. Compounds of the formula I.3A, in which $R^7$ is hydrogen and $R^2$ corresponds to row II-156 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 157. Compounds of the formula I.3A, in which $R^7$ is hydrogen and $R^2$ corresponds to row II-157 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 158. Compounds of the formula I.3A, in which $R^7$ is hydrogen and $R^2$ corresponds to row II-158 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 159. Compounds of the formula I.3A, in which $R^7$ is hydrogen and $R^2$ corresponds to row II-159 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 160. Compounds of the formula I.3A, in which $R^7$ is hydrogen and $R^2$ corresponds to row II-160 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 161. Compounds of the formula I.3A, in which $R^7$ is hydrogen and $R^2$ corresponds to row II-161 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 162. Compounds of the formula I.3A, in which $R^7$ is hydrogen and $R^2$ corresponds to row II-162 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 163. Compounds of the formula I.3A, in which $R^7$ is hydrogen and $R^2$ corresponds to row II-163 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 164. Compounds of the formula I.3A, in which $R^7$ is hydrogen and $R^2$ corresponds to row II-164 of table II, $R^1$ corresponds to row I-1 of table II, the combination of the radicals $R^5$ and $R^6$ corresponds to row III-1 of table III and the combination of the radicals. $L^1$, $L^2$, $L^3$ and $L^4$ for a compound corresponds in each case to one row of table A.

Table 165. Compounds of the formula I.3A, in which $R^7$ is hydrogen and $R^2$ corresponds to row II-165 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 166. Compounds of the formula I.3A, in which $R^7$ is hydrogen and $R^2$ corresponds to row II-166 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 167. Compounds of the formula I.3A, in which $R^7$ is hydrogen and $R^2$ corresponds to row II-167 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 168. Compounds of the formula I.3A, in which $R^7$ is hydrogen and $R^2$ corresponds to row II-168 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 169. Compounds of the formula I.3A, in which $R^7$ is hydrogen and $R^2$ corresponds to row II-169 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 170. Compounds of the formula I.3A, in which $R^7$ is hydrogen and $R^2$ corresponds to row II-170 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 171. Compounds of the formula I.3A, in which $R^7$ is hydrogen and $R^2$ corresponds to row II-171 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 172. Compounds of the formula I.3A, in which $R^7$ is hydrogen and $R^2$ corresponds to row II-172 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 173. Compounds of the formula I.3A, in which $R^7$ is hydrogen and $R^2$ corresponds to row II-173 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 174. Compounds of the formula I.3A, in which $R^7$ is hydrogen and $R^2$ corresponds to row II-174 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 175. Compounds of the formula I.3A, in which $R^7$ is hydrogen and $R^2$ corresponds to row II-175 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 176. Compounds of the formula I.3A, in which $R^7$ is hydrogen and $R^2$ corresponds to row II-176 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 177. Compounds of the formula I.3A, in which $R^7$ is hydrogen and $R^2$ corresponds to row II-177 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 178. Compounds of the formula I.3A, in which $R^7$ is hydrogen and $R^2$ corresponds to row II-178 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 179. Compounds of the formula I.3A, in which $R^7$ is hydrogen and $R^2$ corresponds to row II-179 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 180. Compounds of the formula I.3A, in which $R^7$ is hydrogen and $R^2$ corresponds to row II-180 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 181. Compounds of the formula I.3A, in which $R^7$ is hydrogen and $R^2$ corresponds to row II-181 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 182. Compounds of the formula I.3A, in which $R^7$ is hydrogen and $R^2$ corresponds to row II-182 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 183. Compounds of the formula I.3A, in which $R^7$ is hydrogen and $R^2$ corresponds to row II-183 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 184. Compounds of the formula I.3A, in which $R^7$ is hydrogen and $R^2$ corresponds to row II-184 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 185. Compounds of the formula I.3A, in which $R^7$ is hydrogen and $R^2$ corresponds to row II-185 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 186. Compounds of the formula I.3A, in which $R^7$ is hydrogen and $R^2$ corresponds to row II-186 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 187. Compounds of the formula I.3A, in which $R^7$ is hydrogen and $R^2$ corresponds to row II-187 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 188. Compounds of the formula I.3A, in which $R^7$ is hydrogen and $R^2$ corresponds to row II-188 of table II, $R^1$ corresponds to row I-1 of table. II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 189. Compounds of the formula I.3A, in which $R^7$ is hydrogen and $R^2$ corresponds to row II-189 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 190. Compounds of the formula I.3A, in which $R^7$ is hydrogen and $R^2$ corresponds to row II-190 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 191. Compounds of the formula I.3A, in which $R^7$ is hydrogen and $R^2$ corresponds to row II-191 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 192. Compounds of the formula I.3A, in which $R^7$ is hydrogen and $R^2$ corresponds to row II-192 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 193. Compounds of the formula I.3A, in which $R^7$ is hydrogen and $R^2$ corresponds to row II-193 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 194. Compounds of the formula I.3A, in which $R^7$ is hydrogen and $R^2$ corresponds to row II-194 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 195. Compounds of the formula I.3A, in which $R^7$ is hydrogen and $R^2$ corresponds to row II-195 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 196. Compounds of the formula I.3A, in which $R^7$ is hydrogen and $R^2$ corresponds to row II-196 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 197. Compounds of the formula I.3A, in which $R^7$ is hydrogen and $R^2$ corresponds to row II-197 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 198. Compounds of the formula I.3A, in which $R^7$ is hydrogen and $R^2$ corresponds to row II-198 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 199. Compounds of the formula I.3A, in which $R^7$ is hydrogen and $R^2$ corresponds to row II-199 of table II; $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 200. Compounds of the formula I.3A, in which $R^7$ is hydrogen and $R^2$ corresponds to row II-200 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 201. Compounds of the formula I.3A, in which $R^7$ is hydrogen and $R^2$ corresponds to row II-201 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table. A.

Table 202. Compounds of the formula I.3A, in which $R^7$ is hydrogen and $R^2$ corresponds to row II-202 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 203. Compounds of the formula I.3A, in which $R^7$ is hydrogen and $R^2$ corresponds to row II-203 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 204. Compounds of the formula I.3A, in which $R^7$ is hydrogen and $R^2$ corresponds to row II-204 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 205. Compounds of the formula I.3A, in which $R^7$ is hydrogen and $R^2$ corresponds to row II-205 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 206. Compounds of the formula I.3A, in which $R^7$ is hydrogen and $R^2$ corresponds to row II-206 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 207. Compounds of the formula I.3A, in which $R^7$ is hydrogen and $R^2$ corresponds to row II-207 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 208. Compounds of the formula I.3A, in which $R^7$ is hydrogen and $R^2$ corresponds to row II-208 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 209. Compounds of the formula I.3A, in which $R^7$ is hydrogen and $R^2$ corresponds to row II-209 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 210. Compounds of the formula I.3A, in which $R^7$ is hydrogen and $R^2$ corresponds to row II-210 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 211. Compounds of the formula I.3A, in which $R^7$ is hydrogen and $R^2$ corresponds to row II-211 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 212. Compounds of the formula I.3A, in which $R^7$ is hydrogen and $R^2$ corresponds to row II-212 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 213. Compounds of the formula I.3A, in which $R^7$ is hydrogen and $R^2$ corresponds to row II-213 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 214. Compounds of the formula I.3A, in which $R^7$ is hydrogen and $R^2$ corresponds to row II-214 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 215. Compounds of the formula I.3A, in which $R^7$ is hydrogen and $R^2$ corresponds to row II-215 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 216. Compounds of the formula I.3A, in which $R^7$ is hydrogen and $R^2$ corresponds to row II-216 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 217. Compounds of the formula I.3A, in which $R^7$ is hydrogen and $R^2$ corresponds to row II-217 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 218. Compounds of the formula I.3A, in which $R^7$ is hydrogen and $R^2$ corresponds to row II-218 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 219. Compounds of the formula I.3A, in which $R^7$ is hydrogen and $R^2$ corresponds to row II-219 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 220. Compounds of the formula I.3A, in which $R^7$ is hydrogen and $R^2$ corresponds to row II-220 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 221. Compounds of the formula I.3A, in which $R^7$ is hydrogen and $R^2$ corresponds to row II-221 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 222. Compounds of the formula I.3A, in which $R^7$ is hydrogen and $R^2$ corresponds to row II-222 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 223. Compounds of the formula I.3A, in which $R^7$ is hydrogen and $R^2$ corresponds to row II-223 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 224. Compounds of the formula I.3A, in which $R^7$ is hydrogen and $R^2$ corresponds to row II-224 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 225. Compounds of the formula I.3A, in which $R^7$ is hydrogen and $R^2$ corresponds to row II-225 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 226. Compounds of the formula I.3A, in which $R^7$ is hydrogen and $R^2$ corresponds to row II-226 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 227. Compounds of the formula I.3A, in which $R^7$ is hydrogen and $R^2$ corresponds to row II-227 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 228. Compounds of the formula I.3A, in which $R^7$ is hydrogen and $R^2$ corresponds to row II-228 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 229. Compounds of the formula I.3A, in which $R^7$ is hydrogen and $R^2$ corresponds to row II-229 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 230. Compounds of the formula I.3A, in which $R^7$ is hydrogen and $R^2$ corresponds to row II-230 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 231. Compounds of the formula I.3A, in which $R^7$ is hydrogen and $R^2$ corresponds to row II-231 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 232. Compounds of the formula I.3A, in which $R^7$ is hydrogen and $R^2$ corresponds to row II-232 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 233. Compounds of the formula I.3A, in which $R^7$ is hydrogen and $R^2$ corresponds to row II-233 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 234. Compounds, of the formula I.3A, in which $R^7$ is hydrogen and $R^2$ corresponds to row II-234 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 235. Compounds of the formula I.3A, in which $R^7$ is hydrogen and $R^2$ corresponds to row II-235 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 236. Compounds of the formula I.3A, in which $R^7$ is hydrogen and $R^2$ corresponds to row II-236 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 237. Compounds of the formula I.3A, in which $R^7$ is hydrogen and $R^2$ corresponds to row II-237 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 238. Compounds of the formula I.3A, in which $R^7$ is hydrogen and $R^2$ corresponds to row II-238 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 239. Compounds of the formula I.3A, in which $R^7$ is hydrogen and $R^2$ corresponds to row II-239 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 240. Compounds of the formula I.3A, in which $R^7$ is hydrogen and $R^2$ corresponds to row II-240 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 241. Compounds of the formula I.3A, in which $R^7$ is hydrogen and $R^2$ corresponds to row II-241 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 242. Compounds of the formula I.3A, in which $R^7$ is hydrogen and $R^2$ corresponds to row II-242 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 243. Compounds of the formula I.3A, in which $R^7$ is hydrogen and $R^2$ corresponds to row II-243 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 244. Compounds of the formula I.3A, in which $R^7$ is hydrogen and $R^2$ corresponds to row II-244 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 245. Compounds of the formula I.3A, in which $R^7$ is hydrogen and $R^2$ corresponds to row II-245 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 246. Compounds of the formula I.3A, in which $R^7$ is hydrogen and $R^2$ corresponds to row II-246 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 247. Compounds of the formula I.3A, in which $R^7$ is hydrogen and $R^2$ corresponds to row II-247 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 248. Compounds of the formula I.3A, in which $R^7$ is hydrogen and $R^2$ corresponds to row II-248 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 249. Compounds of the formula I.3A, in which $R^7$ is hydrogen and $R^2$ corresponds to row II-249 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 250. Compounds of the formula I.3A, in which $R^7$ is hydrogen and $R^2$ corresponds to row II-250 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 251. Compounds of the formula I.3A, in which $R^7$ is hydrogen and $R^2$ corresponds to row II-251 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 252. Compounds of the formula I.3A, in which $R^7$ is hydrogen and $R^2$ corresponds to row II-252 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 253. Compounds of the formula I.3A, in which $R^7$ is hydrogen and $R^2$ corresponds to row II-253 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 254. Compounds of the formula I.3A, in which $R^7$ is hydrogen and $R^2$ corresponds to row II-254 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 255. Compounds of the formula I.3A, in which $R^7$ is hydrogen and $R^2$ corresponds to row II-255 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 256. Compounds of the formula I.3A, in which $R^7$ is hydrogen and $R^2$ corresponds to row II-256 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 257. Compounds of the formula I.3A, in which $R^7$ is hydrogen and $R^2$ corresponds to row II-257 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 258. Compounds of the formula I.3A, in which $R^7$ is hydrogen and $R^2$ corresponds to row II-258 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 259. Compounds of the formula I.3A, in which $R^7$ is hydrogen and $R^2$ corresponds to row II-259 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 260. Compounds of the formula I.3A, in which $R^7$ is hydrogen and $R^2$ corresponds to row II-260 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 261. Compounds of the formula I.3A, in which $R^7$ is hydrogen and $R^2$ corresponds to row II-261 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 262. Compounds of the formula I.3A, in which $R^7$ is hydrogen and $R^2$ corresponds to row II-262 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 263. Compounds of the formula I.3A, in which $R^7$ is hydrogen and $R^2$ corresponds to row II-263 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 264. Compounds of the formula I.3A, in which $R^7$ is hydrogen and $R^2$ corresponds to row II-264 of table II, $R^1$ corresponds to row. I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 265. Compounds of the formula I.3A, in which $R^7$ is hydrogen and $R^2$ corresponds to row II-265 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 266. Compounds of the formula I.3A, in which $R^7$ is hydrogen and $R^2$ corresponds to row II-266 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 267. Compounds of the formula I.3A, in which $R^7$ is hydrogen and $R^2$ corresponds to row II-267 of table II, $R^1$ corresponds to row I-1 of table II, the combination of the radicals $R^5$ and $R^6$ corresponds to row III-1 of table III and the combination of the radical $L^1, L^2, L^3$ and $L^4$ for a compound corresponds in each case to one row of table A.

Table 268. Compounds of the formula I.3A, in which $R^7$ is hydrogen and $R^2$ corresponds to row II-268 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 269. Compounds of the formula I.3A, in which $R^7$ is hydrogen and $R^2$ corresponds to row II-269 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 270. Compounds of the formula I.3A, in which $R^7$ is hydrogen and $R^2$ corresponds to row II-270 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 271. Compounds of the formula I.3A, in which $R^7$ is hydrogen and $R^2$ corresponds to row II-271 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 272. Compounds of the formula I.3A, in which $R^7$ is hydrogen and $R^2$ corresponds to row II-272 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 273. Compounds of the formula I.3A, in which $R^7$ is hydrogen and $R^2$ corresponds to row II-273 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 274. Compounds of the formula I.3A, in which $R^7$ is hydrogen and $R^2$ corresponds to row II-274 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 275. Compounds of the formula I.3A, in which $R^7$ is hydrogen and $R^2$ corresponds to row II-275 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 276. Compounds of the formula I.3A, in which $R^7$ is hydrogen and $R^2$ corresponds to row II-276 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 277. Compounds of the formula I.3A, in which $R^7$ is hydrogen and $R^2$ corresponds to row II-277 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 278. Compounds of the formula I.3A, in which $R^7$ is hydrogen and $R^2$ corresponds to row II-278 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 279. Compounds of the formula I.3A, in which $R^7$ is hydrogen and $R^2$ corresponds to row II-279 of table II, $R^1$ corresponds to row I-1 of table the combination of the radicals $R^5$ and $R^6$ corresponds to row III-1 of table III and the combination of the radicals $L^1, L^2, L^3$ and $L^4$ for a compound corresponds in each case to one row of table A.

Table 280. Compounds of the formula I.3A, in which $R^7$ is hydrogen and $R^2$ corresponds to row II-280 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 281. Compounds of the formula I.3A, in which $R^7$ is hydrogen and $R^2$ corresponds to row II-281 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 282. Compounds of the formula I.3A, in which $R^7$ is hydrogen and $R^2$ corresponds to row II-282 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 283. Compounds of the formula I.3A, in which $R^7$ is hydrogen and $R^2$ corresponds to row II-283 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 284. Compounds of the formula I.3A, in which $R^7$ is hydrogen and $R^2$ corresponds to row II-284 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 285. Compounds of the formula I.3A, in which $R^7$ is hydrogen and $R^2$ corresponds to row II-285 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 286. Compounds of the formula I.3A, in which $R^7$ is hydrogen and $R^2$ corresponds to row II-286 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 287. Compounds of the formula I.3A, in which $R^7$ is hydrogen and $R^2$ corresponds to row II-287 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 288. Compounds of the formula I.3A, in which $R^7$ is hydrogen and $R^2$ corresponds to row II-288 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 289. Compounds of the formula I.3A, in which $R^7$ is hydrogen and $R^2$ corresponds to row II-289 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 290. Compounds of the formula I.3A, in which $R^7$ is hydrogen and $R^2$ corresponds to row II-290 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 291. Compounds of the formula I.3A, in which $R^7$ is hydrogen and $R^2$ corresponds to row II-291 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 292. Compounds of the formula I.3A, in which $R^7$ is hydrogen and $R^2$ corresponds to row II-292 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 293. Compounds of the formula I.3A, in which $R^7$ is hydrogen and $R^2$ corresponds to row II-293 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 294. Compounds of the formula I.3A, in which $R^7$ is hydrogen and $R^2$ corresponds to row II-294 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 295. Compounds of the formula I.3A, in which $R^7$ is hydrogen and $R^2$ corresponds to row II-295 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 296. Compounds of the formula I.3A, in which $R^7$ is hydrogen and $R^2$ corresponds to row II-296 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 297. Compounds of the formula I.3A, in which $R^7$ is hydrogen and $R^2$ corresponds to row II-297 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 298. Compounds of the formula I.3A, in which $R^7$ is hydrogen and $R^2$ corresponds to row II-298 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 299. Compounds of the formula I.3A, in which $R^7$ is hydrogen and $R^2$ corresponds to row II-299 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 300. Compounds of the formula I.3A, in which $R^7$ is hydrogen and $R^2$ corresponds to row II-300 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 301. Compounds of the formula I.3A, in which $R^7$ is hydrogen and $R^2$ corresponds to row II-301 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 302. Compounds of the formula I.3A, in which $R^7$ is hydrogen and $R^2$ corresponds to row II-302 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 303. Compounds of the formula I.3A, in which $R^7$ is hydrogen and $R^2$ corresponds to row II-303 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 304. Compounds of the formula I.3A, in which $R^7$ is hydrogen and $R^2$ corresponds to row II-304 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 305. Compounds of the formula I.3A, in which $R^7$ is hydrogen and $R^2$ corresponds to row II-305 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 306. Compounds of the formula I.3A, in which $R^7$ is hydrogen and $R^2$ corresponds to row II-306 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 307. Compounds of the formula I.3A, in which $R^7$ is hydrogen and $R^2$ corresponds to row II-307 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 308. Compounds of the formula I.3A, in which $R^7$ is hydrogen and $R^2$ corresponds to row II-308 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 309. Compounds of the formula I.3A, in which $R^7$ is hydrogen and $R^2$ corresponds to row II-309 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 310. Compounds of the formula I.3A, in which $R^7$ is hydrogen and $R^2$ corresponds to row II-310 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 311. Compounds of the formula I.3A, in which $R^7$ is hydrogen and $R^2$ corresponds to row II-311 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 312. Compounds of the formula I.3A, in which $R^7$ is hydrogen and $R^2$ corresponds to row II-312 of table II, $R^1$ corresponds to row I-1 of table II, the combination of the radicals $R^5$ and $R^6$ corresponds to row III-1 of table III and the combination of the radicals. $L^1, L^2, L^3$ and $L^4$ for a compound corresponds in each case to one row of table A.

Table 313. Compounds of the formula I.3A, in which $R^7$ is hydrogen and $R^2$ corresponds to row II-313 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 314. Compounds of the formula I.3A, in which $R^7$ is hydrogen and $R^2$ corresponds to row II-314 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 315. Compounds of the formula I.3A, in which $R^7$ is hydrogen and $R^2$ corresponds to row II-315 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 316. Compounds of the formula I.3A, in which $R^7$ is hydrogen and $R^2$ corresponds to row II-316 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 317. Compounds of the formula I.3A, in which $R^7$ is hydrogen and $R^2$ corresponds to row II-317 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 318. Compounds of the formula I.3A, in which $R^7$ is hydrogen and $R^2$ corresponds to row II-318 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 319. Compounds of the formula I.3A, in which $R^7$ is hydrogen and $R^2$ corresponds to row II-319 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 320. Compounds of the formula I.3A, in which $R^7$ is hydrogen and $R^2$ corresponds to row II-320 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 321. Compounds of the formula I.3A, in which $R^7$ is hydrogen and $R^2$ corresponds to row II-321 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 322. Compounds of the formula I.3A, in which $R^7$ is hydrogen and $R^2$ corresponds to row II-322 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 323. Compounds of the formula I.3A, in which $R^7$ is hydrogen and $R^2$ corresponds to row II-323 of table II, $R^1$ corresponds to row I-1 of table II, the combination of the radicals $R^5$ and $R^6$ corresponds to row III-1 of table III and the combination of the radicals $L^1, L^2, L^3$ and $L^4$ for a compound corresponds in each case to one row of table A.

Table 324. Compounds of the formula I.3A, in which $R^7$ is hydrogen and $R^2$ corresponds to row II-324 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Table 325. Compounds of the formula I.3A, in which $R^7$ is hydrogen and $R^2$ corresponds to row II-325 of table II, $R^1$ corresponds to row I-1 of table II, the combination of the radicals $R^5$ and $R^6$ corresponds to row III-1 of table III and the combination of the radicals $L^1$, $L^2$, $L^3$ and $L^4$ for a compound corresponds in each case to one row of table A.

Tables 326 to 650. Compounds of the formula I.3A, in which $R^2$, $R^5$, $R^6$ and $R^7$ are as defined in tables 1 to 325, $R^1$ corresponds to row I-2 instead of I-1 in table I and the combination of the radicals $L^1$, $L^2$, $L^3$ and $L^4$ for a compound corresponds in each case to one row of table A.

Tables 651 to 975. Compounds of the formula I.3A, in which $R^2$, $R^5$, $R^6$ and $R^7$ are as defined in tables 1 to 325, $R^1$ corresponds to row I-3 instead of I-1 in table I and the combination of the radicals $L^1$, $L^2$, $L^3$ and $L^4$ for a compound corresponds in each case to one row of table A.

Tables 976 to 1300. Compounds of the formula I.3A, in which $R^2$, $R^5$, $R^6$ and $R^7$ are as defined in tables 1 to 325, $R^1$ corresponds to row I-4 instead of I-1 in table I and the combination of the radicals $L^1$, $L^2$, $L^3$ and $L^4$ for a compound corresponds in each case to one row of table A.

Tables 1301 to 1625. Compounds of the formula I.3A, in which $R^2$, $R^5$, $R^6$ and $R^7$ are as defined in tables 1 to 325, $R^1$ corresponds to row I-5 instead of I-1 in table I and the combination of the radicals $L^1$, $L^2$, $L^3$ and $L^4$ for a compound corresponds in each case to one row of table A.

Tables 1626 to 1950. Compounds of the formula I.3A, in which $R^2$, $R^5$, $R^6$ and $R^7$ are as defined in tables 1 to 325, $R^1$ corresponds to row I-6 instead of I-1 in table I and the combination of the radicals $L^1$, $L^2$, $L^3$ and $L^4$ for a compound corresponds in each case to one row of table A.

Tables 1951 to 2275. Compounds of the formula I.3A, in which $R^2$, $R^5$, $R^6$ and $R^7$ are as defined in tables 1 to 325, $R^1$ corresponds to row I-7 instead of I-1 in table I and the combination of the radicals $L^1$, $L^2$, $L^3$ and $L^4$ for a compound corresponds in each case to one row of table A.

Tables 2276 to 2600. Compounds of the formula I.3A, in which $R^2$, $R^5$, $R^6$ and $R^7$ are as defined in tables 1 to 325, $R^1$ corresponds to row I-8 instead of I-1 in table I and the combination of the radicals $L^1$, $L^2$, $L^3$ and $L^4$ for a compound corresponds in each case to one row of table A.

Tables 2601 to 2925. Compounds of the formula I.3A, in which $R^2$, $R^5$, $R^6$ and $R^7$ are as defined in tables 1 to 325, $R^1$ corresponds to row I-9 instead of I-1 in table I and the combination of the radicals $L^1$, $L^2$, $L^3$ and $L^4$ for a compound corresponds in each case to one row of table A.

Tables 2926 to 3250. Compounds of the formula I.3A, in which $R^2$, $R^5$, $R^6$ and $R^7$ are as defined in tables 1 to 325, $R^1$ corresponds to row I-10 instead of I-1 in tape I and the combination of the radicals $L^1$, $L^2$, $L^3$ and $L^4$ for a compound corresponds in each case to one row of table A.

Tables 3251 to 3575. Compounds of the formula I.3A, in which $R^2$, $R^5$, $R^6$ and $R^7$ are as defined in tables 1 to 325, $R^1$ corresponds to row I-11 instead of I-1 in table I and the combination of the radicals $L^1$, $L^2$, $L^3$ and $L^4$ for a compound corresponds in each case to one row of table A.

Tables 3576 to 3900. Compounds of the formula I.3A, in which $R^2$, $R^5$, $R^6$ and $R^7$ are as defined in tables 1 to 325, $R^1$ corresponds to row I-12 instead of I-1 in table I and the combination of the radicals $L^1$, $L^2$, $L^3$ and $L^4$ for a compound corresponds in each case to one row of table A.

Tables 3901 to 4225. Compounds of the formula I.3A, in which $R^2$, $R^5$, $R^6$ and $R^7$ are as defined in tables 1 to 325, $R^1$ corresponds to row I-13 instead of I-1 in table I and the combination of the radicals $L^1$, $L^2$, $L^3$ and $L^4$ for a compound corresponds in each case to one row of table A.

Tables 4226 to 4550. Compounds of the formula I.3A, in which $R^2$, $R^5$, $R^6$ and $R^7$ are as defined in tables 1 to 325, $R^1$ corresponds to row I-14 instead of I-1 in table I and the combination of the radicals $L^1$, $L^2$, $L^3$ and $L^4$ for a compound corresponds in each case to one row of table A.

Tables 4551 to 4875. Compounds of the formula I.3A, in which $R^2$, $R^5$, $R^6$ and $R^7$ are as defined in tables 1 to 325, $R^1$ corresponds to row I-15 instead of I-1 in table I and the combination of the radicals $L^1$, $L^2$, $L^3$ and $L^4$ for a compound corresponds in each case to one row of table A.

Tables 4876 to 5200. Compounds of the formula I.3A, in which $R^2$, $R^5$, $R^6$ and $R^7$ are as defined in tables 1 to 325, $R^1$ corresponds to row I-16 instead of I-1 in table I and the combination of the radicals $L^1$, $L^2$, $L^3$ and $L^4$ for a compound corresponds in each case to one row of table A.

Tables 5201 to 5525. Compounds of the formula I.3A, in which $R^2$, $R^5$, $R^6$ and $R^7$ are as defined in tables 1 to 325, $R^1$ corresponds to row I-17 instead of I-1 in tableI and the combination of the radicals $L^1$, $L^2$, $L^3$ and $L^4$ for a compound corresponds in each case to one row of table A.

Tables 5526 to 5850. Compounds of the formula I.3A, in which $R^2$, $R^5$, $R^6$ and $R^7$ are as defined in tables 1 to 325, $R^1$ corresponds to row I-18 instead of I-1 in table I and the combination of the radicals $L^1$, $L^2$, $L^3$ and $L^4$ for a compound corresponds in each case to one row of table A.

Tables 5851 to 6175. Compounds of the formula I.3A, in which $R^2$, $R^5$, $R^6$ and $R^7$ are as defined in tables 1 to 325, $R^1$ corresponds to row I-19 instead of I-1 in table I and the combination of the radicals $L^1$, $L^2$, $L^3$ and $L^4$ for a compound corresponds in each case to one row of table A.

Tables 6176 to 12350. Compounds of the formula I.3A, in which $R^1$, $R^2$ and $R^7$ are as defined in tables 1 to 6175, the combination of the radicals $R^5$ and $R^6$ corresponds to row III-2 instead of III-1 in table III and the combination of the radicals $L^1$, $L^2$, $L^3$ and $L^4$ for a compound corresponds in each case to one row of table A.

Tables 12351 to 18525. Compounds of the formula I.3A, in which $R^1$, $R^2$ and $R^7$ are as defined in tables 1 to 6175, the combination of the radicals $R^5$ and $R^6$ corresponds to row III-3 instead of III-1 in table III and the combination of the radicals $L^1$, $L^2$, $L^3$ and $L^4$ for a compound corresponds in each case to one row of table A.

Tables 18526 to 24700. Compounds of the formula I.3A, in which $R^1$, $R^2$ and $R^7$ are as defined in tables 1 to 6175, the combination of the radicals $R^5$ and $R^6$ corresponds to row III-4 instead of III-1 in table III and the combination of the radicals $L^1$, $L^2$, $L^3$ and $L^4$ for a compound corresponds in each case to one row of table A.

Tables 24701 to 30875. Compounds of the formula I.3A, in which $R^1$, $R^2$ and $R^7$ are as defined in tables 1 to 6175, the combination of the radicals $R^5$ and $R^6$ corresponds to row III-5 instead of III-1 in table III and the combination of the radicals $L^1$, $L^2$, $L^3$ and $L^4$ for a compound corresponds in each case to one row of table A.

Tables 30876 to 37050. Compounds of the formula I.3A, in which $R^1$, $R^2$ and $R^7$ are as defined in tables 1 to 6175, the combination of the radicals $R^5$ and $R^6$ corresponds to row III-6 instead of III-1 in table III and the combination of the radicals $L^1$, $L^2$, $L^3$ and $L^4$ for a compound corresponds in each case to one row of table A.

Tables 37051 to 43225. Compounds of the formula I.3A, in which $R^1$, $R^2$ and $R^7$ are as defined in tables 1 to 6175, the combination of the radicals $R^5$ and $R^6$ corresponds to row III-7 instead of III-1 in table III and the combination of the radicals $L^1, L^2, L^3$ and $L^4$ for a compound corresponds in each case to one row of table A.

Tables 43226 to 49400. Compounds of the formula I.3A, in which $R^1$, $R^2$ and $R^7$ are as defined in tables 1 to 6175, the combination of the radicals $R^5$ and $R^6$ corresponds to row III-8 instead of III-1 in table III and the combination of the radicals $L^1, L^2, L^3$ and $L^4$ for a compound corresponds in each case to one row of table A.

Tables 49401 to 55575. Compounds of the formula I.3A, in which $R^1$, $R^2$ and $R^7$ are as defined in tables 1 to 6175, the combination of the radicals $R^5$ and $R^6$ corresponds to row III-9 instead of III-1 in table III and the combination of the radicals $L^1, L^2, L^3$ and $L^4$ for a compound corresponds in each case to one row of table A.

Tables 55576 to 61750. Compounds of the formula I.3A, in which $R^1$, $R^2$ and $R^7$ are as defined in tables 1 to 6175, the combination of the radicals $R^5$ and $R^6$ corresponds to row III-10 instead of III-1 in table III and the combination of the radicals $L^1, L^2, L^3$ and $L^4$ for a compound corresponds in each case to one row of table A.

Tables 61751 to 67925. Compounds of the formula I.3A, in which $R^1$, $R^2$ and $R^7$ are as defined in tables 1 to 6175, the combination of the radicals $R^5$ and $R^6$ corresponds to row III-11 instead of III-1 in table III and the combination of the radicals $L^1, L^2, L^3$ and $L^4$ for a compound corresponds in each case to one row of table A.

Tables 67926 to 74100. Compounds of the formula I.3A, in which $R^1$, $R^2$ and $R^7$ are as defined in tables 1 to 6175, the combination of the radicals $R^5$ and $R^6$ corresponds to row III-12 instead of III-1 in table III and the combination of the radicals $L^1, L^2, L^3$ and $L^4$ for a compound corresponds in each case to one row of table A.

Tables 74101 to 80275. Compounds of the formula I.3A, in which $R^1$, $R^2$ and $R^7$ are as defined in tables 1 to 6175, the combination of the radicals $R^5$ and $R^6$ corresponds to row III-13 instead of III-1 in table III and the combination of the radicals $L^1, L^2, L^3$ and $L^4$ for a compound corresponds in each case to one row of table A.

Tables 80276 to 86450. Compounds of the formula I.3A, in which $R^1$, $R^2$ and $R^7$ are as defined in tables 1 to 6175, the combination of the radicals $R^5$ and $R^6$ corresponds to row III-14 instead of III-1 in table III and the combination of the radicals $L^1, L^2, L^3$ and $L^4$ for a compound corresponds in each case to one row of table A.

Tables 86451 to 92625. Compounds of the formula I.3A, in which $R^1$, $R^2$ and $R^7$ are as defined in tables 1 to 6175, the combination of the radicals $R^5$ and $R^6$ corresponds to row III-15 instead of III-1 in table III and the combination of the radicals $L^1, L^2, L^3$ and $L^4$ for a compound corresponds in each case to one row of table A.

Tables 92626 to 98800. Compounds of the formula I.3A, in which $R^1$, $R^2$ and $R^7$ are as defined in tables 1 to 6175, the combination of the radicals $R^5$ and $R^6$ corresponds to row III-16 instead of III-1 in table III and the combination of the radicals $L^1, L^2, L^3$ and $L^4$ for a compound corresponds in each case to one row of table A.

Tables 98801 to 104975. Compounds of the formula I.3A, in which $R^1$, $R^2$ and $R^7$ are as defined in tables 1 to 6175, the combination of the radicals $R^5$ and $R^6$ corresponds to row III-17 instead of III-1 in table III and the combination of the radicals $L^1, L^2, L^3$ and $L^4$ for a compound corresponds in each case to one row of table A.

Tables 104976 to 111150. Compounds of the formula I.3A, in which $R^1$, $R^2$ and $R^7$ are as defined in tables 1 to 6175, the combination of the radicals $R^5$ and $R^6$ corresponds to row III-18 instead of III-1 in table III and the combination of the radicals $L^1, L^2, L^3$ and $L^4$ for a compound corresponds in each case to one row of table A.

Tables 111151 to 117325. Compounds of the formula I.3A, in which $R^1$, $R^2$ and $R^7$ are as defined in tables 1 to 6175, the combination of the radicals $R^5$ and $R^6$ corresponds to row III-19 instead of III-1 in table III and the combination of the radicals $L^1, L^2, L^3$ and $L^4$ for a compound corresponds in each case to one row of table A.

Tables 117326 to 123500. Compounds of the formula I.3A, in which $R^1$, $R^2$ and $R^7$ are as defined in tables 1 to 6175, the combination of the radicals $R^5$ and $R^6$ corresponds to row III-20 instead of III-1 in table III and the combination of the radicals $L^1, L^2, L^3$ and $L^4$ for a compound corresponds in each case to one row of table A.

Tables 123501 to 129675. Compounds of the formula I.3A, in which $R^1$, $R^2$ and $R^7$ are as defined in tables 1 to 6175, the combination of the radicals $R^5$ and $R^6$ corresponds to row III-21 instead of III-1 in table III and the combination of the radicals $L^1, L^2, L^3$ and $L^4$ for a compound corresponds in each case to one row of table A.

Tables 129676 to 135850. Compounds of the formula I.3A, in which $R^1$, $R^2$ and $R^7$ are as defined in tables 1 to 6175, the combination of the radicals $R^5$ and $R^6$ corresponds to row III-22 instead of III-1 in table III and the combination of the radicals $L^1, L^2, L^3$ and $L^4$ for a compound corresponds in each case to one row of table A.

Tables 135851 to 142025. Compounds of the formula I.3A, in which $R^1$, $R^2$ and $R^7$ are as defined in tables 1 to 6175, the combination of the radicals $R^5$ and $R^6$ corresponds to row III-23 instead of III-1 in table III and the combination of the radicals $L^1, L^2, L^3$ and $L^4$ for a compound corresponds in each case to one row of table A.

Tables 142026 to 148200. Compounds of the formula I.3A, in which $R^1$, $R^2$ and $R^7$ are as defined in tables 1 to 6175, the combination of the radicals $R^5$ and $R^6$ corresponds to row III-24 instead of III-1 in table III and the combination of the radicals $L^1, L^2, L^3$ and $L^4$ for a compound corresponds in each case to one row of table A.

Tables 148201 to 154375. Compounds of the formula I.3A, in which $R^1$, $R^2$ and $R^7$ are as defined in tables 1 to 6175, the combination of the radicals $R^5$ and $R^6$ corresponds to row III-25 instead of III-1 in table III and the combination of the radicals $L^1, L^2, L^3$ and $L^4$ for a compound corresponds in each case to one row of table A.

Tables 154376 to 160550. Compounds of the formula I.3A, in which $R^1$, $R^2$ and $R^7$ are as defined in tables 1 to 6175, the combination of the radicals $R^5$ and $R^6$ corresponds to row III-26 instead of III-1 in table III and the combination of the radicals $L^1, L^2, L^3$ and $L^4$ for a compound corresponds in each case to one row of table A.

Tables 160551 to 166725. Compounds of the formula I.3A, in which $R^1$, $R^2$ and $R^7$ are as defined in tables 1 to 6175, the combination of the radicals $R^5$ and $R^6$ corresponds to row III-27 instead of III-1 in table III and the combination of the radicals $L^1, L^2, L^3$ and $L^4$ for a compound corresponds in each case to one row of table A.

Tables 166726 to 172900. Compounds of the formula I.3A, in which $R^1$, $R^2$ and $R^7$ are as defined in tables 1 to 6175, the combination of the radicals $R^5$ and $R^6$ corresponds to row III-28 instead of III-1 in table III and the combination of the radicals $L^1, L^2, L^3$ and $L^4$ for a compound corresponds in each case to one row of table A.

Tables 172901 to 179075. Compounds of the formula I.3A, in which $R^1$, $R^2$ and $R^7$ are as defined in tables 1 to 6175, the combination of the radicals $R^5$ and $R^6$ corresponds to row III-29 instead of III-1 in table III and the combination of the radicals $L^1$, $L^2$, $L^3$ and $L^4$ for a compound corresponds in each case to one row of table A.

Tables 179076 to 185250. Compounds of the formula I.3A, in which $R^1$, $R^2$ and $R^7$ are as defined in tables 1 to 6175, the combination of the radicals $R^5$ and $R^6$ corresponds to row III-30 instead of III-1 in table III and the combination of the radicals $L^1$, $L^2$, $L^3$ and $L^4$ for a compound corresponds in each case to one row of table A.

Tables 185251 to 191425. Compounds of the formula I.3A, in which $R^1$, $R^2$ and $R^7$ are as defined in tables 1 to 6175, the combination of the radicals $R^5$ and $R^6$ corresponds to row III-31 instead of III-1 in table III and the combination of the radicals $L^1$, $L^2$, $L^3$ and $L^4$ for a compound corresponds in each case to one row of table A.

Tables 191426 to 197600. Compounds of the formula I.3A, in which $R^1$, $R^2$ and $R^7$ are as defined in tables 1 to 6175, the combination of the radicals $R^5$ and $R^6$ corresponds to row III-32 instead of III-1 in table III and the combination of the radicals $L^1$, $L^2$, $L^3$ and $L^4$ for a compound corresponds in each case to one row of table A.

Tables 197601 to 203775. Compounds of the formula I.3A, in which $R^1$, $R^2$ and $R^7$ are as defined in tables 1 to 6175, the combination of the radicals $R^5$ and $R^6$ corresponds to row III-33 instead of III-1 in table III and the combination of the radicals $L^1$, $L^2$, $L^3$ and $L^4$ for a compound corresponds in each case to one row of table A.

Tables 203776 to 209950. Compounds of the formula I.3A, in which $R^1$, $R^2$ and $R^7$ are as defined in tables 1 to 6175, the combination of the radicals $R^5$ and $R^6$ corresponds to row III-34 instead of III-1 in table III and the combination of the radicals $L^1$, $L^2$, $L^3$ and $L^4$ for a compound corresponds in each case to one row of table A.

Tables 209951 to 216125. Compounds of the formula I.3A, in which $R^1$, $R^2$ and $R^7$ are as defined in tables 1 to 6175, the combination of the radicals $R^5$ and $R^6$ corresponds to row III-35 instead of III-1 in table III and the combination of the radicals $L^1$, $L^2$, $L^3$ and $L^4$ for a compound corresponds in each case to one row of table A.

Tables 216126 to 222300. Compounds of the formula I.3A, in which $R^1$, $R^2$ and $R^7$ are as defined in tables 1 to 6175, the combination of the radicals $R^5$ and $R^6$ corresponds to row III-36 instead of III-1 in table III and the combination of the radicals $L^1$, $L^2$, $L^3$ and $L^4$ for a compound corresponds in each case to one row of table A.

Tables 222301 to 228475. Compounds of the formula I.3A, in which $R^1$, $R^2$ and $R^7$ are as defined in tables 1 to 6175, the combination of the radicals $R^5$ and $R^6$ corresponds to row III-37 instead of III-1 in table III and the combination of the radicals $L^1$, $L^2$, $L^3$ and $L^4$ for a compound corresponds in each case to one row of table A.

Tables 228476 to 234650. Compounds of the formula I.3A, in which $R^1$, $R^2$ and $R^7$ are as defined in tables 1 to 6175, the combination of the radicals $R^5$ and $R^6$ corresponds to row III-38 instead of III-1 in table III and the combination of the radicals $L^1$, $L^2$, $L^3$ and $L^4$ for a compound corresponds in each case to one row of table A.

Tables 234651 to 240825. Compounds of the formula I.3A, in which $R^1$, $R^2$ and $R^7$ are as defined in tables 1 to 6175, the combination of the radicals $R^5$ and $R^6$ corresponds to row III-39 instead of III-1 in table III and the combination of the radicals $L^1$, $L^2$, $L^3$ and $L^4$ for a compound corresponds in each case to one row of table A.

Tables 240826 to 247000. Compounds of the formula I.3A, in which $R^1$, $R^2$ and $R^7$ are as defined in tables 1 to 6175, the combination of the radicals $R^5$ and $R^6$ corresponds to row III-40 instead of III-1 in table III and the combination of the radicals $L^1$, $L^2$, $L^3$ and $L^4$ for a compound corresponds in each case to one row of table A.

Tables 247001 to 253175. Compounds of the formula I.3A, in which $R^1$, $R^2$ and $R^7$ are as defined in tables 1 to 6175, the combination of the radicals $R^5$ and $R^6$ corresponds to row III-41 instead of III-1 in table III and the combination of the radicals $L^1$, $L^2$, $L^3$ and $L^4$ for a compound corresponds in each case to one row of table A.

Tables 253176 to 259350. Compounds of the formula I.3A, in which $R^1$, $R^2$ and $R^7$ are as defined in tables 1 to 6175, the combination of the radicals $R^5$ and $R^6$ corresponds to row III-42 instead of III-1 in table III and the combination of the radicals $L^1$, $L^2$, $L^3$ and $L^4$ for a compound corresponds in each case to one row of table A.

Tables 259351 to 265525. Compounds of the formula I.3A, in which $R^1$, $R^2$ and $R^7$ are as defined in tables 1 to 6175, the combination of the radicals $R^5$ and $R^6$ corresponds to row III-43 instead of III-1 in table III and the combination of the radicals $L^1$, $L^2$, $L^3$ and $L^4$ for a compound corresponds in each case to one row of table A.

Tables 265526 to 531050. Compounds of the formula I.3A, in which. $R^1$, $R^2$, $R^5$ and $R^6$ are as defined in tables 1 to 265525, $R^7$ is methyl instead of hydrogen and the combination of the radicals $L^1$, $L^2$, $L^3$ and $L^4$ for a compound corresponds in each case to one row of table A.

Tables 531051 to 1062100. Compounds of the formula I.3B, in which $R^1$, $R^2$, $R^5$, $R^6$ and $R^7$ are as defined in tables 1 to 531050 and the combination of the radicals $L^1$, $L^2$, $L^3$ and $L^4$ for a compound corresponds in each case to one row of table A.

Tables 1062101 to 1593150. Compounds of the formula I.3C, in which $R^1$, $R^2$, $R^5$, $R^6$ and $R^7$ are as defined in tables 1 to 531050 and the combination of the radicals $L^1$, $L^2$, $L^3$ and $L^4$ for a compound corresponds in each case to one row of table A.

Tables 1593151 to 2124200. Compounds of the formula I.3D, in which $R^1$, $R^2$, $R^5$, $R^6$ and $R^7$ are as defined in tables 1 to 531050 and the combination of the radicals $L^1$, $L^2$, $L^3$ and $L^4$ for a compound corresponds in each case to one row of table A.

Tables 2124201 to 2655250. Compounds of the formula I.3E, in which $R^1$, $R^2$, $R^5$, $R^6$ and $R^7$ are as defined in tables 1 to 531050 and the combination of the radicals $L^1$, $L^2$, $L^3$ and $L^4$ for a compound corresponds in each case to one row of table A.

TABLE A

| Row | $L^1$ | $L^2$ | $L^3$ | $L^4$ |
|---|---|---|---|---|
| A-1 | $CH_3$ | F | H | H |
| A-2 | H | H | H | H |
| A-3 | H | $CH_3$ | H | H |
| A-4 | H | $CH_2CH_3$ | H | H |
| A-5 | H | $CHF_2$ | H | H |
| A-6 | H | $CF_3$ | H | H |
| A-7 | H | $OCHF_2$ | H | H |
| A-8 | H | $OCF_3$ | H | H |
| A-9 | H | $OCH_3$ | H | H |
| A-10 | H | Cl | H | H |
| A-11 | H | Br | H | H |
| A-12 | H | F | H | H |
| A-13 | $CH_2CH_3$ | H | H | H |
| A-14 | $CH_2CH_3$ | $CH_3$ | H | H |
| A-15 | $CH_2CH_3$ | $CH_2CH_3$ | H | H |
| A-16 | $CH_2CH_3$ | $CHF_2$ | H | H |
| A-17 | $CH_2CH_3$ | $CF_3$ | H | H |
| A-18 | $CH_2CH_3$ | $OCHF_2$ | H | H |
| A-19 | $CH_2CH_3$ | $OCF_3$ | H | H |

TABLE A-continued

| Row | L¹ | L² | L³ | L⁴ |
|---|---|---|---|---|
| A-20 | CH₂CH₃ | OCH₃ | H | H |
| A-21 | CH₂CH₃ | Cl | H | H |
| A-22 | CH₂CH₃ | Br | H | H |
| A-23 | CH₂CH₃ | F | H | H |
| A-24 | CHF₂ | H | H | H |
| A-25 | CHF₂ | CH₃ | H | H |
| A-26 | CHF₂ | CH₂CH₃ | H | H |
| A-27 | CHF₂ | CHF₂ | H | H |
| A-28 | CHF₂ | CF₃ | H | H |
| A-29 | CHF₂ | OCHF₂ | H | H |
| A-30 | CHF₂ | OCF₃ | H | H |
| A-31 | CHF₂ | OCH₃ | H | H |
| A-32 | CHF₂ | Cl | H | H |
| A-33 | CHF₂ | Br | H | H |
| A-34 | CHF₂ | F | H | H |
| A-35 | CF₃ | H | H | H |
| A-36 | CF₃ | CH₃ | H | H |
| A-37 | CF₃ | CH₂CH₃ | H | H |
| A-38 | CF₃ | CHF₂ | H | H |
| A-39 | CF₃ | CF₃ | H | H |
| A-40 | CF₃ | OCHF₂ | H | H |
| A-41 | CF₃ | OCF₃ | H | H |
| A-42 | CF₃ | OCH₃ | H | H |
| A-43 | CF₃ | Cl | H | H |
| A-44 | CF₃ | Br | H | H |
| A-45 | CF₃ | F | H | H |
| A-46 | OCHF₂ | H | H | H |
| A-47 | OCHF₂ | CH₃ | H | H |
| A-48 | OCHF₂ | CH₂CH₃ | H | H |
| A-49 | OCHF₂ | CHF₂ | H | H |
| A-50 | OCHF₂ | CF₃ | H | H |
| A-51 | OCHF₂ | OCHF₂ | H | H |
| A-52 | OCHF₂ | OCF₃ | H | H |
| A-53 | OCHF₂ | OCH₃ | H | H |
| A-54 | OCHF₂ | Cl | H | H |
| A-55 | OCHF₂ | Br | H | H |
| A-56 | OCHF₂ | F | H | H |
| A-57 | OCF₃ | H | H | H |
| A-58 | OCF₃ | CH₃ | H | H |
| A-59 | OCF₃ | CH₂CH₃ | H | H |
| A-60 | OCF₃ | CHF₂ | H | H |
| A-61 | OCF₃ | CF₃ | H | H |
| A-62 | OCF₃ | OCHF₂ | H | H |
| A-63 | OCF₃ | OCF₃ | H | H |
| A-64 | OCF₃ | OCH₃ | H | H |
| A-65 | OCF₃ | Cl | H | H |
| A-66 | OCF₃ | Br | H | H |
| A-67 | OCF₃ | F | H | H |
| A-68 | OCH₃ | H | H | H |
| A-69 | OCH₃ | CH₃ | H | H |
| A-70 | OCH₃ | CH₂CH₃ | H | H |
| A-71 | OCH₃ | CHF₂ | H | H |
| A-72 | OCH₃ | CF₃ | H | H |
| A-73 | OCH₃ | OCHF₂ | H | H |
| A-74 | OCH₃ | OCF₃ | H | H |
| A-75 | OCH₃ | OCH₃ | H | H |
| A-76 | OCH₃ | Cl | H | H |
| A-77 | OCH₃ | Br | H | H |
| A-78 | OCH₃ | F | H | H |
| A-79 | Cl | H | H | H |
| A-80 | Cl | CH₃ | H | H |
| A-81 | Cl | CH₂CH₃ | H | H |
| A-82 | Cl | CHF₂ | H | H |
| A-83 | Cl | CF₃ | H | H |
| A-84 | Cl | OCHF₂ | H | H |
| A-85 | Cl | OCF₃ | H | H |
| A-86 | Cl | OCH₃ | H | H |
| A-87 | Cl | Cl | H | H |
| A-88 | Cl | Br | H | H |
| A-89 | Cl | F | H | H |
| A-90 | Br | H | H | H |
| A-91 | Br | CH₃ | H | H |
| A-92 | Br | CH₂CH₃ | H | H |
| A-93 | Br | CHF₂ | H | H |
| A-94 | Br | CF₃ | H | H |
| A-95 | Br | OCHF₂ | H | H |
| A-96 | Br | OCF₃ | H | H |
| A-97 | Br | OCH₃ | H | H |
| A-98 | Br | Cl | H | H |
| A-99 | Br | Br | H | H |
| A-100 | Br | F | H | H |
| A-101 | F | H | H | H |
| A-102 | F | CH₃ | H | H |
| A-103 | F | CH₂CH₃ | H | H |
| A-104 | F | CHF₂ | H | H |
| A-105 | F | CF₃ | H | H |
| A-106 | F | OCHF₂ | H | H |
| A-107 | F | OCF₃ | H | H |
| A-108 | F | OCH₃ | H | H |
| A-109 | F | Cl | H | H |
| A-110 | F | Br | H | H |
| A-111 | F | F | H | H |
| A-112 | CH₃ | H | F | H |
| A-113 | CH₃ | CH₃ | F | H |
| A-114 | CH₃ | CH₂CH₃ | F | H |
| A-115 | CH₃ | CHF₂ | F | H |
| A-116 | CH₃ | CF₃ | F | H |
| A-117 | CH₃ | OCHF₂ | F | H |
| A-118 | CH₃ | OCF₃ | F | H |
| A-119 | CH₃ | OCH₃ | F | H |
| A-120 | CH₃ | Cl | F | H |
| A-121 | CH₃ | Br | F | H |
| A-122 | CH₃ | F | F | H |
| A-123 | H | H | F | H |
| A-124 | H | CH₃ | F | H |
| A-125 | H | CH₂CH₃ | F | H |
| A-126 | H | CHF₂ | F | H |
| A-127 | H | CF₃ | F | H |
| A-128 | H | OCHF₂ | F | H |
| A-129 | H | OCF₃ | F | H |
| A-130 | H | OCH₃ | F | H |
| A-131 | H | Cl | F | H |
| A-132 | H | Br | F | H |
| A-133 | H | F | F | H |
| A-134 | CH₂CH₃ | H | F | H |
| A-135 | CH₂CH₃ | CH₃ | F | H |
| A-136 | CH₂CH₃ | CH₂CH₃ | F | H |
| A-137 | CH₂CH₃ | CHF₂ | F | H |
| A-138 | CH₂CH₃ | CF₃ | F | H |
| A-139 | CH₂CH₃ | OCHF₂ | F | H |
| A-140 | CH₂CH₃ | OCF₃ | F | H |
| A-141 | CH₂CH₃ | OCH₃ | F | H |
| A-142 | CH₂CH₃ | Cl | F | H |
| A-143 | CH₂CH₃ | Br | F | H |
| A-144 | CH₂CH₃ | F | F | H |
| A-145 | CHF₂ | H | F | H |
| A-146 | CHF₂ | CH₃ | F | H |
| A-147 | CHF₂ | CH₂CH₃ | F | H |
| A-148 | CHF₂ | CHF₂ | F | H |
| A-149 | CHF₂ | CF₃ | F | H |
| A-150 | CHF₂ | OCHF₂ | F | H |
| A-151 | CHF₂ | OCF₃ | F | H |
| A-152 | CHF₂ | OCH₃ | F | H |
| A-153 | CHF₂ | Cl | F | H |
| A-154 | CHF₂ | Br | F | H |
| A-155 | CHF₂ | F | F | H |
| A-156 | CF₃ | H | F | H |
| A-157 | CF₃ | CH₃ | F | H |
| A-158 | CF₃ | CH₂CH₃ | F | H |
| A-159 | CF₃ | CHF₂ | F | H |
| A-160 | CF₃ | CF₃ | F | H |
| A-161 | CF₃ | OCHF₂ | F | H |
| A-162 | CF₃ | OCF₃ | F | H |
| A-163 | CF₃ | OCH₃ | F | H |
| A-164 | CF₃ | Cl | F | H |
| A-165 | CF₃ | Br | F | H |
| A-166 | CF₃ | F | F | H |
| A-167 | OCHF₂ | H | F | H |
| A-168 | OCHF₂ | CH₃ | F | H |
| A-169 | OCHF₂ | CH₂CH₃ | F | H |
| A-170 | OCHF₂ | CHF₂ | F | H |
| A-171 | OCHF₂ | CF₃ | F | H |
| A-172 | OCHF₂ | OCHF₂ | F | H |
| A-173 | OCHF₂ | OCF₃ | F | H |
| A-174 | OCHF₂ | OCH₃ | F | H |
| A-175 | OCHF₂ | Cl | F | H |

TABLE A-continued

| Row | L¹ | L² | L³ | L⁴ |
|---|---|---|---|---|
| A-176 | OCHF₂ | Br | F | H |
| A-177 | OCHF₂ | F | F | H |
| A-178 | OCF₃ | H | F | H |
| A-179 | OCF₃ | CH₃ | F | H |
| A-180 | OCF₃ | CH₂CH₃ | F | H |
| A-181 | OCF₃ | CHF₂ | F | H |
| A-182 | OCF₃ | CF₃ | F | H |
| A-183 | OCF₃ | OCHF₂ | F | H |
| A-184 | OCF₃ | OCF₃ | F | H |
| A-185 | OCF₃ | OCH₃ | F | H |
| A-186 | OCF₃ | Cl | F | H |
| A-187 | OCF₃ | Br | F | H |
| A-188 | OCF₃ | F | F | H |
| A-189 | OCH₃ | H | F | H |
| A-190 | OCH₃ | CH₃ | F | H |
| A-191 | OCH₃ | CH₂CH₃ | F | H |
| A-192 | OCH₃ | CHF₂ | F | H |
| A-193 | OCH₃ | CF₃ | F | H |
| A-194 | OCH₃ | OCHF₂ | F | H |
| A-195 | OCH₃ | OCF₃ | F | H |
| A-196 | OCH₃ | OCH₃ | F | H |
| A-197 | OCH₃ | Cl | F | H |
| A-198 | OCH₃ | Br | F | H |
| A-199 | OCH₃ | F | F | H |
| A-200 | Cl | H | F | H |
| A-201 | Cl | CH₃ | F | H |
| A-202 | Cl | CH₂CH₃ | F | H |
| A-203 | Cl | CHF₂ | F | H |
| A-204 | Cl | CF₃ | F | H |
| A-205 | Cl | OCHF₂ | F | H |
| A-206 | Cl | OCF₃ | F | H |
| A-207 | Cl | OCH₃ | F | H |
| A-208 | Cl | Cl | F | H |
| A-209 | Cl | Br | F | H |
| A-210 | Cl | F | F | H |
| A-211 | Br | H | F | H |
| A-212 | Br | CH₃ | F | H |
| A-213 | Br | CH₂CH₃ | F | H |
| A-214 | Br | CHF₂ | F | H |
| A-215 | Br | CF₃ | F | H |
| A-216 | Br | OCHF₂ | F | H |
| A-217 | Br | OCF₃ | F | H |
| A-218 | Br | OCH₃ | F | H |
| A-219 | Br | Cl | F | H |
| A-220 | Br | Br | F | H |
| A-221 | Br | F | F | H |
| A-222 | F | H | F | H |
| A-223 | F | CH₃ | F | H |
| A-224 | F | CH₂CH₃ | F | H |
| A-225 | F | CHF₂ | F | H |
| A-226 | F | CF₃ | F | H |
| A-227 | F | OCHF₂ | F | H |
| A-228 | F | OCF₃ | F | H |
| A-229 | F | OCH₃ | F | H |
| A-230 | F | Cl | F | H |
| A-231 | F | Br | F | H |
| A-232 | F | F | F | H |
| A-233 | CH₃ | H | H | F |
| A-234 | CH₃ | CH₃ | H | F |
| A-235 | CH₃ | CH₂CH₃ | H | F |
| A-236 | CH₃ | CHF₂ | H | F |
| A-237 | CH₃ | CF₃ | H | F |
| A-238 | CH₃ | OCHF₂ | H | F |
| A-239 | CH₃ | OCF₃ | H | F |
| A-240 | CH₃ | OCH₃ | H | F |
| A-241 | CH₃ | Cl | H | F |
| A-242 | CH₃ | Br | H | F |
| A-243 | CH₃ | F | H | F |
| A-244 | H | H | H | F |
| A-245 | H | CH₃ | H | F |
| A-246 | H | CH₂CH₃ | H | F |
| A-247 | H | CHF₂ | H | F |
| A-248 | H | CF₃ | H | F |
| A-249 | H | OCHF₂ | H | F |
| A-250 | H | OCF₃ | H | F |
| A-251 | H | OCH₃ | H | F |
| A-252 | H | Cl | H | F |
| A-253 | H | Br | H | F |
| A-254 | H | F | H | F |
| A-255 | CH₂CH₃ | H | H | F |
| A-256 | CH₂CH₃ | CH₃ | H | F |
| A-257 | CH₂CH₃ | CH₂CH₃ | H | F |
| A-258 | CH₂CH₃ | CHF₂ | H | F |
| A-259 | CH₂CH₃ | CF₃ | H | F |
| A-260 | CH₂CH₃ | OCHF₂ | H | F |
| A-261 | CH₂CH₃ | OCF₃ | H | F |
| A-262 | CH₂CH₃ | OCH₃ | H | F |
| A-263 | CH₂CH₃ | Cl | H | F |
| A-264 | CH₂CH₃ | Br | H | F |
| A-265 | CH₂CH₃ | F | H | F |
| A-266 | CHF₂ | H | H | F |
| A-267 | CHF₂ | CH₃ | H | F |
| A-268 | CHF₂ | CH₂CH₃ | H | F |
| A-269 | CHF₂ | CHF₂ | H | F |
| A-270 | CHF₂ | CF₃ | H | F |
| A-271 | CHF₂ | OCHF₂ | H | F |
| A-272 | CHF₂ | OCF₃ | H | F |
| A-273 | CHF₂ | OCH₃ | H | F |
| A-274 | CHF₂ | Cl | H | F |
| A-275 | CHF₂ | Br | H | F |
| A-276 | CHF₂ | F | H | F |
| A-277 | CF₃ | H | H | F |
| A-278 | CF₃ | CH₃ | H | F |
| A-279 | CF₃ | CH₂CH₃ | H | F |
| A-280 | CF₃ | CHF₂ | H | F |
| A-281 | CF₃ | CF₃ | H | F |
| A-282 | CF₃ | OCHF₂ | H | F |
| A-283 | CF₃ | OCF₃ | H | F |
| A-284 | CF₃ | OCH₃ | H | F |
| A-285 | CF₃ | Cl | H | F |
| A-286 | CF₃ | Br | H | F |
| A-287 | CF₃ | F | H | F |
| A-288 | OCHF₂ | H | H | F |
| A-289 | OCHF₂ | CH₃ | H | F |
| A-290 | OCHF₂ | CH₂CH₃ | H | F |
| A-291 | OCHF₂ | CHF₂ | H | F |
| A-292 | OCHF₂ | CF₃ | H | F |
| A-293 | OCHF₂ | OCHF₂ | H | F |
| A-294 | OCHF₂ | OCF₃ | H | F |
| A-295 | OCHF₂ | OCH₃ | H | F |
| A-296 | OCHF₂ | Cl | H | F |
| A-297 | OCHF₂ | Br | H | F |
| A-298 | OCHF₂ | F | H | F |
| A-299 | OCF₃ | H | H | F |
| A-300 | OCF₃ | CH₃ | H | F |
| A-301 | OCF₃ | CH₂CH₃ | H | F |
| A-302 | OCF₃ | CHF₂ | H | F |
| A-303 | OCF₃ | CF₃ | H | F |
| A-304 | OCF₃ | OCHF₂ | H | F |
| A-305 | OCF₃ | OCF₃ | H | F |
| A-306 | OCF₃ | OCH₃ | H | F |
| A-307 | OCF₃ | Cl | H | F |
| A-308 | OCF₃ | Br | H | F |
| A-309 | OCF₃ | F | H | F |
| A-310 | OCH₃ | H | H | F |
| A-311 | OCH₃ | CH₃ | H | F |
| A-312 | OCH₃ | CH₂CH₃ | H | F |
| A-313 | OCH₃ | CHF₂ | H | F |
| A-314 | OCH₃ | CF₃ | H | F |
| A-315 | OCH₃ | OCHF₂ | H | F |
| A-316 | OCH₃ | OCF₃ | H | F |
| A-317 | OCH₃ | OCH₃ | H | F |
| A-318 | OCH₃ | Cl | H | F |
| A-319 | OCH₃ | Br | H | F |
| A-320 | OCH₃ | F | H | F |
| A-321 | Cl | H | H | F |
| A-322 | Cl | CH₃ | H | F |
| A-323 | Cl | CH₂CH₃ | H | F |
| A-324 | Cl | CHF₂ | H | F |
| A-325 | Cl | CF₃ | H | F |
| A-326 | Cl | OCHF₂ | H | F |
| A-327 | Cl | OCF₃ | H | F |
| A-328 | Cl | OCH₃ | H | F |
| A-329 | Cl | Cl | H | F |
| A-330 | Cl | Br | H | F |
| A-331 | Cl | F | H | F |

TABLE A-continued

| Row | L¹ | L² | L³ | L⁴ |
|---|---|---|---|---|
| A-332 | Br | H | H | F |
| A-333 | Br | $CH_3$ | H | F |
| A-334 | Br | $CH_2CH_3$ | H | F |
| A-335 | Br | $CHF_2$ | H | F |
| A-336 | Br | $CF_3$ | H | F |
| A-337 | Br | $OCHF_2$ | H | F |
| A-338 | Br | $OCF_3$ | H | F |
| A-339 | Br | $OCH_3$ | H | F |
| A-340 | Br | Cl | H | F |
| A-341 | Br | Br | H | F |
| A-342 | Br | F | H | F |
| A-343 | F | H | H | F |
| A-344 | F | $CH_3$ | H | F |
| A-345 | F | $CH_2CH_3$ | H | F |
| A-346 | F | $CHF_2$ | H | F |
| A-347 | F | $CF_3$ | H | F |
| A-348 | F | $OCHF_2$ | H | F |
| A-349 | F | $OCF_3$ | H | F |
| A-350 | F | $OCH_3$ | H | F |
| A-351 | F | Cl | H | F |
| A-352 | F | Br | H | F |
| A-353 | F | F | H | F |
| A-354 | $CH_3$ | $CH_3$ | H | $CH_3$ |
| A-355 | $CH_3$ | $CH_3$ | $CH_3$ | H |
| A-356 | $CHF_2$ | $CH_3$ | H | $CH_3$ |
| A-357 | $CH_3$ | $CHF_2$ | $CH_3$ | H |
| A-358 | $CF_3$ | $CH_3$ | H | $CH_3$ |
| A-359 | $CH_3$ | $CF_3$ | $CH_3$ | H |
| A-360 | $OCHF_2$ | $CH_3$ | H | $CH_3$ |
| A-361 | $CH_3$ | $OCHF_2$ | $CH_3$ | H |
| A-362 | $CHF_2$ | $CH_3$ | H | Cl |
| A-363 | $CH_3$ | $CHF_2$ | Cl | H |
| A-364 | $CF_3$ | $CH_3$ | H | Cl |
| A-365 | $CH_3$ | $CF_3$ | Cl | H |
| A-366 | $OCHF_2$ | $CH_3$ | H | Cl |
| A-367 | $CH_3$ | $OCHF_2$ | Cl | H |
| A-368 | $CH_3$ | $CH_3$ | H | Cl |
| A-369 | $CH_3$ | $CH_3$ | Cl | H |
| A-370 | $OCH_3$ | H | $OCH_3$ | H |
| A-371 | $OCH_3$ | $CH_3$ | $OCH_3$ | H |
| A-372 | $OCH_3$ | $CH_2CH_3$ | $OCH_3$ | H |
| A-373 | $OCH_3$ | $CHF_2$ | $OCH_3$ | H |
| A-374 | $OCH_3$ | $CF_3$ | $OCH_3$ | H |
| A-375 | $OCH_3$ | $OCHF_2$ | $OCH_3$ | H |
| A-376 | $OCH_3$ | $OCF_3$ | $OCH_3$ | H |
| A-377 | $OCH_3$ | $OCH_3$ | $OCH_3$ | H |
| A-378 | $OCH_3$ | Cl | $OCH_3$ | H |
| A-379 | $OCH_3$ | Br | $OCH_3$ | H |
| A-380 | $OCH_3$ | F | $OCH_3$ | H |
| A-381 | $OCHF_2$ | H | $OCHF_2$ | H |
| A-382 | $OCHF_2$ | $CH_3$ | $OCHF_2$ | H |
| A-383 | $OCHF_2$ | $OCHF_2$ | $OCHF_2$ | H |
| A-384 | $OCHF_2$ | Cl | $OCHF_2$ | H |
| A-385 | $OCHF_2$ | Br | $OCHF_2$ | H |
| A-386 | $OCHF_2$ | F | $OCHF_2$ | H |

The compounds of the formula I and, respectively, the compositions according to the invention are suitable as fungicides for controlling harmful fungi. They are distinguished by excellent activity against a broad spectrum of phytopathogenic fungi including soilborne pathogens which originate in particular from the classes of the Plasmodiophoramycetes, Peronosporomycetes (syn. Oomycetes), Chytridiomycetes, Zygomycetes, Ascomycetes, Basidiomycetes and Deuteromycetes (syn. Fungi imperfecti). Some of them are systemically active and can be used in crop protection as foliar fungicides, fungicides for seed dressing and soil fungicides. In addition, they are suitable for controlling fungi which, inter alia, attack the wood or the roots of plants.

The compounds I and the compositions according to the invention are of particular importance for the control of a large number of pathogenic fungi on various crop plants such as cereals, for example wheat, rye, barley, triticale, oats or rice; beets, for example sugar beets or fodder beets; pomaceous fruits, stone fruits and soft fruits, for example apples, pears, plums, peaches, almonds, cherries, strawberries, raspberries, currents or gooseberries; leguminous-plants, for example beans, lentils, peas, lucerne or soybeans; oil plants, for example oilseed rape, mustard, olives, sunflowers, coconut, cocoa, castor beans, oil palms, peanuts or soybeans; cucurbits, for example pumpkins, cucumbers or melons; fiber plants, for example cotton, flax, hemp or jute; citrus fruits, for example oranges, lemons, grapefruits or mandarins; vegetable plants, for example spinach, lettuce, asparagus, cabbage plants, carrots, onions, tomatoes, potatoes, pumpkins or bell peppers; laurel plants, for example avocados, cinnamon or camphor; energy and raw material plants, for example corn, soybeans, wheat, oilseed rape, sugar cane or oil palms; corn; tobacco; nuts; coffee; tea; bananas; grape vines (grapes for eating and grapes for wine making); hops; grass, for example lawns; rubber plants; ornamental and forest plants, for example flowers, shrubs, deciduous trees and coniferous trees, and also on the propagation material, for example seeds, and on the harvested material of these plants.

Preferably, the compounds I and the compositions according to the invention are used for controlling a large number of fungal pathogens in agricultural crops, for example potatoes, sugar beets, tobacco, wheat, rye, barley, oats, rice, corn, cotton, soybeans, oilseed rape, leguminous plants, sunflowers, coffee or sugarcane; fruit plants, grapevines and ornamental plants and vegetables, for example cucumbers, tomatoes, beans and cucurbits and also on the propagation material, for example seeds, and the harvested products of these plants.

The term "plant propagation materials" includes all generative parts of the plant, for example seeds, and vegetative plant parts, such as seedlings and tubers (for example potatoes) which can be utilized for propagating a plant. These include seeds, roots, fruits, tubers, bulbs, rhizomes, shoots and other plant parts including seedlings and young plants which are transplanted after germination or after emergence. The young plants can be protected by partial or complete treatment, for example by immersion or watering, against harmful fungi.

The treatment of plant propagation materials with compounds I or the compositions according to the invention is used for controlling a large number of fungal pathogens in cereal crops, for example wheat, rye, barley or oats; rice, corn, cotton and soybeans.

The term crop plants also includes those plants which have been modified by breeding, mutagenesis or genetic engineering methods including the biotechnological agricultural products which are on the market or under development (see, for example, http://www.bio.org/speeches/pubs/er/agri_products.asp). Genetically modified plants are plants whose genetic material has been modified in a manner which does not occur under natural conditions by crossing, mutations or by natural recombination (that is a recombination of the genetic information). In general, one or more genes are integrated into the genetic material of the plant in order to improve the properties of the plant. Such modifications by genetic engineering include post-translational modifications of proteins, oligopeptides or polypeptides, for example by glycosylation or attachment of polymers such as, for example, prenylated, acetylated or farnesylated radicals or PEG radicals.

By way of example, mention may be made of plants which, by breeding and genetic engineering, are tolerant to certain classes of herbicides, such as hydroxyphenylpyruvate dioxygenase (HPPD) inhibitors, acetolactate synthase (ALS) inhibitors, such as, for example, sulfonylureas (EP-A 257 993, U.S. Pat. No. 5,013,659) or imidazolinones (for example U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073), enolpyruvylshikimate 3-phosphate synthase (EPSPS) inhibitors, such as, for example, glyphosate (see, for example, WO 92/00377), glutamine synthetase (GS) inhibitors, such as, for example, gluphosinate (see, for example, EP-A 242 236, EP-A 242 246) or oxynil herbicides (see, for example, U.S. Pat. No. 5,559,024). Clearfield® oilseed rape (BASF SE, Germany), for example, which is tolerant to imidazolinones, for example imazamox, was generated by breeding and mutagenesis. With the aid of genetic engineering methods, crop plants such as soybeans, cotton, corn, beets and oilseed rape were generated which are resistant to glyphosate or glufosinate, and which are obtainable under the trade names RoundupReady® (glyphosate-resistant, Monsanto, U.S.A.) and Liberty Link® (glufosinate-resistant, Bayer CropScience, Germany).

Also included are plants which, owing to interventions by genetic engineering, produce one or more toxins, for example those of the bacterial strain *Bacillus*. Toxins which are produced by such genetically modified plants include, for example, insecticidal proteins of *Bacillus* spp., in particular *B. thuringiensis*, such as the endotoxins Cry1Ab, Cry1Ac, Cry1F, Cry1Fa2, Cry2Ab, Cry3A, Cry3Bb1, Cry9c, Cry34Ab1 or Cry35Ab1; or vegetative insecticidal proteins (VIPs), for example VIP1, VIP2, VIP3, or VIP3A; insecticidal proteins of nematode-colonizing bacteria, for example *Photorhabdus* spp. or *Xenorhabdus* spp.; toxins of animal organisms, for example wasp, spider or scorpion toxins; fungal toxins, for example from Streptomycetes; plant lectins, for example from peas or barley; agglutinins; protease inhibitors, for example trypsin inhibitors, serine protease inhibitors, patatin, cystatin or papain inhibitors; ribosome-inactivating proteins (RIPs), for example ricin, corn-RIP, abrin, luffin, saporin or bryodin; steroid-metabolizing enzymes, for example 3-hydroxysteroid oxidase, ecdysteroid-IDP glycosyl transferase, cholesterol oxidase, ecdyson inhibitors, or HMG-CoA reductase; ion channel blockers, for example inhibitors of sodium channels or calcium channels; juvenile hormone esterase; receptors of the diuretic hormone (helicokinin receptors); stilbene synthase, bibenzyl synthase, chitinases and glucanases. In the plants, these toxins may also be produced as pretoxins, hybrid proteins or truncated or otherwise modified proteins. Hybrid proteins are characterized by a novel combination of different protein domains (see, for example, WO 2002/015701). Further examples of such toxins or genetically modified plants which produce these toxins are disclosed in EP-A 374 753, WO 93/07278, WO 95/34656, EP-A 427 529, EP-A 451 878, WO 03/18810 and WO 03/52073. The methods for producing these genetically modified plants are known to the person skilled in the art and disclosed, for example, in the publications mentioned above. Many of the toxins mentioned above bestow, upon the plants by which they are produced, tolerance to pests from all taxonomic classes of arthropods, in particular to beetles (Coeleropta), dipterans (Diptera) and butterflies (Lepidoptera) and to nematodes (Nematoda). Genetically modified plants which produce one or more genes coding for insecticidal toxins are described, for example, in the publications mentioned above, and some of them are commercially available, such as, for example, YieldGard® (corn varieties producing the toxin Cry1Ab), YieldGard® Plus (corn varieties which produce the toxins Cry1Ab and Cry3Bb1), Starlink® (corn varieties which produce the toxin Cry9c), Herculex® RW (corn varieties which produce the toxins Cry34Ab1, Cry35Ab1 and the enzyme phosphinothricin-N-acetyltransferase [PAT]); NuCOTN® 33B (cotton varieties which produce the toxin Cry1Ac), Bollgard® I (cotton varieties which produce the toxin Cry1Ac), Bollgard® II (cotton varieties which produce the toxins Cry1Ac and Cry2Ab2); VIPCOT® (cotton varieties which produce a VIP toxin); NewLeaf® (potato varieties which produce the toxin Cry3A); Bt-Xtra®, NatureGard®, KnockOut®, BiteGard®, Protecta®, Bt11 (for example Agrisure® CB) and Bt176 from Syngenta Seeds SAS, France (corn varieties which produce the toxin Cry1Ab and the PAT enzyme), MIR604 from Syngenta Seeds SAS, France (corn varieties which produce a Modified version of the toxin Cry3A, see WO 03/018810), MON 863 from Monsanto Europe S.A., Belgium (corn varieties which produce the toxin Cry3Bb1), IPC 531 from Monsanto Europe S.A., Belgium (cotton varieties which produce a modified version of the toxin Cry1Ac) and 1507 from Pioneer Overseas Corporation, Belgium (corn varieties which produce the toxin Cry1F and the PAT enzyme).

Also included are plants which, with the aid of genetic engineering, produce one or more proteins which are more robust or have increased resistance to bacterial, viral or fungal pathogens, such as, for example, pathogenesis-related proteins (PR proteins, see EP-A 0 392 225), resistance proteins (for example potato varieties producing two resistance genes against *Phytophthora infestans* from the wild Mexican potato *Solanum bulbocastanum*) or T4 lysozyme (for example potato varieties which, by producing this protein, are resistant to bacteria such as *Erwinia amylvora*).

Also included are plants whose productivity has been improved with the aid of genetic engineering methods, for example by enhancing the potential yield (for example biomass, grain yield, starch, oil or protein content), tolerance to drought, salt or other limiting environmental factors or resistance to pests and fungal, bacterial and viral pathogens.

Also included are plants whose ingredients have been modified with the aid of genetic engineering methods in particular for improving human or animal diet, for example oil plants producing health-promoting long-chain omega 3 fatty acids or monounsaturated omega 9 fatty acids (for example Nexera® oilseed rape, DOW Agro Sciences, Canada).

Also included are plants which have been modified with the aid of genetic engineering methods for improving the production of raw materials, for example by increasing the amylopectin content of potatoes (Amflora® potato, BASF SE, Germany).

Specifically, the compounds I and, respectively, the compositions according to the invention are suitable for controlling the following plant diseases:

*Albugo* spp. (white rust) on ornamental plants, vegetable crops (for example *A. candida*) and sunflowers (for example *A. tragopogonis*); *Alternaria* spp. (black spot disease, black blotch) on vegetables, oilseed rape (for example *A. brassicola* or *A. brassicae*), sugar beet (for example *A. tenuis*), fruit, rice, soybeans and also on potatoes (for example *A. solani* or *A. alternata*) and tomatoes (for example *A. solani* or *A. alternata*) and *Alternaria* spp. (black head) on wheat; *Aphanornyces* spp. on sugar beet and vegetables; *Ascochyta* spp. on cereals and vegetables, for example *A. tritici* (*Ascochyta* leaf blight) on wheat and A. hordei on barley; *Bipolaris* and *Drechslera* spp. (teleomorph: *Cochliobolus* spp.) for example leaf spot diseases (D. maydis and B. zeicola) on corn, for example glume blotch (*B. sorokiniana*) on cereals and B. oryzae on rice and on lawn; Blumeria (old name: *Erysiphe*) graminis (powdery mildew) on cereals (for example wheat or barley); *Botryosphaeria* spp. ('Black Dead Arm Disease') on grapevines (for example B. obtusa); *Botrytis cinerea* (teleomorph: Botryotinia fuckeliana: gray mold, gray rot) on soft fruit and pomp fruit (inter alia strawberries), vegetables (inter alia lettuce, carrots, celeriac and cabbage), oilseed rape, flowers, grapevines, forest crops and wheat (ear mold); *Bremia lactucae* (downy mildew) on lettuce; *Ceratocystis* (syn. *Ophiostoma*) spp. (blue stain fungus) on deciduous trees and coniferous trees, for example C. ulmi (Dutch elm disease) on elms; *Cercospora* spp. (*Cercospora* leaf spot) on corn (for example C. zeae-maydis), rice, sugar beet (for example *C. beticola*), sugar cane, vegetables, coffee, soybeans (for example *C. sojina* or *C. kikuchii*) and rice; *Cladosporium* spp. on tomato (for example C. fulvum: tomato leaf mold) and cereals, for example C. herbarum (ear rot) on wheat; *Claviceps purpurea* (ergot) on cereals; *Cochliobolus* (anamorph: *Helminthosporium* or *Bipolaris*) spp. (leaf spot) on corn (for example C. carbonum), cereals (for example *C. sativus*, anamorph: *B. sorokiniana*: glume blotch) and rice (for example C. miyabeanus, anamorph: H. oryzae); *Colletotrichum* (teleomorph: *Glomerella*) spp. (anthracnosis) on cotton (for example C. gossypii), corn (for example *C. graminicola*: stem rot and anthracnosis), soft fruit, potatoes (for example C. coccodes: wilt disease), beans (for example *C. lindemuthianum*) and soybeans (for example C. truncatum); *Corticium* spp., for example C. sasakii (sheath blight) on rice; *Corynespora cassiicola* (leaf spot) on soybeans and ornamental plants; *Cycloconium* spp., for example C. oleaginum on olive; *Cylindrocarpon* spp. (for example fruit tree cancer or black foot disease of grapevine, teleomorph: *Nectria* or *Neonectria* spp.) on fruit trees, grapevines (for example C. liriodendri; teleomorph: Neonectria liriodendri, black foot disease) and many ornamental trees; Dematophora (teleomorph: Rosellinia) necatrix (root/stem rot) on soybeans; *Diaporthe* spp. for example *D. phaseolorum* (stem disease) on soybeans; *Drechslera* (syn. *Helminthosporium*, teleomorph: *Pyrenophora*) spp. on corn, cereals, such as barley (for example D. teres, net blotch) and on wheat (for example D. tritici-repentis: DTR leaf spot), rice and lawn; esca disease (dieback of grapevine, apoplexia) on grapevines, caused by Formitiporia (syn. *Phellinus*) punctata, F. mediterranea, Phaeomoniella chlamydospora (old name Phaeoacremonium chlamydosporum), Phaeoacremonium aleophilum and/or *Botryosphaeria obtuse; Elsinoe* spp. on pome fruit (E. pyri) and soft fruit (E. veneta: anthracnosis) and also grapevines (*E. ampelina*: anthracnosis); Entyloma oryzae (leaf smut) on rice; *Epicoccum* spp. (black head) on wheat; *Erysiphe* spp. (powdery mildew) on sugar beet (E. betae), vegetables (for example E. pisi) such as cucumber species (for example *E. cichoracearum*) and cabbage species, such as oilseed rape (for example E. cruciferarum); Eutypa lata (Eutypa cancer or dieback, anamorph: Cytosporina lata, syn. Libertella blepharis) on fruit trees, grapevines and many ornamental trees; *Exserohilum* (syn. *Helminthosporium*) spp. on corn (for example E. turcicum); *Fusarium* (teleomorph: *Gibberella*) spp. (wilt disease, root and stem rot) on various plants, such as for example *F. graminearum* or *F. culmorum* (root rot and silver-top) on cereals (for example wheat or barley), *F. oxysporum* on tomatoes, *F. solani* on soybeans and *F. verticillioides* on corn; *Gaeumannomyces graminis* (take-all) on cereals (for example wheat or barley) and corn; *Gibberella* spp. on cereals (for example G. zeae) and rice (for example G. fujikuroi: bakanae disease); *Glomerella cingulata* on grapevines, pome fruit and other plants and G. gossypii on cotton; Grainstaining complex on rice; *Guignardia bidwellii* (black rot) on grapevines; *Gymnosporangium* spp. on Rosaceae and juniper, for example G. sabinae (pear rust) on pears; *Helminthosporium* spp. (syn. *Drechslera*, teleomorph: *Cochliobolus*) on corn, cereals and rice; *Hemileia* spp., for example H. vastatrix (coffee leaf rust) on coffee; Isariopsis clavispora (syn. Cladosporium vitis) on grapevines; *Macrophomina phaseolina* (syn. phaseoli) (root/stem rot) on soybeans and cotton; *Microdochium* (syn. *Fusarium*) *nivale* (pink snow mold) on cereals (for example wheat or barley); *Microsphaera diffusa* (powdery mildew) on soybeans; *Monilinia* spp., for example *M. laxa*, M. fructicola and *M. fructigena* (blossom and twig blight) on stone fruit and other Rosaceae; *Mycosphaerella* spp. on cereals, bananas, soft fruit and peanuts, such as for example M. graminicola (anamorph: *Septoria tritici*, Septoria leaf blotch) on wheat or M. fijiensis (sigatoka disease) on bananas; *Peronospora* spp. (downy mildew) on cabbage (for example *P. brassicae*), oilseed rape (for example P. parasitica), bulbous plants (for example P. destructor), tobacco (P. tabacina) and soybeans (for example *P. manshurica*); *Phakopsora pachyrhizi* and P. meibomiae (soybean rust) on soybeans; *Phialophora* spp. for example on grapevines (for example P. tracheiphila and P. tetraspora) and soybeans (for example *P. gregata*: stem disease); *Phoma lingam* (root and stem rot) on oilseed rape and cabbage and P. betae (leaf spot) on sugar beet; *Phomopsis* spp. on sunflowers, grapevines (for example P. viticola: dead-arm disease) and soybeans (for example stem canker/stem blight: P. phaseoli, teleomorph: *Diaporthe phaseolorum*); *Physoderma maydis* (brown spot) on corn; *Phytophthora* spp. (wilt disease, root, leaf, stem and fruit rot) on various plants, such as on bell peppers and cucumber species (for example P. capsici), soybeans (for example P. megasperma, syn. *P. sojae*), potatoes and tomatoes (for example *P. infestans*: late blight and brown rot) and deciduous trees (for example P. ramorum: sudden oak death); *Plasmodiophora brassicae* (club-root) on cabbage, oilseed rape, radish and other plants; *Plasmopara* spp., for example *P. viticola* (peronospora of grapevines, downy mildew) on grapevines and *P. halstedii* on sunflowers; *Podosphaera* spp. (powdery mildew) on Rosaceae, hops, pome fruit and soft fruit, for example *P. leucotricha* on apple; *Polymyxa* spp., for example on cereals, such as barley and wheat (P. graminis) and sugar beet (P. betae) and the viral diseases transmitted thereby; *Pseudocercosporella herpotrichoides* (eyespot/stem break, teleomorph: Tapesia yallundae) on cereals, for example wheat or barley; *Pseudoperonospora* (downy mildew) on various plants, for example *P. cubensis* on cucumber species or *P. humili* on hops; Pseudopezicula tracheiphila (angular leaf scorch, anamorph: *Phialophora*) on grapevines; *Puccinia* spp. (rust disease) on various plants, for example P. triticana (also brown rust of wheat), *P. striiformis* (yellow rust), *P. hordei* (dwarf leaf rust of barley), *P. graminis* (black rust) or *P. recondita* (brown rust of rye) on cereals, such as for example wheat, barley or rye, and on asparagus (for example P. asparagi); *Pyrenophora* (anamorph: *Drechslera*) *tritici-repentis* (speckled leaf blotch) on wheat and *P. teres* (net blotch) on barley; *Pyricularia* spp., for example *P. oryzae* (teleomorph: *Magnaporthe grisea*, rice blast) on rice and P. grisea on lawn and cereals; *Pythium* spp. (damping-off disease) on lawn, rice, corn, wheat, cotton, oilseed rape, sunflowers, sugar beet, vegetables and other plants (for example P. ultimum or *P. aphanidermatum*); *Ramularia* spp., for example R. collo-cygni (*Ramularia* leaf and awn spot/physiological leaf spot) on barley and R. beticola on sugar beet; *Rhizoctonla* spp. on cotton, rice, potatoes, lawn, corn, oilseed rape, potatoes, sugar beet, vegetables and on various other plants, for example *R. solani* (root and stem rot) on soybeans, *R. solani* (sheath blight) on rice or *R. cerealis* (sharp eyespot) on wheat or barley; *Rhizopus stolonifer* (soft rot) on strawberries, carrots, cabbage, grapevines and tomato; *Rhynchosporium secalis* (leaf spot) on barley, rye and triticale; Sarocladium oryzae and S. attenuatum (sheath rot) on rice; *Sclerotinia* spp. (stem or white rot) on vegetable and field crops, such as oilseed rape, sunflowers (for example *Sclerotinia sclerotiorum*) and soybeans (for example *S. rolfsii*); *Septoria* spp. on various plants, for example S. glycines (leaf spot) on soybeans, *S. tritici* (*Septoria* leaf blotch) on wheat and *S.* (syn. *Stagonospora*) *nodorum* (leaf blotch and glume blotch) on cereals; *Uncinula* (syn. *Erysiphe*) *necator* (powdery mildew, anamorph: *Oidium tuckeri*) on grapevines; *Setosphaerla* spp. (leaf spot) on corn (for example S. turcicum, syn. *Helminthosporium turcicum*) and lawn; *Sphacelotheca* spp. (head smut) on corn, (for example *S. reiliana*: kernel smut), millet and sugar cane; *Sphaerotheca fuliginea* (powdery mildew) on cucumber species; *Spongospora subterranea* (powdery scab) on potatoes and the viral diseases transmitted thereby; *Stagonospora* spp. on cereals, for example S. nodorum (leaf blotch and glume blotch, teleomorph: *Leptosphaeria* [syn. *Phaeosphaeria]* nodorum) on wheat; Synchytrium endobioticum on potatoes (potato wart disease); *Taphrina* spp., for example T. deformans (curly-leaf disease) on peach and T. pruni (plum-pocket disease) on plums, *Thielaviopsis* spp. (black root rot) on tobacco, pome fruit, vegetable crops, soybeans and cotton, for example T. basicola (syn. Chalara elegans); *Tilletia* spp. (bunt or stinking smut) on cereals, such as for example *T. tritici* (syn. *T. caries*, wheat bunt) and T. controversa (dwarf bunt) on wheat; *Typhula incarnata* (gray snow mold) on barley or wheat; *Urocystis* spp., for example U. occulta (flag smut) on rye; *Uromyces* spp. (rust) on vegetable plants, such as beans (for example *U. appendiculatus*, syn. U. phaseoli) and sugar beet (for example U. betae); *Ustilago* spp. (loose smut) on cereals (for example *U. nuda* and *U. avaenae*), corn (for example *U. maydis*: corn smut) and sugar cane; *Venturia* spp. (scab) on apples (for example *V. inaequalis*) and pears and *Verticillium* spp. (leaf and shoot wilt) on various plants, such as fruit trees and ornamental trees, grapevines, soft fruit, vegetable and field crops, such as for example *V. dahliae* on strawberries, oilseed rape, potatoes and tomatoes.

Moreover, the compounds I and the compositions according to the invention are suitable for controlling harmful fungi in the protection of materials and buildings (for example wood, paper, paint dispersions, fibers or tissues) and in the protection of stored products. In the protection of wood and buildings, particular attention is paid to the following harmful fungi: Ascomycetes, such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichoderma* spp., *Alternaria* spp., *Paecilomyces* spp. and Zygomycetes such as *Mucor* spp., and in addition in the protection of materials to the following yeast fungi: *Candida* spp. and *Saccharomyces cerevisae*.

The compounds of the formula I may be present in various crystal modifications which may differ in their biological activity. These are included in the scope of the present invention.

The compounds I and the compositions according to the invention are suitable for improving plant health. Moreover, the invention relates to a method for improving plant health by treating the plants, the plant propagation material and/or the site at which the plants grow or are intended to grow with an effective amount of the compounds I or the compositions according to the invention.

The term "plant health" comprises states of a plant and/or its harvested material which are determined by various indicators individually or in combination, such as, for example, yield (for example increased biomass and/or increased content of utilizable ingredients), plant vitality (for example increased plant growth and/or greener leaves ("greening effect")), quality (for example increased content or composition of certain ingredients) and tolerance to biotic and/or abiotic stress. The indicators mentioned here for a state of plant health may occur independently of one another or may influence each other.

The compounds I are employed as such or in the form of a composition by treating the harmful fungi, their habitat or the plants or plant propagation materials, for example seed materials to be protected against fungal attack, the soil, areas, materials or spaces with a fungicidally effective amount of the compounds I. The application can be carried out both before and after the infection of the plants, plant propagation materials, for example seed materials, the soil, the areas, materials or spaces by the fungi.

Plant propagation materials can be treated prophylactically during or even before sowing or during or even before transplanting with compounds I as such or with a composition comprising at least one compound I.

The invention furthermore relates to agrochemical compositions comprising a solvent or solid carrier and at least one compound I, and also to their use for controlling harmful fungi.

An agrochemical composition comprises a fungicidally effective amount of a mixture of a compound I. The term "effective amount" refers to an amount of the agrochemical composition or of the compound I which is sufficient for controlling harmful fungi on crop plants or in the protection of materials and buildings and does not cause any significant damage to the treated crop plants. Such an amount may vary within a wide range and is influenced by numerous factors, such as, for example, the harmful fungus to be controlled, the respective crop plant or materials treated, the climatic conditions and compounds.

The compounds I, their N-oxides and their salts can be converted into the types customary for agrochemical compositions, for example solutions, emulsions, suspensions, dusts, powders, pastes and granules. The type of composition depends on the respective intended purpose; in each case, it should ensure a fine and even distribution of the compound according to the invention.

Here, examples of types of compositions are suspensions (SC, OD, FS), pastes, pastilles, wettable powders or dusts (WP, SP, SS, WS, DP, DS) or granules (GR, FG, GG, MG) which may either be water-soluble or dispersible (wettable), and also gels for treating plant propagation materials such as seed (GF).

In general, the composition types (for example SC, OD, FS, WG, SG, WP, SP, SS, WS, GF) are used in diluted form. Composition types such as DP, DS, GR, FG, GG and MG are generally employed in undiluted form.

The agrochemical compositions are prepared in a known manner (see, for example, U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th edition, McGraw-Hill, New York, 1963, 8-57 and ff., WO 91/13546, U.S. Pat. Nos. 4,172, 714, 4,144,050, 3,920,442, 5,180,587, 5,232,701, 5,208,030, GB 2,095,558, U.S. Pat. No. 3,299,566, Klingman: Weed Control as a Science (John Wiley & Sons, New York, 1961), Hance et al.: Weed Control Handbook (8th Ed., Blackwell Scientific Publications, Oxford, 1989) and Mollet, H. and Grubemann, A.: Formulation Technology (Wiley VCH Verlag, Weinheim, 2001).

The agrochemical compositions may furthermore also comprise auxiliaries customary for crop protection compositions, the selection of the auxiliaries depending on the use form or the active compound in question.

Examples of suitable auxiliaries are solvents, solid carriers, surfactants (such as further solubilizers, protective colloids, wetting agents and tackifiers), organic and inorganic thickeners, bactericides, antifreeze agents, antifoams, if appropriate colorants and adhesives (for example for the treatment of seed).

Suitable solvents are water, organic solvents, such as mineral oil fractions having a medium to high boiling point, such as kerosene and diesel oil, furthermore coal tar oils, and also oils of vegetable or animal origin, aliphatic, cyclic and aromatic hydrocarbons, for example paraffins, tetrahydronaphthalene, alkylated naphthalenes and derivatives thereof, alkylated benzenes and derivatives thereof, alcohols, such as methanol, ethanol, propanol, butanol and cyclohexanol, glycols, ketones, such as cyclohexanone, gamma-butyrolactone, dimethyl fatty amides, fatty acids and fatty acid esters and strongly polar solvents, for example amines, such as N-methylpyrrolidone. In principle, it is also possible to use solvent mixtures, and also mixtures of the solvents mentioned above and water.

Solid carriers are mineral earths, such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic substances, fertilizers, such as ammonium sulfate, ammonium phosphate, ammonium nitrate, ureas and vegetable products, such as cereal meal, tree bark meal, sawdust and nutshell meal, cellulose powder or other solid carriers.

Suitable surfactants (adjuvants, wetting agents, tackifiers, dispersants or emulsifiers) are the alkali metal, alkaline earth metal and ammonium salts of aromatic sulfonic acids, for example of lignosulfonic acid (Borresperse® types, Borregaard, Norway), phenolsulfonic acid, naphthalenesulfonic acid (Morwet® types, Akzo Nobel, USA) and dibutylnaphthalenesulfonic acid (Nekal® types, BASF, Germany), and also of fatty acids, alkyl- and alkylarylsulfonates, alkyl, lauryl ether and fatty alcohol sulfates, and also salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octyl phenol ether, ethoxylated isooctylphenol, octylphenol or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfide waste liquors, and also proteins, denatured proteins, polysaccharides (for example methylcellulose), hydrophobically modified starches, polyvinyl alcohol (Mowiol® types, Clariant, Switzerland), polycarboxylates (Sokalan® types, BASF, Germany), polyalkoxylates, polyvinylamine (Lupamin® types, BASF, Germany), polyethyleneimine (Lupasol® types, BASF, Germany), polyvinylpyrrolidone and copolymers thereof.

Examples of thickeners (i.e. compounds which impart modified flow properties to the composition, i.e. high viscosity in the state of rest and low viscosity in motion) are polysaccharides and also organic and inorganic sheet minerals, such as xanthan gum (Kelzan®, CP Kelco, USA), Rhodopol® 23 (Rhodia, France) or Veegum® (R.T. Vanderbilt, USA) or Attaclay® (Engelhard Corp., NJ, USA).

Bactericides can be added for stabilizing the composition. Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivatives, such as alkylisothiazolinones and benzisothiazoiinones (Acticide® MBS from Thor Chemie).

Examples of suitable antifreeze agents are ethylene glycol, propylene glycol, urea and glycerol.

Examples of antifoams are silicone emulsions (such as, for example, Silikon® SRE, Wacker, Germany or Rhodorsil®, Rhodia, France), long-chain alcohols, fatty acids, salts of fatty acids, organofluorine compounds and mixtures thereof.

Examples of colorants are both sparingly water-soluble pigments and water-soluble dyes. Examples which may be mentioned are the dyes and pigments known under the names Rhodarnin B, C. I. Pigment Red 112 and C. I. Solvent Red 1, Pigment blue 15:4, Pigment blue 15:3, Pigment blue 15:2, Pigment blue 15:1, Pigment blue 80, Pigment yellow 1, Pigment yellow 13, Pigment red 48:2, Pigment red 48:1, Pigment red 57:1, Pigment red 53:1, Pigment orange 43, Pigment orange 34, Pigment orange 5, Pigment green 36, Pigment green 7, Pigment white 6, Pigment brown 25, Basic violet 10, Basic violet 49, Acid red 51, Acid red 52, Acid red 14, Acid blue 9, Acid yellow 23, Basic red 10, Basic red 108.

Examples of adhesives are polyvinylpyrrolidone, polyvinyl acetate, polyvinyl alcohol and cellulose ether (Tylose®, Shin-Etsu, Japan).

Suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydro-naphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dustable products can be prepared by mixing or concomitantly grinding the compounds I and, if present further active compounds with at least one solid carrier.

Granules, for example coated granules, impregnated granules and homogeneous granules, can be prepared by binding the active compounds to at least one solid carrier. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

The following are examples of types of composition:
1. Types of Composition for Dilution with Water
  i) Water-Soluble Concentrates (SL, LS)
  10 parts by weight of the active compounds are dissolved with 90 parts by weight of water or with a water-soluble solvent. As an alternative, wetters or other auxiliaries are added. The active compound dissolves upon dilution with water. This gives a composition having an active compound content of 10% by weight.
  ii) Dispersible Concentrates (DC)
  20 parts by weight of the active compounds are dissolved in 70 parts by weight of cyclohexanone with addition of 10 parts by weight of a dispersant, for example polyvinylpyrrolidone. Dilution with water gives a dispersion. The active compound content is 20% by weight.

iii) Emulsifiable Concentrates (EC)

15 parts by weight of the active compounds are dissolved in 75 parts by weight of xylene with addition of calcium dodecylbenzenesulfonate and castor oil ethoxylate (in each case 5 parts by weight). Dilution with water gives an emulsion. The composition has an active compound content of 15% by weight.

iv) Emulsions (EW, EO, ES)

25 parts by weight of the active compounds are dissolved in 35 parts by weight of xylene with addition of calcium dodecylbenzenesulfonate and castor oil ethoxylate (in each case 5 parts by weight). This mixture is added to 30 parts by weight of water by means of an emulsifying machine (e.g. Ultraturrax) and made into a homogeneous emulsion. Dilution with water gives an emulsion. The composition has an active compound content of 25% by weight.

v) Suspensions (SC, OD, FS)

In an agitated ball mill, 20 parts by weight of the active compounds are comminuted with addition of 10 parts by weight of dispersants and wetters and 70 parts by weight of water or an organic solvent to give a fine active compound suspension. Dilution with water gives a stable suspension of the active compound. The active compound content in the composition is 20% by weight.

vi) Water-Dispersible Granules and Water-Soluble Granules (WG, SG)

50 parts by weight of the active compounds are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The composition has an active compound content of 50% by weight.

vii) Water-Dispersible Powders and Water-Soluble Powders (WP, SP, SS, WS)

75 parts by weight of the active compounds are ground in a rotor-stator mill with addition of 25 parts by weight of dispersants, wetters and silica gel. Dilution with water gives a stable dispersion or solution of the active compound. The active compound content of the composition is 75% by weight.

viii) Gels (GF)

20 parts by weight of the active compounds, 10 parts by weight of dispersant, 1 part by weight of gelling agent and 70 parts by weight of water or an organic solvent are ground in a ball mill to give a fine suspension. Dilution with water gives a stable suspension with an active compound content of 20% by weight.

2. Types of Composition to be Applied Undiluted ix) Dusts (DP, DS)

5 parts by weight of the active compounds are ground finely and mixed intimately with 95 parts by weight of finely divided kaolin. This gives a dustable product with an active compound content of 5% by weight.

x) Granules (GR, FG, GG, MG)

0.5 part by weight of the active compounds is ground finely and associated with 99.5 parts by weight of carriers. Current methods are extrusion, spray-drying or the fluidized bed. This gives granules with an active compound content of 0.5% by weight to be applied undiluted.

xi) ULV Solutions (UL)

10 parts by weight of the active compounds are dissolved in 90 parts by weight of an organic solvent, for example xylene. This gives a composition with an active compound content of 10% by weight to be applied undiluted.

In general, the compositions of the compounds according to the invention comprise from 0.01 to 95% by weight, preferably from 0.1 to 90% by weight, of the compounds I. The compounds are preferably employed in a purity of from 90% to 100%, preferably 95% to 100%.

Water-soluble concentrates (LS), suspensions (FS), dusts (DS), water-dispersible and water-soluble powders (WS, SS), emulsions (ES), emulsifiable concentrates (EC) and gels (GF) are usually used for the treatment of plant propagation materials, in particular seed. These compositions can be applied to the propagation materials, in particular seed, in undiluted or, preferably, diluted form. In this case, the corresponding composition can be diluted 2 to 10 times so that in the compositions used for the seed dressing from 0.01 to 60% by weight, preferably from 0.1 to 40% by weight of active compound are present. The application can be carried out before or during sowing. The treatment of plant propagation material, in particular the treatment of seed, is known to the person skilled in the art and is carried out by dusting, coating, pelleting, dipping or drenching the plant propagation material, the treatment preferably being carried out by pelleting, coating and dusting or by furrow treatment, such that, for example, premature germination of the seed is prevented.

For seed treatment, preference is given to using suspensions. Such compositions usually comprise from 1 to 800 g of active compound/l, from 1 to 200 g of surfactants/l, from 0 to 200 g of antifreeze agent/l, from 0 to 400 g of binders/l, from 0 to 200 g of colorants/l and solvents, preferably water.

The compounds can be used as such or in the form of their compositions, for example in the form of directly sprayable solutions, powders, suspensions, dispersions, emulsions, oil dispersions, pastes, dustable products, materials for spreading or granules, by means of spraying, atomizing, dusting, spreading, raking in, immersing or pouring. The types of composition depend entirely on the intended purposes; the intention is to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), by which it is possible to apply compositions comprising over 95% by weight of active compound, or even to apply the active compound without additives.

When used in crop protection, the application rates are from 0.001 to 2.0 kg of active compound per ha, preferably from 0.005 to 2 kg per ha, particularly preferably from 0.05 to 0.9 kg per ha, especially from 0.1 to 0.75 kg per ha, depending on the nature of the desired effect.

In the treatment of plant propagation materials, for example seed, the amounts of active compound used are generally from 0.1 to 1000 g/100 kg of propagation material or seed, preferably from 1 to 1000 g/100 kg, particularly preferably from 1 to 100 g/100 kg, especially from 5 to 100 g/100 kg.

When used in the protection of materials or stored products, the active compound application rate depends on the kind of application area and on the desired effect. Amounts typically applied in the protection of materials are, for example, from 0.001 g to 2 kg, preferably from 0.005 g to 1 kg, of active compound per cubic meter of treated material.

Various types of oils, welters, adjuvants, herbicides, bactericides, other fungicides and/or pesticides may be added to the active compounds or the compositions comprising them, if appropriate not until immediately prior to use (tank mix). These compositions can be admixed with the compositions according to the invention in a weight ratio of from 1:100 to 100:1, preferably from 1:10 to 10:1.

The following are particularly suitable as adjuvants in this context: organically modified polysiloxanes, for example Break Thru S 240®; alcohol alkoxylates, for example Atplus 245®, Atplus MBA 1303®, Plurafac LF 300® and Lutensol ON 30®; EO-PO block polymers, for example Pluronic RPE 2035® and Genapol B®; alcohol ethoxylates, for example Lutensol XP 80®; and sodium dioctylsulfosuccinate, for example Leophen RA®.

The compositions according to the invention in the application form as fungicides can also be present together with other active compounds, for example with herbicides, insecticides, growth regulators, fungicides or else with fertilizers, as premix or if appropriate also only immediately prior to use (tank mix).

When mixing the compounds I or the compositions comprising them with one or more further active compounds, in particular fungicides, it is in many cases possible, for example, to widen the activity spectrum or to prevent the development of resistance. In many cases, synergistic effects are obtained.

The following list of active compounds with which the compounds according to the invention can be applied together is meant to illustrate the possible combinations, but not to limit them:

A) strobilurins:
    azoxystrobin, dimoxystrobin, enestroburin, fluoxastrobin, kresoxim-methyl, metominostrobin, orysastrobin, picoxystrobin, pyraclostrobin, pyribencarb, trifloxystrobin, 2-(2-(6-(3-chloro-2-methylphenoxy)-5-fluoropyrimidin-4-yloxy)phenyl)-2-methoxyimino-N-methylacetamide, methyl 2-(ortho-((2,5-dimethylphenyloxy-methylene)phenyl)-3-methoxyacrylate, methyl 3-methoxy-2-(2-(N-(4-methoxyphenyl)-cyclopropanecarboximidoylsulfanylmethyl)phenyl) acrylate, 2-(2-(3-(2,6-dichloro-phenyl)-1-methylallylideneaminooxymethyl)phenyl)-2-methoxyimino-N-methyl-acetamide;

B) carboxamides:
    carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (metenoxam), ofurace, oxadixyl, oxycarboxin, penthiopyrad, tecloftalam, thifluzamide, tiadinil, 2-amino-4-methylthiazole-5-carboxanilide, 2-chloro-N-(1,1,3-trimethylindan-4-yl)nicotinamide, N-(2',4'-difluorobiphenyl-2-yl)-3-difluoromethyl-1-methyl-1H-pyrazole-4-carboxamide, N-(2',4'-dichlorobiphenyl-2-yl)-3-difluoromethyl-1-methyl-1H-pyrazole-4-carboxamide, N-(2',5'-difluorobiphenyl-2-yl)-3-difluoromethyl-1-methyl-1H-pyrazole-4-carboxamide, N-(2',5'-dichlorobiphenyl-2-yl)-3-difluoromethyl-1-methyl-1H-pyrazole-4-carboxamide, N-(3',5'-difluorobiphenyl-2-yl)-3-difluoromethyl-1-methyl-1H-pyrazole-4-carboxamide, N-(3',5'-dichlorobiphenyl-2-yl)-3-difluoromethyl-1-methyl-1H-pyrazole-4-carboxamide, N-(3'-fluorobiphenyl-2-yl)-3-difluoromethyl-1-methyl-1H-pyrazole-4-carboxamide, N-(3'-chlorobiphenyl-2-yl)-3-difluoromethyl-1-methyl-1H-pyrazole-4-carboxamide, N-(2'-fluorobiphenyl-2-yl)-3-difluoromethyl-1-methyl-1H-pyrazole-4-carboxamide, N-(2'-chlorobiphenyl-2-yl)-3-difluoromethyl-1-methyl-1H-pyrazole-4-carboxamide, N-(3',4',5'-trifluorobiphenyl-2-yl)-3-difluoromethyl-1-methyl-1H-pyrazole-4-carboxamide, N-(2',4',5'-trifluorobiphenyl-2-yl)-3-difluoromethyl-1-methyl-1H-pyrazole-4-carboxamide, N-[2-(1,1,2,3,3,3-hexafluoropropoxy)phenyl]-3-difluoromethyl-1-methyl-1H-pyrazole-4-carboxamide, N-[2-(1,1,2,2-tetrafluoroethoxy)phenyl]-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3-dimethylbutyl)phenyl)-1,3-dimethyl-5-fluoro-1H-pyrazole-4-carboxamide, N-(2-(1,3,3-trimethylbutyl)phenyl)-1,3-dimethyl-5-fluoro-1H-pyrazole-4-carboxamide, N-(4'-chloro-3',5'-difluorobiphenyl-2-yl)-3-di-fluoromethyl-1-methyl-1H-pyrazole-4-carboxamide, N-(4'-chloro-3'.5'-difluorobi-phenyl-2-yl)-3-trifluoromethyl-1-methyl-1H-pyrazole-4-carboxamide, N-(3',4'-dichloro-5'-fluorobiphenyl-2-yl)-3-trifluoromethyl-1-methyl-1H-pyrazole-4-carboxamide, N-(3',5'-difluoro-4'-methylbiphenyl-2-yl)-3-difluoromethyl-1-methyl-1H-pyrazole-4-carboxamide, N-(3',5'-difluoro-4'-methylbiphenyl-2-yl)-3-trifluoromethyl-1-methyl-1H-pyrazole-4-carboxamide, N-(2-bicyclopropyl-2-ylphenyl)-3-difluoromethyl-1-methyl-1H-pyrazole-4-carboxamide, N-(cis-2-bicyclopropyl-2-ylphenyl)-3-difluoromethyl-1-methyl-1H-pyrazole-4-carboxamide, N-(trans-2-bicyclopropyl-2-ylphenyl)-3-difluoromethyl-1-methyl-1H-pyrazole-4-carboxamide, N-[1,2,3,4-tetrahydro-9-(1-methylethyl)-1,4-methanonaphthalen-5-yl]-3-(difluoromethyl)-1-methyl-1H-pyrazole-4-carboxamide;

carboxylic acid morpholides: dimethomorph, flumorph;
benzamides: flumetover, fluopicolide, fluopyram, zoxamide, N-(3-ethyl-3,5,5-tri-mgthylcyclohexyl)-3-formylamino-2-hydroxybenzamide;
other carboxamides: carpropamid, diclocymet, mandipropamid, oxytetracyclin, silthiofam, N-(6-methoxypyridin-3-yl)cyclopropanecarboxamide;

C) azoles:
    triazoles: azaconazole, bitertanole, bromuconazole, cyproconazole, difenoconazole, diniconazole, diniconazole-M, epoxiconazole, fenbuconazole, fluquinconazole, flusilazole, fiutriafole, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenoie, triticonazole, uniconazole, 1-(4-chlorophenyl)-2-([1,2,4]triazol-1-yl)cycloheptanol;
    imidazoles: cyazofamid, imazalil, imazalil sulfate, pefurazoate, prochloraz, triflumizole;
    benzimidazoles: benomyl, carbendazim, fuberidazole, thiabendazole;

others: ethaboxam, etridiazole, hymexazole, 2-(4-chlorophenyl)-N-[4-(3,4-dimethoxyphenypisoxazol-5-yl]-2-prop-2-inyloxy-acetamide;

D) nitrogenous heterocyclyl compounds pyridines: fluazinam, pyrifenox, 3-[5-(4-chlorophenyl)-2,3-dimethylisoxazolidin-3-yl]-pyridine, 3-[5-(4-methylphenyl)-2,3-dimethylisoxazolidin-3-yl]pyridine, 2,3,5,6-tetra-chloro-4-methanesulfonylpyridine, 3,4,5-trichloropyridine-2,6-dicarbonitrile, N-(1-(5-bromo-3-chloropyridin-2-yl)ethyl)-2,4-dichloronicotinamide, N-((5-bromo-3-chloro-pyridin-2-yl)methyl)-2,4-dichloronicotinamide;

pyrimidines: bupirimate, cyprodinil, diflumetorim, fenarimol, ferimzone, mepanipyrim, nitrapyrin, nuarimol, pyrimethanil;

piperazines: triforine;

pyrroles: fludioxonil, fenpiclonil;

morpholines: aldimorph, dodemorph, dodemorph acetate, fenpropimorph, tridemorph;

piperidines: fenpropidin;

dicarboximides: fluoroimide, iprodione, procymidone, vinclozolin;

nonaromatic 5-membered heterocycles: famoxadone, fenamidone, flutianil, octhilinone, probenazole, S-allyl 5-amino-2-isopropyl-3-oxo-4-ortho-tolyl-2,3-dihydro-pyrazole-1-thiocarboxylate;

others: acibenzolar-S-methyl, amisuibrom, anilazine, blasticidin-S, captafol, captan, quinomethionate, dazomet, debacarb, diclomezine, difenzoquat, difenzoquat methylsulfate, fenoxanil, folpet, oxolinic acid, piperalin, proquinazid, pyroquilone, quinoxyfen, triazoxide, tricyclazole, 2-butoxy-6-iodo-3-propylchromen-4-one, 5-chloro-1-(4,6-dimethoxypyrimidin-2-yl)-2-methyl-1H-benzimidazole, 5-chloro-7-(4-methylpiperidin-1-yl)-6-(2,4,6-trifluorophenyl)-[1,2,4]triazolo[1,5-a]pyrimidine, 6-(3,4-dichlorophenyl)-5-methyl-[1,2,4]triazolo[1,5-a]pyrimidin-7-ylamine, 6-(4-tert-butylphenyl)-5-methyl-[1,2,4]triazolo[1,5-a]pyrimidin-7-ylamine, 5-methyl-6-(3,5,5-trimethylhexyl)-[1,2,4]triazolo[1,5-a]pyrimidin-7-ylamine, 5-methyl-6-octyl-[1,2,4]triazolo[1,5-a]pyrimidin-7-ylamine, 6-methyl-5-octyl-[1,2,4]triazolo[1,5-a]-pyrimidin-7-ylamine, 6-ethyl-5-octyl-[1,2,4]triazolo[1,5-a]pyrimidin-7-ylamine, 5-ethyl-6-octyl-[1,2,4]triazolo[1,5-a]pyrimidin-7-ylamine, 5-ethyl-6-(3,5,5-trimethylhexyl)-[1,2,4]triazolo[1,5-a]pyrimidin-7-ylamine, 6-octyl-5-propyl-[1,2,4]triazolo[1,5-a]-pyrimidin-7-ylamine, 5-methoxymethyl-6-octyl-[1,2,4]triazolo[1,5-a]pyrimidin-7-ylamine, 6-octyl-5-trifluoromethyl-[1,2,4]triazolo[1,5-a]pyrimidin-7-ylamine and 5-trifluoromethyl-6-(3,5,5-trimethylhexyl)-[1,2,4]triazolo[1,5-a]pyrimidin-7-ylamine;

E) carbamates and dithiocarbamates thio- and dithiocarbamates: ferbam, mancozeb, maneb, metam, methasulfocarb, metiram, propineb, thiram, zineb, ziram;

carbamates: diethofencarb, benthiavalicarb, iprovalicarb, propamocarb, propamocarb hydrochloride, valiphenal, 4-fluorophenyl N-(1-(1-(4-cyanophenyl)ethanesulfonyl)but-2-yl)carbamate;

F) other fungicides guanidines: dodine, dodine free base, guazatine, guazatine acetate, iminoctadine, iminoctadine triacetate, iminoctadine tris(albesilate);

antibiotics: kasugamycin, kasugamycin hydrochloride hydrate, polyoxins, streptomycin, validamycin A;

nitrophenyl derivatives: binapacryl, dicloran, dinobuton, dinocap, nitrothal isopropyl, tecnazene;

organometallic compounds: fentin salts, such as, for example, fentin acetate, fentin chloride, fentirr hydroxide;

sulfur-containing heterocyclyl compounds: dithianon, isoprothiolane;

organophosphorus compounds: edifenphos, fosetyl, fosetyl aluminum, iprobenfos, phosphorous acid and its salts, pyrazophos, tolclofos-methyl;

organochlorine compounds: chlorothalonil, dichlofluanid, dichlorophen, flusulfamide, hexachlorobenzene, pencycuron, pentachlorophenol and its salts, phthalide, quintozene, thiophanate methyl, tolylfluanid, N-(4-chloro-2-nitrophenyl)-N-ethyl-4-methylbenzenesulfonamide;

inorganic active compounds: phosphorous acid and its salts, Bordeaux mixture, copper salts, such as, for example, copper acetate, copper hydroxide, copper oxychloride, basic copper sulfate, sulfur;

others: biphenyl, bronopol, cyflufenamid, cymoxanil, diphenylamine, metrafenone, mildiomycin, oxine-copper, prohexadione-calcium, spiroxamine, tolylfluanid, N-(cyclopropylmethoxyimino-(6-difluoromethoxy-2,3-difluorophenyl)methyl)-2-phenylacetamide, N'-(4-(4-chloro-3-trifluoromethylphenoxy)-2,5-dimethylphenyl)-N-ethyl-N-methylformamidine, N'-(4-(4-fluoro-3-trifluoromethylphenoxy)-2,5-dimethylphenyl)-N-ethyl-N-methylformamidine, N'-(2-methyl-5-trifluoromethyl-4-(3-trimethylsilanylpropoxy)phenyl)-N-ethyl-N-methylformamidine, N'-(5-difluoromethyl-2-methyl-4-(3-trimethylsilanylpropoxy)phenyl)-N-ethyl-N-methylformamidine, methyl N-(1,2,3,4-tetrahydronaphthalen-1-yl)-2-{1-[2-(5-methyl-3-trifluoromethylpyrazol-1-yl)acetyl]piperidin-4-yl}thiazole-4-carboxamide, methyl (R)—N-(1,2,3,4-tetrahydronaphthalen-1-yl)-2-{1-[2-(5-methyl-3-trifluoromethylpyrazol-1-yl)acetyl]-piperidin-4-yl}thiazole-4-carboxamide, 6-tert-butyl-8-fluoro-2,3-dimethylquinolin-4-yl acetate, 6-tert-butyl-8-fluoro-2,3-dimethylquinolin-4-yl methoxyacetate;

G) growth regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfid, indole-3-acetic acid, maleic hydrazide, mefluidide, mepiquat (mepiquat chloride), metconazole, naphthalene acetic acid, N-6-benzyladenine, paclobutrazole, prohexadione (prohexadione-calcium), prohydrojasmon, thidiazuron, triapenthenol, tributyl phosphorotrithioate, 2,3,5-triiodobenzoic acid, trinexapac-ethyl and uniconazole;

H) herbicides acetamides: acetochlor, alachlor, butachlor, dimethachior, dimethenamid, flufenacet, mefenacet, metolachlor, metazachior, napropamide, naproanilide, pethoxamid, pretilachlor, propachlor, thenylchior;

amino acid analogues: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-p-tefuryl;

bipyridyls: diquat, paraquat;

carbamates and thiocarbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethaifluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bromoxynil, dichlobenil, ioxynil;

imidazolinones: imazamethabenz, imazamox, imazapic, imazapyr, imazaquin, imazethapyr;

phenoxyacetic acids: clomeprop, 2,4-dichlorophenoxyacetic acid (2,4-D), 2,4-DB, dichlorprop, MCPA, MCPA-thioethyl, MCPB, mecoprop;

pyrazines: chloridazone, flufenpyr-ethyl, fluthiacet, norflurazone, pyridate;

pyridines: aminopyralid, clopyralid, diflufenican, dithiopyr, fluridone, fluroxypyr, picloram, picolinafen, thiazopyr;

sulfonylureas: amidosulfuron, azimsulfuron, bensulfuron, chlorimuron-ethyl, chiorsulfuron, cinosulfuron, cyclosulfamuron, ethoxysuifuron, flazasulfuron, fluce-tosulfuron, flupyrsulfuron, foramsulfuron, halosulfuron, imazosulfuron, iodosulfuron, mesosulfuron, metsulfuron-methyl, nicosulfuron, oxasulfuron, primisulfuron, prosul-furon, pyrazosulfuron, rimsulfuron, sulfometuron, sulfosulfuron, thifensulfuron, tria-sulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxypyrimidin-2-yl)urea;

triazines: ametryn, atrazine, cyanazine, dimethametryn, ethiozine, hexazinone, meta-mitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other inhibitors of acetolactate synthase: bispyribac-sodium, cloransuiam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsuiam;

others: amicarbazone, aminotriazole, anilofos, beflubutamid, benazolin, bencarbazone, benfluresate, benzofenap, bentazone, benzobicyclon, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fentrazamide, flumiciorac-pentyl, flumioxazin, flupoxam, fluorochloridone, flurtamone, indanofan, isoxaben, isoxaflutole, lenacil, propanil, propyzamide, quinclorac, quinmerac, mesotrione, methylarsenic acid, naptalam, oxadiargyl, oxadiazon, oxaziclomefone, pentoxazone, pinoxaden, pyraclonil, pyraflufen-ethyl, pyrasulfotol, pyrazoxyfen, pyrazolynate, quinoclamine, saflufenacil, sulcotrion, sulfentrazone, terbacil, tefuryltrione, tembotrione, thiencarbazone, topramezone, 4-hydroxy-3-[2-(2-methoxyethoxymethyl)-6-trifluoromethylpyridine-3-carbonyl]ibicyclo[3.2.1]oct-3-ene-2-one, ethyl (3-[2-chloro-4-fluoro-5-(3-methyl-2,6-dioxo-4-trifluoromethyl-3,6-dihydro-2H-pyrimidin-1-yl)phenoxy]pyridin-2-yloxy)acetate, methyl 6-amino-5-chloro-2-cyclopropylpyrimidine-4-carboxylate, 6-chloro-3-(2-cyclopropyl-6-methylphenoxy)-pyridazin-4-ol, 4-amino-3-chloro-6-(4-chlorophenyl)-5-fluoropyridine-2-carboxylic acid, methyl 4-amino-3-chloro-6-(4-chloro-2-fluoro-3-methoxyphenyl)pyridine-2-carboxylate and methyl 4-amino-3-chloro-6-(4-chloro-3-dimethylamino-2-fluorophenyl)pyridine-2-carboxylate;

I) insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, suiprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyha-lothrin, permethrin, prallethrin, pyrethrin I and II, resmethrin, silafluofen, tau-fluvalinate, tefluthrin, tetramethrin, tralomethrin, transfluthrin, profluthrin, dimefluthrin, inhibitors of insect growth: a) chitin synthesis inhibitors: benzoylureas: chlorfluazuron, cyromazine, diflubenzuron, flucycloxuron, flufenoxuron, hexaflumuron, lufenuron, novaluron, teflubenzuron, triflumuron; buprofezin, diofenolan, hexythiazox, etoxazole, clofentazin; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramate;

nicotine receptor agonists/antagonists: clothianidin, dinotefuran, imidacloprid, thiamethoxam, nitenpyram, acetamiprid, thiacloprid, 1-(2-chlorothiazol-5-ylmethyl)-2-nitrimino-3,5-dimethyl-[1,3,5]triazinane;

GABA antagonists: endosulfan, ethiprol, fipronil, vanilprol, pyrafluprol, pyriprol, 5-amino-1-(2,6-dichloro-4-methylphenyl)-4-sulfinamoyl-1H-pyrazole-3-thiocarboxamide;

macrocyclic lactones: abamectin, emamectin, milbemectin, lepimectin, spinosad, spinetoram;

mitochondrial electron transport chain inhibitors (METI) I acaricides: fenazaquin, pyridaben, tebufenpyrad, tolfenpyrad, flufenerim;

METI II and III substances: acequinocyl, fluacyprim, hydramethylnon;

decouplers: chlorfenapyr;

inhibitors of oxidative phosphorylation: cyhexatin, diafenthiuron, fenbutatin oxide, propargite;

insect molting inhibitors: cryomazine;

mixed function oxidase inhibitors: piperonyl butoxide;

sodium channel blockers: indoxacarb, metaflumizone;

others: benclothiaz, bifenazate, cartap, fionicamid, pyridalyl, pymetrozine, sulfur, thiocyclam, flubendiamid, chlorantraniliprol, cyazypyr (HGW86); cyenopyrafen, flupyrazofos, cyflumetofen, amidoflumet, imicyafos, bistrifiuron, and pyrifluquinazon.

The present invention relates in particular also to fungicidal compositions which comprise at least one compound of the general formula I and at least one further crop protection agent, in particular at least one fungicidal active compound, for example one or more, for example 1 or 2, active compounds of groups A) to F) mentioned above and, if appropriate, one or more agriculturally suitable carriers. With a view to reducing the application rates, these mixtures are of interest, since many show, at a reduced total amount of active compounds applied, an improved activity against harmful fungi, in particular for certain indications. By simultaneous joint or separate application of compound(s) I with at least one active compound of groups A) to I), the fungicidal activity can be increased in a superadditive manner.

In the sense of the present application, joint application means that the at least one compound of the formula I and the at least one further active compound are present simultaneously at the site of action (i.e. the plant-damaging fungi to be controlled and their habitat, such as infected plants, plant propagation materials, in particular seed, soils, materials or spaces and also plants, plant propagation materials, in particular seed, soils, materials or spaces to be protected against fungal attack) in an amount sufficient for an effective control of fungal growth. This can be achieved by applying the compounds I and at least one further active compound jointly in a joint active compound preparation or in at least two separate active compound preparations simultaneously, or by applying the active compounds successively to the site of action, the interval between the individual active compound applications being chosen such that the active compound applied first is, at the time of application of the further active compound(s), present at the site of action in a sufficient amount. The order in which the active compounds are applied is of minor importance.

In binary mixtures, i.e. compositions according to the invention comprising a compound I and a further active compound, for example an active compound of groups A) to I), the weight ratio of compound I to the further active compound lies the weight ratio of compound I to the 1st further active compound depends on the properties of the active compounds in question; usually, it is in the range of from 1:100 to 100:1, frequently in the range of from 1:50 to 50:1, preferably in the range of from 1:20 to 20:1, particularly preferably in the range of from 1:10 to 10:1, especially in the range of from 1:3 to 3:1.

In ternary mixtures, i.e. compositions according to the invention comprising an active compound I and a 1st further active compound and a 2nd further active compound, for example two different active compounds from groups A) to I), the weight ratio of compound I to the 1st further active compound depends on the properties of the respective active compounds; preferably, it is in the range of from 1:50 to 50:1 and in particular in the range of from 1:10 to 10:1. The weight ratio of compound I to the 2nd further active compound is preferably in the range of from 1:50 to 50:1, in particular in the range of from 1:10 to 10:1. The weight ratio of 1st further active compound to 2nd further active compound is preferably in the range of from 1:50 to 50:1, in particular in the range of from 1:10 to 10:1.

The components of the composition according to the invention can be packaged and used individually or as a ready-mix or as a kit of parts.

In one embodiment of the invention, the kits may comprise one or more, and even all, components used for preparing an agrochemical composition according to the invention. For example, these kits may comprise one or more fungicide components and/or an adjuvant component and/or an insecticide component and/or a growth regulator component and/or a herbicide. One or more components may be present combined or preformulated with one another. In the embodiments where more than two components are provided in a kit, the components can be combined with one another and be packaged in a single container, such as a vessel, a bottle, a tin, a bag, a sack or canister. In other embodiments, two or more components of a kit may be packaged separately, i.e. not preformulated or mixed. Kits may comprise one or more separate containers, such as vessels, bottles, tins, bags, sacks or canisters, each container comprising a separate component of the agrochemical composition. The components of the composition according to the invention may be packaged and used individually or as a ready-mix or as a kit of parts. In both forms, a component may be used separately or together with the other components or as a part of a kit of parts according to the invention for preparing the mixture according to the invention.

The user uses the composition according to the invention usually for use in a predosage device, a knapsack sprayer, a spray tank or a spray plane. Here, the agrochemical composition is diluted with water and/or buffer to the desired application concentration, with further auxiliaries being added, if appropriate, thus giving the ready-to-use spray liquor or the agrochemical composition according to the invention. Usually, from 50 to 500 liters of the ready-to-use spray liquor are applied per hectare of agricultural utilized area, preferably from 100 to 400 liters.

According to one embodiment, the user may himself mix individual components, such as, for example, parts of a kit or a two- or three-component mixture of the composition according to the invention in a spray tank and, if appropriate, add further auxiliaries (tank mix).

In a further embodiment, the user may mix both individual components of the composition according to the invention and partially pre-mixed components, for example components comprising compounds I and/or active compounds from groups A) to I), in a spray tank and, if appropriate, add further auxiliaries (tank mix).

In a further embodiment, the user may use both individual components of the composition according to the invention and partially pre-mixed components, for example components comprising compounds I and/or active compounds from groups A) to I), jointly (for example as a tank mix) or in succession.

Preference is given to compositions of a compound I (component 1) with at least one active compound from group A) (component 2) of the strobilurins and in particular selected from the group consisting of azoxystrobin, dimoxystrobin, fluoxastrobin, kresoxim-methyl, orysastrobin, picoxystrobin, pyraclostrobin and trifloxystrobin.

Preference is also given to compositions of a compound I (component 1) with at least one active compound selected from group B) (component 2) of the carboxamides and in particular selected from the group consisting of fenhexamid, metalaxyl, mefenoxam, ofurace, dimethomorph, flumorph, fluopicolid (picobenzamid), zoxamide, carpropamid and mandipropamid.

Preference is also given to compositions of a compound I (component I) with at least one active compound selected from group C) (component 2) of the azoles and in particular selected from the group consisting of cyproconazole, difenoconazole, epoxiconazole, fluquinconazole, flusilazole, flutriafole, metconazole, myclobutanil, penconazole, propiconazole, prothioconazole, triadimefon, triadimenol, tebuconazole, tetraconazole, triticonazole, prochloraz, cyazofamid, benomyl, carbendazim and ethaboxam.

Preference is also given to compositions of a compound I (component 1) with at least one active compound selected from group D) (component 2) of the nitrogenous heterocyclyl compounds and in particular selected from the group consisting of fluazinam, cyprodinil, fenarimol, mepanipyrim, pyrimethanil, triforin, fludioxonil, fodemorph, fenpropimorph, tridemorph, fenpropidin, iprodion, vinclozolin, famoxadone, fenamidone, probenazole, proquinazid, acibenzolar-s-methyl, captafol, folpet, fenoxanil and quinoxyfen.

Preference is also given to compositions of a compound I (component 1) with at least one active compound selected from group E) (component 2) of the carbamates and in particular selected from the group consisting of mancozeb, metiram, propineb, thiram, iprovalicarb, flubenthiavalicarb and propamocarb.

Preference is also given to compositions of a compound I (component 1) with at least one active compound selected from the fungicides of group F) (component 2) and in particular selected from the group consisting of dithianon, fentin salts, such as fentin acetate, fosetyl, fosetyl-aluminum, $H_3PO_3$ and salts thereof, chlorothalonil, dichlofluanid, thiophanate-methyl, copper acetate, copper hydroxide, copper oxychloride, copper sulfate, sulfur, cymoxanil, metrafenone, spiroxamine and 5-chloro-7-(4-methylpiperidin-1-yl)-6-(2,4,6-trifluorophenyl)-[1,2,4]triazolo[1,5-a]pyrimidine.

Accordingly, the present invention furthermore relates to compositions of a compound I (component 1) with a further active compound (component 2), the latter being selected from rows B-1 to B-378 in the column "component 2" of table B.

A further embodiment of the invention relates to the compositions B-1 to B-378 listed in Table B, where a row of Table B corresponds in each case to an agrochemical composition comprising one of the compounds of the formula I individualized in the present description (component 1) and the respective further active compound from the groups A) to F) (component 2) stated in the row in question. The active compounds in the described compositions are in each case preferably present in synergistically active amounts.

TABLE B

Active compound composition, comprising an individualized compound I and a further active compounds from the groups A) to F)

| Row | Component 1 | Component 2 |
|---|---|---|
| B-1 | an individualized compound I | azoxystrobin |
| B-2 | an individualized compound I | dimoxystrobin |
| B-3 | an individualized compound I | enestroburin |
| B-4 | an individualized compound I | fluoxastrobin |
| B-5 | an individualized compound I | kresoxim-methyl |
| B-6 | an individualized compound I | metominostrobin |
| B-7 | an individualized compound I | orysastrobin |
| B-8 | an individualized compound I | picoxystrobin |
| B-9 | an individualized compound I | pyraclostrobin |
| B-10 | an individualized compound I | pyribencarb |
| B-11 | an individualized compound I | trifloxystrobin |
| B-12 | an individualized compound I | 2-(2-(6-(3-chloro-2-methylphenoxy)-5-fluoropyrimidin-4-yloxy)phenyl)-2-methoxyimino-N-methylacetamide |
| B-13 | an individualized compound I | 2-(ortho-((2,5-dimethylphenyloxymethylene)phenyl)-3-methoxyacrylic acid methyl ester |
| B-14 | an individualized compound I | 3-methoxy-2-(2-(N-(4-methoxyphenyl)-cyclopropanecarboximidoylsulfanyl-methyl)phenyl)acrylic acid methyl ester |
| B-15 | an individualized compound I | 2-(2-(3-(2,6-dichlorophenyl)-1-methyallylidene-aminooxymethyl)phenyl)-2-methoxyimino-N-methylacetamide |
| B-16 | an individualized compound I | benalaxyl |
| B-17 | an individualized compound I | benalaxyl-M |
| B-18 | an individualized compound I | benodanil |
| B-19 | an individualized compound I | bixafen |
| B-20 | an individualized compound I | boscalid |
| B-21 | an individualized compound I | carboxin |
| B-22 | an individualized compound I | fenfuram |
| B-23 | an individualized compound I | fenhexamid |
| B-24 | an individualized compound I | flutolanil |
| B-25 | an individualized compound I | furametpyr |
| B-26 | an individualized compound I | isopyrazam |
| B-27 | an individualized compound I | isotianil |
| B-28 | an individualized compound I | kiralaxyl |
| B-29 | an individualized compound I | mepronil |
| B-30 | an individualized compound I | metalaxyl |
| B-31 | an individualized compound I | metalaxyl-M |
| B-32 | an individualized compound I | ofurace |
| B-33 | an individualized compound I | oxadixyl |
| B-34 | an individualized compound I | oxycarboxin |
| B-35 | an individualized compound I | penthiopyrad |
| B-36 | an individualized compound I | tecloftalam |
| B-37 | an individualized compound I | thifluzamide |
| B-38 | an individualized compound I | tiadinil |
| B-39 | an individualized compound I | 2-amino-4-methylthiazole-5-carboxanilide |
| B-40 | an individualized compound I | 2-chloro-N-(1,1,3-trimethylindan-4-yl)-nicotinamide |
| B-41 | an individualized compound I | N-(2',4'-difluorobiphenyl-2-yl)-3-difluoromethyl-1-methyl-1H-pyrazole-4-carboxamide |

TABLE B-continued

Active compound composition, comprising an individualized compound I and a further active compounds from the groups A) to F)

| Row | Component 1 | Component 2 |
|---|---|---|
| B-42 | an individualized compound I | N-(2',4'-dichlorobiphenyl-2-yl)-3-difluoromethyl-1-methyl-1H-pyrazole-4-carboxamide |
| B-43 | an individualized compound I | N-(2',5'-difluorobiphenyl-2-yl)-3-difluoromethyl-1-methyl-1H-pyrazole-4-carboxamide |
| B-44 | an individualized compound I | N-(2',5'-dichlorobiphenyl-2-yl)-3-difluoromethyl-1-methyl-1H-pyrazole-4-carboxamide |
| B-45 | an individualized compound I | N-(3',5'-difluorobiphenyl-2-yl)-3-difluoromethyl-1-methyl-1H-pyrazole-4-carboxamide |
| B-46 | an individualized compound I | N-(3',5'-dichlorobiphenyl-2-yl)-3-difluoromethyl-1-methyl-1H-pyrazole-4-carboxamid |
| B-47 | an individualized compound I | N-(3'-fluorobiphenyl-2-yl)-3-difluoromethyl-1-methyl-1H-pyrazole-4-carboxamide |
| B-48 | an individualized compound I | N-(3'-chlorobiphenyl-2-yl)-3-difluoromethyl-1-methyl-1H-pyrazole-4-carboxamide |
| B-49 | an individualized compound I | N-(2'-fluorobiphenyl-2-yl)-3-difluoromethyl-1-methyl-1H-pyrazole-4-carboxamide |
| B-50 | an individualized compound I | N-(2'-chlorobiphenyl-2-yl)-3-difluoromethyl-1-methyl-1H-pyrazole-4-carboxamide |
| B-51 | an individualized compound I | N-(3',4',5'-trifluorobiphenyl-2-yl)-3-difluoromethyl-1-methyl-1H-pyrazole-4-carboxamide |
| B-52 | an individualized compound I | N-(2',4',5'-trifluorobiphenyl-2-yl)-3-difluoromethyl-1-methyl-1H-pyrazole-4-carboxamide |
| B-53 | an individualized compound I | N-[2-(1,1,2,3,3,3-hexafluoropropoxy)phenyl]-3-difluoromethyl-1-methyl-1H-pyrazole-4-carboxamide |
| B-54 | an individualized compound I | N-[2-(1,1,2,2-tetrafluoroethoxy)phenyl]-3-difluoromethyl-1-methyl-1H-pyrazole-4-carboxamide |
| B-55 | an individualized compound I | N-(4'-trifluoromethylthiobiphenyl-2-yl)-3-difluoromethyl-1-methyl-1H-pyrazole-4-carboxamide |
| B-56 | an individualized compound I | N-(2-(1,3-dimethylbutyl)phenyl)-1,3-dimethyl-5-fluoro-1H-pyrazole-4-carboxamide |
| B-57 | an individualized compound I | N-(2-1,3,3-trimethylbutyl)phenyl)-1,3-dimethyl-5-fluoro-1H-pyrazole-4-carboxamide |
| B-58 | an individualized compound I | N-(4'-chloro-3',5'-difluorobiphenyl-2-yl)-3-difluoromethyl-1-methyl-1H-pyrazole-4-carboxamide |
| B-59 | an individualized compound I | N-(4'-chloro-3',5'-difluorobiphenyl-2-yl)-3-trifluoromethyl-1-methyl-1H-pyrazole-4-carboxamide |
| B-60 | an individualized compound I | N-(3',4'-dichloro-5'-fluorobiphenyl-2-yl)-3-trifluoromethyl-1-methyl-1H-pyrazole-4-carboxamide |
| B-61 | an individualized compound I | N-(3',5'-difluoro-4'-methylbiphenyl-2-yl)-3-difluoromethyl-1-methyl-1H-pyrazole-4-carboxamide |
| B-62 | an individualized compound I | N-(3',5'-difluoro-4'-methylbiphenyl-2-yl)-3-trifluoromethyl-1-methyl-1H-pyrazole-4-carboxamide |
| B-63 | an individualized compound I | N-(2-bicyclopropyl-2-ylphenyl)-3-difluoromethyl-1-methyl-1H-pyrazole-4-carboxamide |
| B-64 | an individualized compound I | N-(cis-2-bicyclopropyl-2-ylphenyl)-3-difluoromethyl-1-methyl-1H-pyrazole-4-carboxamide |
| B-65 | an individualized compound I | N-(trans-2-bicyclopropyl-2-ylphenyl)-3-difluoromethyl-1-methyl-1H-pyrazole-4-carboxamide |
| B-66 | an individualized compound I | N-[1,2,3,4-tetrahydro-9-(1-methylethyl)-1,4-methanonaphthalen-5-yl]-3-(difluoromethyl)-1-methyl-1H-pyrazole-4-carboxamide |
| B-67 | an individualized compound I | dimethomorph |
| B-68 | an individualized compound I | flumorph |
| B-69 | an individualized compound I | flumetover |
| B-70 | an individualized compound I | fluopicolide |
| B-71 | an individualized compound I | fluopyram |
| B-72 | an individualized compound I | zoxamide |
| B-73 | an individualized compound I | N-(3-ethyl-3,5,5-trimethylcyclohexyl)-3-formylamino-2-hydroxybenzamide |
| B-74 | an individualized compound I | carpropamid |
| B-75 | an individualized compound I | diclocymet |
| B-76 | an individualized compound I | mandipropamid |
| B-77 | an individualized compound I | oxytetracyclin |
| B-78 | an individualized compound I | silthiofam |

TABLE B-continued

Active compound composition, comprising an individualized compound I and a further active compounds from the groups A) to F)

| Row | Component 1 | Component 2 |
|---|---|---|
| B-79 | an individualized compound I | N-(6-methoxypyridin-3-yl)cyclopropane-carboxamide |
| B-80 | an individualized compound I | azaconazole |
| B-81 | an individualized compound I | bitertanol |
| B-82 | an individualized compound I | bromuconazole |
| B-83 | an individualized compound I | cyproconazole |
| B-84 | an individualized compound I | difenoconazole |
| B-85 | an individualized compound I | diniconazole |
| B-86 | an individualized compound I | diniconazole-M |
| B-87 | an individualized compound I | epoxiconazole |
| B-88 | an individualized compound I | fenbuconazole |
| B-89 | an individualized compound I | fluquinconazole |
| B-90 | an individualized compound I | flusilazole |
| B-91 | an individualized compound I | flutriafol |
| B-92 | an individualized compound I | hexaconazol |
| B-93 | an individualized compound I | imibenconazole |
| B-94 | an individualized compound I | ipconazole |
| B-95 | an individualized compound I | metconazol |
| B-96 | an individualized compound I | myclobutanil |
| B-97 | an individualized compound I | oxpoconazol |
| B-98 | an individualized compound I | paclobutrazol |
| B-99 | an individualized compound I | penconazole |
| B-100 | an individualized compound I | propiconazole |
| B-101 | an individualized compound I | prothioconazole |
| B-102 | an individualized compound I | simeconazole |
| B-103 | an individualized compound I | tebuconazole |
| B-104 | an individualized compound I | tetraconazole |
| B-105 | an individualized compound I | triadimefon |
| B-106 | an individualized compound I | triadimenol |
| B-107 | an individualized compound I | triticonazole |
| B-108 | an individualized compound I | uniconazol |
| B-109 | an individualized compound I | 1-(4-chlorophenyl)-2-([1,2,4]triazol-1-yl)-cycloheptanol |
| B-110 | an individualized compound I | cyazofamid |
| B-111 | an individualized compound I | imazalil |
| B-112 | an individualized compound I | imazalil-sulfate |
| B-113 | an individualized compound I | pefurazoat |
| B-114 | an individualized compound I | prochloraz |
| B-115 | an individualized compound I | triflumizole |
| B-116 | an individualized compound I | benomyl |
| B-117 | an individualized compound I | carbendazim |
| B-118 | an individualized compound I | fuberidazole |
| B-119 | an individualized compound I | thiabendazole |
| B-120 | an individualized compound I | ethaboxam |
| B-121 | an individualized compound I | etridiazole |
| B-122 | an individualized compound I | hymexazole |
| B-123 | an individualized compound I | 2-(4-chlorophenyl)-N-[4-(3,4-dimethoxyphenyl)isoxazol-5-yl)-2-prop-2-ynyloxyacetamide |
| B-124 | an individualized compound I | fluazinam |
| B-125 | an individualized compound I | pyrifenox |
| B-126 | an individualized compound I | 3-[5-(4-chlorophenyl)-2,3-dimethylisoxazolidin-3-yl]pyridine |
| B-127 | an individualized compound I | 3-[5-(4-methylphenyl)-2,3-dimethylisoxazolidin-3-yl]pyridine |
| B-128 | an individualized compound I | 2,3,5,6-tetrachloro-4-methanesulfonylpyridine |
| B-129 | an individualized compound I | 3,4,5-trichloropyridine-2,6-dicarbonitrile |
| B-130 | an individualized compound I | N-(1-(5-bromo-3-chloropyridin-2-yl)ethyl)-2,4-dichloronicotinamide |
| B-131 | an individualized compound I | N-((5-bromo-3-chloropyridin-2-yl)methyl)-2,4-dichloronicotinamide |
| B-132 | an individualized compound I | bupirimate |
| B-133 | an individualized compound I | cyprodinil |
| B-134 | an individualized compound I | diflumetorim |
| B-135 | an individualized compound I | fenarimol |
| B-136 | an individualized compound I | ferimzone |
| B-137 | an individualized compound I | mepanipyrim |
| B-138 | an individualized compound I | nitrapyrin |
| B-139 | an individualized compound I | nuarimol |
| B-140 | an individualized compound I | pyrimethanil |
| B-141 | an individualized compound I | triforine |
| B-142 | an individualized compound I | fenpiclonil |
| B-143 | an individualized compound I | fludioxonil |
| B-144 | an individualized compound I | aldimorph |
| B-145 | an individualized compound I | dodemorph |

TABLE B-continued

Active compound composition, comprising an individualized compound I and a further active compounds from the groups A) to F)

| Row | Component 1 | Component 2 |
|---|---|---|
| B-146 | an individualized compound I | dodemorph acetate |
| B-147 | an individualized compound I | fenpropimorph |
| B-148 | an individualized compound I | tridemorph |
| B-149 | an individualized compound I | fenpropidin |
| B-150 | an individualized compound I | fluorimid |
| B-151 | an individualized compound I | iprodione |
| B-152 | an individualized compound I | procymidon |
| B-153 | an individualized compound I | vinclozolin |
| B-154 | an individualized compound I | famoxadon |
| B-155 | an individualized compound I | fenamidon |
| B-156 | an individualized compound I | flutianil |
| B-157 | an individualized compound I | octhilinon |
| B-158 | an individualized compound I | probenazole |
| B-159 | an individualized compound I | S-allyl 5-amino-2-isopropyl-4-orthotoluylpyrazol-3-one-1-thiocarboxylate |
| B-160 | an individualized compound I | acibenzolar-S-methyl |
| B-161 | an individualized compound I | amisulbrom |
| B-162 | an individualized compound I | anilazin |
| B-163 | an individualized compound I | blasticidin-S |
| B-164 | an individualized compound I | captafol |
| B-165 | an individualized compound I | captan |
| B-166 | an individualized compound I | chinomethionat |
| B-167 | an individualized compound I | dazomet |
| B-168 | an individualized compound I | debacarb |
| B-169 | an individualized compound I | diclomezine |
| B-170 | an individualized compound I | difenzoquat |
| B-171 | an individualized compound I | difenzoquat methylsulfate |
| B-172 | an individualized compound I | fenoxanil |
| B-173 | an individualized compound I | folpet |
| B-174 | an individualized compound I | oxolinic acid |
| B-175 | an individualized compound I | piperalin |
| B-176 | an individualized compound I | proquinazid |
| B-177 | an individualized compound I | pyroquilon |
| B-178 | an individualized compound I | quinoxyfen |
| B-179 | an individualized compound I | triazoxid |
| B-180 | an individualized compound I | tricyclazole |
| B-181 | an individualized compound I | 2-butoxy-6-iodo-3-propylchromen-4-one |
| B-182 | an individualized compound I | 5-chloro-1-(4,6-dimethoxypyrimidin-2-yl)-2-methyl-1H-benzoimidazole |
| B-183 | an individualized compound I | 5-chloro-7-(4-methylpiperidin-1-yl)-6-(2,4,6-trifluorophenyl)-[1,2,4]triazolo[1,5-a]pyrimidine |
| B-184 | an individualized compound I | 6-(3,4-dichlorophenyl)-5-methyl-[1,2,4]triazolo[1,5-a]pyrimidin-7-ylamine |
| B-185 | an individualized compound I | 6-(4-tert-butylphenyl)-5-methyl-[1,2,4]triazolo[1,5-a]pyrimidin-7-ylamine |
| B-186 | an individualized compound I | 5-methyl-6-(3,5,5-trimethylhexyl)-[1,2,4]triazolo-[1,5-a]pyrimidin-7-ylamine |
| B-187 | an individualized compound I | 5-methyl-6-octyl-[1,2,4]triazolo[1,5-a]pyrimidin-7-ylamine |
| B-188 | an individualized compound I | 6-methyl-5-octyl-[1,2,4]triazolo[1,5-a]pyrimidin-7-ylamine |
| B-189 | an individualized compound I | 6-ethyl-5-octyl-[1,2,4]triazolo[1,5-a]pyrimidin-7-ylamine |
| B-190 | an individualized compound I | 5-ethyl-6-octyl-[1,2,4]triazolo[1,5-a]pyrimidin-7-ylamine |
| B-191 | an individualized compound I | 5-ethyl-6-(3,5,5-trimethylhexyl)-[1,2,4]triazolo[1,5-a]pyrimidin-7-ylamine |
| B-192 | an individualized compound I | 6-octyl-5-propyl-[1,2,4]triazolo[1,5-a]pyrimidin-7-ylamine |
| B-193 | an individualized compound I | 5-methoxymethyl-6-octyl-[1,2,4]triazolo[1,5-a]-pyrimidin-7-ylamine |
| B-194 | an individualized compound I | 6-octyl-5-trifluoromethyl-[1,2,4]triazolo[1,5-a]-pyrimidin-7-ylamine |
| B-195 | an individualized compound I | 5-trifluoromethyl-6-(3,5,5-trimethylhexyl)-[1,2,4]-triazolo[1,5-a]pyrimidin-7-ylamine |
| B-196 | an individualized compound I | ferbam |
| B-197 | an individualized compound I | mancozeb |
| B-198 | an individualized compound I | maneb |
| B-199 | an individualized compound I | metam |
| B-200 | an individualized compound I | methasulphocarb |
| B-201 | an individualized compound I | metiram |
| B-202 | an individualized compound I | propineb |
| B-203 | an individualized compound I | thiram |
| B-204 | an individualized compound I | zineb |
| B-205 | an individualized compound I | ziram |

TABLE B-continued

Active compound composition, comprising an individualized compound I and a further active compounds from the groups A) to F)

| Row | Component 1 | Component 2 |
|---|---|---|
| B-206 | an individualized compound I | diethofencarb |
| B-207 | an individualized compound I | benthiavalicarb |
| B-208 | an individualized compound I | flubenthiavalicarb |
| B-209 | an individualized compound I | iprovalicarb |
| B-210 | an individualized compound I | propamocarb |
| B-211 | an individualized compound I | propamocarb hydrochloride |
| B-212 | an individualized compound I | valiphenal |
| B-213 | an individualized compound I | 4-fluorophenyl N-(1-(1-(4-cyanophenyl)-ethanesulfonyl)but-2-yl)carbamate |
| B-214 | an individualized compound I | dodin |
| B-215 | an individualized compound I | dodin free base |
| B-216 | an individualized compound I | guazatine |
| B-217 | an individualized compound I | guazatine acetate |
| B-218 | an individualized compound I | iminoctadine |
| B-219 | an individualized compound I | iminoctadine triacetate |
| B-220 | an individualized compound I | iminoctadine tris(albesilate) |
| B-221 | an individualized compound I | kasugamycin |
| B-222 | an individualized compound I | kasugamycin hydrochloride hydrate |
| B-223 | an individualized compound I | polyoxin |
| B-224 | an individualized compound I | streptomycin |
| B-225 | an individualized compound I | validamycin A |
| B-226 | an individualized compound I | binapacryl |
| B-227 | an individualized compound I | dicloran |
| B-228 | an individualized compound I | dinobuton |
| B-229 | an individualized compound I | dinocap |
| B-230 | an individualized compound I | nitrothal-isopropyl |
| B-231 | an individualized compound I | tecnazen |
| B-232 | an individualized compound I | fentin salts |
| B-233 | an individualized compound I | dithianon |
| B-234 | an individualized compound I | isoprothiolan |
| B-235 | an individualized compound I | edifenphos |
| B-236 | an individualized compound I | fosetyl, fosetyl aluminum |
| B-237 | an individualized compound I | iprobenfos |
| B-238 | an individualized compound I | phosphorous acid and derivatives |
| B-239 | an individualized compound I | pyrazophos |
| B-240 | an individualized compound I | tolclofos-methyl |
| B-241 | an individualized compound I | chlorthalonil |
| B-242 | an individualized compound I | dichlofluanid |
| B-243 | an individualized compound I | dichlorphen |
| B-244 | an individualized compound I | flusulfamide |
| B-245 | an individualized compound I | hexachlorobenzene |
| B-246 | an individualized compound I | pencycuron |
| B-247 | an individualized compound I | pentachlorophenol and salts |
| B-248 | an individualized compound I | phthalide |
| B-249 | an individualized compound I | quintozene |
| B-250 | an individualized compound I | thiophanate methyl |
| B-251 | an individualized compound I | tolylfluanid |
| B-252 | an individualized compound I | N-(4-chloro-2-nitrophenyl)-N-ethyl-4-methylbenzenesulfonamide |
| B-253 | an individualized compound I | Bordeaux mixture |
| B-254 | an individualized compound I | copper acetate |
| B-255 | an individualized compound I | copper hydroxide |
| B-256 | an individualized compound I | copper oxychloride |
| B-257 | an individualized compound I | basic copper sulfate |
| B-258 | an individualized compound I | sulfur |
| B-259 | an individualized compound I | biphenyl |
| B-260 | an individualized compound I | bronopol |
| B-261 | an individualized compound I | cyflufenamid |
| B-262 | an individualized compound I | cymoxanil |
| B-263 | an individualized compound I | diphenylamin |
| B-264 | an individualized compound I | metrafenon |
| B-265 | an individualized compound I | mildiomycin |
| B-266 | an individualized compound I | oxine-copper |
| B-267 | an individualized compound I | prohexadione-calcium |
| B-268 | an individualized compound I | spiroxamin |
| B-269 | an individualized compound I | tolylfluanid |
| B-270 | an individualized compound I | N-(cyclopropylmethoxyimino-(6-difluoromethoxy-2,3-difluorophenyl)methyl)-2-phenylacetamide |
| B-271 | an individualized compound I | N'-(4-(4-chloro-3-trifluoromethylphenoxy)-2,5-dimethylphenyl)-N-ethyl-N-methylformamidine |
| B-272 | an individualized compound I | N'-(4-(4-fluoro-3-trifluoromethylphenoxy)-2,5-dimethylphenyl)-N-ethyl-N-methylformamidine |
| B-273 | an individualized compound I | N'-(2-methyl-5-trifluoromethyl-4-(3-trimethylsilanylpropoxy)phenyl)-N-ethyl-N-methylformamidine |

TABLE B-continued

Active compound composition, comprising an individualized compound I and a further active compounds from the groups A) to F)

| Row | Component 1 | Component 2 |
|---|---|---|
| B-274 | an individualized compound I | N'-(5-difluoromethyl-2-methyl-4-(3-tri-methylsilanylpropoxy)phenyl)-N-ethyl-N-methylformamidine |
| B-275 | an individualized compound I | methyl N-(1,2,3,4-tetrahydronaphthalene-1-yl)-2-{1-[2-(5-methyl-3-trifluoromethyl-pyrazol-1-yl)acetyl]piperidin-4-yl}thiazole-4-carboxamide |
| B-276 | an individualized compound I | methyl N—(R)-(1,2,3,4-tetrahydronaphthalene-1-yl)-2-{1-[2-(5-methyl-3-trifluoromethylpyrazol-1-yl)acetyl}piperidin-4-yl}thiazole-4-carboxamide |
| B-277 | an individualized compound I | 6-tert-butyl-8-fluoro-2,3-dimethylquinolin-4-y acetate |
| B-278 | an individualized compound I | 6-tert-butyl-8-fluoro-2,3-dimethylquinolin-4-yl methoxyacetate |
| B-279 | an individualized compound I | carbaryl |
| B-280 | an individualized compound I | carbofuran |
| B-281 | an individualized compound I | carbosulfan |
| B-282 | an individualized compound I | methomylthiodicarb |
| B-283 | an individualized compound I | bifenthrin |
| B-284 | an individualized compound I | cyfluthrin |
| B-285 | an individualized compound I | cypermethrin |
| B-286 | an individualized compound I | alpha-cypermethrin |
| B-287 | an individualized compound I | zeta-cypermethrin |
| B-288 | an individualized compound I | deltamethrin |
| B-289 | an individualized compound I | esfenvalerate |
| B-290 | an individualized compound I | lambda-cyhalothrin |
| B-291 | an individualized compound I | permethrin |
| B-292 | an individualized compound I | tefluthrin |
| B-293 | an individualized compound I | diflubenzuron |
| B-294 | an individualized compound I | flufenoxuron |
| B-295 | an individualized compound I | lufenuron |
| B-296 | an individualized compound I | teflubenzuron |
| B-297 | an individualized compound I | spirotetramate |
| B-298 | an individualized compound I | clothianidin |
| B-299 | an individualized compound I | dinotefuran |
| B-300 | an individualized compound I | imidacloprid |
| B-301 | an individualized compound I | thiamethoxam |
| B-302 | an individualized compound I | acetamiprid |
| B-303 | an individualized compound I | thiacloprid |
| B-304 | an individualized compound I | endosulfan |
| B-305 | an individualized compound I | fipronil |
| B-306 | an individualized compound I | abamectin |
| B-307 | an individualized compound I | emamectin |
| B-308 | an individualized compound I | spinosad |
| B-309 | an individualized compound I | spinetoram |
| B-310 | an individualized compound I | hydramethylnon |
| B-311 | an individualized compound I | chlorfenapyr |
| B-312 | an individualized compound I | fenbutatin oxide |
| B-313 | an individualized compound I | indoxacarb |
| B-314 | an individualized compound I | metaflumizon |
| B-315 | an individualized compound I | flonicamid |
| B-316 | an individualized compound I | lubendiamid |
| B-317 | an individualized compound I | chlorantraniliprol |
| B-318 | an individualized compound I | cyazypyr (HGW86) |
| B-319 | an individualized compound I | cyflumetofen |
| B-320 | an individualized compound I | acetochlor |
| B-321 | an individualized compound I | dimethenamid |
| B-322 | an individualized compound I | metolachlor |
| B-323 | an individualized compound I | metazachlor |
| B-324 | an individualized compound I | glyphosate |
| B-325 | an individualized compound I | glufosinate |
| B-326 | an individualized compound I | sulfosate |
| B-327 | an individualized compound I | clodinafop |
| B-328 | an individualized compound I | fenoxaprop |
| B-329 | an individualized compound I | fluazifop |
| B-330 | an individualized compound I | haloxyfop |
| B-331 | an individualized compound I | paraquat |
| B-332 | an individualized compound I | phenmedipham |
| B-333 | an individualized compound I | clethodim |
| B-334 | an individualized compound I | cycloxydim |
| B-335 | an individualized compound I | profoxydim |
| B-336 | an individualized compound I | sethoxydim |
| B-337 | an individualized compound I | tepraloxydim |
| B-338 | an individualized compound I | pendimethalin |
| B-339 | an individualized compound I | prodiamine |
| B-340 | an individualized compound I | trifluralin |

TABLE B-continued

Active compound composition, comprising an individualized compound I and a further active compounds from the groups A) to F)

| Row | Component 1 | Component 2 |
|---|---|---|
| B-341 | an individualized compound I | acifluorfen |
| B-342 | an individualized compound I | bromoxynil |
| B-343 | an individualized compound I | imazamethabenz |
| B-344 | an individualized compound I | imazamox |
| B-345 | an individualized compound I | imazapic |
| B-346 | an individualized compound I | imazapyr |
| B-347 | an individualized compound I | imazaquin |
| B-348 | an individualized compound I | imazethapyr |
| B-349 | an individualized compound I | 2,4-dichlorophenoxyacetic acid (2,4-D) |
| B-350 | an individualized compound I | chloridazon |
| B-351 | an individualized compound I | clopyralid |
| B-352 | an individualized compound I | fluroxypyr |
| B-353 | an individualized compound I | picloram |
| B-354 | an individualized compound I | picolinafen |
| B-355 | an individualized compound I | bensulfuron |
| B-356 | an individualized compound I | chlorimuron-ethyl |
| B-357 | an individualized compound I | cyclosulfamuron |
| B-358 | an individualized compound I | iodosulfuron |
| B-359 | an individualized compound I | mesosulfuron |
| B-360 | an individualized compound I | metsulfuron-methyl |
| B-361 | an individualized compound I | nicosulfuron |
| B-362 | an individualized compound I | rimsulfuron |
| B-363 | an individualized compound I | triflusulfuron |
| B-364 | an individualized compound I | atrazine |
| B-365 | an individualized compound I | hexazinone |
| B-366 | an individualized compound I | diuron |
| B-367 | an individualized compound I | florasulam |
| B-368 | an individualized compound I | pyroxasulfon |
| B-369 | an individualized compound I | bentazone |
| B-370 | an individualized compound I | cinidon-ethlyl |
| B-371 | an individualized compound I | cinmethylin |
| B-372 | an individualized compound I | dicamba |
| B-373 | an individualized compound I | diflufenzopyr |
| B-374 | an individualized compound I | quinclorac |
| B-375 | an individualized compound I | quinmerac |
| B-376 | an individualized compound I | mesotrione |
| B-377 | an individualized compound I | saflufenacil |
| B-378 | an individualized compound I | topramezone |

The active compounds specified above as component 2, their preparation, and their action against harmful fungi are known (cf. http://www.alanwood.net/pesticides/); they are available commercially. The compounds with IUPAC nomenclature, their preparation, and their fungicidal activity are likewise known (cf. Can. J. Plant Sci. 48(6), 587-94, 1968; EP-A 141 31.7; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 05/120234; WO 05/123689; WO 05/123690; WO 05/63721; WO 05/87772; WO 05/87773; WO 06/15866; WO 06/87325; WO 06/87343; WO 07/82098; WO 07/90624).

The compositions for mixtures of active compounds are prepared in a known manner in the form of compositions comprising, in addition to the active compounds, a solvent or a solid carrier, for example in the manner stated for compositions of the compounds I.

With respect to the customary ingredients of such compositions, reference is made to what was said about the compositions comprising the compounds I.

The compositions for mixtures of active compounds are suitable as fungicides for controlling harmful fungi. They have excellent activity against a broad spectrum of phytopathogenic fungi including soil-borne pathogens originating in particular from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Furthermore, reference is made to what was said about the activity of the compounds I and the compositions comprising the compounds I.

SYNTHESIS EXAMPLES

With appropriate modification of the starting materials, the procedures given in the synthesis examples below were used to obtain further compounds I. The compounds produced in this manner are listed in Table C below. The corresponding physical data can be found in Table D.

Example 1

Preparation of N'-(4-{3-(3,4-dichlorophenoxy)-2-[methoxyimino]propoxy}-2,5-dimethylphenyl)-N-ethyl-N-methylformamidine (I-9)

1a) Preparation of O-methyl 1,3-dichloropropan-2-one oxime 7.0 g (55.1 mmol) of 1,3-dichloropropan-2-one were initially charged in 50 ml of ethanol, and 4.6 g (55.1 mmol) of O-methyl hydroxylamine hydrochloride were added with stirring at from 20 to 25° C. This mixture was stirred at from 20 to 25° C. for about 20 hours, adjusted to a pH between 8 and 9 using sat. NaHCO$_3$ solution and extracted with a methyl tert-butyl ether (MTBE)/n-pentane mixture (4:1). After washing with water, the combined organic phases were dried and then freed from the solvent. The title compound (7.2 g) was directly used further.

1b) Preparation of N'-(4-{3-chloro-2-[(E)-methoxyimino]propoxy}-2,5-dimethyl-phenyl)-N-ethyl-N-methylformamidine At from 0 to 5° C., 1.16 g (48.5 mmol) of sodium hydride were added a little at a time with stirring to 10.0 g (48.5 mmol) of N-ethyl-N'-(4-hydroxy-2,5-dimethylphenyl)-N-methylformamidine (cf. WO 2007/031513) in 50 ml of dimethylformamide (DMF), and the mixture was stirred for one hour. At from 0 to 5° C., this solution was added with stirring to a mixture of 15.1 g (97.0 mmol) of O-methyl 1,3-dichloropropan-2-one oxime and 5 ml of DMF, and stirring was continued at from 20 to 25° C. for about 5 hours. The mixture was added to 500 ml of water and extracted with MTBE. The combined organic phases were dried and then freed from the solvent. Chromatography on alumina using cyclohexane/MTBE mixtures gave 7.5 g of the title compound.

1c) Preparation of N''-(4-{3-(3,4-dichlorophenoxy)-2-[methoxyimino]propoxy}-2,5-dimethylphenyl)-N-ethyl-N-methylformamidine At from 20 to 25° C., 2.56 g (22.8 mmol) of potassium tert-butoxide were added a little at a time and with stirring to 3.72 g (22.8 mmol) of 3,4-dichlorophenol dissolved in 10 ml of dimethyl sulfoxide (DMSO), and stirring was continued for 4 hours at from 20 to 25° C. With stirring, this mixture was added dropwise to 6.2 g (19.2 mmol) of the title compound from Example 1b) in 10 ml of DMSO, and stirring was continued for about 20 hours. The reaction mixture was added to 200 ml of water, the pH was adjusted to 10 using Na$_2$CO$_3$ and the mixture was extracted with MTBE. The combined organic phases were dried and then freed from the solvent. Chromatography on alumina using cyclohexane/ethyl acetate mixtures gave 6.4 g of the title compound.

Example 2

Preparation of N'-(4-{2-(3,4-dichlorophenyl)-2-[methoxyimino]-1-methyl-ethoxy}-2,5-dimethylphenyl)-N-ethyl-N-methylformamidine (I-97)

2a) Preparation of 2-chloro-1-(3,4-dichlorophenyl)propan-1-one O-methyl oxime 2.0 g (8.4 mmol) of 2-chloro-1-(3,4-dichlorophenyl)propan-1-one were initially charged in 15 ml of ethanol, and 0.7 g (8.4 mmol) of O-methyl hydroxylamine hydrochloride were added with stirring at from 20 to 25° C. The mixture was stirred for about 20 hours, adjusted to a pH of from 8 to 9 using sat. NaHCO$_3$ solution and extracted with an MTBE/n-pentane mixture (4:1). After washing with water, the combined organic phases were dried and then freed from the solvent. The title compound (1.3 g) was directly used further.

2b) Preparation of N'-(4-{2-(3,4-dichlorophenyl)-2-[methoxyimino]-1-methylethoxy}-2,5-dimethylphenyl)-N-ethyl-N-methylformamidine At from 20 to 25° C., 0.23 g (2.08 mmol) of potassium tert-butoxide were added a little at a time with stirring to 0.43 g (2.08 mmol) of N-ethyl-N'-(4-hydroxy-2,5-dimethyl-phenyl)-N-methylformamidine dissolved in 5 ml of DMSO, and the mixture was stirred at from 20 to 25° C. for about one hour. With stirring, this mixture was added dropwise to 1.11 g (4.17 mmol) of the title compound from Example 2a) in 0.5 ml of DMSO, and the mixture was stirred for about 5 hours. The reaction mixture was added to 40 ml of water and extracted with MTBE. The combined organic phases were dried and then freed from the solvent. Chromatography on alumina using cyclohexane/ethyl acetate mixtures gave 1.26 g of the title compound.

Example 3

Preparation of N-ethyl-N'-(4-{2-[methoxyimino]cyclohexyloxy}-2,5-dimethyl-phenyl)-N-methylformamidine (I-259)

3a) Preparation of 2-chlorocyclohexanone O-methyl oxime 3.0 g (22.6 mmol) of 2-chlorocyclohexanone were initially charged in 30 ml of ethanol, and 1.9 g (22.6 mmol) of O-methyl hydroxylamine hydrochloride were added with stirring at from 20 to 25° C. This mixture was stirred for about 20 hours at from 20 to 25° C., adjusted with sat. NaHCO$_3$ solution to a pH between 7 and 8 and extracted with ethyl acetate. After washing with sat. NaCl solution, the combined organic phases were dried and then freed from the solvent. The title compound (3.4 g) was directly used further.

3b) Preparation of N-ethyl-N'-(4-{2-[methoxyimino]cyclohexyloxy}-2,5-dimethyl-phenyl)-N-methylformamidine At from 0 to 5° C., 239 mg (2.13 mmol) of potassium tert-butoxide and 26 mg 18-crown-6 (0.10 mmol) were added a little at a time and with stirring to 200 mg (0.97 mmol) of N-ethyl-N'-(4-hydroxy-2,5-dimethylphenyl)-N-methylformamidine (cf. WO 2007/031513) in 3 ml of DMSO, and stirring was continued for about 15 minutes. At from 0 to 5° C., a solution of 313 mg (1.94 mmol) of 2-chlorocyclohexanone O-methyl oxime in 0.5 ml of DMSO was added to this mixture with stirring, and stirring was continued for about 20 hours at from 20 to 25° C. With cooling and a little at a time, 50 ml of water were added, and the mixture was extracted with MTBE. The combined organic phases were dried and then freed from the solvent. Cheomatography on alumina using cyclohexane/MTBE mixtures gave 100 mg of the title compound.

TABLE C

Compounds of the formula I.9

| No. | R¹ | R² (# defines the bond to the skeleton) | R³ | R⁵ | R⁶ | L¹ | L² | L³ |
|---|---|---|---|---|---|---|---|---|
| C-1 | $CH_3$ | pyrazol-1-yl | H | $CH_3$ | $CH_2CH_3$ | $CH_3$ | $CH_3$ | H |
| C-2 | $CH_3$ | 1-methylpyrazol-5-yloxymethyl | H | $CH_3$ | $CH_2CH_3$ | $CH_3$ | $CH_3$ | H |
| C-3 | $CH_3$ | [1,2,4]-triazol-1-ylmethyl | H | $CH_3$ | $CH_2CH_3$ | $CH_3$ | $CH_3$ | H |
| C-4 | $CH_3$ | $COOCH_2CH_3$ | H | $CH_3$ | $CH_2CH_3$ | $CH_3$ | $CH_3$ | H |
| C-5 | $CH_3$ | $CH_2OCH_3$ | H | $CH_3$ | $CH_2CH_3$ | $CH_3$ | $CH_3$ | H |
| C-6 | $CH_3$ | $COOCH_3$ | H | $CH_3$ | $CH_2CH_3$ | $CH_3$ | $CH_3$ | H |
| C-7 | $CH_3$ | 3-bromophenoxymethyl | H | $CH_3$ | $CH_2CH_3$ | $CH_3$ | $CH_3$ | H |
| C-8 | $CH_3$ | 3-chlorophenoxymethyl | H | $CH_3$ | $CH_2CH_3$ | $CH_3$ | $CH_3$ | H |
| C-9 | $CH_3$ | 3,4-dichlorophenoxymethyl | H | $CH_3$ | $CH_2CH_3$ | $CH_3$ | $CH_3$ | H |
| C-10 | $CH_3$ | 3-trifluoromethylphenoxymethyl | H | $CH_3$ | $CH_2CH_3$ | $CH_3$ | $CH_3$ | H |
| C-11 | $CH_3$ | 4-chlorophenoxymethyl | H | $CH_3$ | $CH_2CH_3$ | $CH_3$ | $CH_3$ | H |
| C-12 | $CH_3$ | 3-fluorophenoxymethyl | H | $CH_3$ | $CH_2CH_3$ | $CH_3$ | $CH_3$ | H |
| C-13 | $CH_3$ | 4-fluorophenoxymethyl | H | $CH_3$ | $CH_2CH_3$ | $CH_3$ | $CH_3$ | H |
| C-14 | $CH_3$ | 2,4-dichlorophenoxymethyl | H | $CH_3$ | $CH_2CH_3$ | $CH_3$ | $CH_3$ | H |
| C-15 | $CH_3$ | 2-chloro-6-fluorophenoxymethyl | H | $CH_3$ | $CH_2CH_3$ | $CH_3$ | $CH_3$ | H |
| C-16 | $CH_3$ | 3,5-dimethoxyphenoxymethyl | H | $CH_3$ | $CH_2CH_3$ | $CH_3$ | $CH_3$ | H |
| C-17 | $CH_3$ | 3,4-dimethoxyphenoxymethyl | H | $CH_3$ | $CH_2CH_3$ | $CH_3$ | $CH_3$ | H |
| C-18 | $CH_3$ | 3,4-methylenedioxyphenoxymethyl | H | $CH_3$ | $CH_2CH_3$ | $CH_3$ | $CH_3$ | H |
| C-19 | $CH_3$ | (coumarin-7-yloxyethyl) | H | $CH_3$ | $CH_2CH_3$ | $CH_3$ | $CH_3$ | H |
| C-20 | $CH_3$ | (2,2,3,3-tetrafluorobenzodioxin-6-yloxyethyl) | H | $CH_3$ | $CH_2CH_3$ | $CH_3$ | $CH_3$ | H |
| C-21 | $CH_3$ | 3-difluoromethoxyphenoxymethyl | H | $CH_3$ | $CH_2CH_3$ | $CH_3$ | $CH_3$ | H |
| C-22 | $CH_3$ | 4-chloro-3-(phenylcarbonyl)phenoxymethyl | H | $CH_3$ | $CH_2CH_3$ | $CH_3$ | $CH_3$ | H |

TABLE C-continued

Compounds of the formula I.9

| No. | R¹ | R² (# defines the bond to the skeleton) | R³ | R⁵ | R⁶ | L¹ | L² | L³ |
|---|---|---|---|---|---|---|---|---|
| C-23 | $CH_3$ | 4-chloro-3-trifluoromethoxyphenoxymethyl | H | $CH_3$ | $CH_2CH_3$ | $CH_3$ | $CH_3$ | H |
| C-24 | $CH_3$ | 2,3-dichlorophenoxymethyl | H | $CH_3$ | $CH_2CH_3$ | $CH_3$ | $CH_3$ | H |
| C-25 | $CH_3$ | 3,5-dichlorophenoxymethyl | H | $CH_3$ | $CH_2CH_3$ | $CH_3$ | $CH_3$ | H |
| C-26 | $CH_3$ | 3-chloro-4-fluorophenoxymethyl | H | $CH_3$ | $CH_2CH_3$ | $CH_3$ | $CH_3$ | H |
| C-27 | $CH_3$ | 3-chloro-4-ethoxycarbonylphenoxymethyl | H | $CH_3$ | $CH_2CH_3$ | $CH_3$ | $CH_3$ | H |
| C-28 | $CH_3$ | 3-chloro-4-(phenylcarbonyl)phenoxymethyl | H | $CH_3$ | $CH_2CH_3$ | $CH_3$ | $CH_3$ | H |
| C-29 | $CH_3$ | 3-isopropylphenoxymethyl | H | $CH_3$ | $CH_2CH_3$ | $CH_3$ | $CH_3$ | H |
| C-30 | $CH_3$ | 4-tert-butylphenoxymethyl | H | $CH_3$ | $CH_2CH_3$ | $CH_3$ | $CH_3$ | H |
| C-31 | $CH_3$ | (4-methylpyrazol-1-yl)methyl | H | $CH_3$ | $CH_2CH_3$ | $CH_3$ | $CH_3$ | H |
| C-32 | $CH_3$ | 7-chloroquinolin-8-yloxyethyl (shown as structure) | H | $CH_3$ | $CH_2CH_3$ | $CH_3$ | $CH_3$ | H |
| C-33 | $CH_3$ | 7-chloroquinolin-8-yloxyethyl (shown as structure) | H | $CH_3$ | $CH_2CH_3$ | $CH_3$ | $CH_3$ | H |
| C-34 | $CH_3$ | (imidazolazol-1-yl)methyl | H | $CH_3$ | $CH_2CH_3$ | $CH_3$ | $CH_3$ | H |
| C-35 | $CH_3$ | (pyrazol-1-yl)methyl | H | $CH_3$ | $CH_2CH_3$ | $CH_3$ | $CH_3$ | H |
| C-36 | $CH_3$ | (pyridyl-3-oxy)methyl | H | $CH_3$ | $CH_2CH_3$ | $CH_3$ | $CH_3$ | H |
| C-37 | $CH_3$ | (2-methylpyridyl-5-oxy)methyl | H | $CH_3$ | $CH_2CH_3$ | $CH_3$ | $CH_3$ | H |
| C-38 | $CH_3$ | (3-chloropyridyl-5-oxy)methyl | H | $CH_3$ | $CH_2CH_3$ | $CH_3$ | $CH_3$ | H |
| C-39 | $CH_3$ | (2-trifluoromethylpyridyl-5-oxy)methyl | H | $CH_3$ | $CH_2CH_3$ | $CH_3$ | $CH_3$ | H |

TABLE C-continued

Compounds of the formula I.9

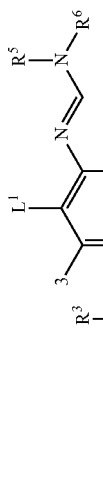

| No. | R¹ | R² (# defines the bond to the skeleton) | R³ | R⁵ | R⁶ | L¹ | L² | L³ |
|---|---|---|---|---|---|---|---|---|
| C-40 | CH₃ | (3-chloro-2-fluoropyridyl-5-oxy)methyl | H | CH₃ | CH₂CH₃ | CH₃ | CH₃ | H |
| C-41 | CH₃ | (pyrimidinyl-5-oxy)methyl | H | CH₃ | CH₂CH₃ | CH₃ | CH₃ | H |
| C-42 | CH₃ | (4-(4-methylphenyl)pyrazol-1-yl)methyl | H | CH₃ | CH₂CH₃ | CH₃ | CH₃ | H |
| C-43 | CH₃ | (3-(4-chlorophenyl)-4-methylpyrazol-1-yl)-methyl | H | CH₃ | CH₂CH₃ | CH₃ | CH₃ | H |
| C-44 | CH₃ | (3,4-dimethylpyrazol-1-yl)methyl | H | CH₃ | CH₂CH₃ | CH₃ | CH₃ | H |
| C-45 | CH₃ | 3-phenylphenoxymethyl | H | CH₃ | CH₂CH₃ | CH₃ | CH₃ | H |
| C-46 | CH₃ | 3-cyanophenoxymethyl | H | CH₃ | CH₂CH₃ | CH₃ | CH₃ | H |
| C-47 | CH₃ | 4-cyanophenoxymethyl | H | CH₃ | CH₂CH₃ | CH₃ | CH₃ | H |
| C-48 | CH₃ | isopropyloxymethyl | H | CH₃ | CH₂CH₃ | CH₃ | CH₃ | H |
| C-49 | CH₃ | cyanoaminomethyl | H | CH₃ | CH₂CH₃ | CH₃ | CH₃ | H |
| C-50 | CH₃ | 2,2,2-trifluoroethoxymethyl | H | CH₃ | CH₂CH₃ | CH₃ | CH₃ | H |
| C-51 | CH₃ | piperidin-1-ylmethyl | H | CH₃ | CH₂CH₃ | CH₃ | CH₃ | H |
| C-52 | CH₃ | morpholin-4-ylmethyl | H | CH₃ | CH₂CH₃ | CH₃ | CH₃ | H |
| C-53 | CH₃ | (4-chlorophenyl)methoxymethyl | H | CH₃ | CH₂CH₃ | CH₃ | CH₃ | H |
| C-54 | CH₃ | (s)-1-methyl-2,2,2-trifluoroethyl-aminomethyl | H | CH₃ | CH₂CH₃ | CH₃ | CH₃ | H |
| C-55 | CH₃ | (r)-1-methyl-2,2,2-trifluoroethyl-aminomethyl | H | CH₃ | CH₂CH₃ | CH₃ | CH₃ | H |
| C-56 | CH₃ | 2-(3,4-dimethoxyphenyl)ethoxymethyl | H | CH₃ | CH₂CH₃ | CH₃ | CH₃ | H |
| C-57 | CH₃ | 2-(3,4-dimethoxyphenyl)ethylamino-methyl | H | CH₃ | CH₂CH₃ | CH₃ | CH₃ | H |
| C-58 | CH₃ | 2-propaneiminoxymethyl | H | CH₃ | CH₂CH₃ | CH₃ | CH₃ | H |
| C-59 | CH₃ | 4-fluoro-3-trifluoromethylphenoxymethyl | H | CH₃ | CH₂CH₃ | Cl | H | H |
| C-60 | CH₃ | CH₂CN | H | CH₃ | CH₂CH₃ | CH₃ | CH₃ | H |
| C-61 | CH₂CH=CH₂ | COOCH₂CH₃ | H | CH₃ | CH₂CH₃ | CH₃ | CH₃ | H |
| C-62 | benzyl | 2,4-dichlorophenyl | H | CH₃ | CH₂CH₃ | CH₃ | CH₃ | H |
| C-63 | CH₃ | CH₃ | COOCH₂CH₃ | CH₃ | CH₂CH₃ | CH₃ | CH₃ | H |
| C-64 | CH₂CH=CH₂ | CH₂COOCH₂CH₃ | H | CH₃ | CH₂CH₃ | CH₃ | CH₃ | H |
| C-65 | CH₃ | CH₃ | H | CH₃ | CH₂CH₃ | CH₃ | CH₃ | H |
| C-66 | E-3-chloroallyl | CH₃ | H | CH₃ | CH₂CH₃ | CH₃ | CH₃ | H |
| C-67 | 4-chlorobenzyl | COOCH₂CH₃ | H | CH₃ | CH₂CH₃ | CH₃ | CH₃ | H |
| C-68 | CH₂CH₃ | COOCH₂CH₃ | H | CH₃ | CH₂CH₃ | CH₃ | CH₃ | H |
| C-69 | CH₂CH₃ | 3-trifluoromethylphenoxymethyl | H | CH₃ | CH₂CH₃ | CH₃ | CH₃ | H |

TABLE C-continued

Compounds of the formula I.9

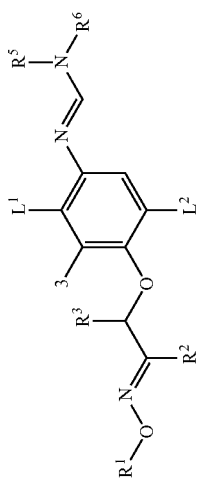

| No. | R¹ | R² (# defines the bond to the skeleton) | R³ | R⁵ | R⁶ | L¹ | L² | L³ |
|---|---|---|---|---|---|---|---|---|
| C-70 | E-3-chloroallyl | 3-trifluoromethylphenoxymethyl | H | CH₃ | CH₂CH₃ | CH₃ | CH₃ | H |
| C-71 | benzyl | 3-trifluoromethylphenoxymethyl | H | CH₃ | CH₂CH₃ | CH₃ | CH₃ | H |
| C-72 | CH₂COOCH₃ | 3-trifluoromethylphenoxymethyl | H | CH₃ | CH₂CH₃ | CH₃ | CH₃ | H |
| C-73 | C(CH₃)₃ | 3-trifluoromethylphenoxymethyl | H | CH₃ | CH₂CH₃ | CH₃ | CH₃ | H |
| C-74 | CH(CH₃)₂ | 3-trifluoromethylphenoxymethyl | H | CH₃ | CH₂CH₃ | CH₃ | CH₃ | H |
| C-75 | CH₂CH₂CH₃ | 3-trifluoromethylphenoxymethyl | H | CH₃ | CH₂CH₃ | CH₃ | CH₃ | H |
| C-76 | CH₂CF₃ | 3-trifluoromethylphenoxymethyl | H | CH₃ | CH₂CH₃ | CH₃ | CH₃ | H |
| C-77 | CH₂OCH₃ | 3-trifluoromethylphenoxymethyl | H | CH₃ | CH₂CH₃ | CH₃ | CH₃ | H |
| C-78 | CH₂CH₃ | 3-trifluoromethylphenoxymethyl | H | CH₃ | CH₂CH₃ | CH₃ | CH₃ | H |
| C-79 | E-3-chloroallyl | 3,4-dichlorophenoxymethyl | H | CH₃ | CH₂CH₃ | CH₃ | CH₃ | H |
| C-80 | benzyl | 3,4-dichlorophenoxymethyl | H | CH₃ | CH₂CH₃ | CH₃ | CH₃ | H |
| C-81 | CH₂COOCH₃ | 3,4-dichlorophenoxymethyl | H | CH₃ | CH₂CH₃ | CH₃ | CH₃ | H |
| C-82 | C(CH₃)₃ | 3,4-dichlorophenoxymethyl | H | CH₃ | CH₂CH₃ | CH₃ | CH₃ | H |
| C-83 | CH(CH₃)₂ | 3,4-dichlorophenoxymethyl | H | CH₃ | CH₂CH₃ | CH₃ | CH₃ | H |
| C-84 | CH₂CH₂CH₃ | 3,4-dichlorophenoxymethyl | H | CH₃ | CH₂CH₃ | CH₃ | CH₃ | H |
| C-85 | CH₂CF₃ | 3,4-dichlorophenoxymethyl | H | CH₃ | CH₂CH₃ | CH₃ | CH₃ | H |
| C-86 | CH₂OCH₃ | 3,4-dichlorophenoxymethyl | H | CH₃ | CH₂CH₃ | CH₃ | CH₃ | H |
| C-87 | CH₂CH₃ | 4-chloro-3-trifluoromethylphenoxymethyl | H | CH₃ | CH₂CH₃ | CH₃ | CH₃ | H |
| C-88 | E-3-chloroallyl | 4-chloro-3-trifluoromethylphenoxymethyl | H | CH₃ | CH₂CH₃ | CH₃ | CH₃ | H |
| C-89 | benzyl | 4-chloro-3-trifluoromethylphenoxymethyl | H | CH₃ | CH₂CH₃ | CH₃ | CH₃ | H |
| C-90 | CH₂COOCH₃ | 4-chloro-3-trifluoromethylphenoxymethyl | H | CH₃ | CH₂CH₃ | CH₃ | CH₃ | H |
| C-91 | C(CH₃)₃ | 4-chloro-3-trifluoromethylphenoxymethyl | H | CH₃ | CH₂CH₃ | CH₃ | CH₃ | H |
| C-92 | CH(CH₃)₂ | 4-chloro-3-trifluoromethylphenoxymethyl | H | CH₃ | CH₂CH₃ | CH₃ | CH₃ | H |
| C-93 | CH₂CH₂CH₃ | 4-chloro-3-trifluoromethylphenoxymethyl | H | CH₃ | CH₂CH₃ | CH₃ | CH₃ | H |
| C-94 | CH₂CF₃ | 4-chloro-3-trifluoromethylphenoxymethyl | H | CH₃ | CH₂CH₃ | CH₃ | CH₃ | H |
| C-95 | CH₂OCH₃ | 4-chloro-3-trifluoromethylphenoxymethyl | H | CH₃ | CH₂CH₃ | CH₃ | CH₃ | H |
| C-96 | CH₃ | 2,4-dichlorophenyl | H | CH₃ | CH₂CH₃ | CH₃ | CH₃ | H |
| C-97 | CH₃ | 3,4-dichlorophenyl | CH₃ | CH₃ | CH₂CH₃ | CH₃ | CH₃ | H |
| C-98 | CH₃ | 4-(methylsulfonylaminophenyl | H | CH₃ | CH₂CH₃ | CH₃ | CH₃ | H |

TABLE C-continued

Compounds of the formula I.9

| No. | R¹ | R² (# defines the bond to the skeleton) | R³ | R⁵ | R⁶ | L¹ | L² | L³ |
|---|---|---|---|---|---|---|---|---|
| C-99 | CH₃ | 2,5-difluorophenyl | H | CH₃ | CH₂CH₃ | CH₃ | CH₃ | H |
| C-100 | CH₃ | 5-chloro-2-methoxyphenyl | H | CH₃ | CH₂CH₃ | CH₃ | CH₃ | H |
| C-101 | CH₃ | 4-tert-butylphenyl | H | CH₃ | CH₂CH₃ | CH₃ | CH₃ | H |
| C-102 | CH₃ | 2-methoxyphenyl | H | CH₃ | CH₂CH₃ | CH₃ | CH₃ | H |
| C-103 | CH₃ | 4-chloro-2-fluoro-5-methylphenyl | H | CH₃ | CH₂CH₃ | CH₃ | CH₃ | H |
| C-104 | CH₃ | 4-methoxyphenyl | H | CH₃ | CH₂CH₃ | CH₃ | CH₃ | H |
| C-105 | CH₃ | 4-trifluoromethylphenyl | H | CH₃ | CH₂CH₃ | CH₃ | CH₃ | H |
| C-106 | CH₃ | 4-phenoxyphenyl | H | CH₃ | CH₂CH₃ | CH₃ | CH₃ | H |
| C-107 | CH₃ | 4-(4-chlorophenoxy)phenyl | H | CH₃ | CH₂CH₃ | CH₃ | CH₃ | H |
| C-108 | CH₃ | 4-(4-chlorophenyl)phenyl | H | CH₃ | CH₂CH₃ | CH₃ | CH₃ | H |
| C-109 | CH₃ | 4-(3-chloro-5-trifluoromethylpyridin-2-yloxy)phenyl | H | CH₃ | CH₂CH₃ | CH₃ | CH₃ | H |
| C-110 | CH₃ | 3-chlorophenyl | H | CH₃ | CH₂CH₃ | CH₃ | CH₃ | H |
| C-111 | CH₃ | 4-chlorophenyl | H | CH₃ | CH₂CH₃ | CH₃ | CH₃ | H |
| C-112 | CH₃ | (6-methyl-3-oxo-3,4-dihydro-2H-benzo[1,4]oxazin-#-yl) | H | CH₃ | CH₂CH₃ | CH₃ | CH₃ | H |
| C-113 | CH₃ | 4-phenylphenyl | H | CH₃ | CH₂CH₃ | CH₃ | CH₃ | H |
| C-114 | CH₃ | 4-(4-chlorophenyl)phenyl | H | CH₃ | CH₂CH₃ | CH₃ | CH₃ | H |
| C-115 | CH₃ | 3,4-dichlorophenyl | H | CH₃ | CH₂CH₃ | CH₃ | CH₃ | H |
| C-116 | CH₃ | 3,4-ethylenedioxyphenyl | H | CH₃ | CH₂CH₃ | CH₃ | CH₃ | H |
| C-117 | CH₃ | 4-chloro-3-trifluoromethylphenoxymethyl | H | CH₃ | CH₂CH₃ | CH₃ | CH₃ | H |
| C-118 | CH₃ | 4-fluoro-3-trifluoromethylphenoxymethyl | H | CH₃ | CH₂CH₃ | CH₃ | CH₃ | H |
| C-119 | CH₃ | 3,5-bistrifluoromethylphenoxymethyl | H | CH₃ | CH₂CH₃ | CH₃ | CH₃ | H |
| C-120 | CH₃ | 2-chloro-5-trifluoromethylphenoxymethyl | H | CH₃ | CH₂CH₃ | CH₃ | CH₃ | H |
| C-121 | CH₃ | 2-fluoro-5-trifluoromethylphenoxymethyl | H | CH₃ | CH₂CH₃ | CH₃ | CH₃ | H |
| C-122 | CH₃ | 3-fluoro-5-trifluoromethylphenoxymethyl | H | CH₃ | CH₂CH₃ | CH₃ | CH₃ | H |

TABLE C-continued

Compounds of the formula I.9

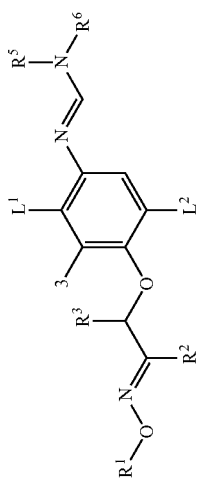

| No. | R$^1$ | R$^2$ (# defines the bond to the skeleton) | R$^3$ | R$^5$ | R$^6$ | L$^1$ | L$^2$ | L$^3$ |
|---|---|---|---|---|---|---|---|---|
| C-123 | CH$_3$ | 2-fluoro-3-trifluoromethylphenoxymethyl | H | CH$_3$ | CH$_2$CH$_3$ | CH$_3$ | CH$_3$ | H |
| C-124 | CH$_3$ | 2-chloro-3-trifluoromethylphenoxymethyl | H | CH$_3$ | CH$_2$CH$_3$ | CH$_3$ | CH$_3$ | H |
| C-125 | CH$_3$ | 3-chloro-2-fluoro-5-trifluoromethylphenoxymethyl | H | CH$_3$ | CH$_2$CH$_3$ | CH$_3$ | CH$_3$ | H |
| C-126 | CH$_3$ | 3-trifluoromethylphenoxymethyl | H | CH$_3$ | CH$_2$CH$_3$ | CH$_3$ | CH$_3$ | H |
| C-127 | CH$_3$ | 3-trifluoromethyl-4-cyanophenoxymethyl | H | CH$_3$ | CH$_2$CH$_3$ | CH$_3$ | CH$_3$ | H |
| C-128 | CH$_3$ | 2,5-dichlorophenoxymethyl | H | CH$_3$ | CH$_2$CH$_3$ | CH$_3$ | CH$_3$ | H |
| C-129 | CH$_3$ | 2,3,6-trichlorophenoxymethyl | H | CH$_3$ | CH$_2$CH$_3$ | CH$_3$ | CH$_3$ | H |
| C-130 | CH$_3$ | 3,4,5-trichlorophenoxymethyl | H | CH$_3$ | CH$_2$CH$_3$ | CH$_3$ | CH$_3$ | H |
| C-131 | CH$_3$ | 2,4,5-trichlorophenoxymethyl | H | CH$_3$ | CH$_2$CH$_3$ | CH$_3$ | CH$_3$ | H |
| C-132 | CH$_3$ | 2,3,4-trichlorophenoxymethyl | H | CH$_3$ | CH$_2$CH$_3$ | CH$_3$ | CH$_3$ | H |
| C-133 | CH$_3$ | 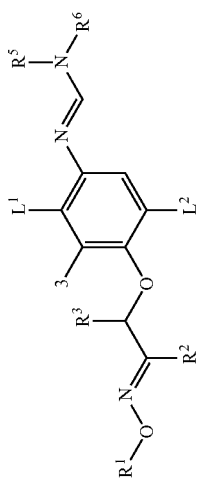 | | CH$_3$ | CH$_2$CH$_3$ | CH$_3$ | CH$_3$ | H |
| C-134 | CH$_3$ | 3-chloro-4-(3-chloro-5-trifluoromethylpyridin-2-yloxy)phenoxymethyl | H | CH$_3$ | CH$_2$CH$_3$ | CH$_3$ | CH$_3$ | H |
| C-135 | CH$_3$ | 3-chloro-4-bromophenoxymethyl | H | CH$_3$ | CH$_2$CH$_3$ | CH$_3$ | CH$_3$ | H |
| C-136 | CH$_3$ | 3-chloro-4-methylphenoxymethyl | H | CH$_3$ | CH$_2$CH$_3$ | CH$_3$ | CH$_3$ | H |
| C-137 | CH$_3$ | 2-chloro-4-trifluoromethylphenoxymethyl | H | CH$_3$ | CH$_2$CH$_3$ | CH$_3$ | CH$_3$ | H |
| C-138 | CH$_3$ | 4-methyl-2,3,5,6-tetrafluorophenoxymethyl | H | CH$_3$ | CH$_2$CH$_3$ | CH$_3$ | CH$_3$ | H |
| C-139 | CH$_3$ | 2,3,5,6-tetrafluoro-4-trifluoromethylphenoxymethyl | H | CH$_3$ | CH$_2$CH$_3$ | CH$_3$ | CH$_3$ | H |
| C-140 | CH$_3$ | 4-methylphenoxymethyl | H | CH$_3$ | CH$_2$CH$_3$ | CH$_3$ | CH$_3$ | H |

TABLE C-continued

Compounds of the formula I.9

| No. | R¹ | R² (# defines the bond to the skeleton) | R³ | R⁵ | R⁶ | L¹ | L² | L³ |
|---|---|---|---|---|---|---|---|---|
| C-141 | CH₃ | 5-chloro-8-quinolinyloxymethyl (via OCH₂#) | H | CH₃ | CH₂CH₃ | CH₃ | CH₃ | H |
| C-142 | CH₃ | 4-chloro-2-phenylphenoxymethyl | H | CH₃ | CH₂CH₃ | CH₃ | CH₃ | H |
| C-143 | CH₃ | 4-chloro-3,5-dimethylphenoxymethyl | H | CH₃ | CH₂CH₃ | CH₃ | CH₃ | H |
| C-144 | CH₃ | 4-chloro-3-methylphenoxymethyl | H | CH₃ | CH₂CH₃ | CH₃ | CH₃ | H |
| C-145 | CH₃ | 4-chloro-3-ethylphenoxymethyl | H | CH₃ | CH₂CH₃ | CH₃ | CH₃ | H |
| C-146 | CH₃ | 2,4-dichloro-5-methoxyphenoxymethyl | H | CH₃ | CH₂CH₃ | CH₃ | CH₃ | H |
| C-147 | CH₃ | 4-chloro-1-naphthoxymethyl | H | CH₃ | CH₂CH₃ | CH₃ | CH₃ | H |
| C-148 | CH₃ | 4-chloro-2,5-dimethylphenoxymethyl | H | CH₃ | CH₂CH₃ | CH₃ | CH₃ | H |
| C-149 | CH₃ | 3,4-difluorophenoxymethyl | H | CH₃ | CH₂CH₃ | CH₃ | CH₃ | H |
| C-150 | CH₃ | 5-bromo-2-chloro-4-iodophenoxymethyl | H | CH₃ | CH₂CH₃ | CH₃ | CH₃ | H |
| C-151 | CH₃ | 5-bromo-2-chloro-4-fluorophenoxymethyl | H | CH₃ | CH₂CH₃ | CH₃ | CH₃ | H |
| C-152 | CH₃ | 3-phenoxyphenoxymethyl | H | CH₃ | CH₂CH₃ | CH₃ | CH₃ | H |
| C-153 | CH₃ | 3-(4-chlorophenoxy)phenoxymethyl | H | CH₃ | CH₂CH₃ | CH₃ | CH₃ | H |
| C-154 | CH₃ | 3,4-dichlorophenoxymethyl | H | —CH₂CH₂CH₂CH₂CH(CH₃)— | | CH₃ | CH₃ | CH₃ |
| C-155 | CH₃ | N-ethyl-N-methylaminomethyl | H | —CH₂CH₂CH₂CH(CH₃)— | | CH₃ | CH₃ | CH₃ |
| C-156 | CH₃ | CH₂OCH₃ | H | —CH₂CH₂CH₂CH(CH₃)— | | CH₃ | CH₃ | H |
| C-157 | CH₃ | NH₂ | H | CH₃ | CH₂CH₃ | CH₃ | CH₃ | H |
| C-158 | CH₃ | (shown structure: 2,3-dichloro-4-(ethoxy)phenyl-NH-C(=O)-C(CH₃)(cyclohexyl)) | H | CH₃ | CH₂CH₃ | CH₃ | CH₃ | H |

TABLE C-continued

Compounds of the formula I.9

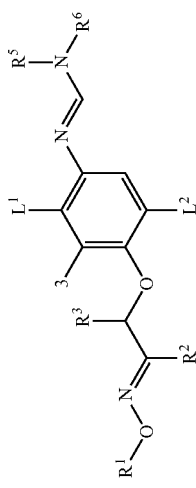

| No. | R¹ | R² (# defines the bond to the skeleton) | R³ | R⁵ | R⁶ | L¹ | L² | L³ |
|---|---|---|---|---|---|---|---|---|
| C-159 | CH₃ | 3-bromophenoxymethyl | H | CH₃ | CH(CH₃)₂ | CH₃ | CH₃ | H |
| C-160 | CH₃ | 3,4-dichlorophenoxymethyl | H | CH₃ | CH(CH₃)₂ | CH₃ | CH₃ | H |
| C-161 | CH₃ | 3-trifluoromethylphenoxymethyl | H | CH₃ | CH(CH₃)₂ | CH₃ | CH₃ | H |
| C-162 | CH₃ | 3-bromophenoxymethyl | H | CH₃ | (CH₂)₂CH₃ | CH₃ | CH₃ | H |
| C-163 | CH₃ | 3,4-dichlorophenoxymethyl | H | CH₃ | (CH₂)₂CH₃ | CH₃ | CH₃ | H |
| C-164 | CH₃ | 3-trifluoromethylphenoxymethyl | H | CH₃ | (CH₂)₂CH₃ | CH₃ | CH₃ | H |
| C-165 | CH₃ | 3-bromophenoxymethyl | H | CH₃ | sec-butyl | CH₃ | CH₃ | H |
| C-166 | CH₃ | 3,4-dichlorophenoxymethyl | H | CH₃ | sec-butyl | CH₃ | CH₃ | H |
| C-167 | CH₃ | 3-trifluoromethylphenoxymethyl | H | CH₃ | sec-butyl | CH₃ | CH₃ | H |
| C-168 | CH₃ | 3-bromophenoxymethyl | H | CH₃ | CH₂CH=CH₂ | CH₃ | CH₃ | H |
| C-169 | CH₃ | 3,4-dichlorophenoxymethyl | H | CH₃ | CH₂CH=CH₂ | CH₃ | CH₃ | H |
| C-170 | CH₃ | 3-trifluoromethylphenoxymethyl | H | CH₃ | CH₂CH=CH₂ | CH₃ | CH₃ | H |
| C-171 | CH₃ | 3-bromophenoxymethyl | H | CH₃ | cyclopropyl | CH₃ | CH₃ | H |
| C-172 | CH₃ | 3,4-dichlorophenoxymethyl | H | CH₃ | cyclopropyl | CH₃ | CH₃ | H |
| C-173 | CH₃ | 3-trifluoromethylphenoxymethyl | H | CH₃ | cyclopropyl | CH₃ | CH₃ | H |
| C-174 | CH₃ | 3-bromophenoxymethyl | H | H | CH(CH₃)CF₃ | CH₃ | CH₃ | H |
| C-175 | CH₃ | 3,4-dichlorophenoxymethyl | H | H | CH(CH₃)CF₃ | CH₃ | CH₃ | H |
| C-176 | CH₃ | 3-trifluoromethylphenoxymethyl | H | H | CH(CH₃)CF₃ | CH₃ | CH₃ | H |
| C-177 | CH₃ | 3-bromophenoxymethyl | H | —CH₂CH₂CH₂CH₂— | | CH₃ | CH₃ | CH₃ |
| C-178 | CH₃ | 3,4-dichlorophenoxymethyl | H | —CH₂CH₂CH₂CH₂— | | CH₃ | CH₃ | CH₃ |
| C-179 | CH₃ | 3-trifluoromethylphenoxymethyl | H | —CH₂CH₂CH₂CH₂— | | CH₃ | CH₃ | CH₃ |
| C-180 | CH₃ | 3-bromophenoxymethyl | H | —CH₂CH₂CH₂CH₂CH₂— | | CH₃ | CH₃ | CH₃ |
| C-181 | CH₃ | 3,4-dichlorophenoxymethyl | H | —CH₂CH₂CH₂CH₂CH₂— | | CH₃ | CH₃ | CH₃ |
| C-182 | CH₃ | 3-trifluoromethylphenoxymethyl | H | —CH₂CH₂CH₂CH₂CH₂— | | CH₃ | CH₃ | CH₃ |
| C-183 | CH₃ | 3-bromophenoxymethyl | H | —CH(CH₃)CH₂CH₂CH₂CH₂— | | CH₃ | CH₃ | CH₃ |
| C-184 | CH₃ | 3,4-dichlorophenoxymethyl | H | —CH(CH₃)CH₂CH₂CH₂CH₂— | | CH₃ | CH₃ | CH₃ |
| C-185 | CH₃ | 3-trifluoromethylphenoxymethyl | H | —CH(CH₃)CH₂CH₂CH₂CH₂— | | CH₃ | CH₃ | CH₃ |
| C-186 | CH₃ | 3-bromophenoxymethyl | H | —CH₂CH₂CH(CH₃)CH₂CH₂— | | CH₃ | CH₃ | CH₃ |
| C-187 | CH₃ | 3,4-dichlorophenoxymethyl | H | —CH₂CH₂CH(CH₃)CH₂CH₂— | | CH₃ | CH₃ | CH₃ |
| C-188 | CH₃ | 3-trifluoromethylphenoxymethyl | H | —CH₂CH₂CH(CH₃)CH₂CH₂— | | CH₃ | CH₃ | CH₃ |
| C-189 | CH₃ | 3-bromophenoxymethyl | H | —CH₂CH₂OCH₂CH₂— | | CH₃ | CH₃ | CH₃ |
| C-190 | CH₃ | 3,4-dichlorophenoxymethyl | H | —CH₂CH₂OCH₂CH₂— | | CH₃ | CH₃ | CH₃ |
| C-191 | CH₃ | 3-trifluoromethylphenoxymethyl | H | —CH₂CH₂OCH₂CH₂— | | CH₃ | CH₃ | CH₃ |
| C-192 | CH₃ | 3-bromophenoxymethyl | H | CH₃ | OCH₃ | CH₃ | CH₃ | H |
| C-193 | CH₃ | 3,4-dichlorophenoxymethyl | H | CH₃ | OCH₃ | CH₃ | CH₃ | H |
| C-194 | CH₃ | 3-trifluoromethylphenoxymethyl | H | CH₃ | OCH₃ | CH₃ | CH₃ | H |
| C-195 | CH₃ | 3,4-dichlorophenoxymethyl | H | CH₃ | CH₂CH₃ | H | H | H |

TABLE C-continued

Compounds of the formula I.9

| No. | $R^1$ | $R^2$ (# defines the bond to the skeleton) | $R^3$ | $R^5$ | $R^6$ | $L^1$ | $L^2$ | $L^3$ |
|---|---|---|---|---|---|---|---|---|
| C-196 | $CH_3$ | 3,4-dichlorophenoxymethyl | H | $CH_3$ | $CH_2CH_3$ | $CH_3$ | H | H |
| C-197 | $CH_3$ | 3,4-dichlorophenoxymethyl | H | $CH_3$ | $CH_2CH_3$ | $CH_2CH_3$ | H | H |
| C-198 | $CH_3$ | 3,4-dichlorophenoxymethyl | H | $CH_3$ | $CH_2CH_3$ | Cl | H | H |
| C-199 | $CH_3$ | 3,4-dichlorophenoxymethyl | H | $CH_3$ | $CH_2CH_3$ | $CF_3$ | H | H |
| C-200 | $CH_3$ | 3,4-dichlorophenoxymethyl | H | $CH_3$ | $CH_2CH_3$ | $CHF_2$ | H | H |
| C-201 | $CH_3$ | 3,4-dichlorophenoxymethyl | H | $CH_3$ | $CH_2CH_3$ | $CH_2F$ | H | H |
| C-202 | $CH_3$ | 3,4-dichlorophenoxymethyl | H | $CH_3$ | $CH_2CH_3$ | H | $CH_3$ | H |
| C-203 | $CH_3$ | 3,4-dichlorophenoxymethyl | H | $CH_3$ | $CH_2CH_3$ | $CH_2CH_3$ | $CH_3$ | H |
| C-204 | $CH_3$ | 3,4-dichlorophenoxymethyl | H | $CH_3$ | $CH_2CH_3$ | $CH(CH_3)_2$ | $CH_3$ | H |
| C-205 | $CH_3$ | 3,4-dichlorophenoxymethyl | H | $CH_3$ | $CH_2CH_3$ | $C(CH_3)_3$ | $CH_3$ | H |
| C-206 | $CH_3$ | 3,4-dichlorophenoxymethyl | H | $CH_3$ | $CH_2CH_3$ | $OCH_3$ | $CH_3$ | H |
| C-207 | $CH_3$ | 3,4-dichlorophenoxymethyl | H | $CH_3$ | $CH_2CH_3$ | $OCH_2CH_3$ | $CH_3$ | H |
| C-208 | $CH_3$ | 3,4-dichlorophenoxymethyl | H | $CH_3$ | $CH_2CH_3$ | Cl | $CH_3$ | H |
| C-209 | $CH_3$ | 3,4-dichlorophenoxymethyl | H | $CH_3$ | $CH_2CH_3$ | Br | $CH_3$ | H |
| C-210 | $CH_3$ | 3,4-dichlorophenoxymethyl | H | $CH_3$ | $CH_2CH_3$ | F | $CH_3$ | H |
| C-211 | $CH_3$ | 3,4-dichlorophenoxymethyl | H | $CH_3$ | $CH_2CH_3$ | CN | $CH_3$ | H |
| C-212 | $CH_3$ | 3,4-dichlorophenoxymethyl | H | $CH_3$ | $CH_2CH_3$ | $CF_3$ | $CH_3$ | H |
| C-213 | $CH_3$ | 3,4-dichlorophenoxymethyl | H | $CH_3$ | $CH_2CH_3$ | $CHF_2$ | $CH_3$ | H |
| C-214 | $CH_3$ | 3,4-dichlorophenoxymethyl | H | $CH_3$ | $CH_2CH_3$ | $CH_2F$ | $CH_3$ | H |
| C-215 | $CH_3$ | 3,4-dichlorophenoxymethyl | H | $CH_3$ | $CH_2CH_3$ | $CH_2CF_3$ | $CH_3$ | H |
| C-216 | $CH_3$ | 3,4-dichlorophenoxymethyl | H | $CH_3$ | $CH_2CH_3$ | $CHFCHF_2$ | $CH_3$ | H |
| C-217 | $CH_3$ | 3,4-dichlorophenoxymethyl | H | $CH_3$ | $CH_2CH_3$ | $OCF_3$ | $CH_3$ | H |
| C-218 | $CH_3$ | 3,4-dichlorophenoxymethyl | H | $CH_3$ | $CH_2CH_3$ | $OCHF_2$ | $CH_3$ | H |
| C-219 | $CH_3$ | 3,4-dichlorophenoxymethyl | H | $CH_3$ | $CH_2CH_3$ | $CCl_3$ | $CH_3$ | H |
| C-220 | $CH_3$ | 3,4-dichlorophenoxymethyl | H | $CH_3$ | $CH_2CH_3$ | $CHCl_2$ | $CH_3$ | H |
| C-221 | $CH_3$ | 3,4-dichlorophenoxymethyl | H | $CH_3$ | $CH_2CH_3$ | H | $CH_2CH_3$ | H |
| C-222 | $CH_3$ | 3,4-dichlorophenoxymethyl | H | $CH_3$ | $CH_2CH_3$ | $CH_3$ | $CH_2CH_3$ | H |
| C-223 | $CH_3$ | 3,4-dichlorophenoxymethyl | H | $CH_3$ | $CH_2CH_3$ | $CH_3$ | $CH(CH_3)_2$ | H |
| C-224 | $CH_3$ | 3,4-dichlorophenoxymethyl | H | $CH_3$ | $CH_2CH_3$ | $OCH_3$ | $OCH_3$ | H |
| C-225 | $CH_3$ | 3,4-dichlorophenoxymethyl | H | $CH_3$ | $CH_2CH_3$ | $OCH_3$ | $OCH_3$ | H |
| C-226 | $CH_3$ | 3,4-dichlorophenoxymethyl | H | $CH_3$ | $CH_2CH_3$ | $CH_3$ | Cl | H |
| C-227 | $CH_3$ | 3,4-dichlorophenoxymethyl | H | $CH_3$ | $CH_2CH_3$ | H | Cl | H |
| C-228 | $CH_3$ | 3,4-dichlorophenoxymethyl | H | $CH_3$ | $CH_2CH_3$ | $CF_3$ | Cl | H |
| C-229 | $CH_3$ | 3,4-dichlorophenoxymethyl | H | $CH_3$ | $CH_2CH_3$ | $OCH_3$ | Cl | H |
| C-230 | $CH_3$ | 3,4-dichlorophenoxymethyl | H | $CH_3$ | $CH_2CH_3$ | $CHF_2$ | Cl | H |
| C-231 | $CH_3$ | 3,4-dichlorophenoxymethyl | H | $CH_3$ | $CH_2CH_3$ | $CFH_2$ | Cl | H |
| C-232 | $CH_3$ | 3,4-dichlorophenoxymethyl | H | $CH_3$ | $CH_2CH_3$ | Cl | Cl | H |
| C-233 | $CH_3$ | 3,4-dichlorophenoxymethyl | H | $CH_3$ | $CH_2CH_3$ | $CH_3$ | Br | H |

TABLE C-continued

Compounds of the formula I.9

| No. | R¹ | R² (# defines the bond to the skeleton) | R³ | R⁵ | R⁶ | L¹ | L² | L³ |
|---|---|---|---|---|---|---|---|---|
| C-234 | CH₃ | 3,4-dichlorophenoxymethyl | H | CH₃ | CH₂CH₃ | H | Br | H |
| C-235 | CH₃ | 3,4-dichlorophenoxymethyl | H | CH₃ | CH₂CH₃ | CF₃ | Br | H |
| C-236 | CH₃ | 3,4-dichlorophenoxymethyl | H | CH₃ | CH₂CH₃ | OCH₃ | Br | H |
| C-237 | CH₃ | 3,4-dichlorophenoxymethyl | H | CH₃ | CH₂CH₃ | CHF₂ | Br | H |
| C-238 | CH₃ | 3,4-dichlorophenoxymethyl | H | CH₃ | CH₂CH₃ | CH₂F | Br | H |
| C-239 | CH₃ | 3,4-dichlorophenoxymethyl | H | CH₃ | CH₂CH₃ | Cl | Br | H |
| C-240 | CH₃ | 3,4-dichlorophenoxymethyl | H | CH₃ | CH₂CH₃ | OCF₃ | Br | H |
| C-241 | CH₃ | 3,4-dichlorophenoxymethyl | H | CH₃ | CH₂CH₃ | H | F | H |
| C-242 | CH₃ | 3,4-dichlorophenoxymethyl | H | CH₃ | CH₂CH₃ | CH₃ | F | H |
| C-243 | CH₃ | 3,4-dichlorophenoxymethyl | H | CH₃ | CH₂CH₃ | H | CF₃ | H |
| C-244 | CH₃ | 3,4-dichlorophenoxymethyl | H | CH₃ | CH₂CH₃ | CH₃ | CH₃ | H |
| C-245 | | —CH₂CH₂— | | CH₃ | CH₂CH₃ | CH₃ | CH₃ | CH₃ |
| C-246 | | —CH₂CH₂— | | CH₃ | CH₂CH₃ | CH₃ | CH₃ | CH₃ |
| C-247 | | —CH₂CH₂CH₂— | | CH₃ | CH₂CH₃ | CH₃ | CH₃ | CH₃ |
| C-248 | CH₃ | —CH₂CH₂— | | CH₃ | CH₂CH₃ | CH₃ | CH₃ | CH₃ |
| C-249 | CH₂CH₃ | —CH₂CH₂— | | CH₃ | CH₂CH₃ | CH₃ | CH₃ | CH₃ |
| C-250 | CH₂CH₂CH₃ | —CH₂CH₂— | | CH₃ | CH₂CH₃ | CH₃ | CH₃ | CH₃ |
| C-251 | CH(CH₃)₂ | —CH₂CH₂— | | CH₃ | CH₂CH₃ | CH₃ | CH₃ | CH₃ |
| C-252 | CH₂CH₂CH₂CH₃ | —CH₂CH₂— | | CH₃ | CH₂CH₃ | CH₃ | CH₃ | CH₃ |
| C-253 | C(CH₃)₃ | —CH₂CH₂— | | CH₃ | CH₂CH₃ | CH₃ | CH₃ | CH₃ |
| C-254 | E-3-chloroallyl | —CH₂CH₂— | | CH₃ | CH₂CH₃ | CH₃ | CH₃ | CH₃ |
| C-255 | benzyl | —CH₂CH₂— | | CH₃ | CH₂CH₃ | CH₃ | CH₃ | CH₃ |
| C-256 | phenyl | —CH₂CH₂— | | CH₃ | CH₂CH₃ | CH₃ | CH₃ | CH₃ |
| C-257 | CH₂OCH₃ | —CH₂CH₂— | | CH₃ | CH₂CH₃ | CH₃ | CH₃ | CH₃ |
| C-258 | CH₂CF₃ | —CH₂CH₂— | | CH₃ | CH₂CH₃ | CH₃ | CH₃ | CH₃ |
| C-259 | CH₃ | —CH₂CH₂CH₂— | | CH₃ | CH₂CH₃ | CH₃ | CH₃ | CH₃ |
| C-260 | CH₂CH₃ | —CH₂CH₂CH₂— | | CH₃ | CH₂CH₃ | CH₃ | CH₃ | CH₃ |
| C-261 | CH₂CH₂CH₃ | —CH₂CH₂CH₂— | | CH₃ | CH₂CH₃ | CH₃ | CH₃ | CH₃ |
| C-262 | CH(CH₃)₂ | —CH₂CH₂CH₂— | | CH₃ | CH₂CH₃ | CH₃ | CH₃ | CH₃ |
| C-263 | CH₂CH₂CH₂CH₃ | —CH₂CH₂CH₂— | | CH₃ | CH₂CH₃ | CH₃ | CH₃ | CH₃ |
| C-264 | C(CH₃)₃ | —CH₂CH₂CH₂— | | CH₃ | CH₂CH₃ | CH₃ | CH₃ | CH₃ |
| C-265 | E-3-chloroallyl | —CH₂CH₂CH₂— | | CH₃ | CH₂CH₃ | CH₃ | CH₃ | CH₃ |
| C-266 | benzyl | —CH₂CH₂CH₂— | | CH₃ | CH₂CH₃ | CH₃ | CH₃ | CH₃ |
| C-267 | phenyl | —CH₂CH₂CH₂— | | CH₃ | CH₂CH₃ | CH₃ | CH₃ | CH₃ |
| C-268 | CH₂OCH₃ | —CH₂CH₂CH₂— | | CH₃ | CH₂CH₃ | CH₃ | CH₃ | CH₃ |
| C-269 | CH₂CF₃ | —CH₂CH₂CH₂— | | CH₃ | CH₂CH₃ | CH₃ | CH₃ | CH₃ |
| C-270 | CH₃ | —CH₂CH₂CH₂CH₂— | | CH₃ | CH₂CH₃ | CH₃ | CH₃ | CH₃ |
| C-271 | CH₂CH₃ | —CH₂CH₂CH₂CH₂— | | CH₃ | CH₂CH₃ | CH₃ | CH₃ | CH₃ |

TABLE C-continued

Compounds of the formula I.9

| No. | R¹ | R² (# defines the bond to the skeleton) | R³ | R⁵ | R⁶ | L¹ | L² | L³ |
|---|---|---|---|---|---|---|---|---|
| C-272 | $CH_2CH_2CH_3$ | —$CH_2CH_2CH_2CH_2$—# | | $CH_3$ | $CH_2CH_3$ | $CH_3$ | $CH_3$ | $CH_3$ |
| C-273 | $CH(CH_3)_2$ | —$CH_2CH_2CH_2CH_2$—# | | $CH_3$ | $CH_2CH_3$ | $CH_3$ | $CH_3$ | $CH_3$ |
| C-274 | $CH_2CH_2CH_2CH_3$ | —$CH_2CH_2CH_2CH_2$—# | | $CH_3$ | $CH_2CH_3$ | $CH_3$ | $CH_3$ | $CH_3$ |
| C-275 | $C(CH_3)_3$ | —$CH_2CH_2CH_2CH_2$—# | | $CH_3$ | $CH_2CH_3$ | $CH_3$ | $CH_3$ | $CH_3$ |
| C-276 | E-3-chloroallyl | —$CH_2CH_2CH_2CH_2$—# | | $CH_3$ | $CH_2CH_3$ | $CH_3$ | $CH_3$ | $CH_3$ |
| C-277 | benzyl | —$CH_2CH_2CH_2CH_2$—# | | $CH_3$ | $CH_2CH_3$ | $CH_3$ | $CH_3$ | $CH_3$ |
| C-278 | phenyl | —$CH_2CH_2CH_2CH_2$—# | | $CH_3$ | $CH_2CH_3$ | $CH_3$ | $CH_3$ | $CH_3$ |
| C-279 | $CH_2OCH_3$ | —$CH_2CH_2CH_2CH_2$—# | | $CH_3$ | $CH_2CH_3$ | $CH_3$ | $CH_3$ | $CH_3$ |
| C-280 | $CH_2CF_3$ | —$CH_2CH_2CH_2CH_2$—# | | $CH_3$ | $CH_2CH_3$ | $CH_3$ | $CH_3$ | $CH_3$ |
| C-281 | $CH_3$ | —(CH)[O-(3,4-dichlorophenyl)]-(CH$_2$)$_2$— | | $CH_3$ | $CH_2CH_3$ | $CH_3$ | $CH_3$ | $CH_3$ |
| C-282 | $CH_3$ | *—(CH)[O-(3-bromophenyl)]-(CH$_2$)$_2$— | | $CH_3$ | $CH_2CH_3$ | $CH_3$ | $CH_3$ | $CH_3$ |
| C-283 | $CH_3$ | *—(CH)[O-(3-trifluoromethylphenyl)]-(CH$_2$)$_2$— | | $CH_3$ | $CH_2CH_3$ | $CH_3$ | $CH_3$ | $CH_3$ |
| C-284 | $CH_3$ | —(CH)[O-(3,4-dichlorophenyl)]-(CH$_2$)$_3$— | | $CH_3$ | $CH_2CH_3$ | $CH_3$ | $CH_3$ | $CH_3$ |
| C-285 | $CH_3$ | *—(CH)[O-(3-bromophenyl)]-(CH$_2$)$_3$— | | $CH_3$ | $CH_2CH_3$ | $CH_3$ | $CH_3$ | $CH_3$ |
| C-286 | $CH_3$ | —(CH)[O-3-(trifluoromethyl)phenyl)]-(CH$_2$)$_3$—* | | $CH_3$ | $CH_2CH_3$ | $CH_3$ | $CH_3$ | $CH_3$ |
| C-287 | | —CH-(4-chlorophenyl)-(CH$_2$)$_2$—* | H | $CH_3$ | $CH_2CH_3$ | $CH_3$ | $CH_3$ | $CH_3$ |
| C-288 | | —CH-((R)-4-chlorophenyl)-(CH$_2$)$_2$—* | H | $CH_3$ | $CH_2CH_3$ | $CH_3$ | $CH_3$ | $CH_3$ |
| C-289 | | —CH-((S)-4-chlorophenyl)-(CH$_2$)$_2$—* | H | $CH_3$ | $CH_2CH_3$ | $CH_3$ | $CH_3$ | $CH_3$ |
| C-290 | | —CH-(3-trifluoromethylphenyl)-(CH$_2$)$_2$—* | | $CH_3$ | $CH_2CH_3$ | $CH_3$ | $CH_3$ | $CH_3$ |
| C-291 | | —CH(-3,4-dimethoxyphenyl)-(CH$_2$)$_2$—* | | $CH_3$ | $CH_2CH_3$ | $CH_3$ | $CH_3$ | $CH_3$ |

C-292

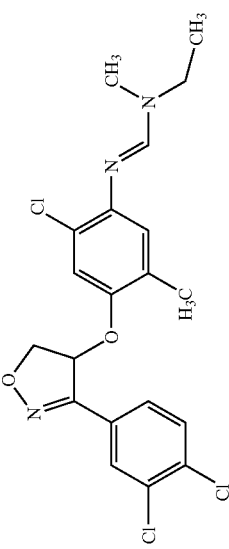

TABLE C-continued

Compounds of the formula I.9

| No. | R¹ | R² (# defines the bond to the skeleton) | R³ | R⁵ | R⁶ | L¹ | L² | L³ |
|---|---|---|---|---|---|---|---|---|
| C-293 | | | | | | | | L.9 |
| C-294 | CH₃ | —CO—CH₂—#* | | | | | | |
| C-295 | CH₃ | —CO—CH₂—#* | H | CH₃ | CH₂CH₃ | CH₃ | CH₃ | H |
| C-296 | | —CO—CH(4-chlorobenzyl)-#* | CH₃ | CH₃ | CH₂CH₃ | CH₃ | CH₃ | H |
| C-297 | | —CO—CH(4-chlorobenzyl)-#* | H | CH₃ | CH₂CH₃ | CH₃ | CH₃ | H |
| C-298 | | 4-fluoro-2-chlorophenoxymethyl | CH₃ | CH₃ | CH₂CH₃ | CH₃ | CH₃ | CH₃ |
| C-299 | | | H | CH₃ | CH₂CH₃ | CH₃ | H | CH₃ |
| C-300 | CH₃ | | H | CH₃ | CH₂CH₃ | CH₃ | H | CH₃ |
| C-301 | CH₃ | 2,4,5-trifluorophenoxymethyl | H | CH₃ | CH₂CH₃ | CH₃ | H | CH₃ |

TABLE C-continued

Compounds of the formula I.9

| No. | R¹ | R² (# defines the bond to the skeleton) | R³ | R⁵ | R⁶ | L¹ | L² | L³ |
|---|---|---|---|---|---|---|---|---|
| C-302 | $CH_3$ | 4,6-dimethyl-2-(1-oxo-1-ethyl)-phenoxymethyl | H | $CH_3$ | $CH_2CH_3$ | $CH_3$ | H | $CH_3$ |
| C-303 | $CH_3$ | 2,6-difluorophenoxymethyl | H | $CH_3$ | $CH_2CH_3$ | $CH_3$ | H | $CH_3$ |
| C-304 | $CH_3$ | 4-fluoro-2-trifluoromethylphenoxymethyl | H | $CH_3$ | $CH_2CH_3$ | $CH_3$ | H | $CH_3$ |
| C-305 | $CH_3$ | 2,4-difluorophenoxymethyl | H | $CH_3$ | $CH_2CH_3$ | $CH_3$ | H | $CH_3$ |
| C-306 | $CH_3$ | 3-chloro-4-fluorophenoxymethyl | H | $CH_3$ | $CH_2CH_3$ | $CH_3$ | H | $CH_3$ |
| C-307 | $CH_3$ | 4-fluoro-2-methylphenoxymethyl | H | $CH_3$ | $CH_2CH_3$ | $CH_3$ | H | $CH_3$ |
| C-308 | $CH_3$ | 2,3,4-trifluorophenoxymethyl | H | $CH_3$ | $CH_2CH_3$ | $CH_3$ | H | $CH_3$ |
| C-309 | $CH_3$ | 2,6-dimethylphenoxymethyl | H | $CH_3$ | $CH_2CH_3$ | $CH_3$ | H | $CH_3$ |
| C-310 | $CH_3$ | 4,5-difluoro-2-methylphenoxymethyl | H | $CH_3$ | $CH_2CH_3$ | $CH_3$ | H | $CH_3$ |
| C-311 | $CH_3$ | 3-bromo-4-fluorophenoxymethyl | H | $CH_3$ | $CH_2CH_3$ | $CH_3$ | H | $CH_3$ |
| C-312 | $CH_3$ | 2-bromo-4,5-difluorophenoxymethyl | H | $CH_3$ | $CH_2CH_3$ | $CH_3$ | H | $CH_3$ |
| C-313 | $CH_3$ | 2,4,6-trifluorophenoxymethyl | H | $CH_3$ | $CH_2CH_3$ | $CH_3$ | H | $CH_3$ |
| C-314 | $CH_3$ | 3,4,5-trifluorophenoxymethyl | H | $CH_3$ | $CH_2CH_3$ | $CH_3$ | H | $CH_3$ |
| C-315 | $CH_3$ | 4-fluoro-3-methylphenoxymethyl | H | $CH_3$ | $CH_2CH_3$ | $CH_3$ | H | $CH_3$ |
| C-316 | $CH_3$ | 2,6-dichloro-4-fluorophenoxymethyl | H | $CH_3$ | $CH_2CH_3$ | $CH_3$ | H | $CH_3$ |
| C-317 | $CH_3$ | 2,6-dichloro-4-methylphenoxymethyl | H | $CH_3$ | $CH_2CH_3$ | $CH_3$ | H | $CH_3$ |
| C-318 | $CH_2CH_3$ | 2-fluoro-5-trifluoromethylphenoxymethyl | H | $CH_3$ | $CH_2CH_3$ | $CH_3$ | H | $CH_3$ |
| C-319 | $CH_2CH_3$ | 4-fluoro-3-trifluoromethylphenoxymethyl | H | $CH_3$ | $CH_2CH_3$ | $CH_3$ | H | $CH_3$ |
| C-320 | $CH_2CH_3$ | 3-bromophenoxymethyl | H | $CH_3$ | $CH_2CH_3$ | $CH_3$ | H | $CH_3$ |
| C-321 | $CH_2CH_3$ | 2,3,6-trichlorophenoxymethyl | H | $CH_3$ | $CH_2CH_3$ | $CH_3$ | H | $CH_3$ |
| C-322 | $CH_2CH_3$ | 2-chloro-6-fluorophenoxymethyl | H | $CH_3$ | $CH_2CH_3$ | $CH_3$ | H | $CH_3$ |
| C-323 | $CH_2CH_3$ | 3,4-difluorophenoxymethyl | H | $CH_3$ | $CH_2CH_3$ | $CH_3$ | H | $CH_3$ |
| C-324 | $CH_2CH_3$ | 3,4-dichlorophenyl | $CH_3$ | $CH_3$ | $CH_2CH_3$ | $CH_3$ | H | $CH_3$ |
| C-325 | $CH_2CH_3$ | 2,4-dichlorophenyl | H | $CH_3$ | $CH_2CH_3$ | $CH_3$ | H | $CH_3$ |
| C-326 | 4-Methoxybenzyl | 3,4-dichlorophenyl | $CH_3$ | $CH_3$ | $CH_2CH_3$ | $CH_3$ | H | $CH_3$ |
| C-327 | 4-Methoxybenzyl | 3,4-dichlorophenyl | H | $CH_3$ | $CH_2CH_3$ | $CH_3$ | H | $CH_3$ |
| C-328 | $CH_3$ | CH=NOCH₃ | H | $CH_3$ | $CH_2CH_3$ | $CH_3$ | H | $CH_3$ |
| C-329 | $CH_3$ | 3-methylpyrazol-1-ylmethyl | H | $CH_3$ | $CH_2CH_3$ | $CH_3$ | H | $CH_3$ |
| C-330 | $CH_3$ | 4-phenylpyrazol-1-ylmethyl | H | $CH_3$ | $CH_2CH_3$ | $CH_3$ | H | $CH_3$ |
| C-331 | Cyclopropylmethyl | $CH_3$ | 3-Trifluoromethylphenyl | $CH_3$ | $CH_2CH_3$ | $CH_3$ | H | $CH_3$ |
| C-332 | Cyclopropylmethyl | $CH_3$ | H | $CH_3$ | $CH_2CH_3$ | $CH_3$ | H | $CH_3$ |
| C-333 | $CH_3$ | methoxycarbonylmethyl | H | $CH_3$ | $CH_2CH_3$ | $CH_3$ | H | $CH_3$ |

TABLE C-continued

Compounds of the formula I.9

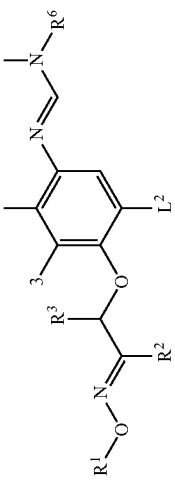

| No. | R¹ | R² (# defines the bond to the skeleton) | R³ | R⁵ | R⁶ | L¹ | L² | L³ |
|---|---|---|---|---|---|---|---|---|
| C-334 | 4-Chlorobenzyl | CH₃ | COOCH₃ | CH₃ | CH₂CH₃ | CH₃ | H | CH₃ |
| C-335 | CH₃ | 4-(4-fluorophenyl)pyrazol-1-ylmethyl | H | CH₃ | CH₂CH₃ | CH₃ | H | CH₃ |
| C-336 | CH₃ | CH₂CH₃ | H | CH₃ | CH₂CH₃ | CH₃ | H | CH₃ |
| C-337 | Cyclopropylmethyl | C(CH₃)₃ | COOCH₃ | CH₃ | CH₂CH₃ | CH₃ | H | CH₃ |
| C-338 | CH₃ | CH₂CH₃ | COOCH₃ | CH₃ | CH₂CH₃ | CH₃ | H | CH₃ |
| C-339 | CH₂CH₃ | CH₃ | COOCH₃ | CH₃ | CH₂CH₃ | CH₃ | H | CH₃ |
| C-340 | CH₃ | CH₃ | CH₃ | CH₃ | CH₂CH₃ | CH₃ | H | CH₃ |
| C-341 | CH₃ | CH₃ | H | CH₃ | CH₂CH₃ | CH₃ | H | CH₃ |
| C-342 | CH₃ | 3,5-bis(2-methylphenyl)pyrazol-1-ylmethyl | | | | | | |
| C-343 | CH₃ |  | H | CH₃ | CH₂CH₃ | CH₃ | H | CH₃ |
| C-344 | CH₃ | 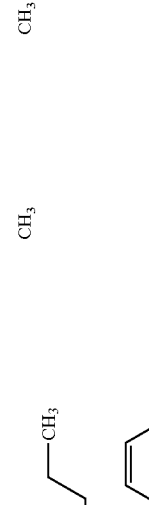 | CH₃ | CH₃ | CH₂CH₃ | CH₃ | H | CH₃ |
| C-345 | CH₃ | 3-(2,4-dichlorophenyl)pyrazol-1-ylmethyl | H | CH₃ | CH₂CH₃ | CH₃ | H | CH₃ |
| C-346 | CH₃ | 4-chloropyrazol-1-ylmethyl | H | CH₃ | CH₂CH₃ | CH₃ | H | CH₃ |
| C-347 | CH₃ | 4-methyl-3-phenylpyrazol-1-ylmethyl | H | CH₃ | CH₂CH₃ | CH₃ | H | CH₃ |
| C-348 | CH₃ | 3,4,5-trimethylpyrazol-1-ylmethyl | | | | | | |

TABLE C-continued

Compounds of the formula I.9

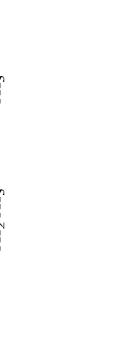

| No. | R¹ | R² (# defines the bond to the skeleton) | R³ | R⁵ | R⁶ | L¹ | L² | L³ |
|---|---|---|---|---|---|---|---|---|
| C-349 | CH₃ | # (indazolylmethyl) | H | CH₃ | CH₂CH₃ | CH₃ | H | CH₃ |
| C-350 | CH₃ | 3-methyl-4-phenylpyrazol-1-ylmethyl | H | CH₃ | CH₂CH₃ | CH₃ | H | CH₃ |
| C-351 | CH₃ | 3,5-dimethylpyrazol-1-ylmethyl | H | CH₃ | CH₂CH₃ | CH₃ | H | CH₃ |
| C-352 | CH₃ | 3-isopropylpyrazol-1-ylmethyl | H | CH₃ | CH₂CH₃ | CH₃ | H | CH₃ |
| C-353 | Allyl | CH₃ | H | CH₃ | CH₂CH₃ | CH₃ | H | CH₃ |
| C-354 | CH₃ | # (oxazolyl-phenyl-Cl) | H | CH₃ | CH₂CH₃ | CH₃ | H | CH₃ |
| C-355 | CH₂CH₃ | CH₃ | H | CH₃ | CH₂CH₃ | CH₃ | H | CH₃ |
| C-356 | CH₂CH(CH₃) | CH₃ | H | CH₃ | CH₂CH₃ | CH₃ | H | CH₃ |
| C-357 | 2-Chlorobenzyl | CH₃ | H | CH₃ | CH₂CH₃ | CH₃ | H | CH₃ |
| C-358 | 3-Chlorobenzyl | CH₃ | H | CH₃ | CH₂CH₃ | CH₃ | H | CH₃ |
| C-359 | CH₃ | # (phenoxypropyl-F) | H | CH₃ | CH₂CH₃ | CH₃ | H | CH₃ |
| C-360 | Benzyl | CH₃ | H | CH₃ | CH₂CH₃ | CH₃ | H | CH₃ |
| C-361 | 4-Cyanobenzyl | CH₃ | H | CH₃ | CH₂CH₃ | CH₃ | H | CH₃ |
| C-362 | 3-Ethoxybenzyl | CH₃ | H | CH₃ | CH₂CH₃ | CH₃ | H | CH₃ |
| C-363 | 3-Fluorobenzyl | CH₃ | H | CH₃ | CH₂CH₃ | CH₃ | H | CH₃ |
| C-364 | 2-Chloro-2-propen-1-yl | CH₃ | H | CH₃ | CH₂CH₃ | CH₃ | H | CH₃ |

TABLE C-continued

Compounds of the formula I.9

| No. | R¹ | R² (# defines the bond to the skeleton) | R³ | R⁵ | R⁶ | L¹ | L² | L³ |
|---|---|---|---|---|---|---|---|---|
| C-365 | 2-Buten-1-yl | CH₃ | H | CH₃ | CH₂CH₃ | CH₃ | H | CH₃ |
| C-366 | 4-(F₂HCO)-C₆H₄-CH(#)(CH₃) | CH₃ | H | CH₃ | CH₂CH₃ | CH₃ | H | CH₃ |
| C-367 | 4-(F₂HCO)-C₆H₄-CH(#)(CH₃) | CH₃ | H | CH₃ | CH₂CH₃ | CH₃ | H | CH₃ |
| C-368 | 2-F-C₆H₄-CH(#)(CH₃) | CH₃ | H | CH₃ | CH₂CH₃ | CH₃ | H | CH₃ |
| C-369 | 2,5-(CH₃)₂-C₆H₃-CH(#)(CH₃) | CH₃ | H | CH₃ | CH₂CH₃ | CH₃ | H | CH₃ |
| C-370 | 2-(CH₃)-C₆H₄-CH(#)(CH₃) | CH₃ | H | CH₃ | CH₂CH₃ | CH₃ | H | CH₃ |

TABLE C-continued

Compounds of the formula I.9

| No. | R¹ | R² (# defines the bond to the skeleton) | R³ | R⁵ | R⁶ | L¹ | L² | L³ |
|---|---|---|---|---|---|---|---|---|
| C-371 | 3-trifluoromethylbenzyl | CH₃ | H | CH₃ | CH₂CH₃ | CH₃ | H | CH₃ |
| C-372 | 3,4-dichlorobenzyl | CH₃ | H | CH₃ | CH₂CH₃ | CH₃ | H | CH₃ |
| C-373 | 4-methylbenzyl | CH₃ | H | CH₃ | CH₂CH₃ | CH₃ | H | CH₃ |
| C-374 | 2-phenylbenzyl | CH₃ | H | CH₃ | CH₂CH₃ | CH₃ | H | CH₃ |
| C-375 | 3-methyl-2-buten-1-yl | CH₃ | H | CH₃ | CH₂CH₃ | CH₃ | H | CH₃ |
| C-376 | CH(CH₃)₂ | CH₃ | H | CH₃ | CH₂CH₃ | CH₃ | H | CH₃ |
| C-377 | (CH₂)₂CH₃ | CH₃ | H | CH₃ | CH₂CH₃ | CH₃ | H | CH₃ |
| C-378 | 4-tert-butylbenzyl | CH₃ | H | CH₃ | CH₂CH₃ | CH₃ | H | CH₃ |
| C-379 | 2,4-difluorobenzyl | CH₃ | H | CH₃ | CH₂CH₃ | CH₃ | H | CH₃ |
| C-380 | (CH₂)₃CH₃ | CH₃ | H | CH₃ | CH₂CH₃ | CH₃ | H | CH₃ |
| C-381 | cyclohexylmethyl | CH₃ | H | CH₃ | CH₂CH₃ | CH₃ | H | CH₃ |
| C-382 | propargyl | CH₃ | H | CH₃ | CH₂CH₃ | CH₃ | H | CH₃ |
| C-383 | (CH₂)₅CH₃ | CH₃ | H | CH₃ | CH₂CH₃ | CH₃ | H | CH₃ |
| C-384 | 2-ethoxyethyl | CH₃ | H | CH₃ | CH₂CH₃ | CH₃ | H | CH₃ |
| C-385 | 1-butyn-3-yl | CH₃ | H | CH₃ | CH₂CH₃ | CH₃ | H | CH₃ |
| C-386 | 5-methyl-3-hexen-1-yl | CH₃ | H | CH₃ | CH₂CH₃ | CH₃ | H | CH₃ |
| C-387 | CH₂CH₃ | CH₃ | 3-Trifluoromethylphenyl | CH₃ | CH₂CH₃ | CH₃ | H | CH₃ |
| C-388 | CH₃ | CH₃ | 3-Trifluoromethylphenyl | CH₃ | CH₂CH₃ | CH₃ | H | CH₃ |
| C-389 | 2-phenoxyethyl | CH₂CH₃ | H | CH₃ | CH₂CH₃ | CH₃ | H | CH₃ |
| C-390 | 4-chlorobenzyl | CH₂CH₃ | H | CH₃ | CH₂CH₃ | CH₃ | H | CH₃ |
| C-391 | CH₂CH₃ | CH(CH₃)₃ | H | CH₃ | CH₂CH₃ | CH₃ | H | CH₃ |
| C-392 | CH₃ | CH₃ | H | CH₃ | CH₂CH₃ | CH₃ | H | CH₃ |
| C-393 | cyclopropylmethyl | CH₃ | CH₃ | CH₃ | CH₂CH₃ | CH₃ | H | CH₃ |
| C-394 | 2-phenoxyethyl | CH₃ | CH₃ | CH₃ | CH₂CH₃ | CH₃ | H | CH₃ |
| C-395 | 4-chlorobenzyl | CH₃ | CH₃ | CH₃ | CH₂CH₃ | CH₃ | H | CH₃ |
| C-396 | CH₂CH₃ | CH₃ | CH₃ | CH₃ | CH₂CH₃ | CH₃ | H | CH₃ |
| C-397 | 2,4-difluorobenzyl | 3,4-dichlorophenyl | H | CH₃ | CH₂CH₃ | CH₃ | H | CH₃ |
| C-398 | 2,4-difluorobenzyl | 2,4-dichlorophenyl | CH₃ | CH₃ | CH₂CH₃ | CH₃ | H | CH₃ |
| C-399 | (1-(4-chlorophenyl)propyl) | 3,4-dichlorophenyl | CH₃ | CH₃ | CH₂CH₃ | CH₃ | H | CH₃ |

TABLE C-continued

Compounds of the formula I.9

| No. | R¹ | R² (# defines the bond to the skeleton) | R³ | R⁵ | R⁶ | L¹ | L² | L³ |
|---|---|---|---|---|---|---|---|---|
| C-400 |  | 2,4-dichlorophenyl | H | CH$_3$ | CH$_2$CH$_3$ | CH$_3$ | H | CH$_3$ |
| C-401 |  | 3,4-dichlorophenyl | CH$_3$ | CH$_3$ | CH$_2$CH$_3$ | CH$_3$ | H | CH$_3$ |
| C-402 |  | 2,4-dichlorophenyl | H | CH$_3$ | CH$_2$CH$_3$ | CH$_3$ | H | CH$_3$ |
| C-403 |  | 3,4-dichlorophenyl | CH$_3$ | CH$_3$ | CH$_2$CH$_3$ | CH$_3$ | H | CH$_3$ |
| C-404 |  | 2,4-dichlorophenyl | H | CH$_3$ | CH$_2$CH$_3$ | CH$_3$ | H | CH$_3$ |
| C-405 | 2-chlorobenzyl | 2,4-dichlorophenyl | H | CH$_3$ | CH$_2$CH$_3$ | CH$_3$ | H | CH$_3$ |
| C-406 | CH$_3$ | 2,4-difluorophenyl | CH$_3$ | CH$_3$ | CH$_2$CH$_3$ | CH$_3$ | H | CH$_3$ |
| C-407 | CH$_3$ | 4-bromophenyl | CH$_3$ | CH$_3$ | CH$_2$CH$_3$ | CH$_3$ | H | CH$_3$ |
| C-408 | CH$_3$ | 3,4-difluorophenyl | H | CH$_3$ | CH$_2$CH$_3$ | CH$_3$ | H | CH$_3$ |

TABLE C-continued

Compounds of the formula I.9

| No. | R¹ | R² (# defines the bond to the skeleton) | R³ | R⁵ | R⁶ | L¹ | L² | L³ |
|---|---|---|---|---|---|---|---|---|
| C-409 | CH₃ | phenyl | CH₃ | CH₃ | CH₂CH₃ | CH₃ | H | CH₃ |
| C-410 | CH₃ | 4-methoxyphenyl | H | CH₃ | CH₂CH₃ | CH₃ | H | CH₃ |
| C-411 | CH₃ | # (2,3-dihydro-1,4-benzodioxin-6-yl) | H | CH₃ | CH₂CH₃ | CH₃ | H | CH₃ |
| C-412 | CH₃ | 4-bromophenyl | H | CH₃ | CH₂CH₃ | CH₃ | H | CH₃ |
| C-413 | CH₃ | 4-phenylphenyl | H | CH₃ | CH₂CH₃ | CH₃ | H | CH₃ |
| C-414 | CH₃ | 4-chlorophenyl | H | CH₃ | CH₂CH₃ | CH₃ | H | CH₃ |
| C-415 | CH₃ | 2,4-difluorophenyl | H | CH₃ | CH₂CH₃ | CH₃ | H | CH₃ |
| C-416 | CH₃ | 4-fluorophenyl | H | CH₃ | CH₂CH₃ | CH₃ | H | CH₃ |
| C-417 | CH₃ | phenyl | H | CH₃ | CH₂CH₃ | CH₃ | H | CH₃ |
| C-418 | CH₃ | # (3,4-dihydroquinolin-2(1H)-one-6-yl) | H | CH₃ | CH₂CH₃ | CH₃ | H | CH₃ |
| C-419 | CH₃ | 4-chloro-2-fluoro-5-methylphenyl | H | CH₃ | CH₂CH₃ | CH₃ | H | CH₃ |
| C-420 | CH₃ | 5-chloro-2-methoxyphenyl | H | CH₃ | CH₂CH₃ | CH₃ | H | CH₃ |
| C-421 | CH₃ | 4-phenylphenyl | CH₃ | CH₃ | CH₂CH₃ | CH₃ | H | CH₃ |
| C-422 | CH₃ | 3-acetamino-2,4-dimethylphenyl | H | CH₃ | CH₂CH₃ | CH₃ | H | CH₃ |
| C-423 | CH₃ | 2,5-dichlorophenyl | CH₃ | CH₃ | CH₂CH₃ | CH₃ | H | CH₃ |
| C-424 | CH₃ | 3-acetaminophenyl | H | CH₃ | CH₂CH₃ | CH₃ | H | CH₃ |
| C-425 | CH₃ | 2,4-dichloro-3-methylphenyl | CH₃ | CH₃ | CH₂CH₃ | CH₃ | H | CH₃ |
| C-426 | CH₃ | 4-fluorophenyl | CH₃ | CH₃ | CH₂CH₃ | CH₃ | H | CH₃ |
| C-427 | CH₃ | 4-tert-butylphenyl | H | CH₃ | CH₂CH₃ | CH₃ | H | CH₃ |
| C-428 | CH₃ | 2,3,4-trichlorophenyl | CH₃ | CH₃ | CH₂CH₃ | CH₃ | H | CH₃ |
| C-429 | CH₃ | 4-chlorophenyl | CH₃ | CH₃ | CH₂CH₃ | CH₃ | H | CH₃ |
| C-430 | CH₃ | 3,4-dichlorophenyl | CH₃ | CH₃ | CH₃ | CH₃ | H | CH₃ |
| C-431 | 2-chlorobenzyl | 3,4-dichlorophenyl | CH₃ | —CH₂CH₂CH₂CH—(CH₃)— | CH₃ | H | CH₃ |
| C-432 | 3-trifluoromethylbenzyl | 3,4-dichlorophenyl | CH₃ | CH₃ | CH₂CH₃ | CH₃ | H | CH₃ |

TABLE C-continued

Compounds of the formula I.9

| No. | R¹ | R² (# defines the bond to the skeleton) | R³ | R⁵ | R⁶ | L¹ | L² | L³ |
|---|---|---|---|---|---|---|---|---|
| C-433 | *H₃C–C(CH₃)(CH₃)–C₆H₄–CH(CH₃)–#* | 2,4-dichlorophenyl | H | CH₃ | CH₂CH₃ | CH₃ | H | CH₃ |
| C-434 | CH₃ | 3,4-dichlorophenyl | CH₃ | CH₃ | CH₂CH₃ | CH₃ | H | CH₃ |
| C-435 | CH₃ | 3-trifluoromethylphenoxymethyl | H | CH₃ | CH₂CH₃ | H | H | H |
| C-436 | CH₃ | 3-bromophenoxymethyl | H | CH₃ | CH₂CH₃ | H | H | H |
| C-437 | CH₃ | 3-trifluoromethylphenoxymethyl | H | CH₃ | CH₂CH₃ | CH₃ | H | H |
| C-438 | CH₃ | 3-bromophenoxymethyl | H | CH₃ | CH₂CH₃ | CH₃ | H | H |
| C-439 | CH₃ | 3-trifluoromethylphenoxymethyl | H | CH₃ | CH₂CH₃ | F | H | H |
| C-440 | CH₃ | 3-bromophenoxymethyl | H | CH₃ | CH₂CH₃ | F | H | H |
| C-441 | CH₃ | 3,4-dichlorophenoxymethyl | H | CH₃ | CH₂CH₃ | CH₃ | H | CH₃ |
| C-442 | 3-trifluoromethylbenzyl | 2,4-dichlorophenyl | H | CH₃ | CH₂CH₃ | CH₃ | H | CH₃ |
| C-443 | 4-chlorobenzyl | 2,4-dichlorophenyl | H | CH₃ | CH₂CH₃ | CH₃ | H | CH₃ |
| C-444 | E-3-chloro-2-propen-1-yl | 2,4-dichlorophenyl | H | CH₃ | CH₂CH₃ | CH₃ | H | CH₃ |
| C-445 | CH₃ | hydroxymethyl | H | CH₃ | CH₂CH₃ | CH₃ | H | CH₃ |
| C-446 | E-3-chloro-2-propen-1-yl | 3,4-dichlorophenyl | CH₃ | CH₃ | CH₂CH₃ | CH₃ | H | CH₃ |
| C-447 | benzyl | 3,4-dichlorophenyl | CH₃ | CH₃ | CH₂CH₃ | CH₃ | H | CH₃ |
| C-448 | 4-chlorobenzyl | 3,4-dichlorophenyl | CH₃ | CH₃ | CH₂CH₃ | CH₃ | H | CH₃ |
| C-449 | CH₃ | 4-cyano-3-trifluoromethyl-phenoxymethyl | H | CH₃ | CH₂CH₃ | CH₃ | H | CH₃ |
| C-450 | CH₃ | *—CH=CHCH₂CH₂—* | | CH₃ | CH₂CH₃ | CH₃ | CH₃ | H |
| C-451 | CH₃ | 4-fluoro-3-trifluoromethyl-phenoxymethyl | H | CH₃ | CH₂CH₃ | H | H | H |
| C-452 | CH₃ | 4-fluoro-3-trifluoromethyl-phenoxymethyl | H | CH₃ | CH₂CH₃ | F | H | H |
| C-453 | CH₂CH₃ | 4-fluoro-3-trifluoromethyl-phenoxymethyl | H | CH₃ | CH₂CH₃ | F | H | H |
| C-454 | CH₃ | 4-fluoro-3-trifluoromethyl-phenoxymethyl | H | CH₃ | CH₂CH₃ | Cl | H | H |
| C-455 | CH₂CH₃ | 4-fluoro-3-trifluoromethyl-phenoxymethyl | H | CH₃ | CH₂CH₃ | Cl | H | H |
| C-456 | CH₃ | 4-fluoro-3-trifluoromethyl-phenoxymethyl | H | CH₃ | CH₂CH₃ | H | H | CF₃ |

*In asymmetric divalent groups, the symbol (*) denotes the bond to position R².

TABLE D

Physical data for compounds of the formula I.9 according to Table C

| No. in Table C | Phys. data ($^1$H-NMR (CDCl$_3$, δ [ppm]); Mp [° C.]; HPLC/MS (R$_t$ [min])) |
|---|---|
| C-2 | $^1$H-NMR (CDCl$_3$): δ = 1.20 (t); 2.10 (s); 2.23 (s); 2.97 (s); 3.30 (br.); 3.45 (s); 3.55 (s); 3.97 (s); 4.60 (s); 4.75 (s); 4.90 (s); 4.99 (s); 5.55 (s); 5.60 (s); 6.50-6.70 (m); 7.30 (s); 7.40 (s). |
| C-3 | $^1$H-NMR (CDCl$_3$): δ = 1.20 (t); 2.10 (s); 2.20 (s); 3.00 (s); 3.37 (br.); 4.00 (s); 4.50 (s); 4.80 (s); 5.10 (s); 5.20 (s); 6.50-6.65 (m); 7.40 (s); 7.97 (s); 8.15. |
| C-4 | $^1$H-NMR (CDCl$_3$): δ = 1.15 (t); 1.30 (t); 2.10 (s); 2.20 (s); 3.00 (s); 3.37 (br.); 4.10 (s); 4.35 (q); 4.87 (s); 6.53 (s); 6.70 (s); 7.40 (s). |
| C-5 | $^1$H-NMR (CDCl$_3$): δ = 1.20 (t); 2.15 (s); 2.20 (s); 2.98 (s); 3.37 (br.); 3.40 (s); 3.90 (s); 3.95 (s); 4.17 (s); 4.32 (s); 4.57 (s); 4.85 (s); 6.50-6.70 (m); 7.40 (s). |
| C-6 | $^1$H-NMR (CDCl$_3$): δ = 1.15 (t); 2.10 (s); 2.20 (s); 3.00 (s); 3.35 (br.); 3.87 (s); 4.10 (s); 4.90 (s); 6.53 (s); 6.70 (s); 7.40 (s). |
| C-7 | $^1$H-NMR (CDCl$_3$): δ = 1.20 (t); 2.05 (s); 2.10 (s); 2.20 (s); 2.98 (s); 3.33 (br.); 3.98 (s); 4.63 (s); 4.70 (s); 4.90 (s); 4.93 (s); 6.55-7.15 (m); 7.40 (s). |
| C-8 | HPLC/MS: R$_t$ = 3.280 |
| C-9 | $^1$H-NMR (CDCl$_3$): δ = 1.20 (t); 2.05 (s); 2.10 (s); 2.23 (s); 2.95 (s); 3.33 (br.); 3.95 (s); 4.60 (s); 4.70 (s); 4.85 (s); 4.87 (s); 6.53 (s); 6.60 (s); 6.70-7.35 (m); 7.37 (s). |
| C-10 | $^1$H-NMR (CDCl$_3$): δ = 1.20 (t); 2.05 (s); 2.10 (s); 2.20 (s); 2.97 (s); 3.35 (br.); 3.98 (s); 4.64 (s); 4.80 (s); 4.90 (s); 4.97 (s); 6.53 (s); 6.63 (s); 7.00-7.40 (m). |
| C-13 | HPLC/MS: R$_t$ = 3.161 |
| C-14 | HPLC/MS: R$_t$ = 3.574 |
| C-15 | HPLC/MS: R$_t$ = 3.328 |
| C-16 | HPLC/MS: R$_t$ = 3.098 |
| C-18 | HPLC/MS: R$_t$ = 3.028 |
| C-19 | HPLC/MS: R$_t$ = 2.825 |
| C-20 | HPLC/MS: R$_t$ = 3.731 |
| C-21 | HPLC/MS: R$_t$ = 3.320 |
| C-23 | HPLC/MS: R$_t$ = 3.703 |
| C-24 | HPLC/MS: R$_t$ = 3.380 |
| C-25 | HPLC/MS: R$_t$ = 3.650 |
| C-26 | HPLC/MS: R$_t$ = 3.447 |
| C-29 | HPLC/MS: R$_t$ = 3.660 |
| C-30 | HPLC/MS: R$_t$ = 3.796 |
| C-31 | HPLC/MS: R$_t$ = 2.477 |
| C-33 | HPLC/MS: R$_t$ = 2.157 |
| C-34 | HPLC/MS: R$_t$ = 1.818 |
| C-35 | HPLC/MS: R$_t$ = 2.434 |
| C-36 | HPLC/MS: R$_t$ = 1.865 |
| C-37 | HPLC/MS: R$_t$ = 2.032 |
| C-38 | HPLC/MS: R$_t$ = 2.872 |
| C-42 | HPLC/MS: R$_t$ = 3.188 |
| C-43 | HPLC/MS: R$_t$ = 3.465 |
| C-44 | HPLC/MS: R$_t$ = 2.605 |
| C-45 | HPLC/MS: R$_t$ = 3.668 |
| C-46 | HPLC/MS: R$_t$ = 3.077 |
| C-47 | HPLC/MS: R$_t$ = 3.026 |
| C-53 | HPLC/MS: R$_t$ = 3.374 |
| C-56 | HPLC/MS: R$_t$ = 3.021 |
| C-57 | HPLC/MS: R$_t$ = 2.168 |
| C-59 | $^1$H-NMR (CDCl$_3$): δ = 1.23 (t); 3.01 (s); 3.23-3.60 (m); 3.96 (s); 4.65-4.78 (m); 4.91-5.05 (m); 6.78 (s); 6.81-6.91 (m); 7.01-7.20 (m). 7.35-7.58 (m); HPLC/MS: R$_t$ = 3.454 |
| C-61 | $^1$H-NMR (CDCl$_3$): δ = 1.20 (t); 1.32 (t); 2.09 (s); 2.20 (s); 2.98 (s); 3.33 (br.); 4.33 (q); 4.80 (m); 4.92 (s); 5.30 (m); 6.00 (m); 6.53 (s); 6.68 (s); 7.38 (s). |
| C-63 | $^1$H-NMR (CDCl$_3$): δ = 1.18 (t); 1.29 (t); 1.98 (s); 2.20 (s); 2.24 (s); 2.97 (s); 3.35 (br.); 3.92 (s); 4.27 (m); 5.13 (s); 6.54 (s); 6.62 (s); 7.38 (s). |
| C-64 | $^1$H-NMR (CDCl$_3$): δ = 1.20 (t); 2.00 (s); 2.15 (s); 2.20 (s); 2.98 (s); 3.33 (br.); 4.50 (s); 4.63 (d); 4.90 (s); 5.30-5.35 (m); 6.00 (m); 6.55 (s); 6.68 (s); 7.38 (s). |
| C-66 | $^1$H-NMR (CDCl$_3$): δ = 1.17 (t); 2.00 (s); 2.15 (s); 2.23 (s); 2.98 (s); 3.35 (br.); 4.50 (s); 4.57 (m); 6.10 (m); 6.27 (m); 6.55 (s); 6.68 (s); 7.38 (s). |
| C-67 | $^1$H-NMR (CDCl$_3$): δ = 1.22 (t); 1.98 (s); 2.16 (s); 2.19 (s); 2.98 (s); 3.35 (br.); 4.49 (s); 5.08 (s); 6.55 (s); 6.63 (s); 7.25-7.43 (m). |
| C-68 | $^1$H-NMR (CDCl$_3$): δ = 1.22 (t); 1.34 (t); 2.13 (s); 2.24 (s); 3.00 (s); 3.35 (br.); 4.35 (m); 4.40 (s); 6.53 (s); 6.72 (s); 7.38 (s). |
| C-69 | $^1$H-NMR (CDCl$_3$): δ = 1.22 (t); 1.32 (t); 2.06 (s); 2.25 (s); 2.98 (s); 3.35 (br.); 4.24 (q); 4.78 (s); 4.92 (s); 6.53 (s); 6.64 (s); 6.95-7.45 (m). |
| C-78 | $^1$H-NMR (CDCl$_3$): δ = 1.22 (t); 1.33 (f); 2.05 (s); 2.21 (s); 2.98 (s); 3.35 (br.); 4.22 (q); 4.72 (s); 4.90 (s); 6.55-7.40 (m). |
| C-82 | $^1$H-NMR (CDCl$_3$): δ = 1.22 (t); 1.30 (d); 2.06 (s); 2.22 (s); 3.02 (s); 3.35 (br.); 4.43 (m); 4.70 (s); 4.89 (s); 6.55-7.40 (m). |
| C-96 | $^1$H-NMR (CDCl$_3$): δ = 1.22 (t); 1.78 (s); 2.24 (s); 3.02 (s); 3.35 (br.); 4.03 (sw); 5.13 (s); 6.49 (s); 6.60 (s); 7.10-7.45 (m). |

TABLE D-continued

Physical data for compounds of the formula I.9 according to Table C

| No. in Table C | Phys. data ($^1$H-NMR (CDCl$_3$, δ [ppm]); Mp [° C.]; HPLC/MS (R$_t$ [min])) |
|---|---|
| C-97 | $^1$H-NMR (CDCl$_3$): δ = 1.20 (t); 1.43 (d); 2.08 (s); 2.23 (s); 3.00 (s); 3.33 (br.); 3.87 (s); 5.10 (q); 6.50 (s); 6.55 (s); 6.87 (s); 7.10-7.40 (m). |
| C-101 | HPLC/MS: R$_t$ = 3.323 |
| C-105 | $^1$H-NMR (CDCl$_3$): δ = 1.20 (t); 2.03 (s); 2.22 (s); 2.98 (s); 3.33 (br.); 3.98 (s); 4.65 (s); 4.78 (s); 4.90 (s); 4.98 (s); 6.52 (s); 6.62 (s); 7.00 (d); 7.38 (s); 7.54 (d). |
| C-107 | HPLC/MS: R$_t$ = 3.407 |
| C-109 | $^1$H-NMR (CDCl$_3$): δ = 1.20 (t); 2.00 (s); 2.20 (s); 2.98 (s); 3.35 (br.); 3.97 (s); 4.70 (s); 4.90 (s); 6.48 (s); 6.70 (s); 7.35 (s); 7.80 (s); 8.30 (s). |
| C-115 | HPLC/MS: R$_t$ = 3.421 |
| C-117 | $^1$H-NMR (CDCl$_3$): δ = 1.20 (t); 2.05 (s); 2.23 (s); 2.98 (s); 3.35 (br.); 3.98 (s); 4.63 (s); 4.73 (s); 4.88 (s); 4.98 (s); 6.55 (s); 6.60 (s); 7.00 (m); 7.20-7.40 (m). |
| C-118 | $^1$H-NMR (CDCl$_3$): δ = 1.20 (t); 2.05 (s); 2.24 (s); 2.98 (s); 3.35 (br.); 3.98 (s); 4.63 (s); 4.75 (s); 4.90 (s); 4.95 (s); 6.55 (s); 6.62 (s); 7.00-7.20 (m); 7.38 (s). |
| C-119 | $^1$H-NMR (CDCl$_3$): δ = 1.20 (t); 2.07 (s); 2.22 (s); 2.98 (s); 3.33 (br.); 3.98 (s); 4.01 (s); 4.63 (s); 4.83 (s); 4.90 (s); 5.03 (s); 6.52 (s); 6.62 (s); 7.35 (s); 7.38 (s); 7.47 (s). |
| C-120 | $^1$H-NMR (CDCl$_3$): δ = 1.20 (t); 2.05 (s); 2.22 (s); 2.98 (s); 3.33 (br.); 3.98 (s); 4.67 (s); 4.85 (s); 4.92 (s); 5.05 (s); 6.53 (s); 6.62 (s); 7.10-7.45 (m). |
| C-121 | $^1$H-NMR (CDCl$_3$): δ = 1.20 (t); 2.03 (s); 2.22 (s); 2.98 (s); 3.33 (br.); 3.98 (s); 4.67 (s); 4.87 (s); 4.92 (s); 5.05 (s); 6.52 (s); 6.62 (s); 7.10-7.40 (m). |
| C-122 | $^1$H-NMR (CDCl$_3$): δ = 1.20 (t); 2.05 (s); 2.22 (s); 2.98 (s); 3.33 (br.); 3.98 (s); 4.63 (s); 4.75 (s); 4.88 (s); 4.97 (s); 6.52 (s); 6.62 (s); 6.70-7.00 (m); 7.37 (s). |
| C-123 | $^1$H-NMR (CDCl$_3$): δ = 1.20 (t); 2.03 (s); 2.22 (s); 2.98 (s); 3.33 (br.); 3.98 (s); 4.67 (s); 4.85 (s); 4.92 (s); 5.05 (s); 6.52 (s); 6.62 (s); 7.10-7.30 (m); 7.38 (s). |
| C-124 | $^1$H-NMR (CDCl$_3$): δ = 1.20 (t); 2.03 (s); 2.20 (s); 2.98 (s); 3.33 (br.); 3.98 (s); 4.72 (s); 4.83 (s); 4.92 (s); 5.05 (s); 6.52 (s); 6.62 (s); 7.10-7.30 (m); 7.38 (s). |
| C-125 | $^1$H-NMR (CDCl$_3$): δ = 1.20 (t); 2.05 (s); 2.22 (s); 2.98 (s); 3.33 (br.); 3.98 (s); 4.67 (s); 4.89 (s); 4.92 (s); 5.05 (s); 6.52 (s); 6.60 (s); 7.10-7.30 (m); 7.38 (s). |
| C-128 | $^1$H-NMR (CDCl$_3$): δ = 1.20 (t); 2.05 (s); 2.10 (s); 2.20 (s); 2.98 (s); 3.33 (br.); 3.98 (s); 4.70 (s); 4.78 (s); 4.92 (s); 5.00 (s); 6.52 (s); 6.63 (s); 6.75 (s); 6.90-7.25 (m); 7.38 (s). |
| C-129 | $^1$H-NMR (CDCl$_3$): δ = 1.20 (t); 2.07 (s); 2.24 (s); 2.98 (s); 3.33 (br.); 3.97 (s); 4.80 (s); 4.97 (s); 6.55 (s); 6.62 (s); 7.10-7.25 (m); 7.38 (s). |
| C-130 | $^1$H-NMR (CDCl$_3$): δ = 1.20 (t); 2.08 (s); 2.24 (s); 2.99 (s); 3.35 (br.); 3.98 (s); 4.72 (s); 4.90 (s); 6.53 (s); 6.59 (s); 6.95-7.45 (m). |
| C-132 | $^1$H-NMR (CDCl$_3$): δ = 1.20 (t); 2.05 (s); 2.22 (s); 2.98 (s); 3.33 (br.); 3.98 (s); 4.70 (s); 4.80 (s); 4.92 (s); 5.00 (s); 6.52 (s); 6.62 (s); 6.83 (m); 7.30 (m); 7.38 (s). |
| C-133 | $^1$H-NMR (CDCl$_3$): δ = 1.20 (t); 1.46 (s); 2.08 (s); 2.24 (s); 2.98 (s); 3.05 (s); 3.35 (br.); 3.93 (s); 4.80 (s); 4.85 (s); 4.95 (s); 5.05 (s); 6.55 (s); 6.62 (s); 7.38 (s). |
| C-134 | $^1$H-NMR (CDCl$_3$): δ = 1.20 (t); 2.08 (s); 2.22 (s); 2.98 (s); 3.35 (br.); 3.98 (s); 4.72 (s); 4.83 (s); 4.92 (s); 5.04 (s); 6.52 (s); 6.62 (s); 7.00-7.25 (m); 7.38 (s); 8.00 (s); 8.28 (s). |
| C-136 | $^1$H-NMR (CDCl$_3$): δ = 1.20 (t); 2.05 (s); 2.10 (s); 2.20 (s); 2.27 (s); 2.98 (s); 3.33 (br.); 3.97 (s); 4.62 (s); 4.70 (s); 4.90 (s); 6.54 (s); 6.62 (s); 6.70-7.10 (m); 7.38 (s). |
| C-137 | $^1$H-NMR (CDCl$_3$): δ = 1.22 (t); 2.06 (s); 2.24 (s); 2.97 (s); 3.35 (br.); 3.97 (s); 4.87 (s); 4.90 (s); 6.52 (s); 6.63 (s); 6.90-7.60 (m). |
| C-139 | $^1$H-NMR (CDCl$_3$): δ = 1.32 (t); 2.07 (s); 2.33 (s); 3.28 (s); 3.50 (br.); 3.98 (s); 4.75 (s); 4.93 (s); 5.00 (s); 5.20 (s); 6.60 (s); 6.72 (s); 7.37 (s). |
| C-142 | $^1$H-NMR (CDCl$_3$): δ = 1.20 (t); 1.98 (s); 2.22 (s); 2.98 (s); 3.33 (br.); 3.94 (s); 4.68 (s); 4.76 (s); 4.93 (s); 4.95 (s); 6.52 (m); 6.90-7.50 (m). |
| C-143 | $^1$H-NMR (CDCl$_3$): δ = 1.20 (t); 2.08 (s); 2.20 (s); 2.32 (s); 2.98 (s); 3.33 (br.); 3.98 (s); 4.62 (s); 4.68 (s); 4.90 (s); 6.52 (s); 6.55 (s); 6.62 (s); 6.69 (s); 7.38 (s). |
| C-144 | $^1$H-NMR (CDCl$_3$): δ = 1.20 (t); 2.03 (s); 2.22 (s); 2.32 (s); 2.98 (s); 3.33 (br.); 3.98 (s); 4.62 (s); 4.69 (s); 4.90 (s); 6.52 (s); 6.62 (s); 6.65-6.80 (m); 7.18 (d); 7.38 (s). |
| C-145 | $^1$H-NMR (CDCl$_3$): δ = 1.20 (t); 2.03 (s); 2.09 (s); 2.20 (s); 2.67 (q); 2.98 (s); 3.33 (br.); 3.96 (s); 4.63 (s); 4.69 (s); 4.90 (s); 4.92 (s); 6.52 (s); 6.60-6.85 (m); 7.20 (d); 7.38 (s). |
| C-146 | $^1$H-NMR (CDCl$_3$): δ = 1.20 (t); 2.05 (s); 2.20 (s); 2.98 (s); 3.33 (br.); 3.85 (s); 3.98 (s); 4.65 (s); 4.80 (s); 4.90 (s); 5.02 (s); 6.50-6.75 (m); 7.33 (s); 7.38 (s). |
| C-147 | $^1$H-NMR (CDCl$_3$): δ = 1.20 (t); 1.99 (s); 2.08 (s); 2.18 (s); 2.98 (s); 3.33 (br.); 4.01 (s); 4.75 (s); 4.90 (s); 4.99 (s); 5.13 (s); 6.50 (s); 6.64 (s); 6.80 (m); 7.30-7.60 (m); 8.20 (m). |

TABLE D-continued

Physical data for compounds of the formula I.9 according to Table C

No. in
Table C   Phys. data ($^1$H-NMR (CDCl$_3$, δ [ppm]); Mp [° C.]; HPLC/MS (R$_t$ [min]))

C-148  $^1$H-NMR (CDCl$_3$): δ = 1.20 (t); 2.00 (s); 2.03 (s); 2.05 (s); 2.20 (s); 2.30 (s);
2.98 (s); 3.33 (br.); 3.98 (s); 4.65 (s); 4.70 (s); 4.90 (s); 4.92 (s);
6.52-6.74 (m); 7.38 (s).

C-149  $^1$H-NMR (CDCl$_3$): δ = 1.20 (t); 2.08 (s); 2.26 (s); 2.97 (s); 3.35 (br.); 3.98 (s);
4.68 (s); 4.90 (s); 6.53 (s); 6.63 (s); 6.70-7.45 (m).

C-151  $^1$H-NMR (CDCl$_3$): δ = 1.20 (t); 2.03 (s); 2.22 (s); 2.98 (s); 3.33 (br.); 3.55 (s);
4.35 (m); 4.84 (m); 6.29 (s); 6.52 (s); 6.60 (s); 7.09 (d); 7.36 (s).

C-152  $^1$H-NMR (CDCl$_3$): δ = 1.20 (t); 2.08 (s); 2.22 (s); 2.97 (s); 3.35 (br.); 3.96 (s);
4.72 (s); 4.90 (s); 6.55-7.45 (m).

C-154  $^1$H-NMR (CDCl$_3$): δ = 1.26 (d); 1.60-2.10 (m); 2.25 (s); 3.55 (m); 3.85 (br.);
3.98 (s); 4.63 (s); 4.70 (s); 4.90 (s); 6.55 (s); 6.62 (s); 6.65-7.30 (m);
7.57 (s).

C-155  $^1$H-NMR (CDCl$_3$): δ = 1.05 (t); 1.28 (d); 1.55-2.30 (m); 2.50 (q); 3.20 (s);
3.55 (m); 3.85 (br.); 3.95 (s); 4.60 (s); 4.80 (s); 6.55 (s); 6.62 (s); 7.60 (s).

C-156  $^1$H-NMR (CDCl$_3$): δ = 1.26 (d); 1.55-2.10 (m); 2.18 (s); 2.24 (s); 3.42 (s);
3.55 (m); 3.85 (br.); 3.98 (s); 4.20 (s); 4.32 (s); 4.59 (s); 4.85 (s); 6.55 (s);
6.62 (s); 7.60 (s).

C-157  $^1$H-NMR (CDCl$_3$): δ = 1.20 (t); 2.18 (s); 2.22 (s); 2.98 (s); 3.33 (br.); 3.80 (s);
4.48 (s); 4.80 (br.); 6.55 (s); 6.70 (s); 7.38 (s).

C-158  $^1$H-NMR (CDCl$_3$): δ = 1.20 (t); 1.28 (s); 1.40-1.70 (m); 2.05 (m); 2.07 (s);
2.22 (s); 2.98 (s); 3.33 (br.); 3.98 (s); 4.67 (s); 4.78 (s); 4.90 (s); 5.01 (s);
6.52 (s); 6.62 (s); 6.97 (d); 7.38 (s); 7.88 (s); 8.23 (d).

C-159  $^1$H-NMR (CDCl$_3$): δ = 1.20 (d); 2.05 (s); 2.22 (s); 2.90 (s); 3.70 (br.);
3.98 (s); 4.72 (s); 4.90 (s); 6.53 (s); 6.62 (s); 6.80-7.50 (m).

C-160  $^1$H-NMR (CDCl$_3$): δ = 1.22 (d); 2.05 (s); 2.22 (s); 2.90 (s); 3.70 (br.);
3.98 (s); 4.72 (s); 4.90 (s); 6.53 (s); 6.62 (s); 6.70-7.50 (m).

C-161  $^1$H-NMR (CDCl$_3$): δ = 1.22 (d); 2.05 (s); 2.22 (s); 2.90 (s); 3.70 (br.);
3.98 (s); 4.78 (s); 4.90 (s); 6.55 (s); 6.62 (s); 7.05-7.50 (m).

C-162  $^1$H-NMR (CDCl$_3$): δ = 0.95 (t); 1.60 (m); 2.07 (s); 2.22 (s); 2.98 (s);
3.25 (br.); 3.98 (s); 4.70 (s); 4.92 (s); 6.53 (s); 6.62 (s); 6.80-7.40 (m).

C-163  $^1$H-NMR (CDCl$_3$): δ = 0.93 (t); 1.60 (m); 2.07 (s); 2.22 (s); 2.98 (s);
3.23 (br.); 3.98 (s); 4.70 (s); 4.90 (s); 6.53 (s); 6.65 (s); 6.80-7.40 (m).

C-164  $^1$H-NMR (CDCl$_3$): δ = 0.95 (t); 1.60 (m); 2.07 (s); 2.22 (s); 2.98 (s);
3.25 (br.); 3.98 (s); 4.78 (s); 4.90 (s); 6.53 (s); 6.62 (s); 7.00-7.40 (m).

C-165  $^1$H-NMR (CDCl$_3$): δ = 0.90 (t); 1.20 (d); 1.55 (m); 2.05 (s); 2.22 (s); 2.87 (s);
3.25 (br.); 3.98 (s); 4.72 (s); 4.90 (s); 6.55 (s); 6.62 (s); 6.80-7.45 (m).

C-166  $^1$H-NMR (CDCl$_3$): δ = 0.90 (t); 1.20 (d); 1.55 (m); 2.07 (s); 2.22 (s); 2.87 (s);
3.25 (br.); 3.98 (s); 4.72 (s); 4.90 (s); 6.55 (s); 6.62 (s); 6.70-7.45 (m).

C-167  $^1$H-NMR (CDCl$_3$): δ = 0.90 (t); 1.20 (d); 1.55 (m); 2.05 (s); 2.22 (s); 2.87 (s);
3.25 (br.); 3.98 (s); 4.78 (s); 4.92 (s); 6.55 (s); 6.62 (s); 7.00-7.45 (m).

C-168  $^1$H-NMR (CDCl$_3$): δ = 2.07 (s); 2.22 (s); 2.96 (s); 3.90 (br.); 3.98 (s);
4.74 (s); 4.90 (s); 5.20 (m); 5.83 (m); 6.55 (s); 6.62 (s); 6.80-7.45 (m).

C-169  $^1$H-NMR (CDCl$_3$): δ = 2.07 (s); 2.22 (s); 2.96 (s); 3.90 (br.); 3.98 (s);
4.70 (s); 4.90 (s); 5.20 (m); 5.83 (m); 6.55 (s); 6.62 (s); 6.70-7.45 (m).

C-170  $^1$H-NMR (CDCl$_3$): δ = 2.07 (s); 2.22 (s); 2.96 (s); 3.90 (br.); 3.98 (s);
4.78 (s); 4.90 (s); 5.23 (m); 5.83 (m); 6.55 (s); 6.62 (s); 6.99-7.45 (m).

C-177  $^1$H-NMR (CDCl$_3$): δ = 1.95 (m); 2.07 (s); 2.23 (s); 3.50 (m); 3.98 (s);
4.73 (s); 4.88 (s); 6.55 (s); 6.60 (s); 6.85-7.20 (m); 7.60 (s).

C-178  $^1$H-NMR (CDCl$_3$): δ = 1.95 (m); 2.05 (s); 2.24 (s); 3.50 (m); 3.98 (s);
4.70 (s); 4.90 (s); 6.54 (s); 6.60 (s); 6.75-7.35 (m); 7.60 (s).

C-179  $^1$H-NMR (CDCl$_3$): δ = 1.95 (m); 2.05 (s); 2.24 (s); 3.50 (m); 3.98 (s);
4.78 (s); 4.90 (s); 6.54 (s); 6.63 (s); 7.10-7.60 (m).

C-180  $^1$H-NMR (CDCl$_3$): δ = 1.60 (m); 2.08 (s); 2.22 (s); 3.43 (br.); 3.98 (s);
4.70 (s); 4.90 (s); 6.54 (s); 6.62 (s); 6.75-7.35 (m).

C-181  $^1$H-NMR (CDCl$_3$): δ = 1.60 (m); 2.06 (s); 2.22 (s); 3.43 (br.); 3.98 (s);
4.70 (s); 4.90 (s); 6.54 (s); 6.61 (s); 6.65-7.35 (m).

C-182  $^1$H-NMR (CDCl$_3$): δ = 1.60 (m); 2.08 (s); 2.24 (s); 3.43 (br.); 3.98 (s);
4.78 (s); 4.92 (s); 6.54 (s); 6.62 (s); 6.99-7.40 (m).

C-183  $^1$H-NMR (CDCl$_3$): δ = 1.23 (d); 1.47-1.49 (m); 1.62-1.71 (m); 2.05 (s);
2.10 (s); 2.22 (s); 3.27 (dtr); 3.53 (br.); 3.945 (s); 3.954 (s); 4.08 (br.); 4.61 (s);
4.69 (s); 4.88 (s); 4.90 (s); 6.53 (s); 6.61 (s); 6.70 (s); 6.78-6.85 (m);
7.05-7.10 (m); 7.34 (s).

C-184  $^1$H-NMR (CDCl$_3$): δ = 1.25 (d); 1.49-1.51 (m); 1.64-1.73 (m); 2.06 (s);
2.09 (s); 2.21 (s); 3.31 (dtr); 3.56 (br.); 3.96 (s); 3.97 (s); 4.09 (br.); 4.61 (s);
4.69 (s); 4.88 (s); 4.90 (s); 6.53 (d); 6.60 (s); 6.69 (s); 6.70-6.79 (m); 6.98 (d);
7.04 (d); 7.28 (d); 7.35 (d).

C-185  $^1$H-NMR (CDCl$_3$): δ = 1.24 (d); 1.48-1.50 (m); 1.63-1.72 (m); 2.05 (s);
2.10 (s); 2.22 (s); 3.30 (dtr); 3.53 (br.); 3.96 (s); 3.97 (s); 4.09 (br.); 4.63 (s);
4.77 (s); 4.90 (s); 4.97 (s); 6.53 (s); 6.62 (s); 6.71 (s); 7.02-7.10 (m);
7.15-7.22 (m); 7.32-7.35 (m).

C-189  $^1$H-NMR (CDCl$_3$): δ = 2.05 (s); 2.10 (s); 2.21 (s); 3.48 (br.); 3.72 (tr);
3.965 (s); 3.974 (s); 4.62 (s); 4.71 (s); 4.89 (s); 4.92 (s); 6.54 (s); 6.62 (s); 6.71 (s);
6.79-6.87 (m); 7.05-7.13 (m); 7.25 (s); 7.37 (s).

TABLE D-continued

Physical data for compounds of the formula I.9 according to Table C

| No. in Table C | Phys. data ($^1$H-NMR (CDCl$_3$, δ [ppm]); Mp [° C.]; HPLC/MS (R$_t$ [min])) |
|---|---|
| C-190 | $^1$H-NMR (CDCl$_3$): δ = 2.06 (s); 2.09 (s); 2.21 (s); 3.49 (br.); 3.73 (tr); 3.96 (s); 4.62 (s); 4.70 (5); 4.89 (s); 4.90 (s); 6.55 (s); 6.61 (s); 6.70 (s); 6.71-6.79 (m); 6.98-7.04 (m); 7.28 (s); 7.30 (s); 7.37 (s). |
| C-191 | $^1$H-NMR (CDCl$_3$): δ = 2.07 (s); 2.22 (s); 3.50 (br.); 3.77 (s); 3.98 (s); 4.80 (s); 4.93 (s); 6.55 (s); 6.63 (s); 7.00-7.40 (m). |
| C-195 | $^1$H-NMR (CDCl$_3$): δ = 1.21 (t); 2.99 (s); 3.35 (br.); 3.98 (s); 4.70 (s); 4.90 (s); 6.70-7.55 (m). |
| C-196 | $^1$H-NMR (CDCl$_3$): δ = 1.21 (t); 2.23 (s); 2.97 (s); 3.35 (br.); 3.98 (s); 4.67 (s); 4.87 (s); 6.60-7.40 (m). |
| C-248 | $^1$H-NMR (CDCl$_3$): δ = 1.19 (t); 1.66-1.91 (m); 1.99-2.16 (m); 2.14 (s); 2.22 (s); 2.38-2.43 (m); 2.98 (s); 3.33 (br.); 3.98 (s); 4.88 (m); 6.52 (s); 6.85 (s); 7.41 (s); |
| C-251 | $^1$H-NMR (CDCl$_3$): δ = 1.19 (t); 1.21 (d); 1.76-1.92 (m); 2.01-2.18 (m); 2.14 (s); 2.22 (s); 2.38-2.44 (m); 2.54-2.63 (m); 2.98 (s); 3.34 (br.); 4.32 (sept); 4.87 (m); 6.52 (s); 6.83 (s); 7.39 (s); |
| C-252 | $^1$H-NMR (CDCl$_3$): δ = 0.93 (t); 1.19 (t); 1.18 (m); 1.61 (m); 1.76-1.91 (m); 1.99-2.16 (m); 2.14 (s); 2.22 (s); 2.38-2.43 (m); 2.54-2.63 (m); 2.98 (s); 3.33 (br.); 4.04 (t); 4.87 (m); 6.52 (s); 6.85 (s); 7.41 (s); |
| C-259 | $^1$H-NMR (CDCl$_3$): δ = 1.19 (t); 1.38-1.51 (m); 1.57-1.79 (m); 1.81-2.38 (m); 2.19 (s); 2.21 (s); 2.98 (s); 3.00-3.09 (m); 3.34 (br.); 3.82 (s); 4.72 (m); 6.54 (s); 6.81 (s); 7.39 (s); |
| C-262 | $^1$H-NMR (CDCl$_3$): δ = 1.19 (t); 1.21 (d); 1.38-1.51 (m); 1.57-1.79 (m); 1.81-2.38 (m); 2.20 (s); 2.21 (s); 2.20-2.31 (m); 2.98 (s); 3.00-3.09 (m); 3.34 (br.); 4.28 (m); 4.72 (m); 6.52 (s); 6.83 (s); 7.39 (s); |
| C-263 | $^1$H-NMR (CDCl$_3$): δ = 0.91 (t); 1.19 (t); 1.18 (m); 1.38-1.49 (m); 1.61 (m); 1.61-1.71 (m); 1.83-2.09 (m); 2.14 (s); 2.20-2.31 (m); 2.22 (s); 2.98 (s); 3.00-3.09 (m); 3.353 (br.); 4.02 (t); 4.72 (m); 6.52 (s); 6.81 (s); 7.39 (s). |
| C-270 | $^1$H-NMR (CDCl$_3$): δ = 1.19 (t); 1.37-1.56 (m); 1.61-1.92 (m); 2.09-2.27 (m); 2.19 (s); 2.21 (s); 2.98 (s); 2.68-2.79 (m); 3.34 (br.); 3.82 (s); 4.87 (m); 6.55 (s); 6.82 (s); 7.39 (s); HPLC/MS: R$_t$ = 3.110 |
| C-299 | HPLC/MS: R$_t$ = 3.331 |
| C-300 | HPLC/MS: R$_t$ = 3.716 |
| C-301 | HPLC/MS: R$_t$ = 3.280 |
| C-302 | HPLC/MS: R$_t$ = 3.342 |
| C-303 | HPLC/MS: R$_t$ = 3.185 |
| C-304 | HPLC/MS: R$_t$ = 3.424 |
| C-305 | HPLC/MS: R$_t$ = 3.193 |
| C-306 | HPLC/MS: R$_t$ = 3.376 |
| C-307 | HPLC/MS: R$_t$ = 3.344 |
| C-308 | HPLC/MS: R$_t$ = 3.290 |
| C-309 | HPLC/MS: R$_t$ = 3.408 |
| C-310 | HPLC/MS: R$_t$ = 3.423 |
| C-311 | HPLC/MS: R$_t$ = 3.558 |
| C-312 | HPLC/MS: R$_t$ = 3.445 |
| C-313 | HPLC/MS: R$_t$ = 3.258 |
| C-314 | HPLC/MS: R$_t$ = 3.365 |
| C-315 | HPLC/MS: R$_t$ = 3.297 |
| C-316 | HPLC/MS: R$_t$ = 3.483 |
| C-317 | HPLC/MS: R$_t$ = 3.619 |
| C-318 | $^1$H-NMR (CDCl$_3$): δ = 1.22 (t); 1.35 (t); 2.07 (s); 2.23 (s); 2.97 (s); 3.35 (br.); 4.22 (m); 4.85 (s); 4.92 (s); 6.53 (s); 6.73 (s); 7.10-7.45 (m). |
| C-319 | $^1$H-NMR (CDCl$_3$): δ = 1.22 (t); 1.32 (t); 2.07 (s); 2.23 (s); 3.03 (s); 3.37 (br.); 4.22 (q); 4.74 (s); 4.92 (s); 6.58 (s); 6.63 (s); 6.85-7.45 (m). |
| C-320 | $^1$H-NMR (CDCl$_3$): δ = 1.22 (t); 1.32 (t); 2.07 (s); 2.23 (s); 3.01 (s); 3.35 (br.); 4.21 (q); 4.72 (s); 4.90 (s); 6.59 (s); 6.63 (s); 6.70-7.45 (m). |
| C-321 | $^1$H-NMR (CDCl$_3$): δ = 1.27 (m); 2.10 (s); 2.28 (s); 3.10 (br.); 3.40 (br.); 4.20 (m); 4.82 (s); 4.99 (s); 6.62 (s); 6.66 (s); 7.15-7.45 (m). |
| C-322 | $^1$H-NMR (CDCl$_3$): δ = 1.22 (t); 1.28 (t); 2.05 (s); 2.24 (s); 3.02 (s); 3.38 (br.); 4.18 (q); 4.83 (s); 4.98 (s); 6.57 (s); 6.63 (s); 6.90-7.45 (m). |
| C-323 | $^1$H-NMR (CDCl$_3$): δ = 1.20 (t); 1.30 (t); 2.05 (s); 2.23 (s); 3.00 (s); 3.35 (br.); 4.22 (q); 4.68 (s); 4.90 (s); 6.54 (s); 6.60-7.40 (m). |
| C-325 | $^1$H-NMR (CDCl$_3$): δ = 1.18 (t); 1.37 (t); 1.78 (s); 2.23 (s); 2.98 (s); 3.35 (br.); 4.27 (q); 5.13 (s); 6.47 (s); 6.60 (s); 7.10-7.45 (m). |
| C-327 | $^1$H-NMR (CDCl$_3$): δ = 1.20 (t); 1.75 (s); 2.20 (s); 3.00 (s); 3.35 (br.); 3.85 (s); 5.15 (s); 5.20 (s); 6.45 (s); 6.55 (s); 6.85-7.45 (m). |
| C-328 | Mp. 61-63° C. |
| C-329 | HPLC/MS: R$_t$ = 2.414 |
| C-330 | HPLC/MS: R$_t$ = 2.933 |
| C-335 | HPLC/MS: R$_t$ = 3.207 |
| C-336 | $^1$H-NMR (CDCl$_3$): δ = 1.18 (m); 2.24 (m); 2.43 (m); 2.98 (s); 3.35 (br.); 3.90 (s); 4.49 (s); 6.61 (s); 6.69 (s); 7.28 (s). |
| C-337 | $^1$H-NMR (CDCl$_3$): δ = 0.33 (m); 0.57 (m); 1.21 (m); 2.18 (s); 2.23 (s); 3.02 (s); 3.40 (br.); 3.92 (s); 4.80 (s); 6.62 (s); 6.81 (s); 7.44 (s). |
| C-338 | $^1$H-NMR (CDCl$_3$): δ = 1.06 (t); 1.21 (t); 2.13 (s); 2.18 (s); 2.40 (m); 2.96 (s); 3.35 (br.); 3.75 (s); 3.87 (s); 6.57 (s); 7.42 (s). |

TABLE D-continued

Physical data for compounds of the formula I.9 according to Table C

No. in
Table C  Phys. data ($^1$H-NMR (CDCl$_3$, δ [ppm]); Mp [° C.]; HPLC/MS (R$_t$ [min]))

C-339  $^1$H-NMR (CDCl$_3$): δ = 1.19 (t); 1.26 (t); 1.93 (s); 2.19 (s); 2.22 (s); 2.96 (s); 3.35 (br.); 3.79 (s); 4.16 (q); 5.16 (s); 6.54 (s); 6.63 (s); 7.38 (s).
C-340  $^1$H-NMR (CDCl$_3$): δ = 1.24 (t); 1.93 (s); 2.19 (s); 2.23 (s); 3.01 (s); 3.35 (br.); 3.81 (s); 3.93 (s); 5.23 (s); 6.62 (s); 6.67 (s); 7.45 (s).
C-341  $^1$H-NMR (CDCl$_3$): δ = 1.18 (t); 1.45 (d); 1.82 (s); 2.17 (s); 2.21 (s); 2.98 (s); 3.35 (br.); 3.86 (s); 4.81 (q); 6.53 (s); 6.73 (s); 7.39 (s).
C-342  HPLC/MS: R$_t$ = 3.727
C-343  HPLC/MS: R$_t$ = 2.909
C-344  HPLC/MS: R$_t$ = 4.034
C-345  HPLC/MS: R$_t$ = 2.489
C-346  HPLC/MS: R$_t$ = 2.733
C-347  HPLC/MS: R$_t$ = 3.150
C-348  HPLC/MS: R$_t$ = 2.319
C-349  HPLC/MS: R$_t$ = 2.883
C-350  HPLC/MS: R$_t$ = 3.058
C-351  HPLC/MS: R$_t$ = 2.347
C-352  HPLC/MS: R$_t$ = 2.833
C-353  HPLC/MS: R$_t$ = 3.027
C-354  HPLC/MS: R$_t$ = 3.277
C-355  HPLC/MS: R$_t$ = 2.645
C-356  HPLC/MS: R$_t$ = 3.128
C-357  HPLC/MS: R$_t$ = 3.257
C-358  HPLC/MS: R$_t$ = 3.258
C-359  HPLC/MS: R$_t$ = 3.329
C-360  HPLC/MS: R$_t$ = 3.094
C-361  HPLC/MS: R$_t$ = 2.912
C-362  HPLC/MS: R$_t$ = 3.216
C-363  HPLC/MS: R$_t$ = 3.140
C-364  HPLC/MS: R$_t$ = 3.200
C-365  HPLC/MS: R$_t$ = 3.221
C-366  HPLC/MS: R$_t$ = 3.937
C-367  HPLC/MS: R$_t$ = 3.575
C-368  HPLC/MS: R$_t$ = 3.555
C-369  HPLC/MS: R$_t$ = 3.783
C-370  HPLC/MS: R$_t$ = 3.462
C-371  HPLC/MS: R$_t$ = 3.618
C-372  HPLC/MS: R$_t$ = 3.702
C-373  HPLC/MS: R$_t$ = 3.513
C-374  HPLC/MS: R$_t$ = 3.792
C-375  HPLC/MS: R$_t$ = 3.377
C-376  HPLC/MS: R$_t$ = 3.166
C-377  HPLC/MS: R$_t$ = 3.167
C-378  HPLC/MS: R$_t$ = 3.907
C-379  HPLC/MS: R$_t$ = 3.414
C-380  HPLC/MS: R$_t$ = 3.388
C-381  HPLC/MS: R$_t$ = 3.827
C-382  HPLC/MS: R$_t$ = 2.858
C-383  HPLC/MS: R$_t$ = 3.793
C-384  HPLC/MS: R$_t$ = 2.824
C-385  HPLC/MS: R$_t$ = 3.054
C-386  HPLC/MS: R$_t$ = 3.810
C-387  $^1$H-NMR (CDCl$_3$): δ = 1.20 (t); 1.31 (t); 1.68 (s); 2.20 (s); 2.29 (s); 3.01 (s); 3.37 (br.); 4.17 (q); 5.81 (s); 6.60 (s); 6.76 (s); 7.20-7.83 (m).
C-388  $^1$H-NMR (CDCl$_3$): δ = 1.31 (t); 1.68 (s); 2.24 (s); 2.30 (s); 2.23 (s); 3.48 (s); 3.93 (s); 5.83 (s); 6.77 (s); 6.83 (s); 7.00-7.80 (m); 8.38 (s).
C-389  $^1$H-NMR (CDCl$_3$): δ = 1.15 (m); 2.17 (s); 2.22 (s); 2.45 (q); 2.97 (s); 3.35 (br.); 4.22 (m); 4.40 (m); 4.47 (s); 6.50-7.40 (m).
C-390  $^1$H-NMR (CDCl$_3$): δ = 1.15 (t); 1.22 (t); 2.14 (s); 2.17 (s); 2.37 (q); 2.99 (s); 3.38 (br.); 4.86 (s); 4.92 (s); 5.10 (s); 6.57 (s); 6.60 (s); 7.30-7.45 (m).
C-391  $^1$H-NMR (CDCl$_3$): δ = 1.20 (m); 2.17 (s); 2.24 (s); 2.43 (q); 2.98 (s); 3.34 (br.); 4.13 (q); 4.83 (s); 6.55 (s); 6.62 (s); 7.39 (s).
C-392  $^1$H-NMR (CDCl$_3$): δ = 1.18 (m); 2.10 (s); 2.16 (s); 2.94 (s); 3.35 (br.); 3.82 (s); 4.58 (s); 6.54 (s); 6.70 (s); 7.37 (s).
C-393  $^1$H-NMR (CDCl$_3$): δ = 0.30 (m); 0.53 (m); 1.15 (t); 1.43 (m); 1.85 (s); 2.20 (m); 2.97 (s); 3.35 (br.); 3.85 (m); 4.80 (m); 6.52 (s); 6.73 (s); 7.38 (s).
C-394  $^1$H-NMR (CDCl$_3$): δ = 1.17 (t); 1.44 (d); 1.82 (s); 2.17 (m); 2.97 (s); 3.35 (br.); 4.15 (m); 4.40 (m); 4.82 (q); 6.50 (s); 6.70 (s); 6.80-7.40 (m).
C-395  $^1$H-NMR (CDCl$_3$): δ = 1.19 (t); 1.45 (d); 1.85 (s); 2.12 (s); 2.17 (s); 2.97 (s); 3.33 (br.); 4.78 (q); 5.06 (s); 6.52 (s); 6.64 (s); 7.20-7.450 (m).
C-396  $^1$H-NMR (CDCl$_3$): δ = 1.22 (m); 1.46 (d); 1.80 (s); 2.16 (m); 2.99 (s); 3.37 (br.); 4.09 (q); 4.82 (q); 6.58 (s); 6.74 (s); 7.42 (s).
C-397  $^1$H-NMR (CDCl$_3$): δ = 1.22 (t); 1.62 (d); 2.07 (s); 2.12 (s); 2.97 (s); 3.35 (br.); 5.30 (s); 5.83 (q); 6.43 (s); 6.48 (s); 6.80-7.50 (m).
C-398  $^1$H-NMR (CDCl$_3$): δ = 1.22 (t); 1.75 (s); 2.20 (s); 2.98 (s); 3.35 (br.); 5.15 (s); 5.28 (s); 6.45 (s); 6.57 (s); 6.80-7.45 (m).

TABLE D-continued

Physical data for compounds of the formula I.9 according to Table C

| No. in Table C | Phys. data ($^1$H-NMR (CDCl$_3$, δ [ppm]); Mp [° C.]; HPLC/MS (R$_t$ [min])) |
|---|---|
| C-400 | $^1$H-NMR (CDCl$_3$): δ = 0.98 (t); 1.20 (t); 1.77 (s); 1.80-2.15 (m); 2.24 (s); 2.97 (s); 3.35 (br.); 5.13 (t); 5.21 (s); 6.47 (s); 6.60 (s); 6.97-7.40 (m). |
| C-402 | $^1$H-NMR (CDCl$_3$): δ = 1.25 (t); 1.62 (d); 1.80 (s); 2.25 (s); 3.05 (br.); 3.38 (br.); 4.78 (s); 5.67 (q); 6.55 (s); 6.63 (s); 6.99-7.45 (m). |
| C-404 | $^1$H-NMR (CDCl$_3$): δ = 1.23 (t); 1.65 (d); 1.77 (s); 2.27 (s); 3.05 (br.); 3.38 (br.); 5.18 (s); 5.38 (q); 6.53 (s); 6.62 (s); 6.99-7.45 (m). |
| C-405 | $^1$H-NMR (CDCl$_3$): δ = 1.20 (t); 1.75 (s); 2.22 (s); 2.98 (s); 3.35 (br.); 5.22 (s); 5.38 (s); 6.46 (s); 6.60 (s); 7.10-7.50 (m). |
| C-406 | HPLC/MS: R$_t$ = 3.006 |
| C-407 | HPLC/MS: R$_t$ = 3.294 |
| C-408 | HPLC/MS: R$_t$ = 3.014 |
| C-409 | HPLC/MS: R$_t$ = 3.000 |
| C-410 | HPLC/MS: R$_t$ = 2.846 |
| C-411 | HPLC/MS: R$_t$ = 2.962 |
| C-412 | HPLC/MS: R$_t$ = 3.251 |
| C-413 | HPLC/MS: R$_t$ = 3.539 |
| C-414 | HPLC/MS: R$_t$ = 3.275 |
| C-415 | HPLC/MS: R$_t$ = 3.032 |
| C-416 | HPLC/MS: R$_t$ = 3.061 |
| C-417 | HPLC/MS: R$_t$ = 2.934 |
| C-418 | HPLC/MS: R$_t$ = 2.561 |
| C-419 | HPLC/MS: R$_t$ = 3.378 |
| C-420 | HPLC/MS: R$_t$ = 3.071 |
| C-421 | HPLC/MS: R$_t$ = 3.582 |
| C-422 | HPLC/MS: R$_t$ = 2.451 |
| C-423 | HPLC/MS: R$_t$ = 3.275 |
| C-424 | HPLC/MS: R$_t$ = 2.627 |
| C-425 | HPLC/MS: R$_t$ = 3.430 |
| C-426 | HPLC/MS: R$_t$ = 2.985 |
| C-427 | HPLC/MS: R$_t$ = 3.574 |
| C-428 | HPLC/MS: R$_t$ = 3.422 |
| C-429 | HPLC/MS: R$_t$ = 3.196 |
| C-433 | $^1$H-NMR (CDCl$_3$): δ = 1.18 (t); 1.35 (s); 1.65 (d); 1.76 (s); 2.23 (s); 2.98 (s); 3.35 (br.); 5.20 (s); 5.37 (q); 6.46 (s); 6.60 (s); 6.99-7.45 (m). |
| C-435 | $^1$H-NMR (CDCl$_3$): δ = 1.20 (t); 2.99 (s); 3.35 (br.); 3.98 (s); 4.75 (s); 4.90 (s); 6.70-7.60 (m). |
| C-436 | $^1$H-NMR (CDCl$_3$): δ = 1.21 (t); 2.99 (s); 3.35 (br.); 3.98 (s); 4.70 (s); 4.90 (s); 6.70-7.50 (m). |
| C-437 | $^1$H-NMR (CDCl$_3$): δ = 1.18 (t); 2.25 (s); 2.95 (s); 3.30 (br.); 3.98 (s); 4.75 (s); 4.90 (s); 6.70-7.40 (m). |
| C-438 | $^1$H-NMR (CDCl$_3$): δ = 1.18 (t); 2.25 (s); 2.95 (s); 3.30 (br.); 3.98 (s); 4.69 (s); 4.88 (s); 6.60-7.40 (m). |
| C-434 | $^1$H-NMR (CDCl$_3$): δ = 1.18 (t); 1.62 (d); 2.09 (s); 2.19 (s); 2.97 (s); 3.33 (br.); 4.07 (s); 5.83 (q); 6.48 (s); 6.53 (s); 7.30-7.60 (m); 7.83 (s). |
| C-439 | $^1$H-NMR (CDCl$_3$): δ = 1.22 (t); 3.00 (s); 3.30 (br.); 3.98 (s); 4.68 (s); 4.90 (s); 6.50-7.60 (m). |
| C-440 | $^1$H-NMR (CDCl$_3$): δ = 1.22 (t); 3.00 (s); 3.30 (br.); 3.98 (s); 4.75 (s); 4.90 (s); 6.50-7.60 (m). |
| C-441 | $^1$H-NMR (CDCl$_3$): δ = 1.22 (t); 3.00 (s); 3.30 (br.); 3.98 (s); 4.66 (s); 4.90 (s); 6.50-7.60 (m). |
| C-442 | $^1$H-NMR (CDCl$_3$): δ = 1.18 (t); 1.75 (s); 2.20 (s); 2.99 (s); 3.35 (br.); 5.18 (s); 5.30 (s); 6.45 (s); 6.55 (s); 7.00-7.70 (m). |
| C-443 | $^1$H-NMR (CDCl$_3$): δ = 1.18 (t); 1.77 (s); 2.22 (s); 3.00 (s); 3.35 (br.); 5.16 (s); 5.23 (s); 6.45 (s); 6.55 (s); 7.00-7.45 (m). |
| C-444 | $^1$H-NMR (CDCl$_3$): δ = 1.18 (t); 1.75 (s); 2.25 (s); 3.00 (s); 3.35 (br.); 4.71 (d); 5.13 (s); 6.15 (m); 6.35 (d); 6.48 (s); 6.58 (s); 7.10-7.45 (m). |
| C-445 | $^1$H-NMR (CDCl$_3$): δ = 1.20 (t); 2.17 (s); 2.22 (s); 2.98 (s); 3.35 (br.); 3.90 (s); 4.53 (s); 4.62 (s); 6.53 (s); 6.70 (s); 7.38 (s). |
| C-446 | $^1$H-NMR (CDCl$_3$): δ = 1.18 (t); 1.62 (d); 2.08 (s); 2.17 (s); 2.98 (s); 3.35 (br.); 4.75 (d); 5.81 (q); 6.20 (m); 6.35 (d); 6.50 (s); 7.25-7.60 (m); 7.53 (s). |
| C-447 | $^1$H-NMR (CDCl$_3$): δ = 1.18 (t); 1.62 (d); 2.07 (s); 2.10 (s); 2.98 (s); 3.35 (br.); 5.30 (s); 5.87 (q); 6.45 (s); 6.50 (s); 7.20-7.85 (m). |
| C-448 | $^1$H-NMR (CDCl$_3$): δ = 1.20 (t); 1.62 (d); 2.08 (s); 2.12 (s); 2.98 (s); 3.35 (br.); 5.08 (q); 5.25 (s); 6.42 (s); 6.74 (s); 7.10-7.80 (m). |
| C-449 | $^1$H-NMR (CDCl$_3$): δ = 1.22 (t); 2.08 (s); 2.23 (s); 2.98 (s); 3.35 (br.); 3.98 (s); 4.85 (s); 4.90 (s); 6.53 (s); 6.60 (s); 7.10-7.80 (m). |
| C-450 | $^1$H-NMR (CDCl$_3$): δ = 1.19 (t); 1.82-2.13 (m); 2.14 (s); 2.20 (s); 2.35 (m); 2.59 (m); 2.98 (s); 3.34 (br.); 3.83 (s); 4.80 (m); 6.32 (m); 6.52 (s); 6.61 (d); 6.90 (s); 7.39 (s); HPLC/MS: R$_t$ = 2.688 |
| C-451 | $^1$H-NMR (CDCl$_3$): δ = 1.20 (t); 3.05 (s); 3.38 (m); 3.96 (m); 4.68 (m); 4.93 (m); 6.75-6.93 (m); 7.00-7.21 (m); 7.45-7.59 (m); HPLC/MS: R$_t$ = 3.257 |
| C-452 | $^1$H-NMR (CDCl$_3$): δ = 1.20 (t); 2.97 (s); 3.25-3.57 (m); 3.92 (m); 4.56-4.71 (m); 4.85-4.93 (m); 6.55-6.88 (m); 6.95-7.18 (m); 7.45-7.61 (m); HPLC/MS: R$_t$ = 3.334 |

TABLE D-continued

Physical data for compounds of the formula I.9 according to Table C

| No. in Table C | Phys. data ($^1$H-NMR (CDCl$_3$, δ [ppm]); Mp [° C.]; HPLC/MS (R$_t$ [min])) |
|---|---|
| C-453 | $^1$H-NMR (CDCl$_3$): δ = 0.94 (t). 1.21 (t); 1.73 (m); 2.97 (s); 3.25-3.57 (m); 4.11 (t); 4.60-4.71 (m); 4.89-4.96 (m); 6.55-6.71 (m); 6.82-6.89 (m); 7.00-7.16 (m); 7.45-7.61 (m); HPLC/MS: R$_t$ = 3.607 |
| C-454 | $^1$H-NMR (CDCl$_3$): δ = 1.22 (t); 2.95 (s); 3.23-3.57 (m); 3.96 (s); 4.60-4.75 (m); 4.85-4.97 (m); 6.65-7.18 (m); 7.35-7.55 (m); HPLC/MS: R$_t$ = 3.397 |
| C-455 | $^1$H-NMR (CDCl$_3$): δ = 0.94 (t). 1.21 (t); 1.76 (m); 3.05 (s); 3.25-3.71 (m); 4.15 (t); 4.62-4.75 (m); 4.91-4.98 (m); 6.70-7.23 (m); 7.45-7.61 (m); HPLC/MS: R$_t$ = 3.738 |
| C-456 | $^1$H-NMR (CDCl$_3$): δ = 1.45 (t); 3.39 (s); 3.61-3.85 (m); 3.99 (s); 4.79 (m); 4.95 (m); 7.01-7.19 (m); 78.47 (s). 7.68 (s). 7.81-7.9 (m); HPLC/MS: R$_t$ = 3.516 |

HPLC column: RP-18 column (Chromolith Speed ROD from Merck KgaA, Germany)

Mobile phase: acetonitrile+0.1% trifluoroacetic acid (TFA)/water+0.1% TFA (gradient 5:95 to 95:5 over 5 min, 40° C.

MS: quadrupole electrospray ionization, 80 V (positive mode)

The abbreviation (br.) denotes broad NMR signals.

In the case of the oximes, E- and Z-isomers are frequently discernible next to one another. In these cases, the NMR signals of the main isomer were specified.

The abbreviation Mp. denotes the melting point.

Examples of the Action Against Harmful Fungi

The fungicidal action of the compounds of the formula I was demonstrated by the following tests:

Microtiter Tests

The compounds and active compounds were formulated separately as a stock solution having a concentration of 10 000 ppm in DMSO.

The measured parameters were compared to the growth of the active compound-free control variant (100%) and the fungus- and active compound-free blank value to determine the relative growth in % of the pathogens in the individual active compounds.

Use Example 1

Activity Against the Gray Mold Pathogen *Bottytis Cinerea*

The stock solution was pipetted into a microtiter plate (MTP) and diluted to the stated active compound concentration using a malt-based aqueous nutrient medium for fungi. An aqueous spore suspension of *Botrytis cinerea* was then added. The plates were placed in a water vapor-saturated chamber at temperatures of 18° C. Using an absorption photometer, the MTPs were measured at 405 nm on day 7 after the inoculation.

In this test, the pathogens which had been treated with 125 ppm of the active compound I-7, I-9, I-10, I-15, I-24, I-25, I-26, I-29, I-43, I-53, I-59, I-66, I-97 or 1-154 showed a growth of at most 10%.

Use Example 2

Activity Against the Late Blight Pathogen *Phytophthora infestans*

The stock solution was pipetted into a microtiter plate (MTP) and diluted to the stated active compound concentration using a pea juice-based aqueous nutrient medium for fungi. An aqueous zoo spore suspension of *Phytophthora infestans* was then added. The plates were placed in a water vapor-saturated chamber at temperatures of 18° C. Using an absorption photometer, the MTPs were measured at 405 nm on day 7 after the inoculation.

In this test, the pathogens which had been treated with 125 ppm of the active compound I-7, I-9, I-10, I-97 or 1-154 showed a growth of at most 10%.

Use Example 3

Activity Against the Rice Blast Pathogen *Pyricularia Oryzae*

The stock solution was pipetted into an MTP and diluted to the stated active compound concentration using a malt-based aqueous nutrient medium for fungi. An aqueous spore suspension of *Pyricularia oryzae* was then added. The plates were placed in a water vapor-saturated chamber at temperatures of 18° C. Using an absorption photometer, the MTPs were measured at 405 nm on day 7 after the inoculation.

In this test, the pathogens which had been treated with 125 ppm of the active compound I-7, I-9, I-10, I-15, I-24, I-25, I-26, I-29, I-47, I-53, I-59, I-64, I-66, I-9.7 or I-154 showed a growth of at most 10%.

Use Example 4

Activity Against the *Septoria* Leaf Spot Pathogen *Septoria tritici*

The stock solution was pipetted into an MTP and diluted to the stated active compound concentration using a malt-based aqueous nutrient medium for fungi. An aqueous spore suspension of *Septoria tritici* was then added. The plates were placed in a water vapor-saturated chamber at temperatures of 18° C. Using an absorption photometer, the MTPs were measured at 405 nm on day 7 after the inoculation.

In this test, the pathogens which had been treated with 125 ppm of the active compound I-5, I-7, I-9, I-10, I-15, I-24, I-25, I-26, I-29, I-43, I-47, I-59, I-97 or I-154 showed a growth of at most 10%.

Greenhouse Tests

The active compounds were prepared separately as a stock solution comprising 19.6 mg of active compound which was made up to 10 ml using a mixture of acetone and/or DMSO, cyclohexanone and the emulsifier Wettol® EM 31 (wetting agent having emulsifying and dispersing action based on ethoxylated castor oil) in a volume ratio of solvent/emulsifier of 99/1. The mixture was then made up to 32 ml with water. This stock solution was diluted with the solvent/emulsifier/water mixture described to the concentration of active compound stated below.

Use Example 5

Activity Against Brown Rust of Wheat Caused by *Puccinia Recondita* on Wheat, Protective Application Leaves of potted wheat seedlings Were sprayed with an aqueous suspension having the active compound concentration stated below. The next day, the treated plants were inoculated with a spore-suspension of brown rust of wheat (*Puccinia recondita*). The plants were then placed in a chamber with high atmospheric humidity (90 to 95%) at 20 to 22° C. for 24 hours. During this time, the spores germinated and the germ tubes penetrated into the leaf tissue. The next day, the test plants were returned to the greenhouse and cultivated at temperatures between 20 and 22° C. and 65 to 70% relative atmospheric humidity for a further 7 days. The extent of the rust fungus development on the leaves was then determined visually in %.

In this test, the plants which had been treated with 600 ppm of the active compound I-2, I-5 to I-10, I-15, I-17, I-21, I-22, I-24, I-31, I-33, I-35, I-37, I-38, I-42, I-43, I-44, I-53, I-59, I-64, I-66, I-97, I-105, I-117 to I-125, I-128 to I-134, I-136, I-139, I-142 to I-149, I-151, I-154 to I-158, I-182, I-252, I-437 or I-450 showed an infection of at most 15%, whereas the untreated plants were 80 to 90% infected.

Use Example 6

Activity Against Brown Rust of Wheat Caused by *Puccinia Recondita* on Wheat, Curative Application Leaves of potted wheat seedlings were inoculated with a spore suspension of brown rust of wheat (*Puccinia recondita*). The pots were then placed in a chamber with high atmospheric humidity (90 to 95%) at 20 to 22° C. for 24 hours. During this time, the spores germinated and the germ tubes penetrated into the leaf tissue. The next day, the infected plants were sprayed to run off point with the active compound solution described above having the active compound concentration stated below. After the spray coating had dried on, the test plants were cultiviated in a greenhouse at temperatures between 20 and 22° C. and 65 to 70% relative atmospheric humidity for 7 days. The extent of the rust fungus development was then determined visually in % infection of the leaf area.

In this test, the plants which had been treated with 600 ppm of the active compound I-2, I-5 to I-10, I-15, I-17, I-21, I-22, I-24, I-31, I-35, I-37, I-38, I-42, I-43, I-44, I-53, I-59, I-64, I-66, I-97, I-105, I-117, I-118, I-120 to I-125, I-128 to I-134, I-136, I-139, I-142 to I-149, I-151, I-156 to I-158, I-182 or 1-450 showed an infection of at most 15%, whereas the untreated plants were 80 to 90% infected.

Use Example 7

Activity Against Gray Mold on Bell Pepper Leaves Caused by *Botrytis Cinerea* 1 Day Protective Application Bell pepper seedlings were, after 2-3 leaves were well-developed, sprayed to runoff point with an aqueous suspension having the concentration of active compounds stated below. After one day, the treated plants were inoculated with a spore suspension of *Botrytis cinerea* in a 2% biomalt solution. The test plants were then placed in a dark climatized chamber at 22 to 24° C. and high atmospheric humidity. After 5 days, the extent of the fungal infection on the leaves could be determined visually in %.

In this test, the plants which had been treated with 600 ppm of the active compounds I-10, I-121, I-131, I-142, I-144, I-146, I-148, I-449, I-151 or I-182 showed an infection of at most 15%, whereas the untreated plants were 80 to 90% infected.

Use Example 8

Activity Against Gray Mold on Bell Pepper Leaves Caused by *Botrytis Cinerea* 7 Days Protective Application Bell pepper seedlings were, after 2-3 leaves were well-developed, sprayed to runoff point with an aqueous suspension having the concentration of active compounds stated below. After 7 days, the treated plants were inoculated with a spore suspension of *Botrytis cinerea* in a 2% biomalt solution. The test plants were then placed in a dark climatized chamber at 22 to 24° C. and high atmospheric humidity. After 5 days, the extent of the fungal infection on the leaves could be determined visually in %.

In this test, the plants which had been treated with 250 ppm of the active compounds I-66 or I-97 showed an infection of at most 15%, whereas the untreated plants were 80 to 90% infected.

Use Example 9

Activity Against Mildew of Wheat Caused by *Erysiphe* [Syn. *Blumeria*] *Graminis* f. sp. *Tritici*

Leaves of potted wheat seedlings were sprayed to runoff point with an aqueous suspension having the concentration of active compounds stated below. The suspension or emulsion was prepared as described above. 24 hours after the spray coating had dried on, the plants were dusted with spores of mildew of wheat (*Erysiphe* [syn. *Blumeria*] *graminis* f. sp. *tritici*). The test plants were then placed in a greenhouse at temperatures between 20 and 24° C. and 60 to 90% relative atmospheric humidity. After 7 days, the extent of the mildew development was determined visually in % infection of the entire leaf area.

In this test, the plants which had been treated with 600 ppm of the active compounds I-2, I-10, I-66, I-121, I-131, I-142, I-144, I-146, I-148, I-149, I-151, I-182, I-437 or I-450, the plants which had been treated with 500 ppm of the active compound I-252 and the plants which had been treated with 300 ppm of the active compound I-97 showed an infection of at most 15%, whereas the untreated plants were 80 to 90% infected.

Use Example 10

Curative Activity Against Soybean Rust Caused by *Phakpsora Pachyrhizi*

Leaves of potted soybean seedlings were inoculated with a spore suspension of soybean rust (*Phakpsora pachyrhizi*). The pots were then placed in a chamber of high atmospheric humidity (90 to 95%) at 23 to 27° C. for 24 hours. During this time, the spores germinated and the germ tubes penetrated into the leaf tissue. The infected plants were then sprayed to runoff point with the solution of active compound described above at the active compound concentration stated below. After the spray coating had dried on, the test plants were cultivated in a greenhouse at temperatures between 23 and 27° C. and 60 to 80% relative atmospheric humidity for 14 days. The extent of the rust fungus development on the leaves was then determined visually in % infection.

In this test, the plants which had been treated with 600 ppm of the active compounds I-2, I-8, I-10, I-66, I-97, I-121, I-131, I-144, I-146, I-148, I-149, I-151, I-182, I-437 or I-450 and the plants which had been treated with 500 ppm of the active compound I-252 showed an infection of at most 15%, whereas the untreated plants were 80 to 90% infected.

Use Example 11

Activity Against Net Blotch of Barley Caused by *Pyrenophora teres* 1 Day Protective Application Leaves of potted barley seedlings were sprayed to runoff point with an aqueous suspension having the concentration of active compounds stated below. 24 hours after the spray coating had dried on, the test plants were inoculated with an aqueous spore suspension of *Pyrenophora* [syn. *Drechslera*] *teres*, the net blotch pathogen. The test plants were then placed in a greenhouse at temperatures between 20 and 24° C. and 70% relative atmospheric humidity. After 6 days, the extent of the disease development was determined visually in % infection of the entire leaf area.

In this test, the plants which had been treated with 600 ppm of the active compounds I-10, I-131, I-144, I-146, I-149 or I-182 and the plants which had been treated with 250 ppm of the active compounds I-10, I-121, I-142 or I-149 showed an infection of at most 15%, whereas the untreated plants were 80 to 90% infected.

Use Example 12

Curative Activity Against *Septoria* Leaf Spot of Wheat Caused by *Septoria Tritici*

Leaves of potted wheat seedlings were inoculated with a spore suspension of the leaf spot pathogen *Septoria tritici*. The test plants were then placed in a greenhouse at temperatures between 20 and 24° C. and a relative atmospheric humidity close to 100% for 4 days and then at temperatures between 16 and 18° C. and a relative atmospheric humidity of about 70%. Six days after the inoculation, the plants were sprayed to runoff point with an aqueous active compound solution having the concentration stated below. After the spray coating had dried on, the plants were replaced. After 21 days, the extent of the development of the disease was determined visually in % infection of the entire leaf area.

In this test, the plants which had been treated with 250 ppm of the active compounds I-121, I-131, I-142, I-144, I-148 or I-149 showed an infection of at most 15%, whereas the untreated plants were 80 to 90% infected.

The invention claimed is:
1. A compound of the formula I

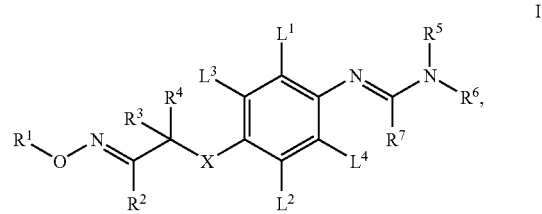

in which the substituents have the following meaning:

$R^1$ is $C_1$-$C_8$-alkyl, $C_2$-$C_8$-alkenyl, $C_2$-$C_8$-alkynyl, $C_3$-$C_8$-cycloalkyl, $C_3$-$C_8$-cyclo-alkenyl, phenyl or a three- to ten-membered saturated, partially unsaturated or aromatic mono- or bicyclic heterocyclyl which, in addition to carbon atoms, contains one to four heteroatoms from the group consisting of O, N and S as ring members;

$R^2$ is amino, $C_1$-$C_8$-alkyl, $C_2$-$C_8$-alkenyl, $C_2$-$C_8$-alkynyl, $C_1$-$C_8$-alkoxy, $C_3$-$C_8$-cycloalkyl, $C_3$-$C_s$-cycloalkenyl, phenyl or a three- to ten-membered saturated, partially unsaturated or aromatic mono- or bicyclic heterocyclyl which, in addition to carbon atoms, contains one to four heteroatoms from the group consisting of O, N and S as ring members, where the groups $R^2$ may be attached directly or via a carbonyl group;

$R^3$ and $R^4$ independently of one another are hydrogen, $C_1$-$C_8$-alkyl, $C_1$-$C_8$-haloalkyl, $C_1$-$C_8$-alkylcarbonyl or $C_1$-$C_8$-alkoxycarbonyl;

$R^5$ and $R^6$ independently of one another are $C_1$-$C_8$-alkyl, $C_1$-$C_8$-haloalkyl, $C_1$-$C_4$-alkoxy or $C_3$-$C_s$-cycloalkyl;

$R^7$ is hydrogen, $C_1$-$C_8$-alkyl, $C_1$-$C_8$-haloalkyl, $C_1$-$C_4$-alkoxy or $C_1$-$C_8$-haloalkoxy; and aliphatic and cyclic groups $R^1$ to $R^6$ may carry one, two, three or up to the maximum possible number of identical or different groups $R^a$ which independently of one another are selected from:

$R^a$ is halogen, hydroxyl, oxo, nitro, cyano, carboxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy, $C_1$-$C_4$-haloalkoxy, $C_3$-$C_6$-cycloalkyl, $C_3$-$C_8$-cycloalkenyl, $C_2$-$C_6$-alkenyloxy, $C_3$-$C_6$-alkynyloxy, $C_1$-$C_4$-alkoxyimino, $C_2$-$C_8$-alkylidene, $C_3$-$C_8$-cycloalkylidene, $C_1$-$C_{12}$-alkylamino, $C_1$-$C_4$-alkoxycarbonyl, $C_1$-$C_4$-alkylcarbonyloxy, $NR^AR^B$, $C_2$-$C_8$-alkylene, $C_2$-$C_8$-oxyalkylene, $C_1$-$C_8$-oxyalkyleneoxy, phenyl, naphthyl or a three- to ten-membered saturated, partially unsaturated or aromatic mono- or bicyclic heterocyclyl which, in addition to carbon atoms, contains one to four heteroatoms from the group consisting of O, N and S as ring members;

where the cyclic groups $R^a$ may be attached directly or via a nitrogen or oxygen atom;

where in the divalent groups $R^a$ the carbon chains may be interrupted by one to four heteroatoms from the group consisting of O, N and S and the free valencies may be attached to the same atom or to two adjacent atoms;

where the aliphatic or cyclic groups $R^a$ for their part may be partially or fully halogenated and/or may carry one, two, three or up to the maximum possible number of identical or different groups $R^b$:

$R^b$ is halogen, hydroxyl, nitro, cyano, carboxyl, $C_1$-$C_4$-alkyl, $C_2$-$C_4$-alkenyl, $C_2$-$C_8$-alkynyl, $C_1$-$C_4$-haloalkyl, $C_1$-$C_4$-alkoxy, $C_1$-$C_4$-haloalkoxy, $C_1$-$C_8$-alkylcarbonylamino, phenyl, phenoxy, pyridyl, pyridyloxy or $C_3$-$C_8$-cycloalkylcarbonylamino;

where the cyclic groups $R^b$ for their part may be partially or fully halogenated and/or may carry one, two, three or up to the maximum possible number of identical or different groups $R^c$:

$R^c$ is halogen, hydroxyl, nitro, cyano, carboxyl, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy or $C_1$-$C_f$-haloalkoxy;

$R^A$ and $R^B$ independently of one another are hydrogen, $C_1$-$C_8$-alkyl, $C_1$-$C_8$-halo-alkyl or $C_1$-$C_8$-alkylcarbonyl;

$L^1$, $L^2$, $L^3$ and $L^4$ independently of one another are hydrogen, halogen, $C_1$-$C_4$-alkyl, $C_1$-$C_4$-haloalkyl, $C_1$-$C_4$-alkoxy or $C_1$-$C_4$-haloalkoxy;

where $R^1$ and $R^2$ or $R^1$ and $R^3$ or $R^2$ and $R^3$ or $R^3$ and $R^4$ and/or $R^5$ and $R^6$ in each case together with the atoms linking them may form a five- to ten-membered saturated or partially unsaturated cyclic group which, in addition to the carbon atoms, may contain one to three heteroatoms from the group consisting of N, O and S and/or may be partially or fully halogenated and/or may carry one, two, three or up to the maximum possible number of identical or different groups $R^a$;

X is oxygen or sulfur;

or an agriculturally acceptable salt of the compounds of the formula I.

2. The compound of the formula I according to claim 1 in which $R^1$ is $C_1$-$C_8$-alkyl, $C_2$-$C_8$-alkenyl, $C_2$-$C_8$-alkynyl, $C_3$-$C_8$-cycloalkyl, phenyl or a five- or six-membered saturated, partially unsaturated or aromatic heterocyclyl which, in addition to carbon atoms, contains one to three heteroatoms from the group consisting of O, N and S as ring members; and $R^2$ is amino, $C_1$-$C_8$-alkyl, $C_2$-$C_8$-alkenyl, $C_2$-$C_8$-alkynyl, $C_1$-$C_8$-alkylcarbonyl, $C_1$-$C_8$-alkoxycarbonyl, $C_3$-$C_8$-cycloalkyl, phenyl or a five- or six-membered saturated, partially unsaturated or aromatic heterocyclyl which, in addition to carbon atoms, contains one to three heteroatoms from the group consisting of O, N and S as ring members;

where aliphatic and cyclic groups $R^1$ to $R^6$ may carry one, two, three or up to the maximum possible number of identical or different groups $R^a$ which independently of one another are selected from:

$R^a$ is halogen, $C_1$-$C_4$-alkyl, $C_1$-$C_4$-haloalkyl, oxo, $C_1$-$C_4$-alkoxyimino, $C_1$-$C_{12}$-alkylamino, $C_1$-$C_4$-alkoxycarbonyl, $C_1$-$C_4$-alkylcarbonyloxy, $C_1$-$C_4$-alkoxy, $C_1$-$C_4$-haloalkoxy, $NR^A R^B$, phenyl or a five- or six-membered saturated, partially unsaturated or aromatic heterocyclyl which, in addition to carbon atoms, contains one to three heteroatoms from the group consisting of O, N and S as ring members, where the cyclic groups $R^a$ may be attached directly or via a nitrogen or oxygen atom;

where the aliphatic and cyclic groups $R^a$ for their part may be partially or fully halogenated and/or may carry one, two, three or up to the maximum possible number of identical or different groups $R^b$;

where $R^1$ and $R^2$ or $R^1$ and $R^3$ or $R^2$ and $R^3$ and/or $R^5$ and $R^6$ also in each case together with the atoms linking them may form cyclic groups according to claim 1; and X is oxygen;

where $R^1$ may not be substituted by heterocyclic groups $R^a$.

3. The compound of the formula I according to claim 1 in which $R^1$ and $R^2$; $R^1$ and $R^3$, $R^2$ and $R^3$ and also $R^3$ and $R^4$ are in each case not able to form a cyclic group.

4. The compound of the formula I according to claim 3 where $R^3$ is optionally $R^a$-substituted $C_1$-$C_8$-alkyl or $C_1$-$C_8$-haloalkyl.

5. The compound of the formula I according to claim 4 where the α carbon atom in $R^1$ does not carry a cyclic group.

6. The compound of the formula I according to claim 5 in which $R^2$ is substituted $C_1$-$C_8$-alkyl which carries a phenyl or heterocyclyl group attached via oxygen and optionally a further one, two, three or four identical of different groups $R^a$.

7. The compound of the formula I according to claim 1 in which $R^2$ is substituted $C_1$-$C_8$-alkyl which carries a phenyl or heterocyclyl group and optionally a further one, two, three or four identical of different groups $R^a$.

8. The compound of the formula I according to claim 1 in which $R^2$ is optionally $R^a$-substituted phenyl or heterocyclyl.

9. A process for preparing a compound of the formula I according to claim 1 wherein a compound of the formula II

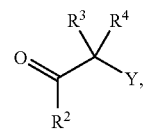

in which Y is a nucleophilically replaceable group, is condensed with a compound of the formula III

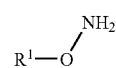

and the resulting compound of the formula IV

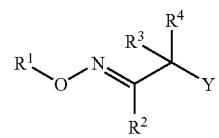

is converted under basic conditions with a compound of the formula V

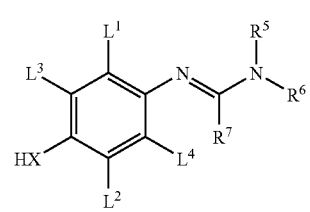

into a compound of the formula I.

10. A process for preparing a compound of the formula I according to claim 1 in which $R^2$ is $CH_2\text{—}R^{2a}$, where $R^{2a}$ is a group $R^a$ attached via oxygen, wherein a compound of the formula II.1

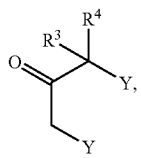
II.1 in which Y are each independently of one another nucleophilically replaceable groups, is condensed with a compound of the formula III,

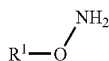
III the resulting compound of the formula IV.1

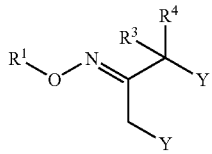
IV.1 is reacted under basic conditions with a compound of the formula V

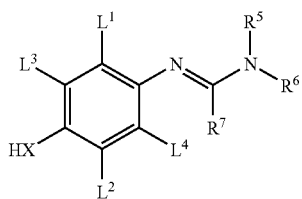
V and the resulting compound of the formula VI

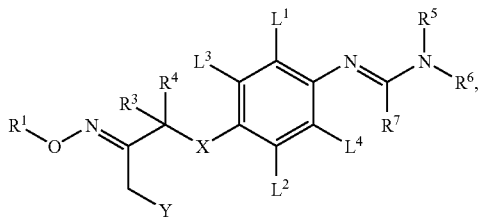
VI in which Y has the meaning given above is reacted with a compound of the formula VII

$H\text{—}R^{2a}$ VII, where $R^{2a}$ has the meaning given above under basic conditions to give a compound of the formula I.1,

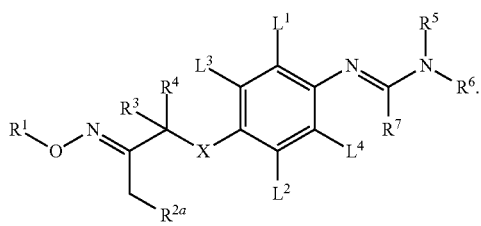
I.1″

11. The compound of the formula VI according to claim 10 in which Y is $C_1$-$C_8$-alkylsulfonyloxy or arylsulfonyloxy.

12. A composition comprising a solvent or solid carrier and a compound of the formula I according to claim 1.

13. The composition according to claim 12, comprising a further active compound.

14. A seed, comprising a compound of the formula I according to claim 1 in an amount of from 1 to 1000 g per 100 kg.

15. A method for controlling phytopathogenic harmful fungi wherein the fungi or the materials, plants, the soil or seed to be protected from fungal attack are treated with an effective amount of a compound of the formula I according to claim 1.

16. The method of claim 15, wherein $R^1$ and $R^2$; $R^1$ and $R^3$, $R^2$ and $R^3$ and also $R^3$ and $R^4$ are in each case not able to form a cyclic group.

17. The method of claim 16, wherein $R^3$ is optionally $R^a$-substituted $C_1$-$C_8$-alkyl or $C_1$-$C_8$-haloalkyl.

18. The method of claim 17, wherein the α carbon atom in $R^1$ does not carry a cyclic group.

19. The method of claim 18, wherein $R^2$ is substituted $C_1$-$C_8$-alkyl which carries a phenyl or heterocyclyl group attached via oxygen and optionally a further one, two, three or four identical of different groups $R^a$.

20. The method of claim 15, wherein $R^2$ is substituted $C_1$-$C_8$-alkyl which carries a phenyl or heterocyclyl group and optionally a further one, two, three or four identical of different groups $R^a$.

* * * * *

UNITED STATES PATENT AND TRADEMARK OFFICE
CERTIFICATE OF CORRECTION

PATENT NO. : 8,426,631 B2  
APPLICATION NO. : 12/739606  
DATED : April 23, 2013  
INVENTOR(S) : Rheinheimer et al.

Page 1 of 1

It is certified that error appears in the above-identified patent and that said Letters Patent is hereby corrected as shown below:

In the Claims

Claim 1, col. 160, line 25: "$C_3$-$C_s$-cycloalkenyl," should be --$C_3$-$C_8$-cycloalkenyl,--.

Claim 1, col. 160, line 36: "$C_3$-$C_s$-cycloalkenyl;" should be --$C_3$-$C_8$-cycloalkenyl;--.

Claim 1, col. 161, line 14: "$C_1$-$C_t$-haloalkoxy;" should be --$C_1$-$C_4$-haloalkoxy;--.

Signed and Sealed this  
Fifteenth Day of October, 2013

Teresa Stanek Rea  
*Deputy Director of the United States Patent and Trademark Office*